(12) United States Patent
McCoull et al.

(10) Patent No.: US 8,673,938 B2
(45) Date of Patent: *Mar. 18, 2014

(54) CHEMICAL COMPOUNDS

(75) Inventors: William McCoull, Macclesfield (GB);
Martin Packer, Macclesfield (GB);
James Stewart Scott, Macclesfield (GB); Paul Robert Owen Whittamore, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 787 days.

This patent is subject to a terminal disclaimer.

(21) Appl. No.: 12/541,565

(22) Filed: Aug. 14, 2009

(65) Prior Publication Data

US 2009/0306075 A1  Dec. 10, 2009

Related U.S. Application Data

(63) Continuation of application No. 11/928,744, filed on Oct. 30, 2007, now Pat. No. 7,964,618.

(60) Provisional application No. 60/864,303, filed on Nov. 3, 2006, provisional application No. 60/864,247, filed on Nov. 3, 2006.

(51) Int. Cl.
*A61K 31/4545* (2006.01)
*C07D 401/04* (2006.01)

(52) U.S. Cl.
USPC .......................................... 514/318; 564/194

(58) Field of Classification Search
USPC .......................................... 546/194; 514/318
See application file for complete search history.

(56) References Cited

U.S. PATENT DOCUMENTS

| | | | |
|---|---|---|---|
| 4,250,178 A | 2/1981 | Bucher et al. | |
| 7,816,391 B2 | 10/2010 | Packer et al. | |
| 7,951,833 B2 | 5/2011 | Tomkinson et al. | |
| 7,964,618 B2 | 6/2011 | McCoull et al. | |
| 2004/0142930 A1 | 7/2004 | Yamada et al. | |
| 2006/0223852 A1 | 10/2006 | Gillespie et al. | |
| 2006/0235028 A1 | 10/2006 | Li et al. | |
| 2008/0269288 A1 | 10/2008 | McCoull et al. | |
| 2009/0221660 A1 | 9/2009 | Tomkinson et al. | |
| 2009/0221663 A1 | 9/2009 | Packer et al. | |
| 2009/0264401 A1 | 10/2009 | Gill et al. | |
| 2009/0312372 A1 | 12/2009 | McCoull et al. | |
| 2010/0022589 A1 | 1/2010 | McCoull et al. | |
| 2011/0028529 A1 | 2/2011 | Tomkinson et al. | |
| 2011/0028530 A1 | 2/2011 | Tomkinson et al. | |
| 2011/0060022 A1 | 3/2011 | Packer et al. | |
| 2011/0092526 A1 | 4/2011 | Bennett et al. | |

FOREIGN PATENT DOCUMENTS

| EP | 0188094 | 7/1986 |
|---|---|---|
| EP | 1219609 | 7/2002 |
| EP | 1600442 | 11/2005 |
| EP | 1889842 | 2/2008 |
| EP | 1894919 | 3/2008 |
| WO | WO 02/20463 | 3/2002 |
| WO | WO 02/34711 | 5/2002 |
| WO | WO 03/015774 | 2/2003 |
| WO | WO 2004/065351 | 8/2004 |
| WO | WO 2004/089470 | 10/2004 |
| WO | WO 2004/089896 | 10/2004 |
| WO | WO 2005/016877 | 2/2005 |
| WO | WO 2005/023761 | 3/2005 |
| WO | WO 2005/054200 | 6/2005 |
| WO | WO 2005/060963 | 7/2005 |
| WO | WO 2005/108359 | 11/2005 |
| WO | WO 2005/121110 | 12/2005 |
| WO | WO 2006/000371 | 1/2006 |
| WO | WO 2006/048750 | 5/2006 |
| WO | WO 2006/050476 | 5/2006 |
| WO | WO 2006/074244 | 7/2006 |
| WO | WO 2006/106054 | 10/2006 |
| WO | WO 2006/106423 | 10/2006 |
| WO | WO 2006/113261 | 10/2006 |
| WO | WO 2006/125958 | 11/2006 |
| WO | WO 2006/132197 | 12/2006 |
| WO | WO 2006/132436 | 12/2006 |
| WO | WO 2006/134467 | 12/2006 |
| WO | WO 2007/007041 | 1/2007 |
| WO | WO 2007/017649 | 2/2007 |
| WO | WO 2007/052843 | 5/2007 |
| WO | WO 2007/053657 | 5/2007 |
| WO | WO 2007/058346 | 5/2007 |
| WO | WO 2007/089683 | 8/2007 |
| WO | WO 2007/107470 | 9/2007 |
| WO | WO 2007/115935 | 10/2007 |

(Continued)

OTHER PUBLICATIONS

Ettmayer et al. "Lessons Learned from Marketed and Investigational Prodrugs." J. Med. Chem., (2004), 47(10): 2393-2404.*

(Continued)

*Primary Examiner* — Patricia L Morris

(74) *Attorney, Agent, or Firm* — Morgan, Lewis & Bockius LLP

(57) ABSTRACT

Compounds of formula (I):

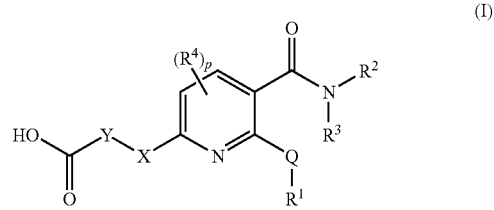

wherein variable groups are defined within; their use in the inhibition of 11βHSD1, processes for making them and pharmaceutical compositions comprising them are described.

3 Claims, No Drawings

(56) References Cited

FOREIGN PATENT DOCUMENTS

| WO | WO 2007/125049 | 11/2007 |
|---|---|---|
| WO | WO 2008/012532 | 1/2008 |
| WO | WO 2008/053194 | 5/2008 |
| WO | WO 2008/099145 | 8/2008 |
| WO | WO 2008/142986 | 11/2008 |
| WO | WO 2009/010416 | 1/2009 |
| WO | WO 2009/060232 | 5/2009 |
| WO | WO 2009/098501 | 8/2009 |
| WO | WO 2009/130496 | 10/2009 |
| WO | WO 2010/087770 | 8/2010 |

OTHER PUBLICATIONS

Stella, Valentino. "Prodrugs as therapeutics." Expert Opin. Ther. Patents (2004), 14(3): 277-280.*

Testa, Bernard. "Prodrug research: futile or fertile?" Biochemical Pharmacology, 68 (2004): 2097-2106.*

Balant ed inWolff et al. Burger's Medicinal Chemistry and Drug Discovery. 5th ed. vol. 1: Principles and Practice. pp. 949-982., 1997.*

Barf et al. "Recent progress in 11-beta-hydroxysteroid dehydrogenase type 1 (11-beta-HSD1) inhibitor development" Drugs of the Future 31(3):231-243 (2006).

Blake et al. "Discovery of 3,3-dimethyl-azetidin-2-ones as potent and selective inhibitors of 11ÿ-HSD1" Gordon Research Conference on Medicinal Chemistry, Colby-Sawyer College, New London, NH, USA (Aug. 2007).

Boyle "Recent advances in the discovery of 11b-HSD1 inhibitors" Current Opinion in Drug Discovery and Development 11:495-511 (2008).

deSchoolmeester et al. "An increase in obesity is associated with increased 11ÿHSD1 activity but not expression in mature human subcutaneous adipocytes" Association for the Study of Obesity (ASO) and Adipose Tissue Discussion Group, Institute of Child Health, London (Nov. 9, 2006).

Jean et al. "Inhibitors of 11â-HSD1: A Potential Treatment for the Metabolic Syndrome" Current Topics in Medicinal Chemistry 8(17): 1508-1523 (2008).

Mayers "11β-hydroxysteroid dehydrogenase type 1: a tale of (fat) mice to men" Abstract and Presentation, Obesity and its Treatment, Society for Medicines Research (Sep. 25, 2008).

Brittain et al. "Polymorphism in pharmaceutical dosage forms" Polymorphism in Pharmaceutical Solids XX (Jan. 1999) pp. 235-238 and 348-361.

Jean et al. "Inhibitors of 11β-HSD1: A Potential Treatment for the Metabolic Syndrome" Current Topics in Medicinal Chemistry 8(17): 1508-1523 (2008).

Katsuno et al. "Sergliflozin, a novel selective inhibitor of low-affinity sodium glucose cotransporter (SGLT2), validates the critical role of SGLT2 in renal glucose reabsorption and modulates plasma glucose level" The Journal of Pharmacology and Experimental Therapeutics 320(1):323-330 (2007).

Morissette et al. "High-throughput crystallization: polymorphs, salts, co-crystals and solvates of pharmaceutical solids" Advanced Drug Delivery Reviews 56:275-300 (2004).

Vippagunta et. al. "Crystalline solids" Advanced Drug Delivery Reviews 48:3-26 (2001) Abstract.

Dostert et al. "Studies on the neuroleptic benzamides I. Synthesis and antidopaminergic properties of new pyrimidine derivatives" European Journal of Medicinal Chemistry 17(5):437-444 (1982).

Hirokawa et al. "Synthesis and structure-affinity relationships of novel N-(1-ethyl-4-methylhexahydro-1,4-diazepin-6-yl)pyridine-3-carboxamides with potent serotonin 5-HT3 and dopamine D2 receptor antagonistic activity" J Med. Chem. 46(5):702-715 (2003).

Hussein et al. "β-Oxoanilides in heterocyclic synthesis: An expeditious synthesis of new polyfunctionally substituted pyridine and pyrazole derivatives" Journal of Heterocyclic Chemistry 45(5):1819-1823 (2008).

Langlois et al. "Studies on the neuroleptic benzamides II. Synthesis and pharmacological evaluation of new 6-azabrendane derivatives" European Journal of Medicinal Chemistry 17(5):445-447 (1982).

Shorvon "Pyrrolidone derivatives" Lancet 358(9296):1885-1892 (2001).

* cited by examiner

CHEMICAL COMPOUNDS

This application is a Continuation Application of U.S. patent application Ser. No. 11/928,744, filed Oct. 30, 2007 (now U.S. Pat. No. 7,964,618), which claims the benefit of U.S. Provisional Application No. 60/864,303, filed Nov. 3, 2006, and U.S. Provisional Application No. 60/864,247, filed Nov. 3, 2006, all of which are herein incorporated by reference in their entirety.

This invention relates to chemical compounds, or pharmaceutically-acceptable salts thereof. These compounds possess human 11-β-hydroxysteroid dehydrogenase type 1 enzyme (11βHSD1) inhibitory activity and accordingly have value in the treatment of disease states including metabolic syndrome and are useful in methods of treatment of a warm-blooded animal, such as man. The invention also relates to processes for the manufacture of said compounds, to pharmaceutical compositions containing them and to their use in the manufacture of medicaments to inhibit 11βHSD1 in a warm-blooded animal, such as man.

Glucocorticoids (cortisol in man, corticosterone in rodents) are counter regulatory hormones i.e. they oppose the actions of insulin (Dallman M F, Strack A M, Akana S F et al. 1993; Front Neuroendocrinol 14, 303-347). They regulate the expression of hepatic enzymes involved in gluconeogenesis and increase substrate supply by releasing glycerol from adipose tissue (increased lipolysis) and amino acids from muscle (decreased protein synthesis and increased protein degradation). Glucocorticoids are also important in the differentiation of pre-adipocytes into mature adipocytes which are able to store triglycerides (Bujalska I J et al. 1999; Endocrinology 140, 3188-3196). This may be critical in disease states where glucocorticoids induced by "stress" are associated with central obesity which itself is a strong risk factor for type 2 diabetes, hypertension and cardiovascular disease (Bjorntorp P & Rosmond R 2000; Int. J. Obesity 24, S80-S85)

It is now well established that glucocorticoid activity is controlled not simply by secretion of cortisol but also at the tissue level by intracellular interconversion of active cortisol and inactive cortisone by the 11-beta hydroxysteroid dehydrogenases, 11βHSD1 (which activates cortisone) and 11βHSD2 (which inactivates cortisol) (Sandeep T C & Walker B R 2001 Trends in Endocrinol & Metab. 12, 446-453). That this mechanism may be important in man was initially shown using carbenoxolone (an anti-ulcer drug which inhibits both 11βHSD1 and 2) treatment which (Walker B R et al. 1995; J. Clin. Endocrinol. Metab. 80, 3155-3159) leads to increased insulin sensitivity indicating that 11βHSD1 may well be regulating the effects of insulin by decreasing tissue levels of active glucocorticoids (Walker B R et al. 1995; J. Clin. Endocrinol. Metab. 80, 3155-3159).

Clinically, Cushing's syndrome is associated with cortisol excess which in turn is associated with glucose intolerance, central obesity (caused by stimulation of pre-adipocyte differentiation in this depot), dyslipidaemia and hypertension. Cushing's syndrome shows a number of clear parallels with metabolic syndrome. Even though the metabolic syndrome is not generally associated with excess circulating cortisol levels (Jessop D S et al. 2001; J. Clin. Endocrinol. Metab. 86, 4109-4114) abnormally high 11βHSD1 activity within tissues would be expected to have the same effect. In obese men it was shown that despite having similar or lower plasma cortisol levels than lean controls, 11βHSD1 activity in subcutaneous fat was greatly enhanced (Rask E et al. 2001; J. Clin. Endocrinol. Metab. 1418-1421). Furthermore, the central fat, associated with the metabolic syndrome expresses much higher levels of 11βHSD1 activity than subcutaneous fat (Bujalska I J et al. 1997; Lancet 349, 1210-1213). Thus there appears to be a link between glucocorticoids, 11βHSD1 and the metabolic syndrome.

11βHSD1 knock-out mice show attenuated glucocorticoid-induced activation of gluconeogenic enzymes in response to fasting and lower plasma glucose levels in response to stress or obesity (Kotelevtsev Y et al. 1997; Proc. Natl. Acad. Sci. USA 94, 14924-14929) indicating the utility of inhibition of 11βHSD1 in lowering of plasma glucose and hepatic glucose output in type 2 diabetes. Furthermore, these mice express an anti-atherogenic lipoprotein profile, having low triglycerides, increased HDL cholesterol and increased apo-lipoprotein AI levels. (Morton N M et al. 2001; J. Biol. Chem. 276, 41293-41300). This phenotype is due to an increased hepatic expression of enzymes of fat catabolism and PPARα. Again this indicates the utility of 11βHSD1 inhibition in treatment of the dyslipidaemia of the metabolic syndrome.

The most convincing demonstration of a link between the metabolic syndrome and 11βHSD1 comes from recent studies of transgenic mice over-expressing 11βHSD1 (Masuzaki H et al. 2001; Science 294, 2166-2170). When expressed under the control of an adipose specific promoter, 11βHSD1 transgenic mice have high adipose levels of corticosterone, central obesity, insulin resistant diabetes, hyperlipidaemia and hyperphagia. Most importantly, the increased levels of 11βHSD1 activity in the fat of these mice are similar to those seen in obese subjects. Hepatic 11βHSD1 activity and plasma corticosterone levels were normal, however, hepatic portal vein levels of corticosterone were increased 3 fold and it is thought that this is the cause of the metabolic effects in liver.

Overall it is now clear that the complete metabolic syndrome can be mimicked in mice simply by overexpressing 11βHSD1 in fat alone at levels similar to those in obese man.

11βHSD1 tissue distribution is widespread and overlapping with that of the glucocorticoid receptor. Thus, 11βHSD1 inhibition could potentially oppose the effects of glucocorticoids in a number of physiological/pathological roles. 11βHSD1 is present in human skeletal muscle and glucocorticoid opposition to the anabolic effects of insulin on protein turnover and glucose metabolism are well documented (Whorwood C B et al. 2001; J. Clin. Endocrinol. Metab. 86, 2296-2308). Skeletal muscle must therefore be an important target for 11βHSD1 based therapy.

Glucocorticoids also decrease insulin secretion and this could exacerbate the effects of glucocorticoid induced insulin resistance. Pancreatic islets express 11βHSD1 and carbenoxolone can inhibit the effects of 11-dehydrocorticosterone on insulin release (Davani B et al. 2000; J. Biol. Chem. 275, 34841-34844). Thus in treatment of diabetes 11βHSD1 inhibitors may not only act at the tissue level on insulin resistance but also increase insulin secretion itself.

Skeletal development and bone function is also regulated by glucocorticoid action. 11βHSD1 is present in human bone osteoclasts and osteoblasts and treatment of healthy volunteers with carbenoxolone showed a decrease in bone resorption markers with no change in bone formation markers (Cooper M S et al 2000; Bone 27, 375-381). Inhibition of 11βHSD1 activity in bone could be used as a protective mechanism in treatment of osteoporosis.

Glucocorticoids may also be involved in diseases of the eye such as glaucoma. 11βHSD1 has been shown to affect intraocular pressure in man and inhibition of 11βHSD1 may be expected to alleviate the increased intraocular pressure associated with glaucoma (Rauz S et al. 2001; Investigative Opthalmology & Visual Science 42, 2037-2042).

There appears to be a convincing link between 11βHSD1 and the metabolic syndrome both in rodents and in humans. Evidence suggests that a drug which specifically inhibits 11βHSD1 in type 2 obese diabetic patients will lower blood glucose by reducing hepatic gluconeogenesis, reduce central obesity, improve the atherogenic lipoprotein phenotype, lower blood pressure and reduce insulin resistance. Insulin effects in muscle will be enhanced and insulin secretion from the beta cells of the islet may also be increased.

Currently there are two main recognised definitions of metabolic syndrome.

1) The Adult Treatment Panel (ATP III 2001 JMA) definition of metabolic syndrome indicates that it is present if the patient has three or more of the following symptoms:

Waist measuring at least 40 inches (102 cm) for men, 35 inches (88 cm) for women;
Serum triglyceride levels of at least 150 mg/dl (1.69 mmol/l);
HDL cholesterol levels of less than 40 mg/dl (1.04 mmol/l) in men, less than 50 mg/dl (1.29 mmol/l) in women;
Blood pressure of at least 135/80 mm Hg; and/or
Blood sugar (serum glucose) of at least 110 mg/dl (6.1 mmol/l).

2) The WHO consultation has recommended the following definition which does not imply causal relationships and is suggested as a working definition to be improved upon in due course:

The patient has at least one of the following conditions: glucose intolerance, impaired glucose tolerance (IGT) or diabetes mellitus and/or insulin resistance; together with two or more of the following:
Raised Arterial Pressure;
Raised plasma triglycerides
Central Obesity
Microalbuminuria We have found that the compounds defined in the present invention, or a pharmaceutically-acceptable salt thereof, are effective 11βHSD1 inhibitors, and accordingly have value in the treatment of disease states associated with metabolic syndrome. We have also found that the compounds of the invention have improved properties, which would make them better candidates for use as pharmaceuticals. For example, in general the compounds of the invention have good oral bioavailability whilst retaining potency. Therefore this group of compounds would be expected to provide superior oral exposure at a lower dose and thereby be particularly suitable for use in the treatment or prevention of a disease or medical condition treatable by inhibiting 11βHSD1. The compounds of the invention may also have superior potency and/or advantageous physical properties and/or favourable toxicity profiles and/or favourable metabolic profiles in comparison with other 11βHSD1 inhibitors known in the art. Accordingly there is provided a compound of formula (1):

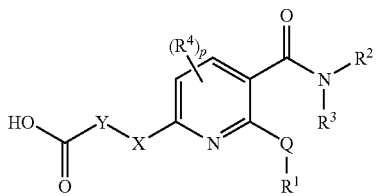

(1)

wherein:
Q is a single bond, —O—, —S— or —N($R^{15}$)— wherein $R^{15}$ is hydrogen, $C_{1-3}$alkyl or $C_{2-3}$alkanoyl or $R^{15}$ and $R^1$ together with the nitrogen atom to which they are attached form a 4-7 membered saturated ring;

$R^1$ is $C_{1-6}$alkyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl, $C_{3-7}$cycloalkyl$C_{2-3}$alkynyl, phenyl, phenyl$C_{1-3}$alkyl, heteroaryl, heteroaryl$C_{1-3}$alkyl, heterocyclyl, or heterocyclyl$C_{1-3}$alkyl [each of which is optionally substituted by 1, 2 or 3 substituents independently selected from $C_{1-3}$alkyl, hydroxy, halo, oxo, cyano, trifluoromethyl, $C_{1-3}$alkoxy, carboxy$C_{1-3}$alkyl, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$C(O)—, $R^{5'}$OC(O)— and ($R^{5'}$)($R^{5''}$)NSO$_2$— (wherein $R^5$ is $C_{1-3}$alkyl optionally substituted by 1, 2 or 3 substituents independently selected from hydroxyl, halo and cyano; and $R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)] and optional substituents for heterocyclyl and the heterocyclyl group in heterocyclyl$C_{1-3}$alkyl are additionally selected from $R^{21}$, $R^{21}$CO—$R^{21}$S(O)$_k$ (wherein k is 0, 1 or 2) and $R^{21}$CH$_2$OC(O)— wherein $R^{21}$ is phenyl optionally substituted by 1 or 2 substituents independently selected from halo, hydroxy, cyano and trifluoromethyl; or when Q is a bond $R^1$ may also be hydrogen;

$R^2$ is selected from $C_{3-7}$cycloalkyl(CH$_2$)$_m$—, and $C_{6-12}$polycycloalkyl(CH$_2$)$_m$— (wherein the cycloalkyl and polycycloalkyl rings optionally contain 1 or 2 ring atoms independently selected from nitrogen, oxygen and sulphur; m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl;

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^4$ is independently selected from halo, $C_{1-2}$alkyl, cyano, $C_{1-2}$alkoxy, and trifluoromethyl;

$R^6$ and $R^7$ are independently selected from hydroxyl, halo, oxo, carboxy, cyano, trifluoromethyl, $R^9$, $R^9$O—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$— wherein a is 0 to 2, $R^9$OC(O)—, ($R^{9'}$)($R^{9''}$)NSO$_2$—, $R^9$SO$_2$N($R^{9''}$)—, ($R^{9'}$)($R^{9''}$)NC(O)N($R^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromoxy, halo, $C_{1-4}$alkoxy, $C_{1-4}$alkoxy$C_{1-4}$alkyl, $C_{1-4}$alkoxy$C_{1-4}$alkyl, amino, N—$C_{1-4}$alkylamino, di-N, N—($C_{1-4}$alkyl)amino, N—$C_{1-4}$alkylcarbamoyl, di-N,N—($C_{1-4}$alkyl)carbamoyl, $C_{1-4}$alkylS(O)$_r$—, $C_{1-4}$alkylS(O)$_r$$C_{1-4}$alkyl (wherein r is 0, 1 and 2)];

$R^9$ is independently $C_{1-3}$alkyl optionally substituted by 1, 2 or 3 substituents independently selected from hydroxyl, halo, $C_{1-4}$alkoxy, carboxy and cyano;

$R^{9'}$, $R^{9''}$ and $R^{9'''}$ are independently selected from hydrogen and $C_{1-3}$alkyl optionally substituted by hydroxyl, halo, $C_{1-4}$alkoxy, carboxy or cyano);

p is 0, 1 or 2;

either X is —O(CH$_2$)$_q$—, —S(CH$_2$)$_q$— or —N(R$^{12}$)(CH$_2$)$_q$— wherein $R^{12}$ is hydrogen, $C_{1-3}$alkyl or $C_{1-3}$alkanoyl and q is 0 or 1; and Y is:

1) a $C_{3-7}$cycloalkdiyl ring, a phenylene ring, an adamantdiyl group, a 5-7 membered saturated heterocyclic ring (linked by a ring carbon atom) containing 1 or 2 ring heteroatoms selected from nitrogen, oxygen and sulphur, or —[C(R$_x$)(R$_y$)]$_v$— (wherein R$_x$ and R$_y$ are independently selected from hydrogen, $C_{1-3}$alkyl, $C_{1-3}$alkoxy and hydroxyl or R$_x$ and R$_y$ together with the carbon atom to which they are attached form a $C_{3-7}$cycloalkdiyl ring and v is 1, 2, 3, 4 or 5) and when v is more than 1 the —[C(R$_x$)(R$_y$)]$_v$— group may optionally be interrupted by a —O—, —S— or —N(R$^{20}$)— group wherein $R^{20}$ is hydrogen or $C_{1-3}$alkyl; or 2) —X—Y— together represents a group of the formula:

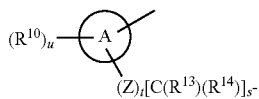

wherein:

ring A is linked to the pyridine group and —(Z)$_t$[C(R$^{13}$)(R$^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

Z is —O—, —S— or —N(R$^{16}$)— wherein $R^{16}$ is hydrogen, $C_{1-3}$alkyl or $C_{1-3}$alkanoyl;

t is 0 or 1 provided that when s is 0 then t is 0;

$R^{10}$ is independently selected from $C_{1-3}$alkyl, $C_{2-3}$alkenyl, $C_{2-3}$alkynyl, hydroxy, halo, oxo, cyano, trifluoromethyl, $C_{1-3}$alkoxy, $C_{1-3}$alkylS(O)$_n$— (wherein n is 0, 1, 2 or 3), $R^{11}$CON($R^{11'}$), ($R^{11'}$)($R^{11''}$)NC(O)—, $R^{11}$OC(O)— and ($R^{11'}$)($R^{11''}$)NSO$_2$— (wherein $R^{11}$ is $C_{1-3}$alkyl optionally substituted by hydroxyl, halo or cyano; and $R^{11'}$ and $R^{11''}$ are independently selected from hydrogen and $C_{1-3}$alkyl optionally substituted by hydroxyl, halo, $C_{1-3}$alkoxy, carboxy or cyano) or $R^{11'}$ and $R^{11''}$ together with the nitrogen atom to which they are attached form a 4-7 membered ring;

u is 0, 1 or 2;

$R^{13}$ and $R^{14}$ are independently selected from hydrogen and $C_{1-3}$alkyl or $R^{13}$ and $R^{14}$ may together with the carbon atom to which they are attached form a $C_{3-7}$cycloalkyl ring; and s is 0, 1 or 2;

or a pharmaceutically-acceptable salt or in vivo hydrolysable ester thereof.

Provided the compound is not:
{(3S)-1-[5-(adamantan-1-ylcarbamoyl)pyridin-2-yl]piperidin-3-yl}acetic acid; or
{(3S)-1-[5-(cyclohexylcarbamoyl)-6-(piperazin-1-yl)pyridin-2-yl]piperidin-3-yl}acetic acid;
or a pharmaceutically-acceptable salt or in vivo hydrolysable ester thereof.

In another aspect there is provided a compound of the formula (1) as herein above defined or a pharmaceutically-acceptable salt thereof.

In another aspect there is provided a compound of formula (1):

wherein:

Q is a single bond, —O—, —S— or —N(R$^{15}$)— wherein $R^{15}$ is hydrogen, $C_{1-3}$alkyl or $C_{2-3}$alkanoyl or $R^{15}$ and $R^1$ together with the nitrogen atom to which they are attached form a 4-7 membered saturated ring;

$R^1$ is $C_{1-6}$alkyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl, $C_{3-7}$cycloalkyl$C_{2-3}$alkynyl, phenyl, phenyl$C_{1-3}$alkyl, heteroaryl, heteroaryl$C_{1-3}$alkyl, heterocyclyl, or heterocyclyl$C_{1-3}$alkyl [each of which is optionally substituted by 1, 2 or 3 substituents independently selected from hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$OC(O)— and ($R^{5'}$)($R^{5''}$)NSO$_2$— (wherein $R^5$ is $C_{1-3}$alkyl optionally substituted by 1, 2 or 3 substituents independently selected from hydroxyl, halo and cyano; and $R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)]; or when Q is a bond $R^1$ may also be hydrogen;

$R^2$ is selected from $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl;

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^4$ is independently selected from halo, $C_{1-2}$alkyl, cyano, $C_{1-2}$alkoxy, and trifluoromethyl;

$R^6$ and $R^7$ are independently selected from hydroxyl, halo, oxo, carboxy, cyano, trifluoromethyl, $R^9$, $R^9$O—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$— wherein a is 0 to 2, $R^9$OC(O)—, ($R^{9'}$)($R^{9''}$)NSO$_2$—, $R^9$SO$_2$N($R^{9''}$)—, ($R^{9'}$)($R^{9''}$)NC(O)N($R^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromoxy, halo, $C_{1-4}$alkoxy, $C_{1-4}$alkoxy$C_{1-4}$alkyl, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_r$—, $C_{1-4}$alkylS(O)$_r$C$_{1-4}$alkyl (wherein r is 0, 1 and 2)];

$R^9$ is independently $C_{1-3}$alkyl optionally substituted by 1, 2 or 3 substituents independently selected from hydroxyl, halo, $C_{1-4}$alkoxy, carboxy and cyano;

$R^{9'}$, $R^{9''}$ and $R^{9'''}$ are independently selected from hydrogen and $C_{1-3}$alkyl optionally substituted by hydroxyl, halo, $C_{1-4}$alkoxy, carboxy or cyano);

p is 0, 1 or 2;

X is —O—, —S— or —N($R^{12}$)— wherein $R^{12}$ is hydrogen, $C_{1-3}$alkyl or $C_{1-3}$alkanoyl;

Y is either:

1) a $C_{3-7}$cycloalkdiyl ring, a 5-7 membered saturated heterocyclic ring (linked by a ring carbon atom) containing 1 or 2 ring heteroatoms selected from nitrogen, oxygen and sulphur, or —[C($R_x$)($R_y$)]$_v$— (wherein $R_x$ and $R_y$ are independently selected from hydrogen, $C_{1-3}$alkyl, $C_{1-3}$alkoxy and hydroxyl or $R_x$ and $R_y$ together with the carbon atom to which they are attached form a $C_{3-7}$cycloalkdiyl ring and v is 1, 2, 3, 4 or 5) and when v is more than 1 the —[C($R_x$)($R_y$)]$_v$— group may optionally be interrupted by a —O—, —S— or —N($R^{20}$)— group wherein $R^{20}$ is hydrogen or $C_{1-3}$alkyl; or 2) —X—Y— together represents a group of the formula:

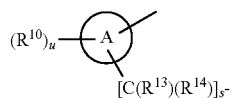

wherein:

ring A is linked to the pyridine group and —[C($R^{13}$)($R^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

$R^{10}$ is independently selected from $C_{1-3}$alkyl, $C_{2-3}$alkenyl, $C_{2-3}$alkynyl, hydroxy, halo, oxo, cyano, trifluoromethyl, $C_{1-3}$alkoxy, $C_{1-3}$alkylS(O)$_n$— (wherein n is 0, 1, 2 or 3), $R^{11}$CON($R^{11'}$), ($R^{11'}$)($R^{11''}$)NC(O)—, $R^{11'}$OC(O)— and ($R^{11'}$)($R^{11''}$)NSO$_2$— (wherein $R^{11}$ is $C_{1-3}$alkyl optionally substituted by hydroxyl, halo or cyano; and $R^{11'}$ and $R^{11''}$ are independently selected from hydrogen and $C_{1-3}$alkyl optionally substituted by hydroxyl, halo, $C_{1-3}$alkoxy, carboxy or cyano) or $R^{11'}$ and $R^{11''}$ together with the nitrogen atom to which they are attached form a 4-7 membered ring;

u is 0, 1 or 2;

$R^{13}$ and $R^{14}$ are independently selected from hydrogen and $C_{1-3}$alkyl or $R^{13}$ and $R^{14}$ may together with the carbon atom to which they are attached form a $C_{3-7}$cycloalkyl ring; and s is 0, 1 or 2;

or a pharmaceutically-acceptable salt thereof.

In this specification the term "alkyl" includes both straight and branched chain alkyl groups but references to individual alkyl groups such as "propyl" are specific for the straight chain version only. For example, "$C_{1-4}$alkyl" includes propyl, isopropyl and t-butyl. However, references to individual alkyl groups such as 'propyl' are specific for the straight chain version only and references to individual branched chain alkyl groups such as 'isopropyl' are specific for the branched chain version only. A similar convention applies to other radicals therefore "$C_{1-4}$alkoxy$C_{1-4}$alkyl" would include 1-($C_{1-4}$alkoxy)propyl, 2-($C_{1-4}$alkoxy)ethyl and 3-($C_{1-4}$alkoxy)butyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A 4-7 membered saturated ring (for example formed between $R^1$ and $R^{15}$ or $R^{5'}$ and $R^{5''}$ and the nitrogen atom to which they are attached) is a monocyclic ring containing the nitrogen atom as the only ring atom.

"Heteroaryl", unless otherwise specified, is a totally unsaturated, monocyclic ring containing 5 or 6 atoms of which at least 1, 2 or 3 ring atoms are independently chosen from nitrogen, sulphur or oxygen, which may, unless otherwise specified, be carbon-linked. A ring nitrogen atom may be optionally oxidised to form the corresponding N-oxide. Examples and suitable values of the term "heteroaryl" are thienyl, furyl, thiazolyl, pyrazolyl, isoxazolyl, imidazolyl, pyrrolyl, thiadiazolyl, isothiazolyl, triazolyl, pyrimidyl, pyrazinyl, pyridazinyl and pyridyl. Particularly "heteroaryl" refers to thienyl, furyl, thiazolyl, pyridyl, imidazolyl or pyrazolyl.

"Heterocyclyl" is a 4-7 saturated, monocyclic ring having 1-3 ring heteroatoms selected from nitrogen, oxygen and sulphur. Examples of heterocyclyl include piperidinyl, piperazinyl, morpholinyl and thiomorpholinyl A polycycloalkyl ring is a ring system in which either at least 2 rings are fused together or in which 2 rings have one ring atom in common (spiro). In particular the polycycloalkyl ring has 2, 3 or 4 rings. An example of a polycycloalkyl ring is adamantyl.

A "saturated mono, bicyclic or bridged ring system optionally containing 1 or 2 additional ring heteroatoms selected from nitrogen, oxygen and sulphur", unless otherwise specified contains 4-14 ring atoms. Particularly a mono ring contains 4-7 ring atoms, a bicyclic ring 6-14 ring atoms and a bridged ring system 6-14 ring atoms. Examples of mono rings include piperidinyl, piperazinyl and morpholinyl. Examples of bicyclic rings include decalin and 2,3,3a,4,5,6,7,7a-octahydro-1H-indene.

Bridged ring systems are ring systems in which there are two or more bonds common to two or more constituent rings. Examples of bridged ring systems include 1,3,3-trimethyl-6-azabicyclo[3.2.1]octane, 2-aza-bicyclo[2.2.1]heptane and 7-azabicyclo(2,2,1)heptane, 1- and 2-adamantanyl.

A "saturated, partially saturated or unsaturated monocyclic ring" is, unless otherwise specified, a 4-7 membered ring. Examples include, cyclopropyl, cyclobutyl, cyclopentyl, cyclopentenyl, cyclohexyl, cyclohexenyl and phenyl.

A "$C_{3-7}$cycloalkdiyl ring" is a saturated monocyclic carbocyclic ring. It is the di-radical of the cycloalkane ring. Adamantdiyl is the di-radical of an adamantane ring system. Phenylene is the diradical of the benzene ring. In a particular aspect the radicals are on different ring atoms.

Examples of "5-7 membered saturated heterocyclic ring (linked by a ring carbon atom) containing 1 or 2 ring heteroatoms selected from nitrogen, oxygen and sulphur" include piperazinyl, piperidinyl and morpholinyl.

A "4-7 membered mono-, bi- or spiro heterocyclic ring system containing a ring nitrogen atom by which it is attached to the pyridine ring and additionally optionally one other ring heteroatom selected from nitrogen, oxygen and sulphur" is a saturated ring system being monocyclic, bicyclic or a spiro ring system having 4 to 7 ring atoms.

Examples of the "4-7 membered mono-, bi- or spiro heterocyclic ring system containing a ring nitrogen atom by which it is attached to the pyridine ring and additionally optionally one other ring heteroatom selected from nitrogen, oxygen and sulphur" include piperidinyl, piperazinyl and morpholinyl.

Examples of a "saturated or partially-saturated 5- or 6-membered ring optionally containing 1, 2 or 3 heteroatoms independently selected from nitrogen, oxygen and sulphur" include piperidinyl, piperazinyl and morpholinyl.

Examples of "$C_{1-4}$alkoxy" include methoxy, ethoxy and propoxy. Examples of "$C_{1-4}$alkoxy$C_{1-4}$alkyl" include methoxymethyl, ethoxymethyl, propoxymethyl, 2-methoxyethyl, 2-ethoxyethyl and 2-propoxyethyl. Examples of "$C_{1-4}$alkylS(O)$_n$ wherein n is 0 to 2" include methylthio, ethylthio, methylsulphinyl, ethylsulphinyl, mesyl and ethylsulphonyl. Examples of "$C_{1-4}$alkylS(O)$_q$$C_{1-4}$alkyl" wherein q is 0 to 2" include methylthio, ethylthio, methylsulphinyl, ethylsulphinyl, mesyl, ethylsulphonyl, methylthiomethyl, ethylthiomethyl, methylsulphinylmethyl, ethylsulphinylmethyl, mesylmethyl and ethylsulphonylmethyl. Examples of "$C_{1-4}$alkanoyl" include propionyl and acetyl. Examples of "N—($C_{1-4}$alkyl)amino" include methylamino and ethylamino. Examples of "N,N—($C_{1-4}$alkyl)$_2$amino" include N,N-dimethylamino, N,N-diethylamino and N-ethyl-N-methylamino. Examples of "$C_{2-4}$alkenyl" are vinyl, allyl and 1-propenyl. Examples of "$C_{2-4}$alkynyl" are ethynyl, 1-propynyl and 2-propynyl. Examples of "N—($C_{1-4}$alkyl)carbamoyl" are methylaminocarbonyl and ethylaminocarbonyl. Examples of "N,N—($C_{1-4}$alkyl)$_2$carbamoyl" are dimethylaminocarbonyl and methylethylaminocarbonyl. Examples of "$C_{3-7}$cycloalkyl$C_{1-3}$alkalkyl" include cyclopropymethyl, 2-cyclopropylethyl, cyclobutylmethyl, cyclopentylmethyl and cyclohexylmethyl. Examples of "$C_{3-7}$cycloalkyl$C_{2-3}$alkalkenyl" include 2-cyclopropylethenyl, 2-cyclopentylethenyl and 2-cyclohexylethenyl. Examples of "$C_{3-7}$cycloalkyl$C_{2-3}$alkalkynyl" include 2-cyclopropylethynyl, 2-cyclopentylethynyl and 2-cyclohexylethynyl.

Examples of "$C_{3-7}$cycloalkyl(CH$_2$)$_m$—" include cyclopropymethyl, 2-cyclopropylethyl, cyclobutylmethyl, cyclopentylmethyl and cyclohexylmethyl. Examples of $C_{6-12}$polycycloalkyl(CH$_2$)$_m$— include norbornyl bicyclo[2.2.2]octane (CH$_2$)$_m$—, bicyclo[3.2.1]octane(CH$_2$)$_m$— and 1- and 2-adamantanyl(CH$_2$)$_m$—.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, tert-butylamine, piperidine, morpholine or tris-(2-hydroxyethyl) amine.

An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $_6$alkanoyloxymethyl esters for example pivaloyloxymethyl, phthalidyl esters, $C_3$ to $_8$cycloalkoxy carbonyloxy$C_1$ to $_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Some compounds of the formula (1) may have chiral centres and/or geometric isomeric centres (E- and Z-isomers), and it is to be understood that the invention encompasses all such optical, diastereoisomers and geometric isomers that possess 11βHSD1 inhibitory activity.

The invention relates to any and all tautomeric forms of the compounds of the formula (1) that possess 11βHSD1 inhibitory activity.

It is also to be understood that certain compounds of the formula (1) can exist in solvated as well as unsolvated forms such as, for example, hydrated forms. It is to be understood that the invention encompasses all such solvated forms, which possess 11βHSD1 inhibitory activity.

In one embodiment of the invention are provided compounds of formula (1). In an alternative embodiment are provided pharmaceutically-acceptable salts of compounds of formula (1).

When a general reference is made to the positions on the pyridine ring, the 2-position refers to the position which is substituted by the -Q-$R^1$ group and the other positions are numbered accordingly.

Particular values of variable groups are as follows. Such values may be used where appropriate with any of the definitions, claims or embodiments defined hereinbefore or hereinafter, for compounds of formula (1):

In one aspect Q is a single bond, —O—, —S— or —N($R^{15}$)— wherein $R^{15}$ is hydrogen, $C_{1-3}$alkyl or $C_{2-3}$alkanoyl or $R^{15}$ and $R^1$ together with the nitrogen atom to which they are attached form a 4-7 membered saturated ring and $R^1$ is $C_{1-6}$alkyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl, $C_{3-7}$cycloalkyl$C_{2-3}$alkynyl, phenyl, phenyl$C_{1-3}$alkyl, heteroaryl, heteroaryl$C_{1-3}$alkyl, heterocyclyl, or heterocyclyl$C_{1-3}$alkyl [each of which is optionally substituted by 1, 2 or 3 substituents independently selected from hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$OC(O)— and ($R^{5'}$)($R^{5''}$)NSO$_2$— (wherein $R^5$ is $C_{1-3}$alkyl optionally substituted by 1, 2 or 3 substituents independently selected from hydroxyl, halo and cyano; and
$R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)].

In one aspect Q is a single bond, —O—, —S— or —N($R^{15}$)— wherein $R^{15}$ is hydrogen, $C_{1-3}$alkyl or $C_{2-3}$alkanoyl or $R^{15}$ and $R^1$ together with the nitrogen atom to which they are attached form a 4-7 membered saturated ring and $R^1$ is $C_{1-6}$alkyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl, $C_{3-7}$cycloalkyl$C_{2-3}$alkynyl, phenyl, heteroaryl, heterocyclyl, or heterocyclyl$C_{1-3}$alkyl [each of which is optionally substituted by 1, 2 or 3 substituents independently selected from hydroxy, halo, oxo, cyano, trifluoromethyl, $C_{1-3}$alkoxy, $C_{1-3}$alkyl $S(O)_n$— (wherein n is 0, 1, 2 or 3), $R^{5'}CON(R^{5'})$—, $(R^{5'})(R^{5''})NC(O)$—, $R^{5'}OC(O)$— and $(R^{5'})(R^{5''})NSO_2$— (wherein $R^5$ is $C_{1-3}$alkyl optionally substituted by 1, 2 or 3 substituents independently selected from hydroxyl, halo and cyano; and $R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)].

In one aspect, Q is O, S or a single bond and $R^1$ is $C_{1-6}$alkyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl or $C_{3-7}$cycloalkyl$C_{2-3}$alkynyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5CON(R^{5'})$—, $(R^{5'})(R^{5''})NC(O)$—, $R^{5'}OC(O)$— and $(R^{5'})(R^{5''})NSO_2$— (wherein $R^5$ is $C_{1-3}$alkyl optionally substituted by 1, 2 or 3 substituents independently selected from hydroxyl, halo and cyano; and $R^{5'}$ and $R^{5''}$ are independently selected from hydrogen and $C_{1-3}$alkyl optionally substituted by 1, 2 or 3 substituents independently hydroxyl, halo, $C_{1-3}$alkoxy, carboxy and cyano or $R^{5'}$ and $R^{5''}$ together with the nitrogen atom to which they are attached form a 4-7 membered saturated ring)].

In another aspect, the invention relates to a compound of the formula (I) as hereinabove defined wherein Q is a single bond.

In another aspect Q is —N($R^{15}$)—.
In one aspect $R^{15}$ is hydrogen.
In another aspect $R^{15}$ is $C_{1-3}$alkyl.
In one aspect $R^{15}$ is methyl.
In one aspect Q is O.
In another aspect Q is S.

In one aspect $R^1$ is $C_{1-6}$alkyl, $C_{3-7}$cycloalkyl, $C_{3-7}$cycloalkyl$C_{1-3}$alkyl, [each of which is optionally substituted by 1, 2 or 3 substituents independently selected from hydroxy, halo, oxo, cyano, trifluoromethyl, $C_{1-3}$alkoxy, $C_{1-3}$alkylS(O)$_n$— (wherein n is 0, 1, 2 or 3).

In another aspect $R^1$ is $C_{1-6}$alkyl, $C_{3-7}$cycloalkyl or $C_{3-7}$cycloalkyl$C_{1-3}$alkyl.

In another aspect $R^1$ is $C_{3-4}$cycloalkyl optionally substituted by 1, 2 or 3 substituents independently selected from $C_{1-3}$alkyl, hydroxy, halo, oxo, cyano, trifluoromethyl and $C_{1-3}$alkoxy.

In another aspect $R^1$ is $C_{3-4}$cycloalkyl.
In another aspect $R^1$ is $C_{3-4}$cycloalkyl$C_{1-2}$alkyl optionally substituted by 1, 2 or 3 substituents independently selected from $C_{1-3}$alkyl, hydroxy, halo, oxo, cyano, trifluoromethyl and $C_{1-3}$alkoxy.

In another aspect $R^1$ is $C_{3-4}$cycloalkyl$C_{1-2}$alkyl.
In another aspect $R^1$ is $C_{1-4}$alkyl optionally substituted by 1, 2 or 3 substituents independently selected from $C_{1-3}$alkyl, hydroxy, halo, oxo, cyano, trifluoromethyl and $C_{1-3}$alkoxy.

In another aspect $R^1$ is $C_{1-4}$alkyl.
In another aspect $R^1$ is propyl optionally substituted by 1 or 2 substituents independently selected from $C_{1-3}$alkyl, hydroxy, halo, oxo, cyano, trifluoromethyl and $C_{1-3}$alkoxy.

In another aspect $R^1$ is propyl.
In another aspect $R^1$ is phenyl$C_{1-3}$alkyl optionally substituted by 1, 2 or 3 substituents independently selected from hydroxy, halo, oxo, cyano, trifluoromethyl and $C_{1-3}$alkoxyIn another aspect $R^1$ is phenyl$C_{1-3}$alkyl.

In another aspect $R^1$ is heteroaryl$C_{1-3}$alkyl optionally substituted by 1, 2 or 3 substituents independently selected from hydroxy, halo, oxo, cyano, trifluoromethyl and $C_{1-3}$alkoxy.

In another aspect $R^1$ is heteroaryl$C_{1-3}$alkyl.
In another aspect $R^1$ is phenyl optionally substituted by 1, 2 or 3 substituents independently selected from hydroxy, halo, oxo, cyano, trifluoromethyl and $C_{1-3}$alkoxy.

In another aspect $R^1$ is phenyl.
In another aspect $R^1$ is heteroaryl optionally substituted by 1, 2 or 3 substituents independently selected from hydroxy, halo, oxo, cyano, trifluoromethyl and $C_{1-3}$alkoxy.

In another aspect $R^1$ is heteroaryl.
In another aspect -Q-$R^1$ is hydrogen.
In one aspect, $R^3$ is $C_{1-4}$alkyl.
In another aspect, $R^3$ is hydrogen, methyl or ethyl.
In another aspect, $R^3$ is hydrogen.
In another aspect, $R^3$ is methyl.
In another aspect, $R^3$ is ethyl.
In one aspect, $R^4$ is methyl.
In one aspect p is 0.
In one aspect, p is 1 or 2.
In another aspect, p is 0 or 1.
In another aspect, p is 1.
In another aspect, p is 2.
In one aspect p is 1 and $R^4$ is in the 5-position.
In one aspect $R^2$ is selected from $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$ as hereinabove defined).

In another aspect $R^2$ is selected from $C_{3-7}$cycloalkyl (CH$_2$)$_m$—, and $C_{6-12}$polycycloalkyl(CH$_2$)$_m$— (wherein m is 0, 1 or 2 and the rings are optionally substituted by 1 or 2 substituents independently selected from $R^6$, wherein $R^6$ is independently selected from hydroxyl, halo and trifluoromethyl).

In another aspect, $R^2$ is selected from $C_{3-7}$cycloalkyl, and $C_{6-12}$polycycloalkyl each of which is independently optionally substituted by 1 $R^6$, wherein $R^6$ is selected from hydroxyl, halo and trifluoromethyl).

In one aspect, $R^2$ is selected from $C_{5-7}$cycloalkyl(CH$_2$)$_m$— and $C_{8-12}$polycycloalkyl(CH$_2$)$_m$— (wherein the rings are optionally substituted by 1, 2 or 3 substituents independently selected from $R^6$) and wherein m is 0, 1 or 2.

In another aspect, $R^2$ is selected from $C_{5-7}$cycloalkyl (CH$_2$)$_m$—, $C_{7-10}$bicycloalkyl(CH$_2$)$_m$— and $C_{10}$tricycloalkyl (CH$_2$)$_m$— (wherein the cycloalkyl, bicycloalkyl and tricycloalkyl rings are optionally substituted by 1, 2 or 3 substituents independently selected from $R^6$) and wherein m is 0, 1 or 2.

In yet another aspect, $R^2$ is selected from $C_{5-7}$cycloalkyl (CH$_2$)$_m$—, $C_{7-10}$bicycloalkyl(CH$_2$)$_m$— and adamantyl (wherein the cycloalkyl, bicycloalkyl and tricycloalkyl rings are optionally substituted by 1, 2 or 3 substituents independently selected from $R^6$) and wherein m is 0, 1 or 2.

In one aspect, m is 0 or 1.
In another aspect, $R^2$ and $R^3$ together with the nitrogen atom to which they are attached form a saturated 5 or 6-membered mono, 6-12 membered bicyclic or 6-12 membered bridged ring system optionally containing 1 or 2 additional ring heteroatoms selected from nitrogen, oxygen and sulphur and which is optionally fused to a saturated, partially-saturated or aryl monocyclic ring wherein the resulting ring system is optionally substituted by 1, 2, or 3 substituents independently selected from $R^7$.

In another aspect, $R^2$ and $R^3$ together with the nitrogen atom to which they are attached form a saturated 5 or 6-membered mono, ring system optionally containing 1 or 2 additional ring heteroatoms selected from nitrogen, oxygen and sulphur and which is optionally fused to a saturated, partially-saturated or aryl monocyclic ring wherein the resulting ring system is optionally substituted by 1, 2, or 3 substituents independently selected from $R^7$.

In another aspect, $R^2$ and $R^3$ together with the nitrogen atom to which they are attached form a saturated 5 or 6-membered mono, ring system optionally containing 1 additional ring heteroatoms selected from nitrogen, oxygen and sulphur and is optionally substituted by 1 or 2 substituents independently selected from $R^7$.

In one aspect, $R^6$ is independently selected from hydroxyl, $R^9O—$, $R^9CO—$ and $R^9C(O)O—$ wherein $R^9$ is as hereinabove defined.

In one aspect, $R^6$ is independently selected from hydroxyl, $R^9O—$, $R^9CO—$ and $R^9C(O)O—$ wherein $R^9$ is $C_{1-3}$alkyl optionally substituted by $C_{1-4}$alkoxy or carboxy.

In another aspect, $R^6$ is independently selected from $R^9CON(R^{9'})—$, $R^9SO_2N(R^{9''})—$ and $(R^{9'})(R^{9''})NC(O)N(R^{9'''})—$;
wherein $R^9$ is as hereinabove defined.

In another aspect, $R^6$ is independently selected from $R^9CON(R^{9'})—$, $R^9SO_2N(R^{9''})—$ and $(R^{9'})(R^{9''})NC(O)N(R^{9'''})—$;
$R^9$ is $C_{1-3}$alkyl optionally substituted by $C_{1-4}$alkoxy or carboxy;
$R^{9'}$, $R^{9''}$ and $R^{9'''}$ are independently selected from hydrogen and $C_{1-3}$alkyl optionally substituted by $C_{1-4}$alkoxy or carboxy).

In another aspect, $R^6$ is independently selected from $(R^{9'})(R^{9''})NC(O)—$ and $(R^{9'})(R^{9''})N—$; wherein $R^{9'}$ and $R^{9''}$ are as hereinabove defined.

In another aspect, $R^6$ is independently selected from $(R^{9'})(R^{9''})NC(O)—$ and $(R^{9'})(R^{9''})N—$; wherein $R^{9'}$ and $R^{9''}$ are independently selected from hydrogen and $C_{1-3}$alkyl optionally substituted by $C_{1-4}$alkoxy or carboxy.

In one aspect $R^6$ is selected from methyl, trifluoromethyl, chloro, fluoro, bromo, methoxy, ethoxy, trifluormethoxy, methanesulfonyl, ethanesulfonyl, methylthio, ethylthio, amino, N-methylamino, N-ethylamino, N-propylamino, N,N-dimethylamino, N,N-methylethylamino or N,N-diethylamino.

In one aspect $R^6$ is selected from hydroxy, halo and trifluoromethyl.

In another aspect, $R^6$ is optionally substituted phenyl, pyridyl or pyrimidyl.

In another aspect, $R^6$ is optionally substituted pyrid-2-yl, pyrid-3-yl or pyrid-4-yl.

In another aspect, $R^6$ is carboxy.

In one aspect $R^7$ is selected from hydroxy, halo and trifluoromethyl.

In one aspect X is —O—, —S— or —N($R^{12}$)— wherein $R^{12}$ is hydrogen, $C_{1-3}$alkyl or $C_{1-3}$alkanoyl.

In one aspect X is —O—.

In another aspect X is —N($R^{12}$)—, wherein $R^{12}$ is as hereinabove defined.

In another aspect X is —N($R^{12}$)—, wherein $R^{12}$ is hydrogen.

In another aspect X is —S—.

In one aspect Y is a $C_{3-7}$cycloalkdiyl ring, a 5-7 membered saturated heterocyclic ring (linked by a ring carbon atom) containing 1 or 2 ring heteroatoms selected from nitrogen, oxygen and sulphur, or —[C($R_x$)($R_y$)]$_v$— (wherein $R_x$ and $R_y$ are independently selected from hydrogen and methyl or $R_x$ and $R_y$ together with the carbon atom to which they are attached form a $C_{3-7}$cycloalkdiyl ring and v is 1, 2, 3, 4 or 5).

In another aspect Y is a $C_{3-7}$cycloalkdiyl ring or a 5-7 membered saturated heterocyclic ring (linked by a ring carbon atom) containing 1 or 2 ring heteroatoms selected from nitrogen, oxygen and sulphur.

In another aspect Y is a $C_{3-7}$cycloalkdiyl ring.

In another aspect Y is a 5-7 membered saturated heterocyclic ring (linked by a ring carbon atom) containing 1 or 2 ring heteroatoms selected from nitrogen, oxygen and sulphur.

In another aspect Y is of the formula —[C($R_x$)($R_y$)]$_v$— (wherein $R_x$ and $R_y$ are independently selected from hydrogen and methyl and v is 1, 2, 3, 4 or 5) and when v is more than 1 the —[C($R_x$)($R_y$)]$_v$— group may optionally be interrupted by a —O—, —S— or —N($R^{20}$)— group wherein $R^{20}$ is hydrogen or $C_{1-3}$alkyl.

In another aspect Y is of the formula —[C($R_x$)($R_y$)]$_v$— (wherein $R_x$ and $R_y$ are independently selected from hydrogen and methyl and v is 1, 2, 3, 4 or 5).

In one aspect —X—Y— together represents a group of the formula:

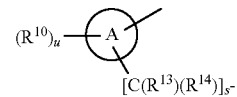

wherein:
ring A is linked to the pyridine group and —[C($R^{13}$)($R^{14}$)]$_s$— is linked to the carboxy group; and
A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;
$R^{10}$ is independently selected from $C_{1-3}$alkyl, hydroxy, halo and trifluoromethyl;
u is 0, or 1;
$R^{13}$ and $R^{14}$ are independently selected from hydrogen and $C_{1-3}$alkyl or $R^{13}$ and $R^{14}$ may together with the carbon atom to which they are attached form a $C_{3-7}$cycloalkyl ring; and
s is 0, 1 or 2.

In another aspect —X—Y— together represents a group of the formula:

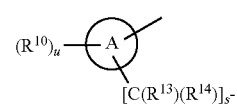

wherein:
ring A is linked to the pyridine group and —[C($R^{13}$)($R^{14}$)]$_s$— is linked to the carboxy group; and
A is a 4-7 membered mono- or bi-heterocyclic ring system containing a ring nitrogen atom by which it is attached to the pyridine ring and additionally optionally one other ring heteroatom selected from nitrogen, oxygen and sulphur;
s u is 0;
$R^{13}$ and $R^{14}$ are independently selected from hydrogen and methyl; and
s is 0, 1 or 2.

In another aspect $R_x$ and $R_y$ are hydrogen.

In another aspect v is 3, 4 or 5.

In one aspect A is a 5 or 6 membered mono-heterocyclic ring containing a ring nitrogen atom by which it is attached to the pyridine ring and additionally optionally one other ring heteroatom selected from nitrogen, oxygen and sulphur.

In another aspect A is piperidino, pyrrolidino, azabicyclo[3.1.0]hexane, morpholino or thiomorpholino.

In another aspect A is piperidino, morpholino or thiomorpholino.

In another aspect A is piperidino.

In another aspect A is piperidino in which the —(Z)$_t$[C(R$^{13}$)(R$^{14}$)]$_s$—COOH group is in the 3-position.

In another aspect A is piperidino in which the —(Z)$_t$[C(R$^{13}$)(R$^{14}$)]$_s$—COOH group is in the 4-position.

In another aspect A is pyrrolidino.

In one aspect Z is —N(R$^{16}$)—, wherein R$^{16}$ is as hereinabove defined.

In another aspect Z is —NH—.

In one aspect t is 0.

In one aspect R$^{10}$ is selected from C$_{1-3}$alkyl, C$_{2-3}$alkenyl, C$_{2-3}$alkynyl, hydroxy, halo, oxo, cyano, trifluoromethyl and alkoxy.

In another aspect R$^{10}$ is selected from C$_{1-3}$alkyl, hydroxy, halo, oxo, cyano, trifluoromethyl and alkoxy.

In another aspect R$^{10}$ is independently selected from C$_{1-3}$alkyl, hydroxy, halo and trifluoromethyl.

In another aspect R$^{10}$ is selected from C$_{1-3}$alkyl and alkoxy.

In one aspect u is 0 or 1.

In another aspect u is 1.

In another aspect u is 0.

In one aspect R$^{13}$ and R$^{14}$ are independently hydrogen or methyl.

In another aspect R$^{13}$ and R$^{14}$ are hydrogen.

In one aspect s is 0 or 1.

In one aspect s is 0.

In another aspect s is 1.

1. A class of compounds of the present invention is of formula (1) wherein:

Q is —O—, —S— or —N(R$^{15}$)— wherein R$^{15}$ is hydrogen, C$_{1-3}$alkyl or C$_{2-3}$alkanoyl or R$^{15}$ and R$^1$ together with the nitrogen atom to which they are attached form a 4-7 membered saturated ring;

R$^1$ is C$_{1-6}$alkyl, C$_{2-6}$alkenyl, C$_{2-6}$alkynyl, C$_{3-7}$cycloalkyl, C$_{3-7}$cycloalkylC$_{1-3}$alkyl, C$_{3-7}$cycloalkylC$_{2-3}$alkenyl, C$_{3-7}$cycloalkylC$_{2-3}$alkynyl, phenyl, heteroaryl, heterocyclyl, or heterocyclylC$_{1-3}$alkyl [each of which is optionally substituted by 1, 2 or 3 substituents independently selected from hydroxy, halo, oxo, cyano, trifluoromethyl, C$_{1-3}$alkoxy, C$_{1-3}$alkylS(O)$_n$— (wherein n is 0, 1, 2 or 3), R$^5$CON(R$^{5'}$)—, (R$^{5'}$)(R$^{5''}$)NC(O)—, R$^5$OC(O)— and (R$^{5'}$)(R$^{5''}$)NSO$_2$— (wherein R$^5$ is C$_{1-3}$alkyl optionally substituted by 1, 2 or 3 substituents independently selected from hydroxyl, halo and cyano; and R$^{5'}$ and R$^{5''}$ are independently selected from hydrogen and C$_{1-3}$alkyl optionally substituted by 1, 2 or 3 substituents independently selected from hydroxyl, halo, C$_{1-3}$alkoxy, carboxy and cyano or R$^{5'}$ and R$^{5''}$ together with the nitrogen atom to which they are attached form a 4-7 membered saturated ring)]; or R$^2$ is selected from C$_{3-7}$cycloalkyl(CH$_2$)$_m$—, and C$_{6-12}$polycycloalkyl(CH$_2$)$_m$— (wherein m is 0, 1 or 2 and the rings are optionally substituted by 1, 2 or 3 substituents independently selected from R$^6$);

R$^3$ is selected from hydrogen, C$_{1-4}$alkyl C$_{3-5}$cycloalkyl and C$_{3-5}$cycloalkylmethyl;

R$^2$ and R$^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from R$^7$;

R$^6$ and R$^7$ are independently selected from hydroxyl, halo, oxo, carboxy, cyano, trifluoromethyl, R$^9$, R$^9$O—, R$^9$CO—, R$^9$C(O)O—, R$^9$CON(R$^{9'}$)—, (R$^{9'}$)(R$^{9''}$)NC(O)—, (R$^{9'}$)(R$^{9''}$)N—, R$^9$S(O)$_a$— wherein a is 0 to 2, R$^9$OC(O)—, (R$^{9'}$)(R$^{9''}$)NSO$_2$—, R$^9$SO$_2$N(R$^{9''}$)—, (R$^{9'}$)(R$^{9''}$)NC(O)N(R$^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from C$_{1-4}$alkyl, hydroxyl, cyano, trifluoromethyl, trifluoromoxy, halo, C$_{1-4}$alkoxy, C$_{1-4}$alkoxyC$_{1-4}$alkyl, C$_{1-4}$alkoxyC$_{1-4}$alkyl, amino, N—C$_{1-4}$alkylamino, di-N, N—(C$_{1-4}$alkyl)amino, N—C$_{1-4}$alkylcarbamoyl, di-N,N—(C$_{1-4}$alkyl)carbamoyl, C$_{1-4}$alkylS(O)$_r$—, C$_{1-4}$alkylS(O)$_r$C$_{1-4}$alkyl (wherein r is 0, 1 and 2)];

R$^9$ is independently C$_{1-3}$alkyl optionally substituted by 1, 2 or 3 substituents independently selected from hydroxyl, halo, C$_{1-4}$alkoxy, carboxy and cyano;

R$^{9'}$, R$^{9''}$ and R$^{9'''}$ are independently selected from hydrogen and C$_{1-3}$alkyl optionally substituted by hydroxyl, halo, C$_{1-4}$alkoxy, carboxy or cyano);

p is 0;

either X is —O—, —S— or —N(R$^{12}$)— wherein R$^{12}$ is hydrogen, C$_{1-3}$alkyl or C$_{1-3}$alkanoyl; and Y is:

1) a C$_{3-7}$cycloalkdiyl ring, a 5-7 membered saturated heterocyclic ring (linked by a ring carbon atom) containing 1 or 2 ring heteroatoms selected from nitrogen, oxygen and sulphur, or —[C(R$_x$)(R$_y$)]$_v$— (wherein R$_x$ and R$_y$ are independently selected from hydrogen, C$_{1-3}$alkyl, C$_{1-3}$alkoxy and hydroxyl or R$_x$ and R$_y$ together with the carbon atom to which they are attached form a C$_{3-7}$cycloalkdiyl ring and v is 1, 2, 3, 4 or 5) and when v is more than 1 the —[C(R$_x$)(R$_y$)]$_v$— group may optionally be interrupted by a —O—, —S— or —N(R$^{20}$)— group wherein R$^{20}$ is hydrogen or C$_{1-3}$alkyl; or 2) —X—Y— together represents a group of the formula:

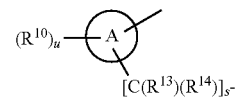

wherein:

ring A is linked to the pyridine group and —[C(R$^{13}$)(R$^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

R$^{10}$ is independently selected from C$_{1-3}$alkyl, C$_{2-3}$alkenyl, C$_{2-3}$alkynyl, hydroxy, halo, oxo, cyano, trifluoromethyl, C$_{1-3}$alkoxy, C$_{1-3}$alkylS(O)$_n$— (wherein n is 0, 1, 2 or 3), R$^{11}$CON(R$^{11'}$), (R$^{11'}$)(R$^{11''}$)NC(O)—, R$^{11'}$OC(O)— and (R$^{11'}$)(R$^{11''}$)NSO$_2$— (wherein R$^{11}$ is C$_{1-3}$alkyl optionally substituted by hydroxyl, halo or cyano; and R$^{11'}$ and R$^{11''}$ are independently selected from hydrogen and C$_{1-3}$alkyl optionally substituted by hydroxyl, halo, C$_{1-3}$alkoxy, carboxy or cyano) or R$^{11'}$ and R$^{11''}$ together with the nitrogen atom to which they are attached form a 4-7 membered ring;

u is 0, 1 or 2;

R$^{13}$ and R$^{14}$ are independently selected from hydrogen and C$_{1-3}$alkyl or R$^{13}$ and R$^{14}$ may together with the carbon atom to which they are attached form a $C_{3-7}$cycloalkyl ring; and s is 0, 1 or 2;

or a pharmaceutically-acceptable salt or in vivo hydrolysable ester thereof.

2. Another class of compounds of the present invention is of formula (1) wherein:

Q is —S—;

$R^1$ is $C_{1-6}$alkyl, $C_{3-7}$cycloalkyl, $C_{3-7}$cycloalkyl$C_{1-3}$alkyl, [each of which is optionally substituted by 1, 2 or 3 substituents independently selected from hydroxy, halo, oxo, cyano, trifluoromethyl, $C_{1-3}$alkoxy, $C_{1-3}$alkylS(O)$_n$— (wherein n is 0, 1, 2 or 3); or $R^2$ is selected from $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen;

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^6$ and $R^7$ are independently selected from hydroxyl, halo, oxo, carboxy, cyano, trifluoromethyl, $R^9$, $R^9$O—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$— wherein a is 0 to 2, $R^{9'}$OC(O)—, ($R^{9'}$)($R^{9''}$)NSO$_2$—, $R^9$SO$_2$N($R^{9'}$)—, ($R^{9'}$)($R^{9''}$)NC(O)N($R^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromoxy, halo, $C_{1-4}$alkoxy, $C_{1-4}$alkoxy$C_{1-4}$alkyl, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_r$—, $C_{1-4}$alkylS(O)$_r$$C_{1-4}$alkyl (wherein r is 0, 1 and 2)];

$R^9$ is independently $C_{1-3}$alkyl optionally substituted by 1, 2 or 3 substituents independently selected from hydroxyl, halo, $C_{1-4}$alkoxy, carboxy and cyano;

$R^{9'}$, $R^{9''}$ and $R^{9'''}$ are independently selected from hydrogen and $C_{1-3}$alkyl optionally substituted by hydroxyl, halo, $C_{1-4}$alkoxy, carboxy or cyano);

p is 0;

either X is —O—, —S— or —N($R^{12}$)— wherein $R^{12}$ is hydrogen, $C_{1-3}$alkyl or $C_{1-3}$alkanoyl; and Y is:

1) a $C_{3-7}$cycloalkdiyl ring, a 5-7 membered saturated heterocyclic ring (linked by a ring carbon atom) containing 1 or 2 ring heteroatoms selected from nitrogen, oxygen and sulphur; or 2) —X—Y— together represents a group of the formula:

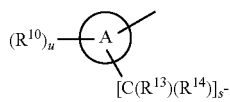

wherein:

ring A is linked to the pyridine group and —[C($R^{13}$)($R^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

$R^{10}$ is independently selected from $C_{1-3}$alkyl, $C_{2-3}$alkenyl, $C_{2-3}$alkynyl, hydroxy, halo, oxo, cyano, trifluoromethyl, $C_{1-3}$alkoxy, $C_{1-3}$alkylS(O)$_n$— (wherein n is 0, 1, 2 or 3), $R^{11}$CON($R^{11'}$), ($R^{11'}$)($R^{11''}$)NC(O)—, $R^{11'}$OC(O)— and ($R^{11'}$)($R^{11''}$)NSO$_2$— (wherein $R^{11}$ is $C_{1-3}$alkyl optionally substituted by hydroxyl, halo or cyano; and $R^{11'}$ and $R^{11''}$ are independently selected from hydrogen and $C_{1-3}$alkyl optionally substituted by hydroxyl, halo, $C_{1-3}$alkoxy, carboxy or cyano) or $R^{11'}$ and $R^{11''}$ together with the nitrogen atom to which they are attached form a 4-7 membered ring;

u is 0, 1 or 2;

$R^{13}$ and $R^{14}$ are independently selected from hydrogen and $C_{1-3}$alkyl or $R^{13}$ and $R^{14}$ may together with the carbon atom to which they are attached form a $C_{3-7}$cycloalkyl ring; and s is 0, 1 or 2;

or a pharmaceutically-acceptable salt or in vivo hydrolysable ester thereof.

3. Another class of compounds of the present invention is of formula (1) wherein:

Q is —S—;

$R^1$ is $C_{1-6}$alkyl, $C_{3-7}$cycloalkyl or $C_{3-7}$cycloalkyl$C_{1-3}$alkyl; or $R^2$ is selected from $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1 or 2 substituents independently selected from $R^6$);

$R^3$ is selected from hydrogen; or $R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1 or 2 substituents independently selected from $R^7$;

$R^6$ and $R^7$ are independently selected from hydroxyl, halo, oxo, carboxy, cyano, trifluoromethyl, $R^9$, $R^9$O—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$— wherein a is 0 to 2, $R^9$OC(O)—, ($R^{9'}$)($R^{9''}$)NSO$_2$—, $R^9$SO$_2$N($R^{9'}$)—, ($R^{9'}$)($R^{9''}$)NC(O)N($R^{9'''}$)—;

$R^{9'}$, $R^{9''}$ and $R^{9'''}$ are independently selected from hydrogen and $C_{1-3}$alkyl optionally substituted by hydroxyl, halo, $C_{1-4}$alkoxy, carboxy or cyano);

p is 0;

either X is —O—, —S— or —N($R^{12}$)— wherein $R^{12}$ is hydrogen, $C_{1-3}$alkyl or $C_{1-3}$alkanoyl; and Y is:

1) a $C_{3-7}$cycloalkdiyl ring or a 5-7 membered saturated heterocyclic ring (linked by a ring carbon atom) containing 1 or 2 ring heteroatoms selected from nitrogen, oxygen and sulphur; or 2) —X—Y— together represents a group of the formula:

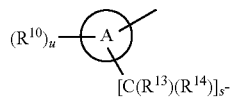

wherein:

ring A is linked to the pyridine group and —[C(R$^{13}$)(R$^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

R$^{10}$ is independently selected from C$_{1-3}$alkyl, C$_{2-3}$alkenyl, C$_{2-3}$alkynyl, hydroxy, halo, oxo, cyano, trifluoromethyl, C$_{1-3}$alkoxy, C$_{1-3}$alkylS(O)$_n$— (wherein n is 0, 1, 2 or 3), R$^{11}$CON(R$^{11'}$), (R$^{11'}$)(R$^{11''}$)NC(O)—, R$^{11'}$OC(O)— and (R$^{11'}$)(R$^{11''}$)NSO$_2$— (wherein R$^{11}$ is C$_{1-3}$alkyl optionally substituted by hydroxyl, halo or cyano; and R$^{11'}$ and R$^{11''}$ are independently selected from hydrogen and C$_{1-3}$alkyl optionally substituted by hydroxyl, halo, C$_{1-3}$alkoxy, carboxy or cyano) or R$^{11'}$ and R$^{11''}$ together with the nitrogen atom to which they are attached form a 4-7 membered ring;

u is 0, or 1;

R$^{13}$ and R$^{14}$ are independently selected from hydrogen and C$_{1-3}$alkyl or R$^{13}$ and R$^{14}$ may together with the carbon atom to which they are attached form a C$_{3-7}$cycloalkyl ring; and s is 0, 1 or 2;

or a pharmaceutically-acceptable salt or in vivo hydrolysable ester thereof.

4. Another class of compounds of the present invention is of formula (1) wherein:

Q is —S—;

R$^1$ is C$_{1-6}$alkyl;

R$^2$ is selected from C$_{3-7}$cycloalkyl(CH$_2$)$_m$—, and C$_{6-12}$polycycloalkyl(CH$_2$)$_m$— (wherein m is 0, 1 or 2 and the rings are optionally substituted by 1 or 2 substituents independently selected from R$^6$);

R$^3$ is selected from hydrogen; or

R$^2$ and R$^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1 or 2 substituents independently selected from R$^7$;

R$^6$ and R$^7$ are independently selected from hydroxyl, halo and trifluoromethyl;

p is 0;

either X is —N(R$^{12}$)— wherein R$^{12}$ is hydrogen; and Y:

1) a C$_{3-7}$cycloalkdiyl ring or a 5-7 membered saturated heterocyclic ring (linked by a ring carbon atom) containing 1 or 2 ring heteroatoms selected from nitrogen, oxygen and sulphur; or 2) —X—Y— together represents a group of the formula:

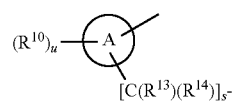

wherein:

ring A is linked to the pyridine group and —[C(R$^{13}$)(R$^{14}$)]$_s$— is linked to the carboxy group; and A is a 4-7 membered mono-, bi- or spiro heterocyclic ring system containing a ring nitrogen atom by which it is attached to the pyridine ring and additionally optionally one other ring heteroatom selected from nitrogen, oxygen and sulphur;

R$^{10}$ is independently selected from C$_{1-3}$alkyl, hydroxy, halo and trifluoromethyl;

u is 0, or 1;

R$^{13}$ and R$^{14}$ are independently selected from hydrogen and C$_{1-3}$alkyl or R$^{13}$ and R$^{14}$ may together with the carbon atom to which they are attached form a C$_{3-7}$cycloalkyl ring; and s is 0, 1 or 2;

or a pharmaceutically-acceptable salt or in vivo hydrolysable ester thereof.

5. Another class of compounds of the present invention is of formula (1) wherein:

Q is —S—;

R$^1$ is C$_{1-6}$alkyl;

R$^2$ is selected from C$_{3-7}$cycloalkyl, and C$_{6-12}$polycycloalkyl each of which is independently optionally substituted by 1 R$^6$;

R$^3$ is selected from hydrogen;

R$^6$ is selected from hydroxyl, halo and trifluoromethyl;

p is 0;

—X—Y— together represents a group of the formula:

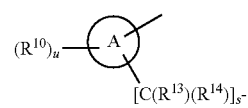

wherein:

ring A is linked to the pyridine group and —[C(R$^{13}$)(R$^{14}$)]$_s$— is linked to the carboxy group; and A is a 4-7 membered mono- or bi-heterocyclic ring system containing a ring nitrogen atom by which it is attached to the pyridine ring and additionally optionally one other ring heteroatom selected from nitrogen, oxygen and sulphur;

u is 0;

R$^{13}$ and R$^{14}$ are independently selected from hydrogen and methyl; and s is 0, 1 or 2;

or a pharmaceutically-acceptable salt or in vivo hydrolysable ester thereof.

6. In another aspect a class of compounds according to the present invention is of the formula (IB):

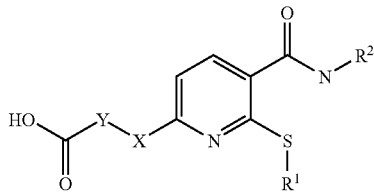

wherein $R^1$, $R^2$, X and Y have any of the definitions given above.

In another aspect of the invention, suitable compounds of the invention are any one or more of the Examples or a pharmaceutically-acceptable salt thereof.

In another aspect the invention relates to: a compound selected from:

2-[(3R)-1-[5-(cyclohexylcarbamoyl)-6-propylsulfanyl-pyridin-2-yl]-3-piperidyl]acetic acid
1-[5-(cyclohexylcarbamoyl)-6-propylsulfanyl-pyridin-2-yl]piperidine-3-carboxylic acid
1-[5-(cyclohexylcarbamoyl)-6-propylsulfanyl-pyridin-2-yl]piperidine-4-carboxylic acid
2-[1-[5-(cyclohexylcarbamoyl)-6-propylsulfanyl-pyridin-2-yl]-4-piperidyl]acetic acid
2-[1-[5-(cyclohexylcarbamoyl)-6-propylsulfanyl-pyridin-2-yl]-3-piperidyl]acetic acid
1-[5-(cyclohexylcarbamoyl)-6-propylsulfanyl-pyridin-2-yl]pyrrolidine-3-carboxylic acid
2-[(3S)-1-[5-(cyclohexylcarbamoyl)-6-propylsulfanyl-pyridin-2-yl]-3-piperidyl]acetic acid
2-[4-[5-(cyclohexylcarbamoyl)-6-propylsulfanyl-pyridin-2-yl]piperazin-1-yl]acetic acid
(3R,5S)-4-[[5-(cyclohexylcarbamoyl)-6-propylsulfanyl-pyridin-2-yl]amino]adamantane-1-carboxylic acid
(3R,5S)-4-[[5-(cyclohexylcarbamoyl)-6-propylsulfanyl-pyridin-2-yl]amino]adamantane-1-carboxylic acid
4-[[5-(cyclohexylcarbamoyl)-6-propylsulfanyl-pyridin-2-yl]-methyl-amino]cyclohexane-1-carboxylic acid
2-[(3S)-1-[5-(cyclohexylcarbamoyl)-6-propylsulfanyl-pyridin-2-yl]pyrrolidin-3-yl]acetic acid
3-[5-(cyclohexylcarbamoyl)-6-propylsulfanyl-pyridin-2-yl]oxybenzoic acid
3-[5-(cyclohexylcarbamoyl)-6-propylsulfanyl-pyridin-2-yl]sulfanylbenzoic acid
4-[5-(cyclohexylcarbamoyl)-6-propylsulfanyl-pyridin-2-yl]sulfanylbenzoic acid
4-[5-(cyclohexylcarbamoyl)-6-propylsulfanyl-pyridin-2-yl]oxybenzoic acid
2-[4-[5-(cyclohexylcarbamoyl)-6-propylsulfanyl-pyridin-2-yl]oxyphenyl]acetic acid
3-[4-[5-(cyclohexylcarbamoyl)-6-propylsulfanyl-pyridin-2-yl]oxyphenyl]propanoic acid
2-[4-[5-(cyclohexylcarbamoyl)-6-propylsulfanyl-pyridin-2-yl]sulfanylphenoxy]acetic acid
2-[4-[5-(cyclohexylcarbamoyl)-6-propylsulfanyl-pyridin-2-yl]oxyphenoxy]acetic acid
2-[4-[5-(cyclohexylcarbamoyl)-6-propylsulfanyl-pyridin-2-yl]oxyphenyl]propanoic acid
2-[4-[5-(cyclohexylcarbamoyl)-6-propylsulfanyl-pyridin-2-yl]sulfanylphenyl]acetic acid
2-[3-[5-(cyclohexylcarbamoyl)-6-propylsulfanyl-pyridin-2-yl]oxyphenyl]acetic acid
2-[5-(cyclohexylcarbamoyl)-6-propylsulfanyl-pyridin-2-yl]sulfanylbenzoic acid
4-[5-(cyclohexylcarbamoyl)-6-propylsulfanyl-pyridin-2-yl]oxycyclohexane-1-carboxylic acid
1-[5-(cyclohexylcarbamoyl)-6-propylsulfanyl-pyridin-2-yl]piperidine-2-carboxylic acid
(2S)-1-[5-(cyclohexylcarbamoyl)-6-propylsulfanyl-pyridin-2-yl]pyrrolidine-2-carboxylic acid
2-[1-[5-(cyclohexylcarbamoyl)-6-propylsulfanyl-pyridin-2-yl]-4-piperidyl]propanoic acid
4-[[[5-(cyclohexylcarbamoyl)-6-propylsulfanyl-pyridin-2-yl]amino]methyl]cyclohexane-1-carboxylic acid
3-[[5-(cyclohexylcarbamoyl)-6-propylsulfanyl-pyridin-2-yl]amino]propanoic acid
1-[5-(cyclohexylcarbamoyl)-6-propylsulfanyl-pyridin-2-yl]azepane-4-carboxylic acid
1-[5-(cyclohexylcarbamoyl)-6-propylsulfanyl-pyridin-2-yl]-4-methyl-piperidine-4-carboxylic acid
(1S,5R)-3-[5-(cyclohexylcarbamoyl)-6-propylsulfanyl-pyridin-2-yl]-3-azabicyclo[3.1.0]hexane-6-carboxylic acid
4-[[5-(cyclohexylcarbamoyl)-6-propylsulfanyl-pyridin-2-yl]amino]cyclohexane-1-carboxylic acid
1-[5-(cyclohexylcarbamoyl)-6-propylsulfanyl-pyridin-2-yl]-4-propan-2-yl-piperidine-4-carboxylic acid
1-[5-(cyclohexylcarbamoyl)-6-propylsulfanyl-pyridin-2-yl]-3-methyl-piperidine-4-carboxylic acid
2-[1-[5-(cyclohexylcarbamoyl)-6-propylsulfanyl-pyridin-2-yl]-3-piperidyl]-2-methyl-propanoic acid
2-[(3R)-1-[5-(cyclohexylcarbamoyl)-6-propylsulfanyl-pyridin-2-yl]pyrrolidin-3-yl]acetic acid
3-[1-[5-(cyclohexylcarbamoyl)-6-propylsulfanyl-pyridin-2-yl]-3-piperidyl]propanoic acid
2-[1-[5-(cyclohexylcarbamoyl)-6-propylsulfanyl-pyridin-2-yl]azetidin-3-yl]oxyacetic acid
1-[1-[5-(cyclohexylcarbamoyl)-6-propylsulfanyl-pyridin-2-yl]-3-piperidyl]cyclobutane-1-carboxylic acid
1-[1-[5-(cyclohexylcarbamoyl)-6-propylsulfanyl-pyridin-2-yl]-3-piperidyl]cyclopropane-1-carboxylic acid
2-[1-[5-(cyclohexylcarbamoyl)-6-propylsulfanyl-pyridin-2-yl]pyrrolidin-3-yl]oxyacetic acid
2-[[1-[5-(cyclohexylcarbamoyl)-6-propylsulfanyl-pyridin-2-yl]-3-piperidyl]oxy]propanoic acid
2-[[1-[5-(cyclohexylcarbamoyl)-6-propylsulfanyl-pyridin-2-yl]-3-piperidyl]oxy]-2-methyl-propanoic acid
2-[[1-[5-(cyclohexylcarbamoyl)-6-propylsulfanyl-pyridin-2-yl]-3-piperidyl]oxy]acetic acid
1-[5-(cyclohexylcarbamoyl)-6-propylsulfanyl-pyridin-2-yl]-3-methyl-piperidine-3-carboxylic acid
2-[1-[5-(cyclohexylcarbamoyl)-6-propylsulfanyl-pyridin-2-yl]-4-piperidyl]-2-methyl-propanoic acid
1-[1-[5-(cyclohexylcarbamoyl)-6-propylsulfanyl-pyridin-2-yl]-4-piperidyl]cyclobutane-1-carboxylic acid
1-[1-[5-(cyclohexylcarbamoyl)-6-propylsulfanyl-pyridin-2-yl]-4-piperidyl]cyclopropane-1-carboxylic acid
4-[5-(cyclohexylcarbamoyl)-6-propylsulfanyl-pyridin-2-yl]morpholine-2-carboxylic acid
2-[(3R)-1-[5-(cyclohexylcarbamoyl)-6-cyclohexylsulfanyl-pyridin-2-yl]pyrrolidin-3-yl]acetic acid
2-[(3R)-1-[5-(cyclohexylcarbamoyl)-6-cyclohexylsulfanyl-pyridin-2-yl]-3-piperidyl]acetic acid
2-[(3S)-1-[5-(cyclohexylcarbamoyl)-6-cyclopentylsulfanyl-pyridin-2-yl]-3-piperidyl]acetic acid
2-[(3S)-1-[5-(cyclohexylcarbamoyl)-6-cyclopentylsulfanyl-pyridin-2-yl]pyrrolidin-3-yl]acetic acid
2-[(3R)-1-[5-(cyclohexylcarbamoyl)-6-cyclopentylsulfanyl-pyridin-2-yl]pyrrolidin-3-yl]acetic acid 2-[(3R)-1-[5-(cyclohexylcarbamoyl)-6-cyclopentylsulfanyl-pyridin-2-yl]-3-piperidyl]acetic acid 1-[1-[5-(cyclohexylcarbamoyl)-6-cyclopentylsulfanyl-pyridin-2-yl]-3-piperidyl]cyclopropane-1-carboxylic acid 2-[(3S)-1-[5-(2-adamantylcarbamoyl)-6-propylsulfanyl-pyridin-2-yl]-3-piperidyl]acetic acid 2-[(3S)-1-[5-(2-adamantylcarbamoyl)-6-propylsulfanyl-pyridin-2-yl]pyrrolidin-3-yl]oxyacetic acid 2-[(3R)-1-[5-(2-adamantylcarbamoyl)-6-propylsulfanyl-pyridin-2-yl]pyrrolidin-3-yl]oxyacetic acid 2-[(3S)-1-[5-(2-adamantylcarbamoyl)-6-propylsulfanyl-pyridin-2-yl]pyrrolidin-3-yl]acetic acid (3R)-1-[5-(2-adamantylcarbamoyl)-6-propylsulfanyl-pyridin-2-yl]pyrrolidine-3-carboxylic acid 2-[(3R)-1-[5-(2-adamantylcarbamoyl)-6-propylsulfanyl-pyridin-2-yl]pyrrolidin-3-yl]acetic acid (2S)-1-[5-(2-adamantylcarbamoyl)-6-propylsulfanyl-pyridin-2-yl]pyrrolidine-2-carboxylic acid (1S,5R)-3-[5-(2-adamantylcarbamoyl)-6-propylsulfanyl-pyridin-2-yl]-3-azabicyclo[3.1.0]hexane-6-carboxylic acid (3S)-1-[5-(2-adamantylcarbamoyl)-6-propylsulfanyl-pyridin-2-yl]pyrrolidine-3-carboxylic acid 4-[5-(2-adamantylcarbamoyl)-6-propylsulfanyl-pyridin-2-yl]morpholine-2-carboxylic acid 2-[(3S)-1-[5-(2-adamantylcarbamoyl)-6-cyclopentylsulfanyl-pyridin-2-yl]pyrrolidin-3-yl]oxyacetic acid 2-[(3R)-1-[5-(2-adamantylcarbamoyl)-6-cyclopentylsulfanyl-pyridin-2-yl]pyrrolidin-3-yl]oxyacetic acid 2-[(3S)-1-[5-(2-adamantylcarbamoyl)-6-cyclohexylsulfanyl-pyridin-2-yl]pyrrolidin-3-yl]oxyacetic acid 2-[(3R)-1-[5-(2-adamantylcarbamoyl)-6-cyclohexylsulfanyl-pyridin-2-yl]pyrrolidin-3-yl]oxyacetic acid 2-[(3R)-1-[5-(2-adamantylcarbamoyl)-6-ethylsulfanyl-pyridin-2-yl]pyrrolidin-3-yl]acetic acid (3R)-1-[5-(2-adamantylcarbamoyl)-6-ethylsulfanyl-pyridin-2-yl]pyrrolidine-3-carboxylic acid (3S)-1-[5-(2-adamantylcarbamoyl)-6-ethylsulfanyl-pyridin-2-yl]pyrrolidine-3-carboxylic acid (1S,5R)-3-[5-(2-adamantylcarbamoyl)-6-ethylsulfanyl-pyridin-2-yl]-3-azabicyclo[3.1.0]hexane-6-carboxylic acid 2-[(3R)-1-[5-(2-adamantylcarbamoyl)-6-methylsulfanyl-pyridin-2-yl]pyrrolidin-3-yl]acetic acid (3R)-1-[5-(2-adamantylcarbamoyl)-6-methylsulfanyl-pyridin-2-yl]pyrrolidine-3-carboxylic acid (1S,5R)-3-[5-(2-adamantylcarbamoyl)-6-methylsulfanyl-pyridin-2-yl]-3-azabicyclo[3.1.0]hexane-6-carboxylic acid 2-[(3S)-1-[5-[((2r,5s)-5-hydroxy-2-adamantyl)carbamoyl]-6-propylsulfanyl-pyridin-2-yl]pyrrolidin-3-yl]acetic acid 4-[[[5-[((2r,5s)-5-hydroxy-2-adamantyl)carbamoyl]-6-propylsulfanyl-pyridin-2-yl]amino]methyl]cyclohexane-1-carboxylic acid 4-[[5-[((2r,5s)-5-hydroxy-2-adamantyl)carbamoyl]-6-propylsulfanyl-pyridin-2-yl]amino]cyclohexane-1-carboxylic acid 4-[[5-[((2r,5s)-5-hydroxy-2-adamantyl)carbamoyl]-6-propylsulfanyl-pyridin-2-yl]amino]cyclohexane-1-carboxylic acid 2-[(3S)-1-[5-[(2r,5s)-5-hydroxy-2-adamantyl]carbamoyl]-6-propylsulfanyl-pyridin-2-yl]-3-piperidyl]acetic acid 1-[5-[[(2r,5s)-5-hydroxy-2-adamantyl]carbamoyl]-6-propylsulfanyl-pyridin-2-yl]piperidine-4-carboxylic acid 2-[(3R)-1-[5-[[(2r,5s)-5-hydroxy-2-adamantyl]carbamoyl]-6-propylsulfanyl-pyridin-2-yl]-3-piperidyl]acetic acid 2-[1-[5-[[(2r,5s)-5-hydroxy-2-adamantyl]carbamoyl]-6-propylsulfanyl-pyridin-2-yl]-4-piperidyl]acetic acid (1R,5S)-3-[5-[[(2r,5s)-5-hydroxy-2-adamantyl]carbamoyl]-6-propylsulfanyl-pyridin-2-yl]-3-azabicyclo[3.1.0]hexane-6-carboxylic acid 1-[5-[[(2r,5s)-5-hydroxy-2-adamantyl]carbamoyl]-6-propylsulfanyl-pyridin-2-yl]-4-methyl-piperidine-4-carboxylic acid 1-[5-[[(2r,5s)-5-hydroxy-2-adamantyl]carbamoyl]-6-propylsulfanyl-pyridin-2-yl]pyrrolidine-3-carboxylic acid 2-[(3R)-1-[5-[[(2r,5s)-5-hydroxy-2-adamantyl]carbamoyl]-6-propylsulfanyl-pyridin-2-yl]pyrrolidin-3-yl]acetic acid 3-[1-[5-[[(2r,5s)-5-hydroxy-2-adamantyl]carbamoyl]-6-propylsulfanyl-pyridin-2-yl]-3-piperidyl]propanoic acid 2-[1-[5-[((2r,5s)-5-hydroxy-2-adamantyl)carbamoyl]-6-propylsulfanyl-pyridin-2-yl]-3-piperidyl]-2-methyl-propanoic acid 2-[(3S)-1-[6-cyclopentylsulfanyl-5-[((2r,5s)-5-hydroxy-2-adamantyl)carbamoyl]pyridin-2-yl]pyrrolidin-3-yl]acetic acid 2-[(3S)-1-[6-cyclopentylsulfanyl-5-[[(2r,5s)-5-hydroxy-2-adamantyl]carbamoyl]pyridin-2-yl]-3-piperidyl]acetic acid 2-[(3R)-1-[6-cyclopentylsulfanyl-5-[((2r,5s)-5-hydroxy-2-adamantyl)carbamoyl]pyridin-2-yl]pyrrolidin-3-yl]acetic acid (3R)-1-[6-cyclopentylsulfanyl-5-[((2r,5s)-5-hydroxy-2-adamantyl)carbamoyl]pyridin-2-yl]pyrrolidine-3-carboxylic acid (2S)-1-[6-cyclopentylsulfanyl-5-[((2r,5s)-5-hydroxy-2-adamantyl)carbamoyl]pyridin-2-yl]pyrrolidine-2-carboxylic acid (1R,5S)-3-[6-cyclopentylsulfanyl-5-[((2r,5s)-5-hydroxy-2-adamantyl)carbamoyl]pyridin-2-yl]-3-azabicyclo[3.1.0]hexane-6-carboxylic acid 1-[6-cyclopentylsulfanyl-5-[((2r,5s)-5-hydroxy-2-adamantyl)carbamoyl]pyridin-2-yl]piperidine-4-carboxylic acid 2-[(3R)-1-[6-cyclohexylsulfanyl-5-[((2r,5s)-5-hydroxy-2-adamantyl)carbamoyl]pyridin-2-yl]pyrrolidin-3-yl]acetic acid (2S)-1-[6-cyclohexylsulfanyl-5-[((2r,5s)-5-hydroxy-2-adamantyl)carbamoyl]pyridin-2-yl]pyrrolidine-2-carboxylic acid (3R)-1-[6-cyclohexylsulfanyl-5-[((2r,5s)-5-hydroxy-2-adamantyl)carbamoyl]pyridin-2-yl]pyrrolidine-3-carboxylic acid 2-[(3S)-1-[6-cyclohexylsulfanyl-5-[[(2r,5s)-5-hydroxy-2-adamantyl]carbamoyl]pyridin-2-yl]-3-piperidyl]acetic acid 2-[(3S)-1-[5-[[(2r,5s)-5-hydroxy-2-adamantyl]carbamoyl]-6-(3-methylbutylsulfanyl)pyridin-2-yl]-3-piperidyl]acetic acid (3R)-1-[5-[((2r,5s)-5-hydroxy-2-adamantyl)carbamoyl]-6-(3-methylbutylsulfanyl)pyridin-2-yl]pyrrolidine-3-carboxylic acid (1R,5S)-3-[5-[((2r,5s)-5-hydroxy-2-adamantyl)carbamoyl]-6-(3-methylbutylsulfanyl)pyridin-2-yl]-3-azabicyclo[3.1.0]hexane-6-carboxylic acid 2-[(3S)-1-[6-benzylsulfanyl-5-[[(2r,5s)-5-hydroxy-2-adamantyl]carbamoyl]pyridin-2-yl]-3-piperidyl]acetic acid 2-[(3S)-1-[5-[[(2r,5s)-5-hydroxy-2-adamantyl]carbamoyl]-6-phenethylsulfanyl-pyridin-2-yl]-3-piperidyl]acetic acid 2-[(3S)-1-[5-[[(2r,5s)-5-hydroxy-2-adamantyl]carbamoyl]-6-propoxy-pyridin-2-yl]-3-piperidyl]acetic acid 2-[1-[5-[((2r,5s)-5-hydroxy-2-adamantyl)carbamoyl]-6-propoxy-pyridin-2-yl]-3-piperidyl]-2-methyl-propanoic acid 5 (1R,5S,6r)-3-(6-(cyclopentylthio)-5-(3-(pyridin-3-yl)pyrrolidine-1-carbonyl)pyridin-2-yl)-3-azabicyclo[3.1.0]hexane-6-carboxylic acid (1S,5R)-3-[6-cyclohexylsulfanyl-5-(3-pyridin-3-ylpyrrolidine-1-carbonyl)pyridin-2-yl]-3-azabicyclo[3.1.0]hexane-6-carboxylic acid
2-[(3S)-1-[6-propylsulfanyl-5-(3-pyridin-3-ylpyrrolidine-1-carbonyl)pyridin-2-yl]-3-piperidyl]acetic acid
2-[(3S)-1-[6-propylsulfanyl-5-(3-pyridin-2-ylpyrrolidine-1-carbonyl)pyridin-2-yl]-3-piperidyl]acetic acid
2-[(3S)-1-[5-(piperidine-1-carbonyl)-6-propylsulfanyl-pyridin-2-yl]-3-piperidyl]acetic acid
2-[(3S)-1-[6-propylsulfanyl-5-(3-pyrazin-2-ylpyrrolidine-1-carbonyl)pyridin-2-yl]-3-piperidyl]acetic acid
2-[(3S)-1-[5-(4,4-difluoropiperidine-1-carbonyl)-6-propylsulfanyl-pyridin-2-yl]-3-piperidyl]acetic acid
2-[(3S)-1-[6-propylsulfanyl-5-[3-(trifluoromethyl)piperidine-1-carbonyl]pyridin-2-yl]-3-piperidyl]acetic acid
2-[(3S)-1-[6-propylsulfanyl-5-[4-(trifluoromethyl)piperidine-1-carbonyl]pyridin-2-yl]-3-piperidyl]acetic acid
2-[(3S)-1-[5-(4-carbamoylpiperidine-1-carbonyl)-6-propylsulfanyl-pyridin-2-yl]-3-piperidyl]acetic acid
2-[(3S)-1-[5-(cyclohexyl-cyclopropyl-carbamoyl)-6-propylsulfanyl-pyridin-2-yl]-3-piperidyl]acetic acid
2-[(3S)-1-[5-(cyclohexyl-(cyclopropylmethyl)carbamoyl)-6-propylsulfanyl-pyridin-2-yl]-3-piperidyl]acetic acid
2-[(3S)-1-[5-(cyclohexyl-ethyl-carbamoyl)-6-propylsulfanyl-pyridin-2-yl]-3-piperidyl]acetic acid
2-[(3S)-1-[5-(cyclohexyl-propan-2-yl-carbamoyl)-6-propylsulfanyl-pyridin-2-yl]-3-piperidyl]acetic acid
2-[(3S)-1-[5-[(4-hydroxycyclohexyl)carbamoyl]-6-propylsulfanyl-pyridin-2-yl]-3-piperidyl]acetic acid
2-[(3S)-1-[6-propylsulfanyl-5-[3-[2-(trifluoromethyl)phenyl]pyrrolidine-1-carbonyl]pyridin-2-yl]-3-piperidyl]acetic acid
2-[(3S)-1-[5-[((2r,5s)-5-methylsulfonyl-2-adamantyl)carbamoyl]-6-propylsulfanyl-pyridin-2-yl]-3-piperidyl]acetic acid
2-[(3S)-1-[6-cyclopentylsulfanyl-5-(3-pyridin-3-ylpyrrolidine-1-carbonyl)pyridin-2-yl]-3-piperidyl]acetic acid
2-[(3R)-1-[5-(cyclohexylcarbamoyl)-6-phenethylsulfanyl-pyridin-2-yl]-3-piperidyl]acetic acid
2-[(3S)-1-[5-(cyclohexylcarbamoyl)-6-phenethylsulfanyl-pyridin-2-yl]-3-piperidyl]acetic acid
2-[(3S)-1-[5-(cyclohexylcarbamoyl)-6-(2-pyridin-3-ylethylsulfanyl)pyridin-2-yl]-3-piperidyl]acetic acid
2-[(3S)-1-[5-(cyclohexylcarbamoyl)-6-(2-pyrazin-2-ylethylsulfanyl)pyridin-2-yl]-3-piperidyl]acetic acid
2-[(3S)-1-[5-(cyclohexylcarbamoyl)pyridin-2-yl]-3-piperidyl]acetic acid
2-[(3S)-1-[5-(cyclohexylcarbamoyl)-6-[2-(4-fluorophenyl)ethoxy]pyridin-2-yl]-3-piperidyl]acetic acid
2-[(3S)-1-[5-(cyclohexylcarbamoyl)-6-(3-methylbutoxy)pyridin-2-yl]-3-piperidyl]acetic acid
2-[(3S)-1-[5-(cyclohexylcarbamoyl)-6-(3-phenylpropoxy)pyridin-2-yl]-3-piperidyl]acetic acid
2-[(3S)-1-[5-(cyclohexylcarbamoyl)-6-(2-pyridin-3-ylethoxy)pyridin-2-yl]-3-piperidyl]acetic acid
2-[(3S)-1-[5-(cyclohexylcarbamoyl)-6-methoxy-pyridin-2-yl]-3-piperidyl]acetic acid
2-[(3S)-1-[5-(cyclohexylcarbamoyl)-6-propoxy-pyridin-2-yl]-3-piperidyl]acetic acid
2-[(3S)-1-[5-(cyclohexylcarbamoyl)-6-(1-piperidyl)pyridin-2-yl]-3-piperidyl]acetic acid
2-[(3S)-1-[6-[2-(4-chlorophenyl)ethylamino]-5-(cyclohexylcarbamoyl)pyridin-2-yl]-3-piperidyl]acetic acid
2-[(3S)-1-[5-(cyclohexylcarbamoyl)-6-[3-(4-fluorophenyl)pyrrolidin-1-yl]pyridin-2-yl]-3-piperidyl]acetic acid
2-[(3S)-1-[5-(cyclohexylcarbamoyl)-6-(3,4-dihydro-1H-isoquinolin-2-yl)pyridin-2-yl]-3-piperidyl]acetic acid
2-[(3S)-1-[5-(cyclohexylcarbamoyl)-6-(3,4-dihydro-1H-isoquinolin-2-yl)pyridin-2-yl]-3-piperidyl]acetic acid
2-[(3S)-1-[5-(cyclohexylcarbamoyl)-6-(4-phenylpiperazin-1-yl)pyridin-2-yl]-3-piperidyl]acetic acid
2-[(3S)-1-[5-(cyclohexylcarbamoyl)-6-[4-(4-fluorobenzoyl)piperazin-1-yl]pyridin-2-yl]-3-piperidyl]acetic acid
2-[(3S)-1-[6-(4-acetylpiperazin-1-yl)-5-(cyclohexylcarbamoyl)pyridin-2-yl]-3-piperidyl]acetic acid
2-[(3S)-1-[5-(cyclohexylcarbamoyl)-6-(4-ethylsulfonylpiperazin-1-yl)pyridin-2-yl]-3-piperidyl]acetic acid
2-[(3S)-1-[6-[4-(benzenesulfonyl)piperazin-1-yl]-5-(cyclohexylcarbamoyl)pyridin-2-yl]-3-piperidyl]acetic acid
2-[(3S)-1-[5-(cyclohexylcarbamoyl)-6-(4-phenylmethoxycarbonylpiperazin-1-yl)pyridin-2-yl]-3-piperidyl]acetic acid
2-[(3S)-1-[5-(cyclohexylcarbamoyl)-6-propylamino-pyridin-2-yl]-3-piperidyl]acetic acid
2-[(3S)-1-[5-(cyclohexylcarbamoyl)-6-(phenethylamino)pyridin-2-yl]-3-piperidyl]acetic acid
2-[(3S)-1-[5-(cyclohexylcarbamoyl)-6-(methyl-phenethyl-amino)pyridin-2-yl]-3-piperidyl]acetic acid
2-[(3S)-1-[5-(cyclohexylcarbamoyl)-6-(methyl-propyl-amino)pyridin-2-yl]-3-piperidyl]acetic acid
2-[(3S)-1-[5-(cyclohexylcarbamoyl)-6-pyrrolidin-1-yl-pyridin-2-yl]-3-piperidyl]acetic acid
2-[(3S)-1-[5-(cyclohexylcarbamoyl)-6-morpholin-4-yl-pyridin-2-yl]-3-piperidyl]acetic acid
2-[(3S)-1-[5-(cyclohexyl-methyl-carbamoyl)-6-propylamino-pyridin-2-yl]-3-piperidyl]acetic acid
2-[(3S)-1-[5-(cyclohexyl-methyl-carbamoyl)-6-(methyl-propyl-amino)pyridin-2-yl]-3-piperidyl]acetic acid
2-[(3S)-1-[5-(cyclohexylcarbamoyl)-6-methyl-pyridin-2-yl]-3-piperidyl]acetic acid
2-[(3S)-1-[5-(1-adamantylcarbamoyl)-6-methyl-pyridin-2-yl]-3-piperidyl]acetic acid
2-[(3S)-1-[5-(2-adamantylcarbamoyl)-6-methyl-pyridin-2-yl]-3-piperidyl]acetic acid
2-[(3S)-1-[5-(2-adamantylcarbamoyl)-6-butyl-pyridin-2-yl]-3-piperidyl]acetic acid
3-[5-(2-adamantylcarbamoyl)-6-butyl-pyridin-2-yl]-3-azabicyclo[3.1.0]hexane-6-carboxylic acid
2-[(3S)-1-[6-butyl-5-(cyclohexylcarbamoyl)pyridin-2-yl]-3-piperidyl]acetic acid
2-[(3S)-1-[5-(cyclohexylcarbamoyl)-6-cyclopropyl-pyridin-2-yl]-3-piperidyl]acetic acid
2-[(3S)-1-[5-(2-adamantylcarbamoyl)-6-cyclopropyl-pyridin-2-yl]-3-piperidyl]acetic acid
2-[(3S)-1-[6-cyclopropyl-5-[[(2r,5s)-5-hydroxy-2-adamantyl]carbamoyl]pyridin-2-yl]-3-piperidyl]acetic acid
2-[(3R)-1-[5-(cyclohexyl-methyl-carbamoyl)-6-propylsulfanyl-pyridin-2-yl]-3-piperidyl]acetic acid
2-[(3S)-1-[5-(cyclohexyl-methyl-carbamoyl)-6-propylsulfanyl-pyridin-2-yl]-3-piperidyl]acetic acid
[(3S)-1-{5-[((2r,5s)-5-methoxyadamantan-2-yl)(methyl)carbamoyl]-6-(propylthio)pyridin-2-yl}piperidin-3-yl]acetic acid
[(3S)-1-{5-[((2r,5s)-5-hydroxyadamantan-2-yl)(methyl)carbamoyl]-6-(propylthio)pyridin-2-yl}piperidin-3-yl]acetic acid
{(3S)-1-[5-(adamantan-1-ylcarbamoyl)-6-(propylthio)pyridin-2-yl]piperidin-3-yl}acetic acid
{(3S)-1-[6-(propylthio)-5-(tetrahydro-2H-pyran-4-ylcarbamoyl)pyridin-2-yl]piperidin-3-yl}acetic acid
[(3S)-1-{5-[methyl(tetrahydro-2H-pyran-4-yl)carbamoyl]-6-(propylthio)pyridin-2-yl}piperidin-3-yl]acetic acid 2-[(3S)-1-[6-cyclohexylsulfanyl-5-[[(2r,5s)-5-(difluoromethoxy)-2-adamantyl]carbamoyl]pyridin-2-yl]pyrrolidin-3-yl]acetic acid 2-[(3S)-1-[6-cyclohexylsulfanyl-5-[[(2r,5s)-5-(difluoromethoxy)-2-adamantyl]carbamoyl]pyridin-2-yl]-3-piperidyl]acetic acid 2-[(3S)-1-[6-cyclopentylsulfanyl-5-[[(2r,5s)-5-(difluoromethoxy)-2-adamantyl]carbamoyl]pyridin-2-yl]pyrrolidin-3-yl]acetic acid 2-[(3S)-1-[6-cyclopentylsulfanyl-5-[[(2r,5s)-5-(difluoromethoxy)-2-adamantyl]carbamoyl]pyridin-2-yl]-3-piperidyl]acetic acid 2-[(3S)-1-[5-[[(2r,5s)-5-(difluoromethoxy)-2-adamantyl]carbamoyl]-6-propylsulfanyl-pyridin-2-yl]-3-piperidyl]acetic acid 2-[(3S)-1-[5-[[(2r,5s)-5-(difluoromethoxy)-2-adamantyl]carbamoyl]-6-propylsulfanyl-pyridin-2-yl]pyrrolidin-3-yl]acetic acid 2-[(3S)-1-[5-[[(2r,5s)-5-(difluoromethoxy)-2-adamantyl]carbamoyl]-6-propoxy-pyridin-2-yl]-3-piperidyl]acetic acid (3R)-1-[6-cyclopentylsulfanyl-5-[[(2r,5s)-5-(difluoromethoxy)-2-adamantyl]carbamoyl]pyridin-2-yl]pyrrolidine-3-carboxylic acid (1R,5S)-3-[6-cyclopentylsulfanyl-5-[[(2r,5s)-5-(difluoromethoxy)-2-adamantyl]carbamoyl]pyridin-2-yl]-3-azabicyclo[3.1.0]hexane-6-carboxylic acid 2-[(3R)-1-[5-[[(2r,5s)-5-(difluoromethoxy)-2-adamantyl]carbamoyl]-6-propylsulfanyl-pyridin-2-yl]pyrrolidin-3-yl]acetic acid 1-[5-[[(2r,5s)-5-(difluoromethoxy)-2-adamantyl]carbamoyl]-6-propylsulfanyl-pyridin-2-yl]pyrrolidine-3-carboxylic acid (S)-2-(1-(5-(cyclohexylcarbamoyl)-3-fluoro-6-(propylthio)pyridin-2-yl)piperidin-3-yl)acetic acid and (R)-2-(1-(5-(cyclohexylcarbamoyl)-3-fluoro-6-(propylthio)pyridin-2-yl)piperidin-3-yl)acetic acid and pharmaceutically-acceptable salts thereof.

Another aspect of the present invention provides a process for preparing a compound of formula (1) or a pharmaceutically acceptable salt thereof which process [wherein Z is —X—Y—COOH and other variable groups are, unless otherwise specified, as defined in formula (1)] comprises any one of processes a) to e):

a) reaction of a compound of Formula (2) with a compound of Formula (3):

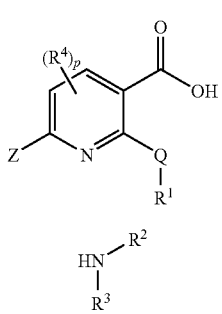

(2)

(3)

b) reaction of a compound of Formula (4) with a compound of Formula (5):

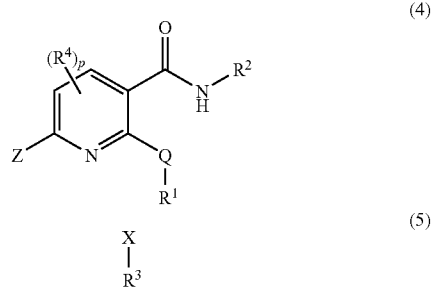

(4)

(5)

wherein X is a leaving group; or c) reaction of a compound of Formula (6) with a compound of Formula (7):

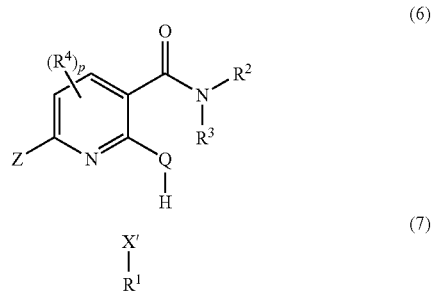

(6)

(7)

wherein X' is a leaving group; or d) reaction of a compound of Formula (8) with a compound of Formula (9):

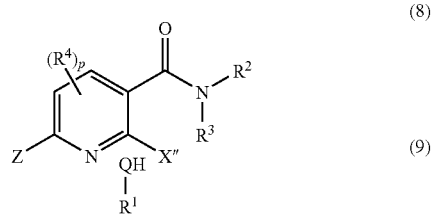

(8)

(9)

wherein X" is a leaving group; or e) reaction of a compound of Formula (10) with a compound of Formula (11):

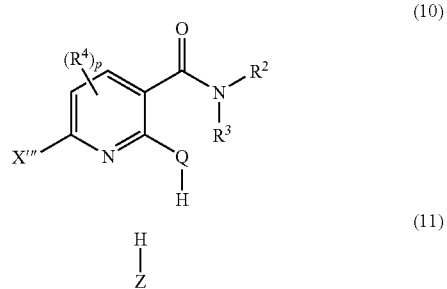

(10)

(11)

wherein X''' is a leaving group;

and thereafter if necessary or desirable:
i) converting a compound of the formula (1) into another compound of the formula (1);
ii) removing any protecting groups;
iii) resolving enantiomers;
iv) forming a pharmaceutically-acceptable salt or in vivo hydrolysable ester thereof.

Examples of conversions of a compound of Formula (1) into another compound of Formula (1), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions.

Suitable conditions for the above processes a) to e) are as follows.

Process a) is typically carried out in a suitable solvent such as dichloromethane or N,N-dimethylformamide for example with either the in situ formation of the acyl halide using a suitable reagent such as oxalyl chloride for example or with the addition of a suitable coupling agent (or combination of agents) to form an active ester such as HOBT and EDAC for example, optionally in the presence of a suitable base such as triethylamine or N,N-di-iso-propylamine for example. Typically the reaction is carried out at ambient or elevated temperature between 0-60° C.

Process b) is typically carried out in a suitable solvent such as dichloromethane or THF for example using a strong base (such as sodium hydride or lithium or potassium hexamethyldisilylazides) and a suitable alkylating agent (such as alkyl iodide). Typically the reaction is carried out at ambient or temperature. Suitable examples of leaving groups (X) are chloro, bromo, iodo, mesylate, tosylate or triflate. Others are known to the art.

Process c) may be carried out in a suitable solvent such as acetonitrile, butyronitrile or methanol for example, typically with the addition of a suitable base such as potassium carbonate or sodium hydroxide for example. Typically the reaction is carried out at elevated temperature, using Microwave or conventional heating, for example at temperatures between 100-140° C. In certain cases the reactions can be carried out at ambient temperature. Suitable examples of leaving groups (X') are chloro, bromo, iodo, mesylate, tosylate or triflate. Others are known to the art.

Process d) may be carried out in a suitable solvent such as acetonitrile, butyronitrile, DMF or THF for example, typically with the addition of a suitable base such as potassium carbonate or sodium hexamethyldisilylazide for example. Typically the reaction is carried out at ambient or elevated temperature between 30-180° C. (achieved using conventional heating or microwave irradiation). Suitable examples of leaving groups (X") are fluoro, and chloro. Others are known to the art.

Process e) may be carried out in a suitable solvent such as acetonitrile, butyronitrile, DMF or THF for example, typically with the addition of a suitable base such as potassium carbonate or sodium hexamethyldisilylazide for example. Typically the reaction is carried out at ambient or elevated temperature between 30-180° C. (achieved using conventional heating or microwave irradiation). Suitable examples of leaving groups (X''') are fluoro, and chloro. Others are known to the art.

It will be appreciated that the intermediates required to synthesise compounds of formula (1) may be commercially available, may be known to the art or may be prepared by known procedures and/or by the procedures described above a)-e). It will be appreciated that the sequence in which these processes are carried out, will be determined by the type of compound of formula (1) being synthesised. For example, reaction of a compound of Formula (12) with appropriate nucleophilic reagents (Nu) resulting in displacement of leaving groups ($X^1$ and $X^2$) to generate compounds of types (13) or (14) which would be potentially useful intermediates in the synthesis of compounds of formula (1)

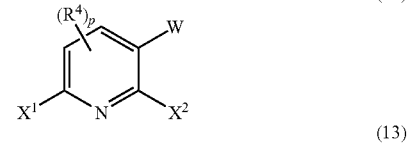

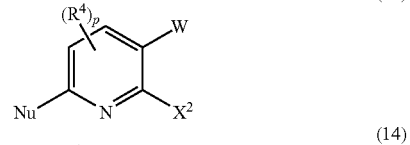

wherein $X^1$ and $X^2$ are leaving groups (typically fluoro or chloro) and W is an amide or alternatively a group that may be converted into an amide by processes known to the art (for example an ester which may be hydrolysed to an acid that may be subsequently transformed into an amide);

It will be appreciated to those skilled in the art that the nature of $X^1$ and $X^2$, the nature of W, the nature and position of any $R^4$ substituents and reaction conditions such as solvent and temperature and any additional catalysts (for example palladium & copper ligands) may affect the order in which the groups are $X^1$ and $X^2$ are displaced and in turn the order in which the reactions are required to be carried out in order to deliver the required compounds. It will be appreciated that examples of pyridines with appropriate substitution in the 4 and 6-positions are known to the art and that they may also be used as starting points for the synthesis of compounds of type (1).

It will be appreciated that when Q is H, the required compounds may be accessed from intermediates of type (15) according to the processes described above.

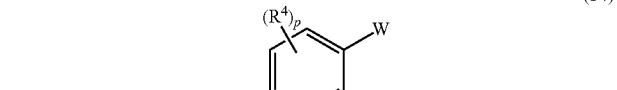

It will be appreciated that certain of the various substituents in the compounds of the present invention, and in intermediates in their preparation, may be introduced by standard aromatic substitution reactions or generated by conventional functional group modifications either prior to or immediately following the processes mentioned above, and as such are included in the process aspect of the invention. Such reactions and modifications include, introduction of a substituent by means of an aromatic substitution reaction, reduction of substituents, oxidation of substituents and alkylation of substituents, for example, alkylation reactions such as conversion of a secondary amide to a primary amide typically carried out using strong base (such as sodium hydride or lithium or potassium hexamethyldisilylazides) and a suitable alkylating agent (such as methyl iodide). The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example hydroxylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess 11βHSD1 inhibitory activity. These properties may be assessed using the following assay.

Assays

The conversion of cortisone to the active steroid cortisol by 11βHSD1 oxo-reductase activity, can be measured using a competitive homogeneous time resolved fluorescence assay (HTRF) (CisBio International, R&D, Administration and Europe Office, In Vitro Technologies—HTRF®/Bioassays BP 84175, 30204 Bagnols/Cèze Cedex, France. Cortisol bulk HTRF kit: Cat No. 62CORPEC).

The evaluation of compounds described herein was carried out using a baculovirus expressed N terminal 6-His tagged full length human 11βHSD1 enzyme(*1). The enzyme was purified from a detergent solubilised cell lysate, using a copper chelate column. Inhibitors of 11βHSD1 reduce the conversion of cortisone to cortisol, which is identified by an increase in signal, in the above assay.

Compounds to be tested were dissolved in dimethyl sulphoxide (DMSO) to 10 mM and diluted further in assay buffer containing 1% DMSO to 10 fold the final assay concentration. Diluted compounds were then plated into black 384 well plates (Matrix, Hudson N.H., USA).

The assay was carried out in a total volume of 20 µl consisting of cortisone (Sigma, Poole, Dorset, UK, 160 nM), glucose-6-phosphate (Roche Diagnostics, 1 mM), NADPH (Sigma, Poole, Dorset, 100 µM), glucose-6-phosphate dehydrogenase (Roche Diagnostics, 12.5 µg/ml), EDTA (Sigma, Poole, Dorset, UK, 1 mM), assay buffer ($K_2HPO_4/KH_2PO_4$, 100 mM) pH 7.5, recombinant 11βHSD1 [using an appropriate dilution to give a viable assay window—an example of a suitable dilution may be 1 in 1000 dilution of stock enzyme] plus test compound. The assay plates were incubated for 25 minutes at 37° C. after which time the reaction was stopped by the addition of 10 µl of 0.5 mM glycerrhetinic acid plus conjugated cortisol (XL665 or D2). 10 µl of anti-cortisol Cryptate was then added and the plates sealed and incubated for 6 hours at room temperature. Fluorescence at 665 nm and 620 nm was measured and the 665 nm:620 nm ratio calculated using an Envision plate reader.

This data was then used to calculate $IC_{50}$ values for each compound (Origin 7.5, Microcal software, Northampton Mass., USA).

*1 The Journal of Biological Chemistry, Vol. 26, No 25, pp 16653-16658

Compounds of the present invention typically show an $IC_{50}$ of less than 30 µM, and preferably less than 5 µM.

The following table displays IC50 values for selected compounds:

| Ex No | IC 50 (uM) | Ex. No | IC 50 (uM) | Ex. No | IC 50 (uM) | Ex. No | IC 50 (uM) |
|---|---|---|---|---|---|---|---|
| 1 | 0.095 | 4 | 0.198 | 6 | 0.157 | | |
| 7 | 0.007 | 60 | 0.008 | 81 | 0.009 | 121 | 0.031 |
| 25 | 0.250 | 68 | 0.006 | 91 | 0.006 | 136 | 0.120 |

| Ex No | IC 50 (uM) | Ex. No | IC 50 (uM) | Ex. No | IC 50 (uM) | Ex. No | IC 50 (uM) |
|---|---|---|---|---|---|---|---|
| 30 | 0.240 | 74 | 0.006 | 99 | 0.007 | 158 | 0.079 |
| 42 | 0.021 | 75 | 0.006 | 112 | 0.016 | 162 | 0.006 |
| 54 | 0.035 | 78 | 0.009 | 117 | 0.100 | 177 | 0.020 |

The following table displays % inhibition of human 11-βHSD at a test concentration of 30 μM of compound:

| Ex. No. | % @30 uM |
|---|---|
| 1 | 87 |
| 2 | 84 |
| 3 | 87 |
| 4 | 77 |
| 5 | 86 |
| 6 | 98 |
| 7 | 87 |
| 8 | 78 |
| 9 | 92 |
| 10 | 88 |
| 11 | 83 |
| 12 | 81 |
| 13 | 94 |
| 14 | 78 |
| 15 | 73 |
| 16 | 43 |
| 17 | 89 |
| 18 | 81 |
| 19 | 61 |
| 20 | 89 |
| 21 | 88 |
| 22 | 65 |
| 23 | 78 |
| 24 | 77 |
| 25 | 93 |
| 26 | 76 |
| 27 | 94 |
| 28 | 86 |
| 29 | 88 |
| 30 | 84 |
| 31 | 94 |
| 32 | 89 |
| 33 | 80 |
| 34 | 86 |
| 35 | 93 |
| 36 | 89 |
| 37 | 89 |
| 38 | 87 |
| 39 | 74 |
| 40 | 87 |
| 41 | 82 |
| 42 | 84 |
| 43 | 92 |
| 44 | 85 |
| 45 | 85 |
| 46 | 83 |
| 47 | 90 |
| 48 | 75 |
| 49 | 77 |
| 50 | 81 |
| 51 | 90 |
| 52 | 92 |
| 53 | 82 |
| 54 | 85 |
| 55 | 89 |
| 56 | 97 |
| 57 | 97 |
| 58 | 83 |
| 59 | 94 |
| 60 | 87 |
| 61 | 91 |
| 62 | 89 |
| 63 | 91 |
| 64 | 89 |
| 65 | 89 |
| 66 | 89 |
| 67 | 88 |
| 68 | 89 |
| 69 | 91 |
| 70 | 95 |
| 71 | 92 |
| 72 | 84 |
| 73 | 92 |
| 74 | 93 |
| 74a | 90 |
| 75 | 87 |
| 76 | 87 |
| 77 | 99 |
| 78 | 96 |
| 79 | 90 |
| 80 | 94 |
| 81 | 96 |
| 82 | 95 |
| 83 | 87 |
| 84 | 101 |
| 85 | 89 |
| 86 | 90 |
| 87 | 91 |
| 88 | 89 |
| 89 | 85 |
| 90 | 88 |
| 91 | 88 |
| 92 | 89 |
| 93 | 85 |
| 94 | 90 |
| 95 | 88 |
| 96 | 88 |
| 97 | 97 |
| 98 | 95 |
| 99 | 96 |
| 100 | 92 |
| 101 | 100 |
| 102 | 89 |
| 103 | 90 |
| 104 | 87 |
| 105 | 92 |
| 106 | 95 |
| 107 | 90 |
| 108 | 88 |
| 109 | 88 |
| 110 | 95 |
| 111 | 93 |
| 112 | 96 |
| 113 | 90 |
| 114 | 101 |
| 115 | 93 |
| 116 | 89 |
| 117 | 101 |
| 118 | 101 |
| 119 | 99 |
| 120 | 104 |
| 121 | 97 |
| 122 | 88 |
| 123 | 94 |
| 124 | 92 |
| 125 | 102 |
| 126 | 87 |
| 126b | 99 |
| 127 | 96 |
| 128 | 91 |
| 129 | 82 |
| 130 | 91 |
| 131 | 91 |
| 132 | 98 |
| 133 | 58 |
| 135 | 92 |
| 136 | 89 |
| 137 | 99 |
| 138 | 98 |
| 139 | 89 |
| 140 | 88 |
| 141 | 96 |

-continued

| Ex. No. | % @30 uM |
|---|---|
| 142 | 94 |
| 143 | 95 |
| 144 | 93 |
| 145 | 84 |
| 146 | 58 |
| 147 | 86 |
| 148 | 56 |
| 149 | 83 |
| 150 | 74 |
| 151 | 83 |
| 152 | 81 |
| 153 | 92 |
| 154 | 97 |
| 155 | 94 |
| 156 | 78 |
| 157 | 91 |
| 158 | 88 |
| 159 | 55 |
| 160 | 80 |
| 161 | 84 |
| 162 | 89 |
| 163 | 93 |
| 164 | 87 |
| 165 | 95 |
| 166 | 95 |
| 167 | 95 |
| 168 | 108 |
| 169 | 100 |
| 170 | 92 |
| 171 | 97 |
| 172 | 88 |
| 173 | 92 |
| 174 | 92 |
| 175 | 91 |
| 176 | 92 |
| 177 | 88 |
| 178 | 93 |
| 179 | 87 |
| 180 | 95 |
| 181 | 93 |
| 182 | 91 |
| 183 | 88 |
| 184 | 94 |
| 185 | 97 |
| 186 | 104 |
| 187 | 90 |

The compounds:
{(3S)-1-[5-(adamantan-1-ylcarbamoyl)pyridin-2-yl]piperidin-3-yl}acetic acid; and
{(3S)-1-[5-(cyclohexylcarbamoyl)-6-(piperazin-1-yl)pyridin-2-yl]piperidin-3-yl}acetic acid
did not achieve 50% inhibition of the enzyme at less than or equal to 30 micromolar and hence are not preferred compounds of the invention.

The compound 2-[(3S)-1-[5-(2-adamantylcarbamoyl)pyridin-2-yl]-3-piperidyl]acetic acid achieved 50% inhibition in one assay, but in a subsequent 3 assays did not and hence is also not a preferred aspect of the invention.

In one aspect the invention does not relate to 2-[(3S)-1-[5-(2-adamantylcarbamoyl)pyridin-2-yl]-3-piperidyl]acetic acid.

The oral bioavailability of the compounds of the invention may be tested as follows:

Determination of Bioavailability in PK Studies

Compounds are dosed intravenously at 2 mg/kg (2 ml/kg) and orally at 5 mg/kg (5 ml/kg) in a 25% HPBCD in sorrensons buffer pH 5.5 formulation. Blood samples (200 ul) are taken Predose, 0.25, 0.5, 1, 2, 3, 4, 5, 6, 8 and 24 h post dose for both routes and plasma prepared by centrifugation. Plasma samples are analysed as below. PK parameters (clearance, volume of distribution, bioavailability, fraction absorbed etc.) are calculated by standard PK methods using suitable PK software (WinNon-Lin).

Bioanalysis of Plasma Samples

The guidelines described are for the manual preparation of plasma samples following single compound or cassette dosing of project compounds to all PK species used within discovery DMPK. Analysis by open access (LC-MS/MS) or manual approaches (LC-MS) is described.

Contents
1. Materials
2. Generic Extraction Method
3. Example Sample List Using Generic Plate Layout
4. Open Access Batch Submission and System Checks
5. Acceptance Criteria for Batch Pass 1. Materials
Solvents: Methanol, acetonitrile and DMSO
Water: Purified or HPLC grade
1 ml shallow 96-well plates OR eppendorf tubes
2 ml deep well 96-well plates plus lids
Blank (control) plasma 2. Generic Extraction Method
Solubilise compound(s) to 1 mg/ml using DMSO taking into account salt factors if any. The DMSO stock(s) may be used to make all calibration & quality control (QC) samples:
2.i Single compound analysis
2.i.a Preparation of calibration and QC samples:
1. Prepare standard solutions as follows:

| Stock diluted ng/ml | Volume methanol ml | Volume stock ml | Standard conc. ng/ml | Post plasma dilution conc. ng/ml |
|---|---|---|---|---|
| 1 mg/ml | 0.9 | 0.1 | 100,000 | 10,000 |
| 100,000 | 0.5 | 0.5 | 50,000 | 5,000 |
| 50,000 | 0.75 | 0.5 | 20,000 | 2,000 |
| 20,000 | 0.5 | 0.5 | 10,000 | 1,000 |
| 10,000 | 0.5 | 0.5 | 5,000 | 500 |
| 5,000 | 2 | 0.5 | 1,000 | 100 |
| 1,000 | 0.5 | 0.5 | 500 | 50 |
| 500 | 0.75 | 0.5 | 200 | 20 |
| 200 | 0.5 | 0.5 | 100 | 10 |
| 100 | 0.5 | 0.5 | 50 | 5 |
| 50 | 0.5 | 0.5 | 10 | 1 |

2. Transfer 50 ul blank plasma to a well of a 1 ml 96-well plate (shallow well)
3. Transfer 5 ul of each of the standard solutions to further wells of the plate
4. Add 50 ul blank plasma to each of these wells.
5. To generate the QC samples, add three aliquots of 5 ul of the 100 ng/ml, 1000 ng/ml and 10,000 ng/ml standard solutions to the plate (3 QCs at each concentration).
6. Add 50 ul blank plasma to each of these.
7. Transfer 50 ul of each PK sample to the 1 ml 96-well plate
8. Add 5 ul methanol (–compound) to each of the PK samples
9. Ensure all dose formulations are well mixed by vortex mixing.
10. Dilute intravenous (IV) and oral dose (PO) formulations of expected concentration to 10 ug/ml in methanol. (For example, a formulation made to an expected concentration of 2 mg/ml would be diluted 1:200 to give 10 ug/ml solution).
11. Add 6×50 ul aliquots of plasma to the plate. Add 5 ul of diluted IV formulation to three of the wells, repeat with PO formulation and remaining 3 wells.

12. Precipitate proteins by adding 100 ul acetonitrile containing a project related internal standard (at 1 ug/ml) to all calibration, QC, PK and formulation samples.
13. Vortex mix the plate before centrifugation at 4,000 g for 10 minutes.
14. Transfer 100 ul of the supernatant to the wells of a 2 ml 96-well plate (see following plate map). Care should be taken not to disturb the pellet.
15. Add ~1.5 ml of 50:50 Methanol:Water into the last well.
16. For analysis on triple quad systems: add 400 ul water (HPLC grade) to each sample. Gently mix.
17. Add 100 ul of the 100,000 ng/ml stock of each of the standard solutions to the 2 ml plate and add 900 ul water. Add a sample of internal standard to a further well (see plate map). These are for compound tuning (denoted on the plate map as tune solutions)
18. For analysis on platform systems: add 100 ul water (HPLC grade) to each sample. Gently mix.
19. Manually tune all compounds using compound solutions prepared to 5,000 ng/ml (add 100 ul of the 50,000 ng/ml standard solutions to 900 ul water)

2.ii Cassette dose analysis
2.iia Preparation of calibration and QC samples:
Note: For cassette dosing, the amount of methanol required to dilute the 1 mg/ml stock will be adjusted according to the number of compounds present.
1. Add 100 ul of each 1 mg/ml stock required to a vial.
2. Add the required volume of methanol to yield a total volume of 1 ml.
3. Perform all further steps as for single compound analysis (steps 2-16 above).

2.iii In cases where PK samples exceed the Upper limit of Quantification (ULOQ).
1. Prepare a further calibration curve and QC samples as above (steps 1-6).
2. Transfer <50 ul (e.g. 25 ul) of the PK samples that exceed the ULOQ.
3. Add enough control plasma to these samples to yield a final plasma volume of 50 ul. Make a note of the dilution made.
4. Transfer 50 ul of all remaining PK samples.
5. Prepare all formulation samples and extract all samples as described above. (steps 8-16)

Note: Upper concentrations used to generate the calibration curve may be reviewed, however, care must be taken to avoid saturation of the HPLC column or MS equipment. It is for this reason that dilution of PK samples is recommended.

2.1v In cases of poor sensitivity (high Lower Limit of Quantification).
Note: High LLOQ is taken as when most of the plasma concentrations lie below the lower limit of quantification or where the LLOQ is greater the 10 ng/ml. The following methods should be applied when either of these scenarios is encountered.

According to a further aspect of the invention there is provided a pharmaceutical composition, which comprises a compound of the Examples, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In general, compositions in a form suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

We have found that the compounds defined in the present invention, or a pharmaceutically-acceptable salt thereof, are effective 11βHSD1 inhibitors, and accordingly have value in the treatment of disease states associated with metabolic syndrome.

It is to be understood that where the term "metabolic syndrome" is used herein, this relates to metabolic syndrome as defined in 1) and/or 2) or any other recognised definition of this syndrome. Synonyms for "metabolic syndrome" used in the art include Reaven's Syndrome, Insulin Resistance Syndrome and Syndrome X. It is to be understood that where the term "metabolic syndrome" is used herein it also refers to Reaven's Syndrome, Insulin Resistance Syndrome and Syndrome X.

According to a further aspect of the present invention there is provided a compound of formula (1), or a pharmaceutically-acceptable salt thereof, as defined hereinbefore for use in a method of prophylactic or therapeutic treatment of a warm-blooded animal, such as man.

Thus according to this aspect of the invention there is provided a compound of formula (1), or a pharmaceutically-acceptable salt thereof, as defined hereinbefore for use as a medicament.

According to another feature of the invention there is provided the use of a compound of formula (1), or a pharmaceutically-acceptable salt thereof, as defined hereinbefore in the manufacture of a medicament for use in the production of an 11βHSD1 inhibitory effect in a warm-blooded animal, such as man.

Where production of or producing an 11βHSD1 inhibitory effect is referred to suitably this refers to the treatment of metabolic syndrome. Alternatively, where production of an 11βHSD1 inhibitory effect is referred to this refers to the treatment of diabetes, obesity, hyperlipidaemia, hyperglycaemia, hyperinsulinemia or hypertension, particularly diabetes and obesity. Alternatively, where production of an 11βHSD1 inhibitory effect is referred to this refers to the treatment of glaucoma, osteoporosis, tuberculosis, dementia, cognitive disorders or depression.

Alternatively, where production of an 11βHSD1 inhibitory effect is referred to this refers to the treatment of cognitive disorders, such as improving the cognitive ability of an individual, for example by improvement of verbal fluency, verbal memory or logical memory, or for treatment of mild cognitive disorders. See for example WO03/086410 and references contained therein, and Proceedings of National Academy of Sciences (PNAS), 2001, 98(8), 4717-4721.

Alternatively, where production of an 11βHSD1 inhibitory effect is referred to this refers to the treatment of, delaying the onset of and/or reducing the risk of atherosclerosis—see for example J. Experimental Medicine, 2005, 202(4), 517-527.

Alternatively, where production of an 11βHSD1 inhibitory effect is referred to this refers to the treatment of Alzheimers and/or neurodegenerative disorders.

According to a further feature of this aspect of the invention there is provided a method for producing an 11βHSD1 inhibitory effect in a warm-blooded animal, such as man, in need of such treatment which comprises administering to said animal an effective amount of a compound of formula (1), or a pharmaceutically-acceptable salt thereof.

In addition to their use in therapeutic medicine, the compounds of formula (1), or a pharmaceutically-salt thereof, are also useful as pharmacological tools in the development and standardisation of in vitro and in vivo test systems for the evaluation of the effects of inhibitors of 11βHSD1 in laboratory animals such as cats, dogs, rabbits, monkeys, rats and mice, as part of the search for new therapeutic agents.

The inhibition of 11βHSD1 described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example agents than might be co-administered with 11βHSD1 inhibitors, particularly those of the present invention, may include the following main categories of treatment:

1) Insulin and insulin analogues;
2) Insulin secretagogues including sulphonylureas (for example glibenclamide, glipizide), prandial glucose regulators (for example repaglinide, nateglinide), glucagon-like peptide 1 agonist (GLP1 agonist) (for example exenatide, liraglutide) and dipeptidyl peptidase IV inhibitors (DPP-IV inhibitors);
3) Insulin sensitising agents including PPARγ agonists (for example pioglitazone and rosiglitazone);
4) Agents that suppress hepatic glucose output (for example metformin);
5) Agents designed to reduce the absorption of glucose from the intestine (for example acarbose);
6) Agents designed to treat the complications of prolonged hyperglycaemia; e.g. aldose reductase inhibitors
7) Other anti-diabetic agents including phosotyrosine phosphatase inhibitors, glucose 6-phosphatase inhibitors, glucagon receptor antagonists, glucokinase activators, glycogen phosphorylase inhibitors, fructose 1,6 bisphosphastase inhibitors, glutamine:fructose-6-phosphate amidotransferase inhibitors
8) Anti-obesity agents (for example sibutramine and orlistat);
9) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); ileal bile acid absorption inhibitors (IBATi), cholesterol ester transfer protein inhibitors and nicotinic acid and analogues (niacin and slow release formulations);
10) Antihypertensive agents such as, β blockers (eg atenolol, inderal); ACE inhibitors (eg lisinopril); calcium antagonists (eg. nifedipine); angiotensin receptor antagonists (eg candesartan), α antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;
12) Anti-inflammatory agents, such as non-steroidal anti-inflammatory drugs (eg. aspirin) and steroidal anti-inflammatory agents (eg. cortisone); and
13) Agents that prevent the reabsorption of glucose by the kidney (SGLT inhibitors).

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:
(i) temperatures are given in degrees Celsius (° C.); operations were carried out at room or ambient temperature, that is, at a temperature in the range of 18-25° C. and under an atmosphere of an inert gas such as argon;
(ii) evaporation of solvent was carried out using a rotary evaporator under reduced pressure (600-4000 Pa; 4.5-30 mmHg) with a bath temperature of up to 60° C.;
(iii) chromatography means flash chromatography on silica gel;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data ($^1$H) is in the form of delta values for major diagnostic protons, given in parts per million (ppm) relative to tetramethylsilane (TMS), determined at 300 or 400 MHz (unless otherwise stated) using perdeuterio dimethyl sulfoxide (DMSO-$d_6$) as solvent, unless otherwise stated; peak multiplicities are shown thus: s, singlet; d, doublet; dd, doublet of doublets; dt, doublet of triplets; dm, doublet of multiplets; t, triplet, m, multiplet; br, broad;
(vii) chemical symbols have their usual meanings; SI units and symbols are used;
(viii) solvent ratios are given in volume:volume (v/v) terms;
(ix) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported;
(x) The following abbreviations may be used below or in the process section hereinbefore:

$Et_2O$ diethyl ether

DMF dimethylformamide

DCM dichloromethane

DME 1,2-dimethoxyethane

MeOH methanol

EtOH ethanol $H_2O$ water

TFA trifluoroacetic acid

THF tetrahydrofuran

DMSO dimethylsulfoxide

HOBt 1-hydroxybenzotriazole

EDCI (EDAC) 1-ethyl-3-(3-dimethylaminopropyl)carbodi-imide hydrochloride

DIPEA diisopropylethylamine

DEAD diethyl azodicarboxylate

EtOAc ethyl acetate $NaHCO_3$ sodium bicarbonate $K_3PO_4$ potassium phosphate $MgSO_4$ magnesium sulfate PS polymer supported BINAP 2,2'-bis(diphenylphosphino)-1,1'binaphthyl Dppf 1,1'-bis(diphenylphosphino)ferrocene dba dibenzylidineacetone PS-CDI polymer supported carbonyldiimidazole

Example 1

2-[(3R)-1-[5-(Cyclohexylcarbamoyl)-6-propylsulfanyl-pyridin-2-yl]-3-piperidyl]acetic acid

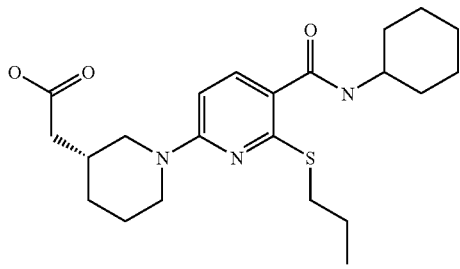 [SMILES: CCCSc1nc(N2CCC[C@H](CC(=O)O)C2)ccc1C(=O)NC1CCCCC1]

6-chloro-N-cyclohexyl-2-propylsulfanyl-pyridine-3-carboxamide (Intermediate 2, 1.88 g, 6.03 mmol), Methyl-(R)-3-Piperidine Acetate hydrochloride (1.17 g, 6.03 mmol), $K_2CO_3$ (2.50 g, 18.08 mmol) and butyronitrile were mixed in a microwave tube and stirred at 170° C. for 2 hours. The mixture changed from a poorly soluble white mixture to an orange solution. The reaction was stopped and most of the butyronitrile was evaporated under reduced pressure. Water (20 mL) was added and the product was extracted with EtOAc (2×40 mL), washed with brine (10 mL), dried over $MgSO_4$, filtered and evaporated under reduced pressure to give an orange oil. It was preloaded on Celite and purification by flash column chromatography ($SiO_2$, eluent gradient: 0% to 50%, hexane:EtOAc) afforded the title compound as a slightly yellow oil which crystallised to give a white solid (1.44 g, 55%).

The solid was taken in THF (20 mL), water was added (10 mL) followed by LiOH (281 mg). The reaction was stirred at room temperature for three hours. The solution was acidified with 2 N HCl between pH 4 and pH 5 and the product extracted in EtOAc (2×40 mL). The solution was washed with brine (10 mL), dried over $MgSO_4$ and the organic phase evaporated under reduced pressure to give a white solid (1.38 g, 99%).

$^1$H NMR (400.13 MHz, DMSO-$d_6$) δ0.95 (3H, t), 1.11 (1H, m), 1.26 (3H, m), 1.30 (1H, m), 1.43 (1H, m), 1.59 (2H, t), 1.65-1.72 (2H, m), 1.69-1.73 (1H, m), 1.77 (3H, m), 1.83-1.85 (1H, m), 2.12-2.25 (2H, m), 2.71-2.77 (1H, m), 2.86-3.02 (3H, m), 3.63-3.67 (1H, m), 4.20 (1H, d), 4.29 (1H, d), 6.47 (1H, d), 7.61 (1H, d), 7.79 (1H, d)

MS m/e MH$^+$ 420

The following Examples were prepared in a similar manner to Example 1, using Intermediate 2 and an appropriate aminoester starting material:

| Compound | Ex | Name | $^1$H NMR δ | MS m/e MH$^+$ |
|---|---|---|---|---|
|  | 2 | 1-[5-(cyclohexylcarbamoyl)-6-propylsulfanyl-pyridin-2-yl]piperidine-3-carboxylic acid | 1H NMR (400.13 MHz, CDCl3) 0.95 (3H, t), 1.11-1.37 (6H, m), 1.46-1.57 (2H, m), 1.65-1.78 (5H, m), 1.92-1.97 (2H, m), 2.03-2.07 (1H, m), 2.50-2.57 (1H, m), 3.02-3.12 (3H, m), 3.42 (1H, q), 3.88-3.95 (1H, m), 4.03 (1H, m), 4.36-4.41 (1H, m), 6.33 (1H, d), 6.49 (1H, d), 7.73 (1H, d) | 406 |
|  | 3 | 1-[5-(cyclohexylcarbamoyl)-6-propylsulfanyl-pyridin-2-yl]piperidine-4-carboxylic acid | 1H NMR (300.072 MHz, CDCl3) 0.95-1.01 (3H, m), 1.14 (1H, m), 1.19-1.22 (2H, m), 1.23 (1H, d), 1.31-1.41 (2H, m), 1.52-1.56 (1H, m), 1.62-1.72 (4H, m), 1.65-1.73 (1H, m), 1.76-1.80 (1H, m), 1.92-1.97 (3H, m), 2.00-2.01 (1H, m), 2.55-2.62 (1H, m), 3.03-3.09 (4H, m), 3.91 (1H, s), 4.13-4.18 (2H, m), 6.40 (2H, m), 7.74 (1H, d) | 406 |
|  | 4 | 2-[1-[5-(cyclohexylcarbamoyl)-6-propylsulfanyl-pyridin-2-yl]-4-piperidyl]acetic acid | 1H NMR (300.072 MHz, CDCl3) 0.95 (3H, t), 1.16-1.33 (7H, t), 1.34-1.41 (2H, m), 1.54 (1H, d), 1.62-1.71 (4H, m), 1.77-1.81 (2H, m), 1.91-1.96 (2H, m), 2.24 (2H, d), 2.83-2.90 (2H, m), 3.06 (2H, t), 3.92 (1H, m), 4.29 (2H, d), 6.29 (1H, d), 6.47 (1H, d), 7.72 (1H, d) | 420 |

-continued

| Compound | Ex | Name | ¹H NMR δ | MS m/e MH⁺ |
|---|---|---|---|---|
| | 5 | 2-[1-[5-(cyclohexylcar-bamoyl)-6-propylsulfanyl-pyridin-2-yl]-3-piperidyl]acetic acid | 1H NMR (400.13 MHz, CDCl3) 0.95 (3H, t), 1.15-1.40 (7H, m), 1.50-1.59 (2H, m), 1.62-1.69 (4H, m), 1.82-1.98 (3H, m), 2.01-2.07 (1H, m), 2.20-2.25 (2H, m), 2.75 (1H, t), 2.92-3.13 (3H, m), 3.91 (1H, s), 4.15-4.21 (2H, m), 6.32 (1H, d), 6.50 (1H, d), 7.73 (1H, d) | 420 |
| | 6 | 1-[5-(cyclohexylcar-bamoyl)-6-propylsulfanyl-pyridin-2-yl]pyrrolidine-3-carboxylic acid | 1H NMR (400.13 MHz, CDCl3) 0.95 (3H, t), 1.09-1.40 (7H, m), 1.64-1.70 (4H, m), 1.88-1.97 (2H, m), 2.23 (2H, m), 3.04-3.18 (3H, m), 3.42-3.46 (1H, m), 3.54-3.60 (1H, m), 3.69 (1H, d), 3.91 (1H, s), 5.98 (1H, d), 6.55 (1H, d), 7.72 (1H, d) | 392 |
| | 7 | 2-[(3S)-1-[5-(cyclohexylcar-bamoyl)-6-propylsulfanyl-pyridin-2-yl]-3-piperidyl]acetic acid | 1H NMR (400.13 MHz, DMSO-d6) 0.95 (3H, t), 1.05-1.18 (1H, m), 1.15-1.35 (5H, m), 1.41-1.49 (1H, m), 1.55-1.90 (10H, m), 2.12-2.26 (2H, m), 2.71-2.77 (1H, m), 2.85-3.01 (3H, m), 3.63-3.66 (1H, m), 4.20 (1H, d), 4.29 (1H, d), 6.47 (1H, d), 7.61 (1H, d), 7.79 (1H, d), 12.15 (1H, s) | 420 |
| | 8 | 2-[4-[5-(cyclohexylcar-bamoyl)-6-propylsulfanyl-pyridin-2-yl]piperazin-1-yl]acetic acid | 1H NMR (300.072 MHz, CDCl3) 0.83-0.85 (1H, m), 0.91-0.97 (3H, m), 1.19-1.24 (6H, m), 1.2S (1H, s), 1.28-1.35 (1H, m), 1.33 (2H, m), 1.65 (1H, m), 1.91 (1H, d), 2.99 (2H, t), 3.14 (2H, m), 3.53-3.57 (2H, m), 3.66-3.70 (1H, m), 3.80 (3H, m), 3.87 (2H, m), 6.25 (1H, d), 6.49-6.50 (1H, m), 7.68 (1H, d) | 421 |
| | 9 | (3R,5S)-4-[[5-(cyclohexylcar-bamoyl)-6-propylsulfanyl-pyridin-2-yl]amino]ada-mantane-1-carboxylic acid | ¹H NMR (400.13 MHz, DMSO-d₆) 0.98 (3H, t), 1.11-1.19 (1H, m), 1.20-1.31 (4H, m), 1.55-1.64 (5H, m), 1.68-1.82 (10H, m), 1.95-2.00 (1H, m), 2.08-2.13 (4H, m), 2.96 (2H, t), 3.60-3.70 (1H, m), 4.02-4.15 (1H, m), 6.34 (1H, d), 6.94 (1H, d), 7.48 (1H, d), 7.60 (1H, d), 11.85 (1H, s) | 472 |

-continued

| Compound | Ex | Name | ¹H NMR δ | MS m/e MH⁺ |
|---|---|---|---|---|
| | 10 | (3R,5S)-4-[[5-(cyclohexylcar-bamoyl)-6-propylsulfanyl-pyridin-2-yl]amino]ada-mantane-1-carboxylic acid | ¹H NMR (400.13 MHz, DMSO-d₆) 0.96 (3H, t), 1.08-1.16 (1H, m), 1.18-1.36 (4H, m), 1.46 (2H, d), 1.53-1.62 (3H, m), 1.68-1.75 (6H, m), 1.92 (5H, s), 1.95-2.10 (4H, m), 2.95 (2H, t), 3.58-3.70 (1H, m), 4.05-4.07 (1H, m), 6.34 (1H, d), 6.96 (1H, d), 7.48 (1H, d), 7.66 (1H, d), 12.14 (1H, s) | 472 |
| | 11 | 4-[[5-(cyclohexylcar-bamoyl)-6-propylsulfanyl-pyridin-2-yl]-methyl-amino]cyclohex-ane-1-carboxylic acid | 1H NMR (400.13 MHz, DMSO-d₆) 0.99 (3H, t), 1.11-1.17 (1H, m), 1.24-1.34 (4H, m), 1.43-1.53 (2H, m), 1.57-1.67 (7H, m), 1.72 (2H, d), 1.79 (2H, d), 2.00-2.03 (2H, m), 2.18-2.28 (1H, m), 2.87 (3H, s), 2.95-2.99 (2H, m), 3.65 (1H, d), 4.50 (1H, s), 6.31 (1H, d), 7.62 (1H, d), 7.68 (1H, d), 12.03 (1H, s) | 434 |
| | 12 | 2-[(3S)-1-[5-(cyclohexylcar-bamoyl)-6-propylsulfanyl-pyridin-2-yl]pyrrolidin-3-yl]acetic acid | 1H NMR (400.13 MHz, DMSO-d₆) 0.96 (3H, t), 1.09-1.2 (1H, m), 1.22-1.35 (4H, m), 1.58-1.85 (8H, m), 2.12-2.2 (1H, m), 2.31-2.45 (2H, m), 2.52-2.64 (1H, m), 2.98 (2H, t), 3.09 (1H, dd), 3.34-3.41 (1H, m), 3.5-3.8 (3H, m), 6.10 (1H, d), 7.62 (1H, d), 7.68 (1H, s), 12.2 (1H, s). | 406; HPLC tR = 2.62 min. |
| | 13 | 3-[5-(cyclohexylcar-bamoyl)-6-propylsulfanyl-pyridin-2-yl]oxybenzoic acid | 1H NMR (300.073 MHz, DMSO-d6) 0.58 (t, 3H), 1.06-1.38 (m, 7H), 1.51-1.63 (m, 1H), 1.65-1.86 (m, 4H), 2.54 (t, 2H), 3.60-3.74 (m, 1H), 6.82 (d, 1H), 7.43 (d, 1H), 7.57 (t, 1H), 7.65 (s, 1H), 7.78-7.87 (m, 2H), 8.13 (d, 1H), 12.57-13.46 (m, 1H) | 415 |
| | 14 | 3-[5-(cyclohexylcar-bamoyl)-6-propylsulfanyl-pyridin2-yl]sulfanylbenzoic acid | 1H NMR (300.073 MHz, DMSO-d6) 0.71 (t, 3H), 1.04-1.42 (m, 7H), 1.49-1.84 (m, 5H), 2.57 (t, 2H), 3.57-3.72 (m, 1H), 7.00 (d, 1H), 7.58 (d, 1H), 7.61 (t, 1H), 7.80 (d, 1H), 8.03 (d, 1H), 8.06 (s, 1H), 8.16 (d, 1H), 12.73-13.56 (m, 1H) | 431 |

-continued

| Compound | Ex | Name | ¹H NMR δ | MS m/e MH⁺ |
|---|---|---|---|---|
|  | 15 | 4-[5-(cyclohexylcarbamoyl)-6-propylsulfanyl-pyridin-2-yl]sulfanylbenzoic acid | 1H NMR (300.073 MHz, DMSO-d6) 0.71 (t, 3H), 1.05-1.38 (m, 7H), 1.50-1.62 (m, 1H), 1.65-1.84 (m, 4H), 2.61 (t, 2H), 3.66 (d, 1H), 7.03 (d, 1H), 7.59 (d, 1H), 7.65 (d, 2H), 7.99 (d, 2H), 8.17 (d, 1H), 13.26 (s, 1H) | 431 |
|  | 16 | 4-[5-(cyclohexylcarbamoyl)-6-propylsulfanyl-pyridin-2-yl]oxybenzoic acid | 1H NMR (300.073 MHz, DMSO-d6) 0.60 (t, 3H), 1.06-1.39 (m, 7H), 1.50-1.63 (m, 1H), 1.64-1.87 (m, 4H), 2.56 (t, 2H), 3.58-3.73 (m, 1H), 6.82 (d, 1H), 7.25 (d, 2H), 7.84 (d, 1H), 8.00 (d, 2H), 8.13 (d, 1H) | 415 |
|  | 17 | 2-[4-[5-(cyclohexylcarbamoyl)-6-propylsulfanyl-pyridin-2-yl]oxyphenyl]acetic acid | 1H NMR (300.072 MHz, CDCl3) 0.73 (t, 3H), 1.14-1.50 (m, 7H), 1.55-1.81 (m, 3H), 1.95-2.07 (m, 2H), 2.75 (t, 2H), 3.66 (s, 2H), 3.91-4.07 (m, 1H), 6.33 (d, 1H), 6.62 (d, 1H), 7.08 (d, 2H), 7.31 (d, 2H), 7.92 (d, 1H) | 429 |
|  | 18 | 3-[4-[5-(cyclohexylcarbamoyl)-6-propylsulfanyl-pyridin-2-yl]oxyphenyl]propanoic acid | 1H NMR (300.073 MHz, DMSO-d6) 0.64 (t, 3H), 1.01-1.38 (m, 7H), 1.50-1.63 (m, 1H), 1.65-1.89 (m, 4H), 2.51 (t, 2H), 2.57 (t, 2H), 2.82 (t, 2H), 3.58-3.75 (m, 1H), 6.70 (d, 1H), 7.04 (d, 2H), 7.27 (d, 2H), 7.79 (d, 1H), 8.08 (d, 1H) | 443 |
|  | 19 | 2-[4-[5-(cyclohexylcarbamoyl)-6-propylsulfanyl-pyridin-2-yl]sulfanylphenoxy]acetic acid | 1H NMR (300.072 MHz, CDCl3) 0.91 (t, 3H), 1.18-1.67 (m, 7H), 1.68-1.81 (m, 2H), 1.93-2.08 (m, 2H), 2.91 (t, 2H), 3.88-4.10 (m, 1H), 4.69 (s, 2H), 4.88-5.49 (m, 1H), 6.45 (d, 1H), 6.64 (d, 1H), 6.95 (d, 2H), 7.50 (d, 2H), 7.67 (d, 1H) | 461 |

-continued

| Compound | Ex | Name | ¹H NMR δ | MS m/e MH⁺ |
|---|---|---|---|---|
| | 20 | 2-[4-[5-(cyclohexylcarbamoyl)-6-propylsulfanylpyridin-2-yl]oxyphenoxy]acetic acid | 1H NMR (300.072 MHz, CDCl3) 0.77 (t, 3H), 1.12-1.52 (m, 7H), 1.56-1.68 (m, 1H), 1.69-1.80 (m, 2H), 1.93-2.08 (m, 2H), 2.77 (t, 2H), 3.91-4.07 (m, 1H), 4.67 (s, 2H), 6.38 (d, 1H), 6.60 (d, 1H), 6.94 (d, 2H), 7.06 (d, 2H), 7.92 (d, 1H) | 445 |
| | 21 | 2-[4-[5-(cyclohexylcarbamoyl)-6-propylsulfanylpyridin-2-yl]oxyphenyl]propanoic acid | 1H NMR (300.072 MHz, CDCl3) 0.71 (t, 3H), 1.14-1.50 (m, 7H), 1.53 (d, 3H), 1.57-1.67 (m, 1H), 1.67-1.80 (m, 2H), 1.94-2.08 (m, 2H), 2.73 (t, 2H), 3.77 (q, 1H), 3.92-4.07 (m, 1H), 6.33 (d, 1H), 6.62 (d, 1H), 7.08 (d, 2H), 7.34 (d, 2H), 7.92 (d, 1H) | 443 |
| | 22 | 2-[4-[5-(cyclohexylcarbamoyl)-6-propylsulfanylpyridin-2-yl]sulfanylphenyl]acetic acid | 1H NMR (300.072 MHz, CDCl3) 0.88 (t, 3H), 1.13-1.81 (m, 10H), 1.91-2.08 (m, 2H), 2.88 (t, 2H), 3.64 (s, 2H), 3.87-4.05 (m, 1H), 6.40 (d, 1H), 6.68 (d, 1H), 7.31 (d, 2H), 7.51 (d, 2H), 7.64 (d, 1H) | 445 |
| | 23 | 2-[3-[5-(cyclohexylcarbamoyl)-6-propylsulfanylpyridin-2-yl]oxyphenyl]acetic acid | 1H NMR (400.132 MHz, CDCl3) 0.71 (t, 3H), 1.14-1.49 (m, 7H), 1.56-1.66 (m, 1H), 1.68-1.80 (m, 2H), 1.95-2.06 (m, 2H), 2.74 (t, 2H), 3.65 (s, 2H), 3.92-4.06 (m, 1H), 6.35 (d, 1H), 6.62 (d, 1H), 7.01-7.09 (m, 2H), 7.14 (d, 1H), 7.35 (t, 1H), 7.91 (d, 1H) | 429 |
| | 24 | 2-[5-(cyclohexylcarbamoyl)-6-propylsulfanylpyridin-2-yl]sulfanylbenzoic acid | 1H NMR (300.072 MHz, CDCl3) 0.81 (t, 3H), 1.13-1.51 (m, 7H), 1.57-1.69 (m, 1H), 1.67-1.81 (m, 2H), 1.94-2.08 (m, 2H), 2.77 (t, 2H), 3.90-4.08 (m, 1H), 6.29 (d, 1H), 7.01 (d, 1H), 7.42-7.53 (m, 2H), 7.57 (d, 1H), 7.72 (d, 1H), 8.02 (d, 1H) | 431 |

-continued

| Compound | Ex | Name | ¹H NMR δ | MS m/e MH⁺ |
|---|---|---|---|---|
| | 25 | 4-[5-(cyclohexylcarbamoyl)-6-propylsulfanyl-pyridin-2-yl]oxycyclohexane-1-carboxylic acid | 1H NMR (300.073 MHz, DMSO-d6) 0.98 (t, 3H), 1.06-2.15 (m, 20H), 2.20-2.33 (m, 1H), 2.99 (t, 2H), 3.57-3.74 (m, 1H), 4.88-5.03 (m, 1H), 6.44 (d, 1H), 7.68 (d, 1H), 7.99 (d, 1H), 11.98-12.22 (m, 1H) | 421 |
| | 26 | 1-[5-(cyclohexylcarbamoyl)-6-propylsulfanyl-pyridin-2-yl]piperidine-2-carboxylic acid | 1H NMR (400.13 MHz, DMSO-d6) 0.94 (3H, t), 1.08-1.13 (1H, m), 1.21-1.33 (4H, m), 1.41-1.47 (1H, m), 1.52-1.67 (4H, m), 1.68-1.80 (4H, m), 2.24 (2H, d), 2.91 (2H, t), 3.09-3.17 (2H, m), 3.60-3.66 (2H, m), 4.11 (1H, s), 5.02 (1H, s), 6.42 (1H, d), 7.59 (1H, d), 7.78 (1H, d) | 406 HPLC tR = 1.47 min. |
| | 27 | (2S)-1-[5-(cyclohexylcarbamoyl)-6-propylsulfanyl-pyridin-2-yl]pyrrolidine-2-carboxylic acid | 1H NMR (400.13 MHz, CDCl3) 1.00-1.05 (3H, m), 1.22-1.31 (4H, m), 1.40-1.46 (2H, m), 1.59-1.64 (1H, m), 1.67-1.77 (3H, m), 1.97-2.04 (2H, m), 2.10-2.19 (3H, m), 2.47 (1H, s), 2.99-3.06 (1H, m), 3.16-3.23 (1H, m), 3.37-3.41 (1H, m), 3.55-3.59 (1H, m), 3.96-4.01 (1H, m), 4.65 (1H, d), 6.20-6.23 (1H, m), 6.51 (1H, d), 7.84 (1H, d) | 392 HPLC tR = 1.48 min. |
| | 28 | 2-[1-[5-(cyclohexylcarbamoyl)-6-propylsulfanyl-pyridin-2-yl]-4-piperidyl]propanoic acid | 1H NMR (400.13 MHz, DMSO-d6) 0.95 (3H, t), 1.03 (3H, d), 1.12-1.18 (2H, m), 1.20-1.23 (2H, m), 1.26 (3H, d), 1.57-1.63 (4H, m), 1.68-1.73 (4H, m), 1.75-1.80 (2H, m), 2.18 (1H, t), 2.81-2.89 (2H, m), 2.93 (2H, t), 3.61-3.67 (1H, m), 4.40 (1H, d), 4.44 (1H, s), 6.51 (1H, d), 7.61 (1H, d), 7.80 (1H, d) | 434 HPLC tR = 1.55 min. |
| | 29 | 4-[[[5-(cyclohexylcarbamoyl)-6-propylsulfanyl-pyridin-2-yl]amino]methyl]cyclohexane-1-carboxylic acid | 1H NMR (400.13 MHz, DMSO-d6) 0.94-0.99 (5H, m), 1.1-1.22 (1H, m), 1.23-1.40 (6H, m), 1.53-1.69 (4H, m), 1.71-1.81 (6H, m), 1.91 (2H, d), 2.10-2.16 (1H, m), 2.94-2.96 (2H, t), 3.16 (2H, d), 3.55-3.65 (1H, m), 6.14 (1H, d), 7.15 (1H, s), 7.47 (1H, d), 7.69 (1H, d), 12.20 (1H, s) | 434; HPLC tR = 2.65 min. |

-continued

| Compound | Ex | Name | ¹H NMR δ | MS m/e MH⁺ |
|---|---|---|---|---|
| | 30 | 3-[[5-(cyclohexylcarbamoyl)-6-propylsulfanyl-pyridin-2-yl]amino] propanoic acid | 1H NMR (400.13 MHz, DMSO-d6) 0.95 (3H, t), 1.09-1.15 (1H, m), 1.25-1.29 (5H, m), 1.55-1.65 (4H, m), 1.70-1.77 (4H, m), 2.96 (2H, t), 3.52 (2H, t), 3.58-3.70 (1H, m), 6.16 (1H, d), 7.49 (1H, d), 7.71 (1H, d) | 366; HPLC tR = 2.21 min. |
| | 31 | 1-[5-(cyclohexylcarbamoyl)-6-propylsulfanyl-pyridin-2-yl]azepane-4-carboxylic acid | 1H NMR (400.13 MHz, CDCl3) 0.95 (3H, t), 1.16-1.26 (3H, m), 1.31-1.41 (2H, m), 1.52-1.74 (7H, m), 1.82-1.96 (5H, m), 2.10-2.17 (1H, m), 2.40-2.46 (1H, m), 3.00-3.11 (2H, m), 3.35-3.45 (1H, m), 3.55-3.65 (1H, m), 3.70-3.85 (2H, m), 3.88-3.96 (1H, m), 6.14 (1H, d), 6.44 (1H, d), 7.71 (1H, d) | 420; HPLC tR = 2.64 min. |
| | 32 | 1-[5-(cyclohexylcarbamoyl)-6-propylsulfanyl-pyridin-2-yl]-4-methyl-piperidine-4-carboxylic acid | 1H NMR (400.13 MHz, DMSO-d6) 0.96 (3H, t), 1.10 (3H, s), 1.22-1.33 (7H, m), 1.56-1.65 (3H, m), 1.71-1.77 (4H, m), 2.00 (2H, d), 2.91 (2H, t), 3.15-3.22 (2H, m), 3.62-3.65 (1H, m), 4.00 (2H, d), 6.50 (1H, d), 7.61 (1H, d), 7.80 (1H, d) | 420; HPLC tR = 2.75 min. |
| | 33 | (1S,5R)-3-[5-(cyclohexylcarbamoyl)-6-propylsulfanyl-pyridin-2-yl]-3-aza-bicyclo[3.1.0] hexane-6-carboxylic acid | 1H NMR (400.13 MHz, DMSO-d6) 0.95-1.00 (3H, t), 1.10-1.17 (1H, m), 1.24-1.28 (4H, m), 1.40 (1H, t), 1.58-1.78 (7H, m), 2.19 (2H, s), 2.97 (2H, t), 3.50 (2H, d), 3.65 (1H, s), 3.79 (2H, d), 6.13 (1H, d), 7.62 (1H, d), 7.76 (1H, d) | 404; HPLC tR = 2.55 min. |
| | 34 | 4-[[5-(cyclohexylcarbamoyl)-6-propylsulfanyl-pyridin-2-yl]amino]cyclohexane-1-carboxylic acid | 1H NMR (400.13 MHz, DMSO-d6) 0.97 (3H, t), 1.15 (2H, m), 1.24-1.30 (6H, m), 1.37-1.44 (2H, m), 1.57-1.66 (3H, m), 1.70-1.78 (4H, m), 1.95-2.03 (4H, m), 2.15-2.25 (1H, m), 2.97 (2H, t), 3.64 (1H, s), 3.71-3.77 (1H, m), 6.14 (1H, d), 7.48 (1H, d), 7.63 (1H, d) | 420; HPLC tR = 2.52 min. |

-continued

| Compound | Ex | Name | ¹H NMR δ | MS m/e MH⁺ |
|---|---|---|---|---|
| | 35 | 4-[5-(cyclohexylcar-bamoyl)-6-propylsulfanyl-pyridin-2-yl]-4-propan-2-yl-piperidine-4-carboxylic acid | 1H NMR (300.072 MHz, CDCl3) 0.87 (6H, d), 0.96 (3H, t), 1.14-1.39 (7H, m), 1.54-1.63 (1H, m), 1.69-1.76 (5H, m), 1.92-1.96 (2H, m), 2.08 (2H, d), 2.78 (2H, t), 3.05 (2H, t), 3.92-4.00 (1H, m), 4.20 (2H, d), 6.21-6.29 (1H, d), 6.40 (1H, d), 7.72 (1H, d) | 448; HPLC tR = 2.99 min. |
| | 36 | 1-[5-(cyclohexylcar-bamoyl)-6-propylsulfanyl-pyridin-2-yl]-4-propan-2-yl-piperidine-4-carboxylic acid | 1H NMR (300.072 MHz, CDCl3) 0.90-1.16 (6H, m), 1.20-1.38 (6H, m), 1.52-1.68 (5H, m), 1.85-1.91 (4H, m), 3.04-3.11 (2H, m), 3.26 (1H, d), 3.55-3.70 (3H, m), 3.88-4.00 (2H, m), 6.34 (1H, d), 6.40 (1H, d), 7.72 (1H, d) | 420; HPLC tR = 2.60 min. |
| | 37 | 2-[1-[5-(cyclohexylcar-bamoyl)-6-propylsulfanyl-pyridin-2-yl]-3-piperidyl]-2-methyl-propanoic acid | 1H NMR (300.073 MHz, DMSO-d6) 0.95 (3H, t), 1.09 (3H, s), 1.14 (3H, s), 1.24-1.53 (6H, m), 1.55-1.63 (5H, m), 1.71-1.79 (6H, m), 2.64-2.87 (3H, m), 3.05-3.12 (1H, m), 3.62 (1H, s), 4.33 (1H, d), 4.43 (1H, d), 6.42 (1H, d), 7.58 (1H, d), 7.74 (1H, d), 12.20 (1H, s) | 448; HPLC tR = 2.93 min. |
| | 38 | 2-[(3R)-1-[5-(cyclohexylcar-bamoyl)-6-propylsulfanyl-pyridin-2-yl]pyrrolidin-3-yl]acetic acid | 1H NMR (300.073 MHz, DMSO-d6) 0.94 (3H, t), 1.06-1.18 (1H, m), 1.22-1.34 (4H, m), 1.55-1.78 (8H, m), 2.12-2.19 (1H, m), 2.40 (2H, d), 2.55-2.62 (1H, m), 2.96 (2H, t), 3.09 (1H, t), 3.39-3.43 (1H, m), 3.53-3.68 (3H, m), 6.09 (1H, d), 7.60-7.62 (1H, d), 7.68 (1H, d) | 406; HPLC tR = 2.57 min. |
| | 39 | 3-[1-[5-(cyclohexylcar-bamoyl)-6-propylsulfanyl-pyridin-2-yl]-3-piperidyl]propanoic acid | 1H NMR (300.073 MHz, DMSO-d6) 0.96 (3H, t), 1.11-1.30 (6H, m), 1.37-1.50 (4H, m), 1.55-1.64 (4H, m), 1.69-1.79 (5H, m), 2.28 (2H, t), 2.59-2.67 (1H, m), 2.91-3.02 (3H, m), 3.60 (1H, s), 4.19 (1H, d), 4.27 (1H, d), 6.48 (1H, d), 7.57-7.60 (1H, d), 7.72 (1H, d), 12.00 (1H, s) | 434; HPLC tR = 2.75 min. |

-continued

| Compound | Ex | Name | ¹H NMR δ | MS m/e MH⁺ |
|---|---|---|---|---|
| | 40 | 2-[1-[5-(cyclohexylcar-bamoyl)-6-propylsulfanyl-pyridin-2-yl]azetidin-3-yl]oxyacetic acid | 1H NMR (400.13 MHz, DMSO-d6) 0.96 (3H, t), 1.10-1.20 (1H, m), 1.24-1.28 (2H, m), 1.26-1.31 (3H, m), 1.58-1.66 (3H, m), 1.72-1.80 (4H, m), 1.85 (1H, s), 2.96 (2H, t), 3.71 (1H, s), 3.84-3.88 (2H, m), 4.17 (2H, t), 4.55-4.58 (1H, m), 6.04 (1H, d), 7.60 (1H, d), 7.75 (1H, d) | 408; HPLC tR = 2.37 min. |
| | 41 | 1-[1-[5-(cyclohexylcar-bamoyl)-6-propylsulfanyl-pyridin-2-yl]-3-piperidyl]cyclo-butane-1-carboxylic acid | 1H NMR (400.13 MHz, DMSO-d6) 0.96 (3H, t), 1.10-1.19 (1H, m), 1.22-1.34 (5H, m), 1.35-1.45 (1H, m), 1.56-1.64 (3H, m), 1.72-1.83 (9H, m), 2.09-2.13 (2H, m), 2.27-2.34 (2H, m), 2.67-2.90 (3H, m), 3.04-3.11 (1H, m), 3.66 (1H, s), 4.30 (1H, d), 4.53 (1H, d), 6.48 (1H, d), 7.60-7.62 (1H, m), 7.74 (1H, d), 12.20 (1H, s) | 460; HPLC tR = 2.97 min. |
| | 42 | 1-[1-[5-(cyclohexylcar-bamoyl)-6-propylsulfanyl-pyridin-2-yl]-3-piperidyl]cyclo-propane-1-carboxylic acid | 1H NMR (400.13 MHz, DMSO-d6) 0.79-0.83 (2H, m), 0.96 (3H, t), 1.04-1.20 (3H, m), 1.25-1.50 (6H, m), 1.53-1.78 (10H, m), 2.73--3.04 (4H, m), 3.65 (1H, s), 4.39-4.45 (2H, m), 6.50 (1H, d), 7.60-7.62 (1H, d), 7.79 (1H, d), 12.21 (1H, s) | 446; HPLC tR = 1.87 min. |
| | 43 | 2-[1-[5-(cyclohexylcar-bamoyl)-6-propylsulfanyl-pyridin-2-yl]pyrrolidin-3-yl]oxyacetic acid | 1H NMR (400.13 MHz, DMSO-d6) 0.97 (3H, t), 1.12-1.21 (1H, m), 1.27 (4H, m), 1.59-1.66 (3H, m), 1.68-1.74 (2H, m), 1.76-1.82 (2H, m), 2.04-2.13 (2H, m), 3.00 (2H, t), 3.45 (1H, q), 3.53-3.57 (3H, m), 3.66 (1H, s), 4.06 (2H, s), 4.31 (1H, s), 6.14 (1H, d), 7.63 (1H, d), 7.69 (1H, d) | 422; HPLC tR = 2.42 min. |
| | 44 | 2-[[5-(cyclohexylcar-bamoyl)-6-propylsulfanyl-pyridin-2-yl]-3-piperidyl]oxy]propanoic acid | 1H NMR (400.13 MHz, DMSO-d6) 0.95-1.00 (3H, m), 1.09-1.12 (1H, m), 1.16-1.43 (7H, m), 1.40-1.45 (1H, m), 1.58-1.68 (4H, m), 1.71-1.79 (5H, m), 1.94-2.02 (1H, m), 2.91-3.05 (3H, m), 3.20-3.40 (3H, m), 3.65 (1H, s), 4.09-4.17 (2H, m), 6.47-6.53 (1H, m), 7.60 (1H, d), 7.74 (1H, d), 12.50 (1H, s) | 450; HPLC tR = 2.63 min. |

-continued

| Compound | Ex | Name | ¹H NMR δ | MS m/e MH⁺ |
|---|---|---|---|---|
| | 45 | 2-[[5-(cyclohexylcarbamoyl)-6-propylsulfanyl-pyridin-2-yl]-3-piperidyl]oxy]-2-methyl-propanoic acid | 1H NMR (400.13 MHz, DMSO-d6) 0.97 (3H, t), 1.09-1.18 (1H, m), 1.15-1.28 (4H, m), 1.37 (6H, d), 1.42-1.51 (2H, m), 1.54-1.66 (3H, m), 1.68-1.80 (5H, m), 1.99-2.10 (1H, m), 2.86-2.93 (2H, m), 3.00-3.08 (2H, m), 3.33-3.37 (1H, m), 3.66 (1H, s), 4.08 (1H, d), 4.31 (1H, d), 6.45 (1H, d), 7.60 (1H, d), 7.74 (1H, d), 12.50 (1H, s) | 464; HPLC tR = 2.84 min. |
| | 46 | 2-[[5-(cyclohexylcarbamoyl)-6-propylsulfanyl-pyridin-2-yl]-3-piperidyl]oxy]acetic acid | 1H NMR (400.13 MHz, DMSO-d6) 0.97 (3H, t), 1.18 (1H, m), 1.20-1.27 (4H, m), 1.39-1.45 (1H, m), 1.51-1.67 (4H, m), 1.70-1.79 (4H, m), 1.98-2.02 (1H, m), 2.93-3.01 (2H, m), 3.18-3.30 (2H, m), 3.41-3.47 (2H, m), 3.66 (1H, m), 3.82-3.87 (1H, m), 4.08-4.09 (2H, s), 4.14-4.18 (1H, m), 6.52 (1H, d), 7.60 (1H, d), 7.74 (1H, d), 12.50 (1H, s) | 436; HPLC tR = 2.51 min. |
| | 47 | 1-[5-(cyclohexylcarbamoyl)-6-propylsulfanyl-pyridin-2-yl]-3-methyl-piperidine-3-carboxylic acid | 1H NMR (400.13 MHz, DMSO-d6) 0.97 (3H, t), 1.12 (4H, s), 1.27-1.32 (4H, m), 1.48-1.55 (1H, m), 1.65-1.85 (7H, m), 2.03 (1H, s), 2.06 (1H, s), 2.94-2.96 (2H, m), 3.25-3.35 (2H, m), 3.65 (1H, s), 3.82 (1H, d), 4.10 (1H, d), 5.75 (1H, s), 6.50 (1H, d), 7.60 (1H, d), 7.71 (1H, d) | 420; HPLC tR = 2.76 min. |
| | 48 | 2-[1-[5-(cyclohexylcarbamoyl)-6-propylsulfanyl-pyridin-2-yl]-4-piperidyl]-2-methyl-propanoic acid | 1H NMR (400.13 MHz, DMSO-d6) 0.96 (3H, t), 1.05 (6H, s), 1.17-1.31 (7H, m), 1.57-1.66 (5H, m), 1.72-1.84 (5H, m), 2.81 (2H, t), 2.95 (2H, t), 3.65-3.67 (1H, m), 4.46 (2H, d), 6.49 (1H, d), 7.59-7.62 (1H, d), 7.74 (1H, d), 12.09 (1H, s) | 448; HPLC tR = 2.90 min. |

-continued

| Compound | Ex | Name | ¹H NMR δ | MS m/e MH⁺ |
|---|---|---|---|---|
| | 49 | 1-[1-[5-(cyclohexylcarbamoyl)-6-propylsulfanyl-pyridin-2-yl]-4-piperidyl]cyclobutane-1-carboxylic acid | 1H NMR (400.13 MHz, DMSO-d6) 0.96 (3H, t), 1.11-1.29 (7H, m), 1.56-1.80 (11H, m), 1.90-2.01 (3H, m), 2.21-2.31 (2H, m), 2.84 (2H, t), 2.95 (2H, t), 3.65-3.67 (1H, m), 4.47 (2H, d), 6.50 (1H, d), 7.60 (1H, d), 7.74 (1H, d), 11.95 (1H, s) | 460; HPLC tR = 2.98 min. |
| | 50 | 1-[1-[5-(cyclohexylcarbamoyl)-6-propylsulfanyl-pyridin-2-yl]-4-piperidyl]cyclopropane-1-carboxylic acid | 1H NMR (400.13 MHz, DMSO-d6) 0.73-0.75 (2H, m), 0.94-1.01 (5H, m), 1.11-1.16 (1H, m), 1.27-1.34 (4H, m), 1.43-1.52 (2H, m), 1.57-1.66 (6H, m), 1.72-1.79 (4H, m), 2.80 (2H, t), 2.94 (2H, t), 3.66 (1H, s), 4.42-4.46 (2H, d), 6.49 (1H, d), 7.59-7.61 (1H, d), 7.73 (1H, d), 12.00 (1H, s) | 446; HPLC tR = 2.87 min. |
| | 51 | 4-[5-(cyclohexylcarbamoyl)-6-propylsulfanyl-pyridin-2-yl]morpholine-2-carboxylic acid | 1H NMR (400.13 MHz, DMSO-d6) 0.96 (3H, t), 1.07-1.19 (1H, m), 1.24-1.31 (4H, m), 1.57-1.66 (3H, m), 1.71-1.79 (4H, m), 2.95 (2H, t), 3.32-3.37 (2H, m), 3.61-3.67 (2H, m), 3.78-3.81 (1H, m), 3.97-4.02 (1H, m), 4.19-4.22 (2H, m), 6.55 (1H, d), 7.66 (1H, d), 7.81 (1H, d), 12.92 (1H, s) | 408; HPLC tR = 2.30 min. |

Intermediate 1

2,6-dichloro-N-cyclohexyl-pyridine-3-carboxamide

To a solution of 2,6-dichloronicotinic acid (5.005 g, 26.18 mmol) in DCM (60 ML) was added a few drops of DMF followed by the addition dropwise of oxalyl chloride (2.27 mL, 26.18 mmol). The reaction was stirred at room temperature for two hours until gas bubbling had stopped. The solvent was evaporated under reduced pressure to give an oil. DCM (60 mL) was added and the reaction mixture was cooled in an ice bath. Cyclohexylamine (5.98 mL, 52.36 mmol) was added slowly keeping the temperature below 15° C. The reaction was stirred at room temperature overnight.

The reaction mixture was extracted in DCM and washed with sat bicarb (30 mL), water (30 mL) and brine. The solvent was evaporated under reduced pressure to give a brown/red solid. It was recrystallised in hexane/ethyl acetate and filtered to give a white solid (6.986 g, 25.6 mmol, 98%)

¹H NMR (400.13 MHz, DMSO-d₆) δ1.12-1.18 (1H, m), 1.21-1.25 (1H, m), 1.29 (2H, m), 1.30-1.34 (1H, m), 1.55-1.59 (1H, m), 1.70-1.73 (2H, m), 1.84 (2H, m, 3.69-3.77 (1H, m), 7.62-7.64 (1H, d), 7.93 (1H, d), 8.46 (1H, d)
MS m/e MH⁺ 273

Intermediate 2

6-chloro-N-cyclohexyl-2-propylsulfanyl-pyridine-3-carboxamide

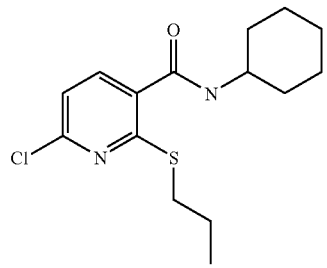 [SMILES: CCCSc1nc(Cl)ccc1C(=O)NC1CCCCC1]

To a solution of propane thiol (2.975 mL, 32.89 mmol)l in DMF (25 mL) was added slowly a solution of 1N NaHMDS in THF (33 ml, 33.00 mmol). The mixture was stirred for ten minutes at room temperature and then added slowly to a solution of 2,6-dichloro-N-cyclohexyl-pyridine-3-carboxamide (Intermediate 1, 8.95 g, 32.89 mmol) in DMF (50 mL). The reaction was stirred at room temperature for two hours. The reaction was stopped and most of the THF and DMF was evaporated. The product was extracted with DCM (150 mL), washed with water (2×25 ml) and brine (25 mL). The solution was dried over MgSO4 and evaporated under reduced pressure to give a slightly pink solid. The solid was triturated in hexane and filtered; all of the coloured impurity went into solution to leave a white solid (7.84 g, 76%).

$^1$H NMR (300.072 MHz, DMSO-d$_6$) δ 0.98 (3H, t), 1.21-1.25 (1H, m), 1.28 (3H, d), 1.59-1.68 (3H, m), 1.71 (1H, d), 1.73-1.74 (1H, m), 1.83 (2H, d), 3.04 (2H, t), 3.61-3.74 (1H, m), 7.26 (1H, d), 7.73 (1H, d), 8.30 (1H, d)

MS m/e MH$^+$ 313

The following Examples were prepared in a similar manner to Example 1, using Intermediate 3 and an appropriate aminoester starting material:

| Compound | Ex | Name | $^1$H NMR δ | MS m/e MH$^+$ |
|---|---|---|---|---|
| | 52 | 2-[(3S)-1-[5-(cyclohexylcarbamoyl)-6-cyclopentylsulfanyl-pyridin-2-yl]-3-piperidyl]acetic acid | 1H NMR (400.13 MHz, DMSO-d6) 1.05-1.35 (7H, m), 1.44 (3H, d), 1.54-1.88 (11H, m), 2.06-2.25 (4H, m), 2.73 (1H, d), 2.91-2.98 (1H, m), 3.60-3.65 (1H, m), 3.88-3.95 (1H, m), 4.20 (1H, d), 4.29 (1H, d), 6.47 (1H, d), 7.61 (1H, d), 7.78 (1H, d), 12.14 (1H, s) | 446 |
| | 53 | 2-[(3S)-1-[5-(cyclohexylcarbamoyl)-6-cyclopentylsulfanyl-pyridin-2-yl]pyrrolidin-3-yl]acetic acid | 1H NMR (400.13 MHz, DMSO-d6) 1.11-1.16 (1H, m), 1.2-1.37 (4H, m), 1.43-1.85 (12H, m), 2.03-2.2 (3H, m), 2.35-2.46 (2H, m), 2.53-2.6 (1H, m), 3.08 (1H, dd), 3.36-3.43 (1H, m), 3.5-3.78 (3H, m), 3.9-4.01 (1H, m), 6.09 (1H, d), 7.62 (1H, d), 7.67 (1H, s), 12.2 (1H, s). | 432; HPLC tR = 2.81 min. |
| | 54 | 2-[(3R)-1-[5-(cyclohexylcarbamoyl)-6-cyclopentylsulfanyl-pyridin-2-yl]pyrrolidin-3-yl]acetic acid | 1H NMR (400.13 MHz, DMSO-d6) 1.07-1.18 (2H, m), 1.20-1.35 (4H, m), 1.45-1.85 (11H, m), 2.10-2.17 (3H, m), 2.42 (2H, d), 2.54-2.64 (1H, m), 3.07-3.12 (1H, m), 3.35-3.44 (1H, m), 3.55-3.73 (3H, m), 3.93-4.00 (1H, m), 6.09 (1H, d), 7.62 (1H, d), 7.67 (1H, d), 12.15 (1H, s) | 432; HPLC tR = 2.73 min |
| | 55 | 2-[(3R)-1-[5-(cyclohexylcarbamoyl)-6-cyclopentylsulfanyl-pyridin-2-yl]-3-piperidyl]acetic acid | 1H NMR (400.13 MHz, DMSO-d6) 1.11-1.33 (6H, m), 1.43-1.89 (15H, m), 2.07-2.25 (4H, m), 2.71-2.78 (1H, m), 2.92-3.00 (1H, m), 3.59-3.70 (1H, m), 3.89-3.97 (1H, m), 4.15-4.22 (1H, m), 4.25-4.32 (1H, m), 6.46 (1H, d), 7.60 (1H, d), 7.72 (1H, d), 12.07 (1H, s) | 446; HPLC tR = 2.80 min. |

| Compound | Ex | Name | ¹H NMR δ | MS m/e MH⁺ |
|---|---|---|---|---|
| | 56 | 1-[1-[5-(cyclohexylcarbamoyl)-6-cyclopentylsulfanyl-pyridin-2-yl]-3-piperidyl]cyclopropane-1-carboxylic acid | 1H NMR (300.073 MHz, DMSO-d6) 0.73 (1H, s), 1.00 (2H, s), 1.23-1.30 (3H, m), 1.06-1.54 (3H, m), 1.46-1.76 (17H, m), 2.01-2.12 (2H, m), 2.77 (1H, m), 3.61 (1H, s), 3.85-4.02 (1H, m), 4.34-4.38 (2H, m), 6.46 (1H, d), 7.60 (1H, d), 7.76 (1H, d) | 472; HPLC tR = 3.03 min. |

Intermediate 3

6-chloro-N-cyclohexyl-2-(cyclopentylthio)nicotinamide

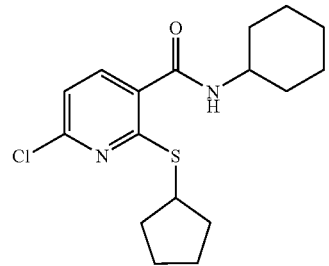 [SMILES: O=C(NC1CCCCC1)c1ccc(Cl)nc1SC1CCCC1]

Cyclopentanethiol (7.84 mL, 73.22 mmol) was added in one portion to 2,6-dichloro-N-cyclohexylnicotinamide (20 g, 73.22 mmol) and sodium carbonate (23.28 g, 219.65 mmol) in DMF (150 mL). The resulting suspension was stirred at 60° C. for 3 hours. The mixture was cooled, evaporated, DCM (250 mL) was added and the mixture was washed with water (3×100 mL) and brine (50 mL), dried (MgSO₄), filtered and evaporated to a sticky pale yellow solid. This was triturated with 4:1 hexane:ethyl acetate, filtered and dried to give 6-chloro-N-cyclohexyl-2-(cyclopentylthio)nicotinamide (13.8 g, 55.6%) as a white solid.

1H NMR (400.13 MHz, DMSO-d₆) δ 1.1-1.38 (5H, m), 1.46-1.78 (9H, m), 1.8-1.89 (2H, m), 2.1-2.21 (2H, m), 3.62-3.73 (1H, m), 3.86-3.95 (1H, m), 7.25 (1H, d), 7.73 (1H, d), 8.29 (1H, d)

m/z (ESI+) (M+H)+=339; HPLC $t_R$=3.16 min.

The following Examples were prepared in a similar manner to Example 1, using Intermediate 4 and an appropriate aminoester starting material:

| Compound | Ex | Name | ¹H NMR δ | MS m/e MH⁺ |
|---|---|---|---|---|
| | 57 | 2-[(3R)-1-[5-(cyclohexylcarbamoyl)-6-cyclohexylsulfanyl-pyridin-2-yl]pyrrolidin-3-yl]acetic acid | 1H NMR (400.13 MHz, DMSO-d6) 1.14-1.40 (10H, m), 1.55-1.81 (9H, m), 2.00-2.03 (2H, m), 2.14-2.18 (1H, m), 2.38-2.47 (2H, m), 2.55-2.63 (1H, m), 3.07-3.11 (1H, m), 3.34-3.43 (1H, m), 3.53 -3.75 (4H, m), 6.09 (1H, d), 7.60 (1H, d), 7.66 (1H, d), 12.15 (1H, s) | 446; HPLC tR = 2.85 min. |
| | 58 | 2-[(3R)-1-[5-(cyclohexylcarbamoyl)-6-cyclohexylsulfanyl-pyridin-2-yl]-3-piperidyl]acetic acid | 1H NMR (400.13 MHz, DMSO-d6) 1.11-1.49 (12H, m), 1.57-1.92 (11H, m), 1.96-2.04 (2H, m), 2.12-2.27 (2H, m), 2.72-2.79 (1H, m), 2.93-3.00 (1H, m), 3.63-3.71 (2H, m), 4.16-4.27 (2H, m), 6.46 (1H, d), 7.59 (1H, d), 7.72 (1H, d), 12.08 (1H, s) | 460; HPLC tR = 2.97 min. |

Intermediate 4

6-chloro-N-cyclohexyl-2-cyclohexylsulfanyl-pyridine-3-carboxamide

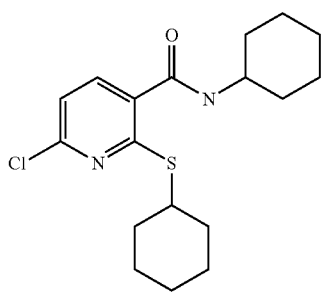 [SMILES: O=C(NC1CCCCC1)c1ccc(Cl)nc1SC1CCCCC1]

This intermediate was prepared in an analogous manner to that of intermediate 3

1H NMR (400.13 MHz, DMSO-$d_6$) δ 1.08-1.47 (10H, m), 1.54-1.63 (2H, m), 1.66-1.76 (4H, m), 1.78-1.86 (2H, m), 1.99-2.01 (2H, m), 3.66-3.75 (2H, m), 7.25 (1H, d), 7.71 (1H, d), 8.29 (1H, d)

m/z (ESI+) (M+H)+=353; HPLC $t_R$=3.14 min

The following Examples were prepared in a similar manner to Example 1, using Intermediate 6 and an appropriate aminoester starting material:

| Compound | Ex | Name | ¹H NMR δ | MS m/e MH⁺ |
|---|---|---|---|---|
|  | 59 | 2-[(3S)-1-[5-(2-adamantylcarbamoyl)-6-propylsulfanyl-pyridin-2-yl]-3-piperidyl]acetic acid | 1H NMR (300.072 MHz, CDCl₃) 1.02 (3H, t), 1.30-1.39 (1H, m), 1.52-1.61 (1H, m), 1.66-1.81 (8H, m), 1.83-2.10 (11H, m), 2.32 (2H, d), 2.78-2.89 (1H, m), 2.97-3.06 (1H, m), 3.09-3.26 (2H, m), 4.20-4.31 (3H, m), 6.38 (1H, d), 7.20 (1H, d), 7.91 (1H, d) | 472 |
|  | 60 | 2-[(3S)-1-[5-(2-adamantylcarbamoyl)-6-propylsulfanyl-pyridin-2-yl]pyrrolidin-3-yl]oxyacetic acid | 1H NMR (400.13 MHz, CDCl3) 1.04 (3H, t), 1.67-2.1 (16H, m), 2.12-2.32 (2H, m), 3.20-3.24 (2H, m), 3.60-3.75 (4H, m), 4.17 (2H, s), 4.23-4.29 (1H, m), 4.34-4.38 (1H, m), 6.10 (1H, d), 7.14 (1H, d), 7.91 (1H, d) | 474; HPLC tR = 2.99 min. |
|  | 61 | 2-[(3R)-1-[5-(2-adamantylcarbamoyl)-6-propylsulfanyl-pyridin-2-yl]pyrrolidin-3-yl]oxyacetic acid | 1H NMR (400.13 MHz, DMSO-d6) 0.98 (3H, t), 1.4-1.49 (2H, m), 1.51-1.61 (2H, m), 1.61-1.68 (2H, m), 1.69-1.81 (6H, m), 1.81-1.85 (2H, m), 1.95-2.03 (4H, s), 3.0 (2H, t), 3.36-3.44 (1H, m), 3.45-3.58 (3H, m), 3.88-3.93 (1H, m), 4.02 (2H, s), 4.2-4.3 (1H, m), 6.1 (1H, d), 7.5 (1H, d), 7.6 (1H, d), 12.5 (1H, s). | 474; HPLC tR = 3.01 min. |

-continued

| Compound | Ex | Name | ¹H NMR δ | MS m/e MH⁺ |
|---|---|---|---|---|
| | 62 | 2-[(3S)-1-[5-(2-adamantylcarbamoyl)-6-propylsulfanyl-pyridin-2-yl]pyrrolidin-3-yl]acetic acid | 1H NMR (400.13 MHz, DMSO-d6) 0.97 (3H, t), 1.5-158 (2H, m), 1.59-1.89 (11H, m), 1.9-1.97 (2H, m), 2.04-2.09 (2H, m), 2.12-2.2 (1H, m), 2.41-2.46 (2H, m), 2.54-2.63 (1H, m), 3.04 (2H, t), 3.1 (1H, dd), 3.37-3.41 (1H, m), 3.52-3.6 (1H, m), 3.70-3.74 (1H, m), 3.93-4.0 (1H, m), 6.13 (1H, d), 7.56 (1H, m), 7.65 (1H, d), 12.2 (1H, s). | 458; HPLC tR = 3.16 min. |
| | 63 | (3R)-1-[5-(2-adamantylcarbamoyl)-6-propylsulfanyl-pyridin-2-yl]pyrrolidine-3-carboxylic acid | 1H NMR (300.072 MHz, CDCl3) 1.03 (t, 3H), 1.61-2.09 (m, 16H), 2.24-2.42 (m, 2H), 3.17-3.31 (m, 3H), 3.48-3.72 (m, 2H), 3.79 (d, 2H), 4.21-4.31 (m, 1H), 6.09 (d, 1H), 7.15 (d, 1H), 7.90 (d, 1H) | 444 |
| | 64 | 2-[(3R)-1-[5-(2-adamantylcarbamoyl)-6-propylsulfanyl-pyridin-2-yl]pyrrolidin-3-yl]acetic acid | 1H NMR (300.073 MHz, DMSO-d6) 0.94 (t, 3H), 1.45-2.23 (m, 18H), 2.19 (d, 2H), 2.49-2.63 (m, 1H), 2.96-3.10 (m, 3H), 3.28-3.44 (m, 1H), 3.46-3.59 (m, 1H), 3.60-3.70 (m, 1H), 3.91-3.98 (m, 1H), 6.08 (d, 1H), 7.56 (d, 1H), 7.62 (d, 1H) | 458 |
| | 65 | (2S)-1-[5-(2-adamantylcarbamoyl)-6-propylsulfanyl-pyridin-2-yl]pyrrolidine-2-carboxylic acid | 1H NMR (300.073 MHz, DMSO-d6) 0.95 (t, 3H), 1.42-2.14 (m, 19H), 2.20-2.37 (m, 1H), 2.81-2.97 (m, 1H), 2.99-3.14 (m, 1H), 3.37-3.59 (m, 2H), 3.90-3.98 (m, 1H), 4.49 (d, 1H), 6.17 (d, 1H), 7.56-7.69 (m, 2H), 12.21-12.66 (m, 1H) | 444 |

| Compound | Ex | Name | ¹H NMR δ | MS m/e MH⁺ |
|---|---|---|---|---|
| | 66 | (1S,5R)-3-[5-(2-adamantylcarbamoyl)-6-propylsulfanyl pyridin-2-yl]-3-azabicyclo[3.1.0]hexane-6-carboxylic acid | 1H NMR (300.073 MHz, DMSO-d6) 0.96 (t, 3H), 1.38 (s, 1H), 1.50 (d, 2H), 1.56-1.86 (m, iGH), 1.91 (s, 2H), 2.05 (d, 2H), 2.22 (s, 2H), 3.01 (t, 2H), 3.49 (d, 2H), 3.78 (d, 2H), 3.89-3.99 (m, 1H), 6.14 (d, 1H), 7.53-7.70 (m, 2H), 11.80-12.82 (m, 1H) | 456 |
| | 67 | (3S)-1-[5-(2-adamantylcarbamoyl)-6-propylsulfanyl-pyridin-2-yl]pyrrolidine-3-carboxylic acid | 1H NMR (300.072 MHz, CDCl₃) 1.03 (t, 3H), 1.60-2.11 (m, 16H), 2.21-2.41 (m, 2H), 3.15-3.29 (m, 3H), 3.46-3.71 (m, 2H), 3.75 (d, 2H), 4.26 (d, 1H), 6.05 (d, 1H), 7.18 (d, 1H), 7.89 (d, 1H) | 444 |
| | 68 | 4-[5-(2-adamantylcarbamoyl)-6-propylsulfanyl-pyridin-2-yl]morpholine-2-carboxylic acid | 1H NMR (400.13 MHz, DMSO-d6) 0.97 (3H, t), 1.52 (2H, t), 1.58-1.66 (2H, m), 1.72-1.79 (2H, m), 1.81-1.84 (6H, m), 1.92-1.96 (2H, m), 2.06-2.09 (2H, m), 3.00 (2H, d), 3.33-3.39 (2H, m), 3.61-3.67 (1H, m), 3.77-3.80 (1H, m), 3.96-4.02 (2H, m), 4.19-4.23 (2H, m), 6.56 (1H, d), 7.67 (1H, d), 7.72 (1H, d), 12.90 (1H, s) | 460; HPLC tR = 2.76 min. |

Intermediate 5

N-(2-adamantyl)-2,6-dichloro-pyridine-3-carboxamide

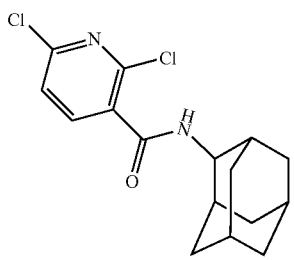 [SMILES: O=C(NC1C2CC3CC(C2)CC1C3)c1ccc(Cl)nc1Cl]

Oxalyl chloride (8.72 ml, 100.00 mmol) was added dropwise to 2,6-dichloronicotinic acid (9.60 g, 50 mmol) and N,N-dimethylformamide (0.039 ml, 0.50 mmol) in DCM at 20° C. over a period of 10 minutes under nitrogen. The resulting suspension was stirred at 20° C. for 2 hours. The resulting mixture was evaporated to dryness and the residue was azeotroped with toluene to afford the crude acid chloride, which was dissolved in DCM (25 mL) and added portionwise to a stirred solution of 2-adamantanamine hydrochloride (9.39 g, 50.00 mmol) and N-Ethyldiisopropylamine (26.1 ml, 150.00 mmol) in DCM cooled to 0° C., over a period of 15 minutes under nitrogen. The resulting suspension was stirred at 20° C. for 2 hours.

The reaction mixture was evaporated to dryness, stirred with water (50 mL) for 10 mins and the precipitate was collected by filtration, washed with water (2×25 mL) and dried under vacuum to afford N-(2-adamantyl)-2,6-dichloro-pyridine-3-carboxamide (16.01 g, 98%) as a cream solid, which was used without further purification 1H NMR (400.132 MHz, CDCl3) δ 1.69-1.76 (2H, m), 1.79 (2H, s), 1.82-1.96 (8H, m), 2.07 (2H, s), 4.27 (1H, d), 6.92-7.01 (1H, m), 7.39 (1H, d), 8.19 (1H, d)

m/z (ESI+) (M+H)+=325; HPLC $t_R$=2.66 min.

Intermediate 6

N-(2-adamantyl)-6-chloro-2-propylsulfanyl-pyridine-3-carboxamide

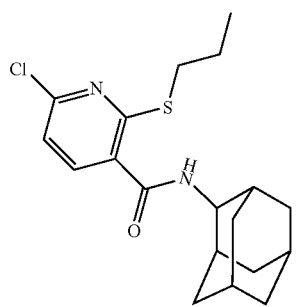 [SMILES: CCCSc1nc(Cl)ccc1C(=O)NC1C2CC3CC(C2)CC1C3]

Propanethiol (1.45 mL, 16 mmol) was added to N-(2-adamantyl)-2,6-dichloro-pyridine-3-carboxamide (5.2 g, 16 mmol), and sodium carbonate (5.09 g, 48 mmol) in DMF (50 mL) at 20° C. under nitrogen. The resulting suspension was stirred at 60° C. for 3 hours. The reaction mixture was diluted with EtOAc (400 mL) and washed with water (3×50 mL), and saturated brine (25 mL). The organic layer was dried over MgSO4, filtered and evaporated to afford crude product which was recrystallised from 15% ethyl acetate/hexane to give N-(2-adamantyl)-6-chloro-2-propylsulfanyl-pyridine-3-carboxamide (4.9 g, 84%)

1H NMR (300.072 MHz, CDCl3) δ 1.06 (t, 3H), 1.63-1.84 (m, 6H), 1.85-1.99 (m, 8H), 2.02-2.14 (m, 2H), 3.24 (t, 2H), 4.22-4.31 (m, 1H), 6.85-6.96 (m, 1H), 7.06 (d, 1H), 7.90 (d, 1H)

m/z (ESI+) (M+H)+=365; HPLC $t_R$=3.23 min.

The following Examples were prepared in a similar manner to Example 1, using Intermediate 7 and an appropriate aminoester starting material:

| Compound | Ex | Name | ¹H NMR δ | MS m/e MH+ |
|---|---|---|---|---|
|  | 69 | 2-[(3S)-1-[5-(2-adamantylcarbamoyl)-6-cyclopentylsulfanyl-pyridin-2-yl]pyrrolidin-3-yl]oxyacetic acid | 1H NMR (400.13 MHz, CDCl3) 1.6-2.07 (20 H, m), 2.13-2.21 (4H, m), 3.60-3.75 (4H, m), 4.15-4.25 (2H, m), 4.18 (2H, s), 4.35-4.37 (1H, m), 6.10 (1H, d), 7.15 (1H, d), 7.90 (1H, d) | 500; HPLC tR = 3.19 min. |
|  | 70 | 2-[(3R)-1-[5-(2-adamantylcarbamoyl)-6-cyclopentylsulfanyl-pyridin-2-yl]pyrrolidin-3-yl]oxyacetic acid | 1H NMR (400.13 MHz, CDCl3) 1.6-2.07 (20 H, m), 2.13-2.21 (4H, m), 3.60-3.75 (4H, m), 4.15-4.25 (2H, m), 4.18 (2H, s), 4.35-4.37 (1H, m), 6.10 (1H, d), 7.15 (1H, d), 7.90 (1H, d) | 500; HPLC tR = 3.21 min. |

Intermediate 7

N-(2-adamantyl)-6-chloro-2-cyclopentylsulfanyl-pyridine-3-carboxamide

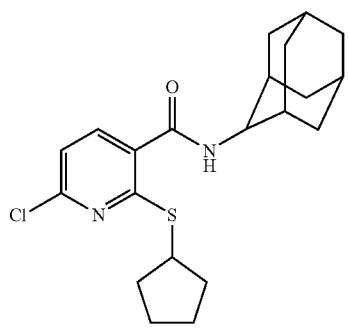 [SMILES: O=C(NC1C2CC3CC(C2)CC1C3)c1ccc(Cl)nc1SC1CCCC1]

Anhydrous Sodium carbonate (2.201 mL, 52.58 mmol) was added in one portion to N-(2-adamantyl)-2,6-dichloro-pyridine-3-carboxamide (5.7 g, 17.53 mmol) and cyclopentyl mercaptan (1.885 mL, 17.53 mmol) in DMF (50 mL) under nitrogen. The resulting suspension was stirred at 60° C. for 6 hours.

The reaction mixture was concentrated and diluted with DCM (150 mL), and washed sequentially with water (2×75 mL) and saturated brine (75 mL). The organic layer was dried over MgSO4, filtered and evaporated to afford crude product. This was triturated with 4:1 isohexane:EtOAc to give the desired product (5.6 g, 82%) as a white powder.

1H NMR (400.13 MHz, CDCl$_3$) δ 1.60-1.94 (18H, m), 2.02-2.1 (2H, m), 2.21-2.27 (2H, m), 4.12-4.19 (1H, m), 4.26 (1H, d), 6.90 (1H, d), 7.05 (1H, d), 7.89 (1H, d)

m/z (ESI+) (M+H)+=391; HPLC t$_R$=3.62 min.

The following Examples were prepared in a similar manner to Example 1, using Intermediate 8 and an appropriate aminoester starting material:

| Compound | Ex | Name | $^1$H NMR δ | MS m/e MH$^+$ |
|---|---|---|---|---|
| | 71 | 2-[(3S)-1-[5-(2-adamantylcarbamoyl)-6-cyclohexylsulfanyl-pyridin-2-yl]pyrrolidin-3-yl]oxyacetic acid | 1H NMR (400.13 MHz, CDCl3) 1.3-2.3 (26H, m), 3.57-3.78 (4H, m), 3.94-4.05 (1H, m), 4.17 (2H, s), 4.25-4.3 (1H, m), 4.35-4.4 (1H, m), 6.10 (1H, d), 7.28 (1H, d), 7.93 (1H, d) | 514; HPLC tR = 3.36 min. |
| | 72 | 2-[(3R)-1-[5-(2-adamantylcarbamoyl)-6-cyclohexylsulfanyl-pyridin-2-yl]pyrrolidin-3-yl]oxyacetic acid | 1H NMR (400.13 MHz, DMSO-d6) 1.2-1.49 (5H, m), 1.51-1.64 (3H, m), 1.66-1.9 (10H, m), 1.9-1.96 (2H, m), 2.06-2.2 (6H, m), 3.4-3.5 (1H, m), 3.53-3.62 (3H, m), 3.78-3.88 (1H, m), 3.92-4.0 (1H, m), 4.07 (2H, s), 4.3-4.35 (1H, s), 6.16 (1H, d), 7.58 (1H, d), 7.64 (1H, d), 12.5 (1H, s). | 514; HPLC tR = 3.38 min. |

Intermediate 8

N-(2-adamantyl)-6-chloro-2-cyclohexylsulfanyl-pyridine-3-carboxamide

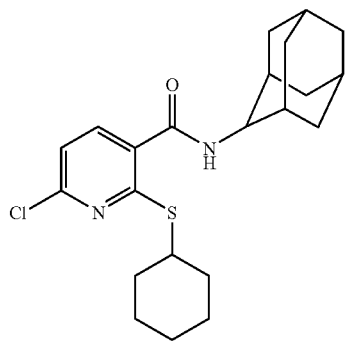 [SMILES: O=C(NC1C2CC3CC(C2)CC1C3)c1ccc(Cl)nc1SC1CCCCC1]

Anhydrous sodium carbonate (2.201 mL, 52.58 mmol) was added in one portion to N-(2-adamantyl)-2,6-dichloro-pyridine-3-carboxamide (5.7 g, 17.53 mmol) and cyclohexyl mercaptan (2.14 mL, 17.53 mmol) in DMF (50 mL) under nitrogen. The resulting suspension was stirred at 60° C. for 6 hours.

The reaction mixture was concentrated and diluted with DCM (150 mL), and washed sequentially with water (2×75 mL) and saturated brine (75 mL). The organic layer was dried over MgSO4, filtered and evaporated to afford crude product. This was triturated with 4:1 isohexane:EtOAc to give the desired product (6.5 g, 92%) as a white powder.

1H NMR (400.13 MHz, DMSO-$d_6$) δ 1.31 (1H, s), 1.36-1.42 (2H, m), 1.42 (2H, d), 1.45 (1H, s), 1.49 (1H, d), 1.53 (1H, s), 1.58 (1H, t), 1.70 (4H, d), 1.77 (1H, s), 1.82 (6H, d), 1.95 (2H, s), 1.97-2.00 (2H, m), 2.06-2.09 (2H, m), 3.76 (1H, t), 3.99 (1H, t), 7.25 (1H, d), 7.69-7.71 (1H, m), 8.28 (1H, d) m/z (ESI+) (M+H)+=405; HPLC $t_R$=3.77 min.

The following Examples were prepared in a similar manner to Example 1, using Intermediate 9 and an appropriate aminoester starting material:

| Compound | Ex | Name | 1H NMR δ | MS m/e MH+ |
|---|---|---|---|---|
|  | 73 | 2-[(3R)-1-[5-(2-adamantylcarbamoyl)-6-ethylsulfanyl-pyridin-2-yl]pyrrolidin-3-yl]acetic acid | 1H NMR (300.072 MHz, CDCl3) 1.38 (t, 3H), 1.61-1.80 (m, 5H), 1.81-2.09 (m, 9H), 2.19-2.33 (m, 1H), 2.54 (d, 2H), 2.74 (quintet, 1H), 3.09-3.22 (m, 1H), 3.24 (q, 2H), 3.49 (q, 1H), 3.60-3.73 (m, 1H), 3.80 (t, 1H), 4.22-4.33 (m, 1H), 4.42-4.82 (m, 1H), 6.08 (d, 1H), 7.09 (d, 1H), 7.89 (d, 1H) | 444 |
|  | 74 | (3R)-1-[5-(2-adamantylcarbamoyl)-6-ethylsulfanyl-pyridin-2-yl]pyrrolidine-3-carboxylic acid | 1H NMR (300.072 MHz, CDCl3) 1.38 (t, 3H), 1.63-1.80 (m, 4H), 1.81-2.08 (m, 10H), 2.28-2.40 (m, 2H), 3.24 (q, 3H), 3.48-3.60 (m, 1H), 3.61-3.72 (m, 1H), 3.80 (d, 2H), 4.22-4.30 (m, 1H), 6.09 (d, 1H), 7.07 (d, 1H), 7.89 (d, 1H) | 430 |

-continued

| Compound | Ex | Name | ¹H NMR δ | MS m/e MH+ |
|---|---|---|---|---|
|  | 74b | (3S)-1-[5-(2-adamantylcarbamoyl)-6-ethylsulfanyl-pyridin-2-yl]pyrrolidine-3-carboxylic acid | 1H NMR (300.072 MHz, CDCl3) 1.38 (t, 3H), 1.63-1.80 (m, 4H), 1.81-2.08 (m, 10H), 2.28-2.40 (m, 2H), 3.24 (q, 3H), 3.48-3.60 (m, 1H), 3.61-3.72 (m, 1H), 3.80 (d, 2H), 4.22-4.30 (m, 1H), 6.09 (d, 1H), 7.07 (d, 1H), 7.89 (d, 1H) | 430 |
|  | 75 | (1S,5R)-3-[5-(2-adamantylcarbamoyl)-6-ethylsulfanyl-pyridin-2-yl]-3-azabicyclo[3.1.0]hexane-6-carboxylic acid | 1H NMR (300.072 MHz, CDCl3) 1.38 (t, 3H), 1.58-1.63 (m, 1H), 1.64-1.81 (m, 4H), 1.81-2.09 (m, 10H), 2.33 (s, 2H), 3.21 (q, 2H), 3.58 (d, 2H), 3.88 (d, 2H), 4.22-4.28 (m, 1H), 6.06 (d, 1H), 7.01 (d, 1H), 7.87 (d, 1H) | 442 |

Intermediate 9

N-(2-adamantyl)-6-chloro-2-ethylsulfanyl-pyridine-3-carboxamide

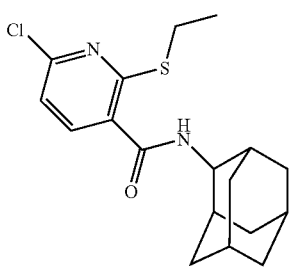 [SMILES: CCSc1nc(Cl)ccc1C(=O)NC1C2CC3CC(C2)CC1C3]

Ethanethiol (0.433 mL, 5.84 mmol) was added to N-(2-adamantyl)-2,6-dichloro-pyridine-3-carboxamide (2 g, 6.15 mmol), and sodium carbonate (1.955 g, 18.45 mmol) in DMF (12 mL) at 20° C. under nitrogen. The resulting suspension was stirred at 60° C. for 3 hours. The reaction mixture was diluted with EtOAc (100 mL) and washed with water (3×20 mL), and saturated brine (25 mL). The organic layer was dried over MgSO4, filtered and evaporated to afford crude product which was recrystallised from 15% ethyl acetate/hexane to give N-(2-adamantyl)-6-chloro-2-ethylsulfanyl-pyridine-3-carboxamide (1.489 g, 69%)

¹H NMR (300.072 MHz, CDCl3) δ 1.40 (t, 3H), 1.66-1.81 (m, 4H), 1.85-1.96 (m, 8H), 2.03-2.12 (m, 2H), 3.26 (q, 2H), 4.22-4.31 (m, 1H), 6.78-6.89 (m, 1H), 7.06 (d, 1H), 7.89 (d, 1H)

m/z (ESI+) (M+H)+=351; HPLC $t_R$=3.05 min.

The following Examples were prepared in a similar manner to Example 1, using Intermediate 10 and an appropriate aminoester starting material:

| Compound | Ex | Name | ¹H NMR δ | MS m/e MH⁺ |
|---|---|---|---|---|
| | 76 | 2-[(3R)-1-[5-(2-adamantylcarbamoyl)-6-methylsulfanyl-pyridin-2-yl]pyrrolidin-3-yl]acetic acid | 1H NMR (300.072 MHz, CDCl3) 1.61-1.82 (m, 5H), 1.81-2.11 (m, 10H), 2.17-2.31 (m, 1H), 2.53 (d, 2H), 2.58 (s, 3H), 2.65-2.79 (m, 1H), 3.10-3.22 (m, 1H), 3.40-3.55 (m, 1H), 3.59-3.72 (m, 1H), 3.74-3.87 (m, 1H), 4.20-4.32 (m, 1H), 6.06 (d, 1H), 6.97 (d, 1H), 7.85 (d, 1H) | 430 |
| | 77 | (3R)-1-[5-(2-adamantylcarbamoyl)-6-methylsulfanyl-pyridin-2-yl]pyrrolidine-3-carboxylic acid | 1H NMR (300.072 MHz, CDCl3) 1.62-1.80 (m, 4H), 1.81-2.10 (m, 10H), 2.26-2.40 (m, 2H), 2.58 (s, 3H), 3.25 (quintet, 1H), 3.49-3.61 (m, 1H), 3.61-3.74 (m, 1H), 3.81 (d, 2H), 4.20-4.30 (m, 1H), 6.08 (d, 1H), 6.96 (d, 1H), 7.86 (d, 1H) | 416 |
| | 78 | (1S,5R)-3-[5-(2-adamantylcarbamoyl)-6-methylsulfanyl-pyridin-2-yl]-3-azabicyclo[3.1.0]hexane-6-carboxylic acid | 1H NMR (300.072 MHz, CDCl3) 1.53-2.10 (m, 15H), 2.34 (s, 2H), 2.56 (s, 3H), 3.59 (d, 2H), 3.90 (d, 2H), 4.18-4.31 (m, 1H), 6.05 (d, 1H), 6.90 (d, 1H), 7.84 (d, 1H) | 428 |

Intermediate 10

N-(2-adamantyl)-6-chloro-2-methylsulfanyl-pyridine-3-carboxamide

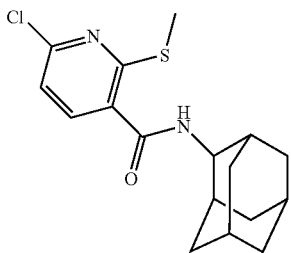 [SMILES: CSc1nc(Cl)ccc1C(=O)NC1C2CC3CC(C2)CC1C3]

Sodium thiomethoxide (0.409 g, 5.84 mmol) was added to N-(2-adamantyl)-2,6-dichloro-pyridine-3-carboxamide (2 g, 6.15 mmol) in DMA (10 mL) at 20° C. under nitrogen. The resulting suspension was stirred at 60° C. for 3 hours. The reaction mixture was diluted with EtOAc (100 mL) and washed with water (3×20 mL), and saturated brine (25 mL). The organic layer was dried over MgSO4, filtered and evaporated to afford crude product which was purified by crystallisation from EtOAc/isohexane to afford N-(2-adamantyl)-6-chloro-2-methylsulfanyl-pyridine-3-carboxamide (1.150 g, 55.5%) as a white solid $^1$H NMR (300.072 MHz, CDCl3) δ 1.65-1.82 (m, 4H), 1.85-1.98 (m, 8H), 2.01-2.12 (m, 2H), 2.61 (s, 3H), 4.22-4.33 (m, 1H), 6.73-6.82 (m, 1H), 7.07 (d, 1H), 7.87 (d, 1H)

m/z (ESI+) (M+H)+=337; HPLC $t_R$=2.97 min.

The following Examples were prepared in a similar manner to Example 1, using Intermediate 12 and an appropriate aminoester starting material:

| Compound | Ex | Name | $^1$H NMR δ | MS m/e MH+ |
|---|---|---|---|---|
| | 79 | 2-[(3S)-1-[5-[((2r,5s)-5-hydroxy-2-adamantyl)carbamoyl]-6-propylsulfanyl-pyridin-2-yl]pyrrolidin-3-yl]acetic acid | 1H NMR (400.13 MHz, DMSO-d6) 0.99 (3H, t), 1.35-1.43 (2H, m), 1.59-1.8 (9H, m), 1.96-2.14 (5H, m), 2.16-2.28 (1H, m), 2.41-2.47 (2H, m), 2.53-2.63 (1H, m), 3.06 (2H, t), 3.10 (1H, dd), 3.4-3.5 (1H, m), 3.56-3.65 (1H, m), 3.71-3.8 (1H, m), 3.9-3.97 (1H, m), 4.42 (1H, s), 6.17 (1H, d), 7.57 (1H, d), 7.69 (1H, d), 12.2 (1H, s). | 474; HPLC tR = 2.08 min. |
| | 80 | 4-[[[5-[((2r,5s)-5-hydroxy-2-adamantyl)carbamoyl]-6-propylsulfanyl-pyridin-2-yl]amino]methyl]cyclohexane-1-carboxylic acid | 1H NMR (300.073 MHz, DMSO-d6) 0.96 (t, 3H), 1.15-1.42 (m, 4H), 1.43-2.21 (m, 21H), 3.00 (t, 2H), 3.10-3.20 (m, 2H), 3.19-3.65 (m, 1H), 3.79-3.89 (m, 1H), 6.16 (d, 1H), 6.96-7.09 (m, 1H), 7.42-7.52 (m, 2H), 11.32-12.50 (m, 1H) | 502 |

-continued

| Compound | Ex | Name | ¹H NMR δ | MS m/e MH⁺ |
|---|---|---|---|---|
| | 81 | 4-[[5-[((2r,5s)-5-hydroxy-2-adamantyl)carbamoyl]-6-propylsulfanyl-pyridin-2-yl]amino]cycloexane-1-carboxylic acid | 1H NMR (300.073 MHz, DMSO-d6) 0.96 (t, 3H), 1.13-1.49 (m, 7H), 1.51-1.75 (m, 8H), 1.86-2.07 (m, 9H), 2.09-2.22 (m, 1H), 2.99 (t, 2H), 3.64-3.79 (m, 1H), 3.80-3.89 (m, 1H), 6.14 (d, 1H), 6.85 (d, 1H), 7.42-7.51 (m, 2H) | 488 |
| | 82 | 4-[[5-[((2r,5s)-5-hydroxy-2-adamantyl)carbamoyl]-6-propylsulfanyl-pyridin-2-yl]amino]cyclohexane-1-carboxylic acid | 1H NMR (300.073 MHz, DMSO-d6) 0.95 (t, 3H), 1.32 (d, 2H), 1.47-1.80 (m, 13H), 1.81-2.09 (m, 8H), 2.33-2.45 (m, 1H), 2.98 (t, 2H), 3.80-3.88 (m, 1H), 3.88-4.02 (m, 1H), 4.20-4.56 (m, 1H), 6.21 (d, 1H), 6.88 (d, 1H), 7.41- 7.52 (m, 2H) | 488 |
| | 83 | 2-[(3S)-1-[5-[(2r,5s)-5-hydroxy-2-adamantyl]carbamoyl]-6-propylsulfanyl-pyridin-2-yl]-3-piperidyl]acetic acid | 1H NMR (400.13 MHz, DMSO-d6) 0.95 (3H, t), 1.24-1.48 (4H, m), 1.56-1.72 (9H, m), 1.81-1.88 (2H, m), 1.93-2.07 (5H, d), 2.13-2.27 (2H, m), 2.72-2.78 (1H, m), 2.90-3.06 (3H, m), 3.83-3.88 (1H, m), 4.20 (1H, d), 4.29 (1H, d), 4.43 (1H, s), 6.49 (1H, d), 7.61 (1H, d), 7.67 (1H, d), 12.16 (1H, s) | 488; HPLC tR = 2.19 min |

| Compound | Ex | Name | ¹H NMR δ | MS m/e MH⁺ |
|---|---|---|---|---|
| | 84 | 1-[5-[[(2r,5s)-5-hydroxy-2-adamantyl]carbamoyl]-6-propylsulfanyl-pyridin-2-yl]piperidine-4-carboxylic acid | 1H NMR (400.13 MHz, DMSO-d6) 0.96 (3H, t), 1.29-1.36 (2H, m), 1.44-1.75 (9H, m), 1.82-1.89 (2H, m), 1.93-2.07 (6H, m), 2.52-2.59 (1H, m), 2.96-3.10 (4H, m), 3.84-3.88 (1H, m), 4.23-4.30 (2H, m), 4.43 (1H, s), 6.55 (1H, d), 7.61 (1H, d), 7.69 (1H, d), 12.28 (1H, s) | 474; HPLC tR = 2.06 min |
| | 85 | 2-[(3R)-1-[5-[[(2r,5s)-5-hydroxy-2-adamantyl]carbamoyl)-6-propylsulfanyl-pyridin-2-yl]-3-piperidyl]acetic acid | 1H NMR (400.13 MHz, DMSO-d6) 0.95 (3H, t), 1.22-1.49 (4H, m), 1.55-1.74 (6H, m), 1.78-1.90 (3H, m), 1.92-2.07 (7H, m), 2.17-2.20 (2H, m), 2.72-2.78 (1H, m), 2.90-3.06 (3H, m), 3.84-3.88 (1H, m), 4.17-4.24 (1H, m), 4.26-4.33 (1H, m), 4.43 (1H, s), 6.49 (1H, d), 7.61 (1H, d), 7.67 (1H, d), 12.16 (1H, s) | 488; HPLC tR = 2.21 min |
| | 86 | 2-[1-[5-[[(2r,5s)-5-hydroxy-2-adamantyl]carbamoyl]-6-propylsulfanyl-pyridin-2-yl]-4-piperidyl]acetic acid | 1H NMR (400.13 MHz, DMSO-d6) 0.95 (3H, t), 1.09-1.20 (2H, m), 1.29-1.36 (2H, m), 1.5-1.74 (10H, m), 1.92-2.06 (6H, m), 2.17 (2H, d), 2.88-2.99 (4H, m), 3.83-3.89 (1H, m), 4.32-4.39 (2H, m), 4.43 (1H, s), 6.52 (1H, d), 7.61 (1H, d), 7.66 (1H, d), 12.11 (1H, s) | 488; HPLC tR = 2.13 min |
| | 87 | (1R,5S)-3-[5-[[(2r,5s)-5-hydroxy-2-adamantyl]carbamoyl)-6-propylsulfanyl-pyridin-2-yl]-3-azabicyclo [3.1.0] hexane-6-carboxylic acid | 1H NMR (400.13 MHz, DMSO-d6) 0.97 (3H, t), 1.29-1.40 (3H, m), 1.58-1.74 (8H, m), 1.92-2.06 (5H, m), 2.18-2.21 (2H, m), 3.01 (2H, t), 3.50 (2H, d), 3.79 (2H, d), 3.83-3.88 (1H, m), 4.43 (1H, s), 6.15 (1H, d), 7.61 (1H, d), 7.64 (1H, d), 12.28 (1H, s) | 472; HPLC tR = 2.03 min |

-continued

| Compound | Ex | Name | ¹H NMR δ | MS m/e MH⁺ |
|---|---|---|---|---|
| | 88 | 1-[5-[[(2r,5s)-5-hydroxy-2-adamantyl]carbamoyl]-6-propylsulfanyl-pyridin-2-yl]-4-methyl-piperidine-4-carboxylic acid | 1H NMR (400.13 MHz, DMSO-d6) 0.96 (3H, t), 1.17 (3H, s), 1.31-1.40 (4H, m), 1.57-1.74 (8H, m), 1.92-2.07 (7H, m), 2.95-3.01 (2H, m), 3.19-3.26 (2H, m), 3.84-3.88 (1H, m), 3.95-4.03 (2H, m), 4.43 (1H, s), 6.54 (1H, d), 7.61 (1H, d), 7.68 (1H, d), 12.44 (1H, s) | 488; HPLC tR = 2.22 min |
| | 89 | 1-[5-[[(2r,5s)-5-hydroxy-2-adamantyl]carbamoyl]-6-propylsulfanyl-pyridin-2-yl]pyrrolidine-3-carboxylic acid | 1H NMR (400.13 MHz, DMSO-d6) 0.96 (3H, t), 1.30-1.38 (2H, m), 1.59-1.74 (8H, m), 1.93-2.07 (5H, m), 2.11-2.28 (2H, m), 3.00-3.04 (2H, m), 3.17-3.25 (1H, m), 3.42-3.56 (2H, m), 3.60-3.70 (2H, m), 3.84-3.89 (1H, m), 4.43 (1H, s), 6.17 (1H, d), 7.61 (1H, d), 7.64 (1H, d), 12.53 (1H, s) | 460; HPLC tR = 2.02 min |
| | 90 | 2-[(3R)-1-[5-[[(2r,5s)-5-hydroxy-2-adamantyl]carbamoyl]-6-propylsulfanyl-pyridin-2-yl]pyrrolidin-3-yl]acetic acid | 1H NMR (400.13 MHz, DMSO-d6) 0.96 (3H, t), 1.31-1.38 (2H, m), 1.59-1.73 (9H, m), 1.92-2.08 (5H, d), 2.14-2.18 (1H, m), 2.41-2.47 (2H, m), 2.53-2.59 (1H, m), 3.00-3.05 (2H, m), 3.08-3.12 (1H, m), 3.38-3.43 (1H, m), 3.52-3.60 (1H, m), 3.68-3.76 (1H, m), 3.87-3.88 (1H, m), 4.37 (1H, s), 6.13 (1H, d), 7.53 (1H, d), 7.64 (1H, d), 12.18 (1H, s) | 474; HPLC tR = 2.11 min |
| | 91 | 3-[1-[5-[[(2r,5s)-5-hydroxy-2-adamantyl]carbamoyl)-6-propylsulfanyl-pyridin-2-yl]-3-piperidyl]propanoic acid | 1H NMR (400.13 MHz, DMSO-d6) 0.97 (3H, t), 1.17-1.22 (2H, m), 1.31-1.57 (6H, m), 1.59-1.75 (8H, m), 1.79-1.87 (1H, m), 1.93-2.08 (5H, m), 2.29 (2H, t), 2.63-2.69 (1H, m), 2.91-3.07 (3H, m), 3.85-3.89 (1H, m), 4.17-4.23 (1H, m), 4.27-4.33 (1H, m), 4.37 (1H, s), 6.51 (1H, d), 7.60 (2H, d), 12.00 (1H, s) | 500; HPLC tR = 2.30 min |

| Compound | Ex | Name | ¹H NMR δ | MS m/e MH⁺ |
|---|---|---|---|---|
| | 92 | 2-[1-[5-[((2r,5s)-5-hydroxy-2-adamantyl)carbamoyl]-6-propylsulfanyl-pyridin-2-yl]-3-piperidyl]-2-methyl-propanoic acid | 1H NMR (400.13 MHz, DMSO-d6) 0.96 (3H, t), 1.09-1.10 (3H, s), 1.15 (3H, s), 1.31-1.41 (4H, m), 1.55-1.66 (6H, m), 1.71 (4H, m), 1.95-2.04 (5H, m), 2.66 (1H, t), 2.80 (1H, t), 2.87-2.91 (1H, m), 3.09-3.16 (1H, m), 3.40 (2H, q), 3.86 (1H, s), 4.35 (1H, d), 4.45 (1H, d), 6.46 (1H, d), 7.60 (1H, d), 7.68 (1H, d), 12.25 (1H, s) | 516; HPLC tR = 2.44 min. |

Intermediate 11

2,6-dichloro-N-((2r,5s)-5-hydroxyadamantan-2-yl)nicotinamide

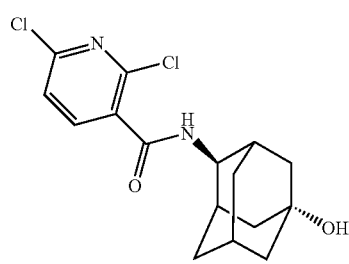 [SMILES: O=C(N[C@H]1C2CC3CC1C[C@](O)(C3)C2)c1ccc(Cl)nc1Cl]

A solution of 2,6-dichloronicotinoyl chloride (25.2 g, 119.60 mmol) in DCM (100 mL) was added dropwise to a stirred suspension of 4-aminoadamantan-1-ol (20.00 g, 119.6 mmol) and N-Ethyldiisopropylamine (24.83 mL, 143.52 mmol) in THF (400 mL) at 20° C., over a period of 30 minutes under nitrogen. The resulting suspension was stirred at room temperature for 18 hours. The reaction mixture was diluted with EtOAc (500 mL), and washed sequentially with water (100 mL) and saturated brine (50 mL). The organic layer was dried over MgSO4, filtered and evaporated to afford the crude product. The crude product was purified by flash silica chromatography, elution gradient 0 to 100% EtOAc in DCM. Pure fractions were evaporated to dryness to afford 2,6-dichloro-N-(5-hydroxyadamantan-2-yl)nicotinamide (20.65 g, 51%) as a white solid.

1H NMR (400.13 MHz, DMSO-d6) δ 1.31-1.38 (2H, m), 1.60-1.67 (4H, d), 1.69-1.76 (2H, m), 1.87-1.94 (2H, m), 1.99-2.00 (1H, m), 2.04-2.09 (2H, m), 3.91-3.96 (1H, m), 4.47 (1H, s), 7.64 (1H, d), 7.95 (1H, d), 8.49 (1H, d)

m/z (ESI−) (M−H)−=339; HPLC $t_R$=1.59 min.

Intermediate 12

6-chloro-N-((2r,5s)-5-hydroxy-2-adamantyl)-2-propylsulfanyl-pyridine-3-carboxamide

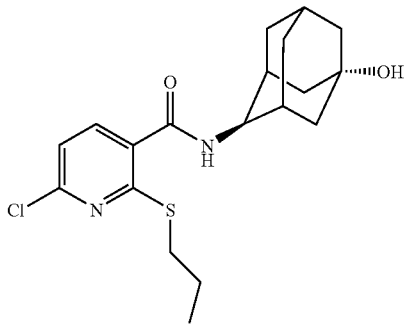 [SMILES: CCCSc1nc(Cl)ccc1C(=O)N[C@H]1C2CC3CC1C[C@](O)(C3)C2]

1-Propanethiol (1.327 mL, 14.65 mmol) was added in one portion to 2,6-dichloro-N-(5-hydroxy-2-adamantyl)pyridine-3-carboxamide (5 g, 14.65 mmol) and sodium carbonate (4.66 g, 43.96 mmol) in DMF (50 mL). The resulting suspension was stirred at 60° C. for 3 hours. The mixture was cooled, evaporated, DCM (250 mL) was added and the mixture was washed with water (3×50 mL) and brine (50 mL), dried (MgSO4), filtered and evaporated to a sticky pale yellow solid. This was triturated with 4:1 hexane:ethyl acetate, filtered and dried to give the desired product as a white solid (5.0 g, 90%).

1H NMR (400.13 MHz, DMSO-d6) δ 0.92 (3H, t), 1.22-1.3 (2H, m), 1.5-1.7 (8H, m), 1.85-1.96 (3H, m), 1.97-2.03 (2H, s), 3.0 (2H, t), 3.83-3.9 (1H, m), 4.34 (1H, s), 7.2 (1H, d), 7.65 (1H, d), 8.18 (1H, d)

m/z (ESI+) (M+H)+=381; HPLC $t_R$=2.34 min.

The following Examples were prepared in a similar manner to Example 1, using Intermediate 13 and an appropriate aminoester starting material:

| Compound | Ex | Name | ¹H NMR δ | MS m/e MH⁺ |
|---|---|---|---|---|
| | 93 | 2-[(3S)-1-[6-cyclopentylsulfanyl-5-[((2r,5s)-5-hydroxy-2-adamantyl)carbamoyl]-pyridin-2-yl]pyrrolidin-3-yl]acetic acid | 1H NMR (400.13 MHz, DMSO-d6) 1.33-1.4 (2H, m), 1.45-1.78 (13H, m), 1.9-2.2 (8H, m), 2.36-2.48 (2H, m), 2.53-2.58 (1H, m), 3.08 (1H, dd), 3.37-3.41 (1H, m), 3.5-3.62 (1H, m), 3.63-3.75 (1H, m), 3.84-3.9 (1H, m), 3.95-4.04 (1H, m), 4.37 (1H, s), 6.12 (1H, d), 7.52 (1H, m), 7.64 (1H, d), 12.2 (1H, s). | 500; HPLC tR = 2.25 min. |
| | 94 | 2-[(3S)-1-[6-cyclopentylsulfanyl-5-[[(2r,5s)-5-hydroxy-2-adamantyl]carbamoyl]-pyridin-2-piperidyl]acetic acid | 1H NMR (400.13 MHz, DMSO-d6) 1.22-1.74 (17H, d), 1.82-2.26 (11H, m), 2.72-2.79 (1H, m), 2.92-3.01 (1H, m), 3.84-3.89 (1H, m), 3.93-4.01 (1H, m), 4.15-4.22 (1H, m), 4.26-4.32 (1H, m), 4.37 (1H, s), 6.48 (1H, d), 7.60 (1H, d), 7.61 (1H, d), 12.08 (1H, s) | 514; HPLC tR = 2.34 min |
| | 95 | 2-[(3R)-1-[6-cyclopentylsulfanyl-5-[((2r,5s)-5-hydroxy-2-adamantyl)carbamoyl]-pyridin-2-yl]pyrrolidin-3-yl]acetic acid | 1H NMR (400.13 MHz, DMSO-d6) 1.31-1.37 (2H, m), 1.49-1.73 (13H, m), 1.94-2.18 (8H, m), 2.42 (2H, d), 2.53-2.60 (1H, m), 3.08-3.12 (1H, m), 3.36-3.44 (1H, m), 3.53-3.60 (1H, m), 3.68-3.75 (1H, m), 3.84-3.89 (1H, m), 3.96-4.04 (1H, m), 4.37 (1H, s), 6.12 (1H, d), 7.52 (1H, d), 7.64 (1H, d), 12.14 (1H, s) | 500; HPLC tR = 2.22 min. |
| | 96 | (3R)-1-[6-cyclopentylsulfanyl-5-[((2r,5s)-5-hydroxy-2-adamantyl)carbamoyl]-pyridin-2-yl]pyrrolidine-3-carboxylic acid | 1H NMR (400.13 MHz, DMSO-d6) 1.31-1.38 (2H, m), 1.50-1.73 (12H, m), 1.92-2.38 (9H, m), 3.19-3.24 (1H, m), 3.46-3.53 (2H, m), 3.61-3.68 (2H, m), 3.84-3.89 (1H, m), 3.97-4.05 (1H, m), 4.37 (1H, s), 6.17 (1H, d), 7.54 (1H, d), 7.64 (1H, d), 12.46 (1H, s) | 486; HPLC tR = 2.14 min. |

-continued

| Compound | Ex | Name | ¹H NMR δ | MS m/e MH⁺ |
|---|---|---|---|---|
| | 97 | (2S)-1-[6-cyclopentylsulfanyl-5-[((2r,5s)-5-hydroxy-2-adamantyl)carbamoyl]-pyridin-2-yl]pyrrolidine-2-carboxylic acid | 1H NMR (400.13 MHz, DMSO-d6) 1.32-1.73 (14H, m), 1.92-2.07 (9H, m), 2.17-2.34 (2H, m), 3.41-3.57 (2H, m), 3.84-3.89 (1H, m), 3.95-4.02 (1H, m), 4.36 (1H, s), 4.50-4.55 (1H, m), 6.18 (1H, d), 7.58-7.63 (2H, m), 12.40 (1H, s) | 486; HPLC tR = 2.06 min. |
| | 98 | (1R,5S)-3-[6-cyclopentylsulfanyl-5-[((2r,5s)-5-hydroxy-2-adamantyl)carbamoyl]-pyridin-2-yl]-3-azabicyclo [3.1.0] hexane-6-carboxylic acid | 1H NMR (400.13 MHz, DMSO-d6) 1.32-1.39 (3H, m), 1.49-1.72 (12H, m), 1.93-2.04 (5H, m), 2.09-2.21 (4H, m), 3.48-3.53 (2H, m), 3.78-3.88 (3H, m), 3.95-4.02 (1H, m), 4.36 (1H, s), 6.14 (1H, d), 7.56 (1H, d), 7.61 (1H, d), 12.19 (1H, s) | 498; HPLC tR = 2.15 min. |
| | 99 | 1-[6-cyclopentylsulfanyl-5-[((2r,5s)-5-hydroxy-2-adamantyl)carbamoyl)-pyridin-2-yl]piperidine-4-carboxylic acid | 1H NMR (400.13 MHz, DMSO-d6) 1.30-1.37 (2H, m), 1.47-1.73 (14H, m), 1.84-1.88 (2H, m), 1.94-2.14 (7H, m), 2.52-2.62 (1H, m), 3.03-3.10 (2H, m), 3.84-3.89 (1H, m), 3.93-4.00 (1H, m), 4.22-4.29 (2H, m), 4.36 (1H, s), 6.53 (1H, d), 7.59-7.64 (2H, m), 12.19 (1H, s) | 500; HPLC tR = 2.21 min. |

Intermediate 13

6-chloro-2-cyclopentylsulfanyl-N-((2r,5s)-5-hydroxy-2-adamantyl)pyridine-3-carboxamide

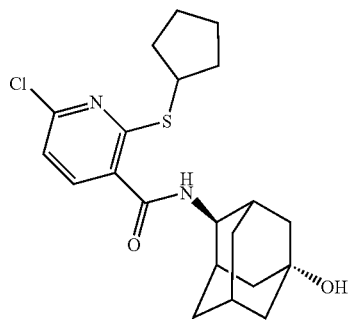 [SMILES: O=C(N[C@H]1C2CC3CC1C[C@](O)(C3)C2)c1ccc(Cl)nc1SC1CCCC1]

This intermediate was prepared in an analogous manner to that of intermediate 12

1H NMR (400.13 MHz, DMSO-d6) δ 1.31-1.37 (2H, m), 1.47-1.74 (12H, m), 1.94-2.00 (3H, m), 2.04-2.09 (2H, m), 2.12-2.20 (2H, m), 3.90-3.97 (2H, m), 4.39 (1H, s), 7.25 (1H, d), 7.71 (1H, d), 8.22 (1H, d)

m/z (ESI+) (M+H)+=407; HPLC $t_R$=2.52 min.

The following Examples were prepared in a similar manner to Example 1, using Intermediate 14 and an appropriate aminoester starting material:

| Compound | Ex | Name | ¹H NMR δ | MS m/e MH⁺ |
|---|---|---|---|---|
| | 100 | 2-[(3R)-1-[6-cyclohexylsulfanyl-5-[((2r,5s)-5-hydroxy-2-adamantyl)carbamoyl]-pyridin-2-yl]pyrrolidin-3-yl]acetic acid | 1H NMR (300.072 MHz, CDCl3) 1.21-1.85 (m, 16H), 1.85-1.99 (m, 4H), 2.05-2.36 (m, 6H), 2.48-2.58 (m, 2H), 2.74 (quintet, 1H), 3.17 (t, 1H), 3.48 (q, 1H), 3.57-3.70 (m, 1H), 3.74-3.87 (m, 1H), 3.92-4.05 (m, 1H), 4.18-4.27 (m, 1H), 6.08 (d, 1H), 7.22 (d, 1H), 7.92 (d, 1H) | 514 |
| | 101 | (2S)-1-[6-cyclohexylsulfanyl-5-[((2r,5s)-5-hydroxy-2-adamantyl)carbamoyl]-pyridin-2-yl]pyrrolidine-2-carboxylic acid | 1H NMR (300.073 MHz, DMSO-d6) 1.13-1.76 (m, 17H), 1.80-2.11 (m, 10H), 2.16-2.39 (m, 1H), 2.94-3.66 (m, 1H), 3.74-3.89 (m, 2H), 4.39 (s, 1H), 4.47 (d, 1H), 6.15 (d, 1H), 7.53-7.64 (m, 2H) | 500 |
| | 102 | (3R)-1-[6-cyclohexylsulfanyl-5-[((2r,5s)-5-hydroxy-2-adamantyl)carbamoyl]-pyridin-2-yl]pyrrolidine-3-carboxylic acid | 1H NMR (300.073 MHz, DMSO-d6) 1.16-1.50 (m, 7H), 1.49-1.84 (m, 9H), 1.85-2.10 (m, 7H), 2.10-2.29 (m, 2H), 3.03-3.55 (m, 3H), 3.56-3.69 (m, 2H), 3.71-3.91 (m, 2H), 4.30-4.48 (m, 1H), 6.15 (d, 1H), 7.55 (d, 1H), 7.60 (d, 1H) | 500 |
| | 103 | 2-[(3S)-1-[6-cyclohexylsulfanyl-5-[[(2r,5s)-5-hydroxy-2-adamantyl]carbamoyl]-piperidyl]acetic acid | 1H NMR (400.13 MHz, DMSO-d6) 1.25-1.46 (9H, m), 1.55-1.76 (10H, m), 1.80-2.07 (9H, m), 2.13-2.27 (2H, m), 2.73-2.79 (1H, m), 2.93-3.01 (1H, m), 3.68-3.77 (1H, m), 3.84-3.89 (1H, m), 4.17-4.28 (2H, m), 4.37 (1H, s), 6.48 (1H, d), 7.58-7.63 (2H, m), 12.09 (1H, s) | 528; HPLC tR = 2.47 min |

Intermediate 14

6-chloro-2-cyclohexylsulfanyl-N-((2r,5s)-5-hydroxy-2-adamantyl)pyridine-3-carboxamide

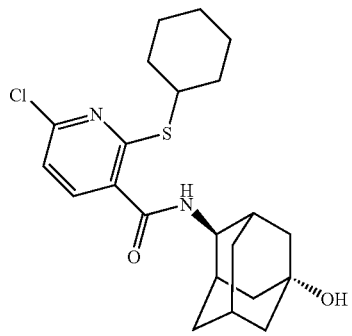 [SMILES: O=C(N[C@H]1C2CC3CC1C[C@](O)(C3)C2)c1ccc(Cl)nc1SC1CCCCC1]

This intermediate was prepared in an analogous manner to that of intermediate 12

1H NMR (400.13 MHz, DMSO-d6) δ 1.32-1.48 (7H, m), 1.56-1.74 (9H, m), 1.92-2.09 (7H, m), 3.74-3.79 (1H, m), 3.88-3.93 (1H, m), 4.39 (1H, s), 7.25 (1H, d), 7.70 (1H, d), 8.23 (1H, d)

m/z (ESI+) (M+H)+=421; HPLC $t_R$=2.64 min.

The following Examples were prepared in a similar manner to Example 1, using Intermediate 15 and an appropriate aminoester starting material:

| Compound | Ex | Name | $^1$H NMR δ | MS m/e MH+ |
|---|---|---|---|---|
| | 104 | 2-[(3S)-1-[5-[[(2r,5s)-5-hydroxy-2-adamantyl]carbamoyl]-6-(3-methylbutylsulfanyl)pyridin-2-yl]-3-piperidyl]acetic acid | 1H NMR (400.13 MHz, DMSO-d6) 0.89 (6H, d), 1.22-1.56 (6H, m), 1.59 - 1.74 (8H, m), 1.79 -2.06 (7H, m), 2.12-2.26 (2H, m), 2.73-2.79 (1H, m), 2.92-3.00 (2H, m), 3.03-3.11 (1H, m), 3.83-3.88 (1H, m), 4.21-4.29 (2H, m), 4.43 (1H, s), 6.49 (1H, d), 7.61 (1H, d), 7.67 (1H, d), 12.16 (1H, s) | 516; HPLC tR = 2.46 min. |
| | 105 | (3R)-1-[5-[((2r,5s)-5-hydroxy-2-adamantyl)carbamoyl]-6-(3-methylbutylsulfanyl-pyridin-2-yl]pyrrolidine-3-carboxylic acid | 1H NMR (400.13 MHz, DMSO-d6) 0.91 (6H, d), 1.31-1.38 (2H, m), 1.49 - 1.56 (2H, m), 1.62-1.73 (7H, m), 1.92-2.08 (5H, m), 2.16-2.25 (2H, m), 3.04-3.10 (2H, m), 3.17-3.24 (1H, m), 3.45-3.53 (2H, m), 3.65-3.69 (2H, m), 3.87-3.88 (1H, m), 4.37 (1H, s), 6.17 (1H, d), 7.55 (1H, d), 7.64 (1H, d), 12.45 (1H, s) | 488; HPLC tR = 2.25 min. |
| | 106 | (1R,5S)-3-[5-[[(2r,5s)-5-hydroxy-2-adamantyl)carbamoyl]-6-(3-methylbutylsulfanyl)pyridin-2-yl]-3-azabicyclo[3.1.0]hexane-6-carboxylic acid | 1H NMR (400.13 MHz, DMSO-d6) 0.91 (6H, d), 1.30-1.40 (3H, m), 1.48-1.54 (2H, m), 1.62-1.73 (7H, m), 1.92-2.07 (5H, m), 2.18-2.22 (2H, m), 3.04-3.08 (2H, m), 3.47-3.54 (2H, m), 3.79 - 3.87 (3H, m), 4.37 (1H, s), 6.15 (1H, d), 7.57-7.62 (2H, m), 12.20 (1H, s) | 500; HPLC tR = 2.26 min. |

Intermediate 15

6-chloro-N-((2r,5 s)-5-hydroxy-2-adamantyl)-2-(3-methylbutylsulfanyl)pyridine-3-carboxamide

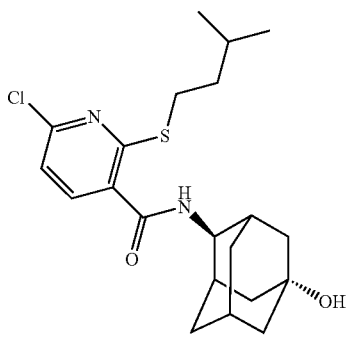 [SMILES: CC(C)CCSc1nc(Cl)ccc1C(=O)N[C@H]1C2CC3CC1C[C@](O)(C3)C2]

This intermediate was prepared in an analogous manner to that of intermediate 12

1H NMR (400.13 MHz, DMSO-d6) δ 0.86-0.98 (6H, m), 1.30-1.38 (2H, m), 1.48-1.53 (2H, m), 1.62-1.74 (7H, m), 1.94-2.00 (3H, m), 2.07-2.10 (2H, m), 3.07-3.11 (2H, m), 3.89-3.94 (1H, m), 4.39 (1H, s), 7.26 (1H, d), 7.72 (1H, d), 8.23 (1H, d)

m/z (ESI+) (M+H)+=409; HPLC $t_R$=2.61 min.

The following Example was prepared in a similar manner to Example 1, using Intermediate 16 and an appropriate aminoester starting material:

Intermediate 16

2-benzylsulfanyl-6-chloro-N-((2r,5s)-5-hydroxy-2-adamantyl)pyridine-3-carboxamide

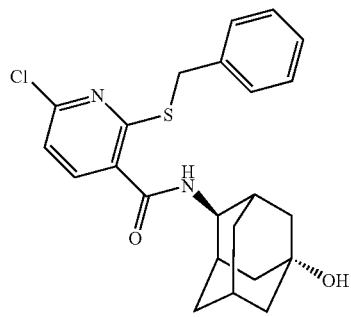 [SMILES: O=C(N[C@H]1C2CC3CC1C[C@](O)(C3)C2)c1ccc(Cl)nc1SCc1ccccc1]

This intermediate was prepared in an analogous manner to that of intermediate 12

$^1$H NMR (400.13 MHz, DMSO-$d_6$) δ1.28-1.35 (2H, m), 1.58-1.73 (6H, m), 1.89-2.06 (5H, m), 3.86-3.90 (1H, m), 4.33 (2H, s), 4.44 (1H, s), 7.21-7.25 (1H, m), 7.28-7.32 (3H, m), 7.40-7.44 (2H, m), 7.78 (1H, d), 8.30 (1H, d)

m/z (ESI+) (M+H)+=429; HPLC $t_R$=2.44 min.

The following Example was prepared in a similar manner to Example 1, using Intermediate 17 and an appropriate aminoester starting material:

| Compound | Ex | Name | $^1$H NMR δ | MS m/e MH+ |
|---|---|---|---|---|
|  | 107 | 2-[(3S)-1-[6-benzylsulfanyl-5-[[(2r,5s)-5-hydroxy-2-adamantyl]carbamoyl]-pyridin-2-yl]-3-piperidyl]acetic acid | 1H NMR (400.13 MHz, DMSO-d6) 1.21-1.46 (4H, m), 1.57-1.73 (8H, m), 1.78-2.05 (7H, m), 2.11-2.24 (2H, m), 2.72-2.80 (1H, m), 2.92-3.00 (1H, m), 3.82-3.87 (1H, m), 4.17-4.35 (4H, m), 6.51 (1H, d), 7.19-7.23 (1H, m), 7.26-7.28 (2H, m), 7.35-7.37 (2H, m), 7.65-7.70 (2H, m) | 536; HPLC tR = 2.30 min |

| Compound | Ex | Name | ¹H NMR δ | MS m/e MH⁺ |
|---|---|---|---|---|
|  | 108 | 2-[(3S)-1-[5-[[(2r,5s)-5-hydroxy-2-adamantyl]carbamoyl]-6-phenethylsulfanyl-pyridin-2-yl]-3-piperidyl]acetic acid | 1H NMR (400.13 MHz, DMSO-d6) 1.21-1.51 (4H, m), 1.59-1.74 (7H, m), 1.79-2.06 (8H, m), 2.10-2.22 (2H, m), 2.74-2.80 (1H, m), 2.87-3.02 (3H, m), 3.22-3.40 (2H, m), 3.83-3.88 (1H, m), 4.24-4.30 (1H, m), 4.43 (1H, s), 6.52 (1H, d), 7.18-7.31 (5H, m), 7.62-7.68 (2H, d), 12.17 (1H, s) | 550; HPLC tR = 2.41 min |

Intermediate 17

6-chloro-N-((2r,5 s)-5-hydroxy-2-adamantyl)-2-phenethylsulfanyl-pyridine-3-carboxamide

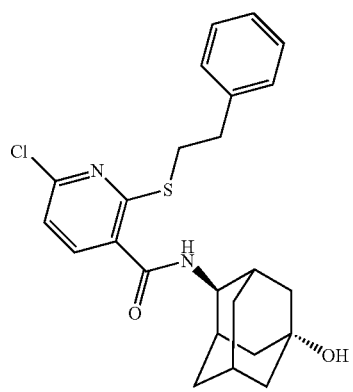 [SMILES: O=C(N[C@H]1C2CC3CC1C[C@](O)(C3)C2)c1ccc(Cl)nc1SCCc1ccccc1]

¹H NMR (400.13 MHz, DMSO-d₆) δ1.29-1.37 (2H, m), 1.60-1.66 (4H, m), 1.68-1.75 (2H, m), 1.91-2.08 (5H, m), 2.89-2.93 (2H, m), 3.27-3.33 (2H, m), 3.87-3.92 (1H, m), 4.46 (1H, s), 7.20-7.26 (1H, m), 7.30-7.34 (5H, m), 7.77 (1H, d), 8.30 (1H, d)

m/z (ESI+) (M+H)+=443; HPLC t$_R$=2.59 min

The following Examples were prepared in a similar manner to Example 1, using Intermediate 18 and an appropriate aminoester starting material:

| Compound | Ex | Name | ¹H NMR δ | MS m/e MH⁺ |
|---|---|---|---|---|
|  | 109 | 2-[(3S)-1-[5-[[(2r,5s)-5-hydroxy-2-adamantyl]carbamoyl]-6-propoxy-pyridin-2-yl]-3-piperidyl]acetic acid | 1H NMR (400.13 MHz, DMSO-d6) 1.00 (3H, t), 1.23-1.34 (1H, m), 1.38-1.51 (3H, m), 1.63-1.93 (13H, m), 1.99-2.08 (3H, m), 2.13-2.28 (2H, m), 2.79-2.86 (1H, m), 2.98-3.06 (1H, m), 3.97-4.02 (1H, m), 4.09-4.16 (1H, m), 4.22-4.28 (1H, m), 4.32-4.40 (2H, m), 4.42 (1H, s), 6.44 (1H, d), 7.96 (1H, d), 8.03 (1H, d), 12.09 (1H, s) | 472; HPLC tR = 2.21 min |

| Compound | Ex | Name | ¹H NMR δ | MS m/e MH⁺ |
|---|---|---|---|---|
| 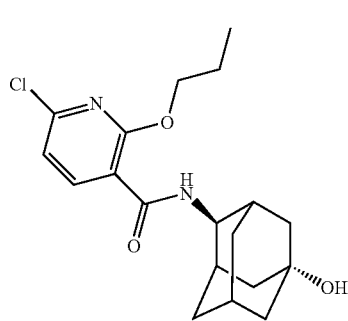 [SMILES: CCCOc1nc(Cl)ccc1C(=O)N[C@H]1C2CC3CC1C[C@](O)(C3)C2] | 110 | 2-[1-[5-[((2r,5s)-5-hydroxy-2-adamantyl)carbamoyl]-6-propoxy-pyridin-2-yl]-3-piperidyl]-2-methyl-propanoic acid | 1H NMR (400.13 MHz, DMSO-d6) 0.99 (3H, t), 1.10 (3H, s), 1.15 (3H, s), 1.39 (2H, t), 1.47 (2H, d), 1.66 (5H, m), 1.73 (6H, m), 1.78-1.86 (2H, m), 2.02-2.07 (3H, m), 2.69 (1H, t), 2.84 (1H, t), 3.90-3.95 (1H, m), 4.25-4.28 (1H, m), 4.34-4.40 (2H, m), 4.42 (1H, s), 4.46-4.50 (1H, m), 6.41 (1H, d), 7.96 (1H, d), 8.03 (1H, d), 12.19 (1H, s) | 500; HPLC tR = 2.44 min. |

Intermediate 18

6-chloro-N-((2r,5s)-5-hydroxy-2-adamantyl)-2-propoxy-pyridine-3-carboxamide

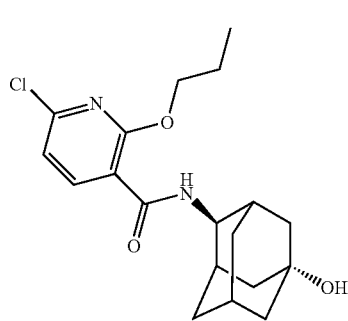 [SMILES: CCCOc1nc(Cl)ccc1C(=O)N[C@H]1C2CC3CC1C[C@](O)(C3)C2]

Bis-sodium hexamethyldisilylamide 1.0M in THF (1 ml, 1 mmol) was added to 2,6-dichloro-N-(5-hydroxyadamantan-2-yl)nicotinamide (341 mg, 1 mmol) and heated at 150° C. for 2 hours. The reaction mixture was diluted with EtOAc (60 mL), and washed sequentially with water (20 mL) and saturated brine (20 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford 6-chloro-N-(5-hydroxyadamantan-2-yl)-2-propoxynicotinamide (341 mgs, 93%) as a white solid.

¹H NMR (400.13 MHz, DMSO-d₆) δ0.99 (3H, t), 1.41-1.45 (2H, m), 1.64-1.67 (4H, m), 1.72-1.84 (5H, m), 2.01-2.08 (3H, m), 3.96-4.01 (1H, m), 4.34 (2H, t), 4.49 (1H, s), 7.22 (1H, d), 8.10 (1H, d), 8.16 (1H, d)

m/z (ESI+) (M+H)+=365; HPLC t_R=2.39 min

Example 111

(1R,5S,6r)-3-(6-(Cyclopentylthio)-5-(3-(pyridin-3-yl)pyrrolidine-1-carbonyl)pyridin-2-yl)-3-azabicyclo[3.1.0]hexane-6-carboxylic acid

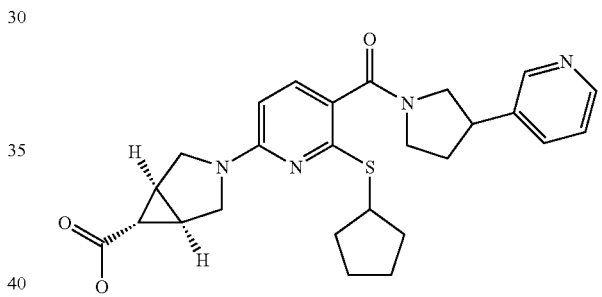

Lithium hydroxide monohydrate (102 mg, 2.44 mmol) was added to a stirred solution of (1R,5 S,6r)-methyl 3-(6-(cyclopentylthio)-5-(3-(pyridin-3-yl)pyrrolidine-1-carbonyl)pyridin-2-yl)-3-azabicyclo[3.1.0]hexane-6-carboxylate (400 mg, 0.81 mmol) in methanol (5 mL)/water (2 mL). The resulting solution was stirred at ambient temperature for 24 hours. The bulk of the organic solvent was removed in vacuo and the resulting solution was acidified with 1N citric acid. The resulting suspension was extracted with EtOAc (3×30 ml). The combined organic layers were washed with HCl solution (pH3, 30 mL), sat brine (30 mL) then dried (MgSO₄), filtered and evaporated to yield (1R,5S,6r)-3-(6-(cyclopentylthio)-5-(3-(pyridin-3-yl)pyrrolidine-1-carbonyl)pyridin-2-yl)-3-azabicyclo[3.1.0]hexane-6-carboxylic acid (195 mg, 50%)

1H NMR (400.13 MHz, DMSO-d6) 1.25 (1H, s), 1.40 (1H, s), 1.50-1.72 (6H, m), 1.90-2.10 (1H, m), 2.10-2.20 (3H, m), 2.29-2.35 (1H, m), 3.30-3.55 (5H, m), 3.64 (1H, s), 3.72-3.95 (3H, m), 4.01-4.07 (1H, m), 6.16 (1H, d), 7.30-7.80 (2H, m), 7.71 (1H, s), 8.40-8.60 (2H, m), 12.18 (1H, s)

m/z (ESI+) (M+H)+=479

The (1R,5S,6r)-methyl 3-(6-(cyclopentylthio)-5-(3-(pyridin-3-yl)pyrrolidine-1-carbonyl)pyridin-2-yl)-3-azabicyclo[3.1.0]hexane-6-carboxylate used as starting material was prepared as described below Oxalyl chloride (0.274 mL, 3.15 mmol) was added dropwise to a stirred solution of 2-(cyclopentylthio)-6-((1R,5S,6r)-6-(methoxycarbonyl)-3-azabicyclo[3.1.0]hexan-3-yl)nicotinic acid (380 mg, 1.05 mmol) in DCM (5 mL)/DMF (1 drop) at 0° C., under nitrogen. The resulting solution was allowed to warm to ambient temperature and stirred for 2 hours. The reaction mixture was evaporated to dryness and redissolved in DCM (8 mL). The solution was cooled to 0° C. then treated with a solution of 3-pyrrolidin-3-ylpyridine (171 mg, 1.15 mmol) and triethylamine (0.438 mL, 3.15 mmol) in DCM (5 mL). The resulting reaction was allowed to warm to ambient temperature and stirred at this temperature for 2 hours. The reaction mixture was diluted with DCM (50 mL), and washed sequentially with 1N citric acid (30 mL), water (30 mL), and saturated brine (30 mL). The organic layer was dried over MgSO4, filtered and evaporated to afford crude product. The crude product was purified by flash silica chromatography, elution gradient 0 to 5% MeOH in DCM. Pure fractions were evaporated to dryness to afford (1R,5S,6r)-methyl 3-(6-(cyclopentylthio)-5-(3-(pyridin-3-yl)pyrrolidine-1-carbonyl)pyridin-2-yl)-3-azabicyclo[3.1.0]hexane-6-carboxylate (400 mg, 77%) as a yellow oil.

m/z (ESI+) (M+H)+=493; HPLC t$_R$=1.84 min.

1H NMR (400.13 MHz, CDCl3) δ 1.58-1.70 (4H, m), 1.71-1.80 (3H, m), 2.11-2.20 (3H, m), 2.25 (2H, s), 2.36 (1H, s), 3.40-3.60 (4H, m), 3.69 (4H, s), 3.74-3.87 (4H, m), 4.05-4.12 (2H, m), 5.99 (1H, d), 7.20-7.30 (2H, m), 7.57 (1H, s), 8.40-8.60 (1H, m)

The 2-(cyclopentylthio)-6-((1R,5S,6r)-6-(methoxycarbonyl)-3-azabicyclo[3.1.0]hexan-3-yl)nicotinic acid used as starting material was prepared as described below A solution of (1R,5S,6r)-methyl 3-(5-(tert-butoxycarbonyl)-6-(cyclopentylthio)pyridin-2-yl)-3-azabicyclo[3.1.0]hexane-6-carboxylate (Intermediate 21, 968 mg, 2.31 mmol) in hydrogen chloride (4M in dioxane) (30 ml, 120.00 mmol) was stirred at ambient temperature for 5 hours. The solvent was removed in vacuo to yield 2-(cyclopentylthio)-6-((1R,5S,6r)-6-(methoxycarbonyl)-3-azabicyclo[3.1.0]hexan-3-yl)nicotinic acid (760 mg, 91%) as a yellow solid.

m/z (ESI+) (M+H)+=363; HPLC t$_R$=2.48 min.

1H NMR (300.072 MHz, CDCl3) δ 1.50-1.80 (7H, m), 2.10-2.25 (2H, m), 2.29 (2H, s), 3.61-3.71 (5H, m), 3.80-4.00 (2H, m), 4.02-4.11 (1H, m), 6.00 (1H, d), 8.03 (1H, d)

Intermediate 19 tert-butyl 2,6-dichloropyridine-3-carboxylate

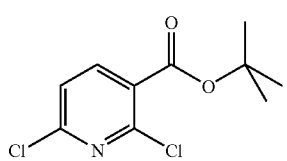

A suspension of 2,6-dichloronicotinic acid (15 g, 78.13 mmol) in Toluene (170 mL) was warmed to 90° C. under nitrogen. To this suspension was added N,N-dimethylformamide di-tert-butyl acetal (74.9 mL, 312.50 mmol) dropwise. The resulting solution was stirred at 90° C. for 5 hours. The reaction mixture was evaporated to dryness and redissolved in EtOAc (200 mL), and washed sequentially with saturated NaHCO3 (100 mL) and saturated brine (50 mL). The organic layer was dried over MgSO4, filtered and evaporated to afford crude product. The crude product was purified by flash silica chromatography, elution gradient 10 to 30% EtOAc in isohexane. Pure fractions were evaporated to dryness to afford tert-butyl 2,6-dichloronicotinate (17.13 g, 88%) as a pale yellow oil.

1H NMR (300.073 MHz, DMSO-d6) δ 1.54 (9H, s), 7.67 (1H, d), 8.23 (1H, d)

Intermediate 20 methyl (1R,5S)-3-[6-chloro-5-[(2-methylpropan-2-yl)oxycarbonyl]pyridin-2-yl]-3-azabicyclo[3.1.0]hexane-6-carboxylate

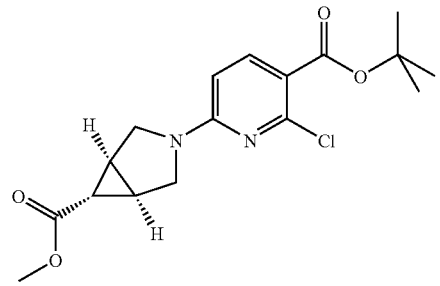 [SMILES: COC(=O)[C@H]1[C@@H]2CN(c3ccc(C(=O)OC(C)(C)C)c(Cl)n3)C[C@@H]21]

A suspension of (1R,5S,6r)-methyl 3-azabicyclo[3.1.0]hexane-6-carboxylate (2.99 g, 21.16 mmol), tert-butyl 2,6-dichloronicotinate (5 g, 20.15 mmol) and triethylamine (3.37 mL, 24.18 mmol) in DMA (50 mL) was stirred at ambient temperature overnight. The reaction mixture was evaporated to dryness and redissolved in EtOAc (150 mL), and washed sequentially with 1N citric acid (50 mL), water (50 mL), and saturated brine (50 mL). The organic layer was dried over MgSO4, filtered and evaporated to afford crude product. The crude product was purified by flash silica chromatography, elution gradient 10 to 30% EtOAc in isohexane. Pure fractions were evaporated to afford (1R,5S,6r)-methyl 3-(5-(tert-butoxycarbonyl)-6-chloropyridin-2-yl)-3-azabicyclo[3.1.0]hexane-6-carboxylate (2.18 g, 31%)

1H NMR (400.13 MHz, CDCl3) δ 1.47 (1H, t), 1.50 (9H, s), 2.19-2.21 (2H, m), 3.50-3.53 (2H, m), 3.62 (3H, s), 3.77 (2H, d), 6.12 (1H, d), 7.86 (1H, d)

m/z (ESI+) (M+H)+=353; HPLC t$_R$=2.75 min.

Intermediate 21 methyl (1R,5S)-3-[6-cyclopentylsulfanyl-5-[(2-methylpropan-2-yl)oxycarbonyl]pyridin-2-yl]-3-azabicyclo[3.1.0]hexane-6-carboxylate

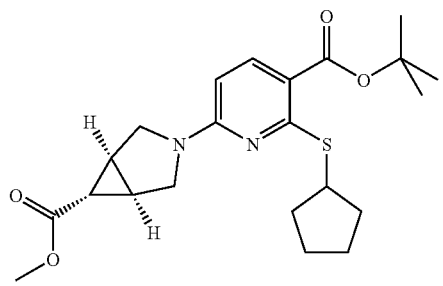 [SMILES: COC(=O)[C@H]1[C@@H]2CN(c3ccc(C(=O)OC(C)(C)C)c(SC4CCCC4)n3)C[C@@H]21]

Cyclopentanethiol (1.157 mL, 10.81 mmol) was added to a stirred suspension of potassium tert-butoxide (0.416 g, 3.71 mmol) in DMA (4 ml). The resulting suspension was stirred at ambient temperature for 10 minutes under nitrogen then treated with a solution of (1R,5S,6r)-methyl 3-(5-(tert-butoxycarbonyl)-6-chloropyridin-2-yl)-3-azabicyclo[3.1.0] hexane-6-carboxylate (1.09 g, 3.09 mmol) in DMA (5 ml). The resulting reaction was stirred at ambient temperature for 2 hours then treated with sat NH4Cl solution (15 ml). The reaction mixture was diluted with EtOAc (75 mL), and washed sequentially with saturated NH4Cl (25 mL), water (50 mL), and saturated brine (50 mL). The organic layer was dried over MgSO4, filtered and evaporated to afford crude product. The crude product was purified by flash silica chromatography, elution gradient 10 to 30% EtOAc in isohexane. Pure fractions were evaporated to dryness to afford (1R,5S, 6r)-methyl 3-(5-(tert-butoxycarbonyl)-6-(cyclopentylthio) pyridin-2-yl)-3-azabicyclo[3.1.0]hexane-6-carboxylate (0.968 g, 74.9%) as a colourless oil.

1H NMR (300.072 MHz, CDCl3) δ 1.55-1.82 (16H, m), 2.10-2.22 (2H, m), 2.27 (2H, t), 3.60 (2H, d), 3.70 (3H, s), 3.87 (2H, d), 4.00-4.08 (1H, m), 5.95 (1H, d), 7.90 (1H, d)

m/z (ESI+) (M+H)+=419; HPLC $t_R$=3.43 min.

The following Examples were prepared in a similar manner to Example 111, using Intermediate 22 and an appropriate aminoester starting material:

| Compound | Ex | Name | $^1$H NMR δ | MS m/e MH+ |
|---|---|---|---|---|
| | 112 | (1S,5R)-3-[6-cyclohexyl-sulfanyl-5-(3-pyridin-3-ylpyrrolidine-1-carbonyl)pyridin-2-yl]-3-azabicyclo[3.1.0]hexane-6-carboxylic acid | 1H NMR (400.13 MHz, DMSO-d6) 1.20-1.32 (4H, m), 1.38-1.45 (4H, m), 1.60 (1H, d), 1.72 (2H, s), 1.95-2.05 (3H, m), 2.18 (2H, s), 2.29-2.35 (1H, m), 3.25-3.49 (4H, m), 3.71 (4H, d), 6.16 (1H, d), 7.34 (2H, d), 7.65-7.80 (1H, m), 8.45-8.50 (2H, m), 11.80 (1H, br s) | 493 |

Intermediate 22 methyl (1R,5S)-3-[6-cyclohexylsulfanyl-5-[(2-methylpropan-2-yl)oxycarbonyl]pyridin-2-yl]-3-azabicyclo[3.1.0]hexane-6-carboxylate

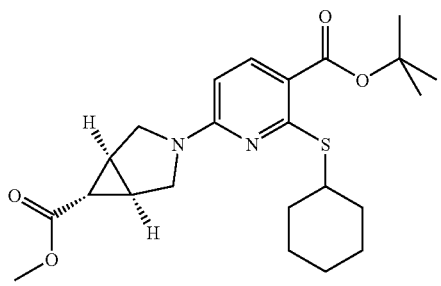 [SMILES: COC(=O)[C@H]1[C@@H]2CN(c3ccc(C(=O)OC(C)(C)C)c(SC4CCCCC4)n3)C[C@@H]21]

Intermediate 22 was prepared from intermediate 20 using an analogous method to that used to prepare intermediate 21

1H NMR (400.13 MHz, CDCl3) δ 1.24-1.46 (5H, m), 1.49 (9H, s), 1.52 (1H, t), 1.55-1.65 (1H, m), 1.73-1.76 (2H, m), 2.00-2.10 (2H, m), 2.20-2.22 (2H, m), 3.52 (2H, d), 3.63 (3H, s), 3.70-3.85 (3H, m), 5.87 (1H, d), 7.83 (1H, d)

m/z (ESI+) (M+H)+=433; HPLC $t_R$=3.60 min.

The following Examples were prepared in a similar manner to Example 111, using Intermediate 24 and an appropriate aminoester starting material:

| Compound | Ex | Name | ¹H NMR δ | MS m/e MH⁺ |
|---|---|---|---|---|
| | 113 | 2-[(3S)-1-[6-propylsulfanyl-5-(3-pyridin-3-ylpyrrolidine-1-carbonyl)pyridin-2-yl]-3-piperidyl]acetic acid | 1H NMR (500.13 MHz, DMSO-d6) 0.99 (3H, t), 1.28-1.38 (1H, m), 1.51-1.54 (1H, m), 1.66-1.74 (3H, m), 1.86-1.90 (1H, m), 1.94-1.98 (1H, m), 2.01-2.05 (1H, m), 2.17-2.28 (2H, m), 2.34-2.38 (1H, m), 2.80-2.86 (1H, m), 3.00-3.07 (1H, m), 3.09-3.13 (2H, m), 3.38-3.45 (1H, m), 3.47-3.54 (2H, m), 3.57-3.64 (1H, m), 3.82-3.86 (1H, m), 4.07-4.13 (1H, m), 4.20-4.24 (1H, m), 6.48 (1H, d), 7.31-7.35 (2H, m), 7.69 (1H, d), 8.44-8.46 (1H, m), 8.53 (1H, d), 11.50 (1H, s) | 469 |
| | 114 | 2-[(3S)-1-[6-propylsulfanyl-5-(3-pyridin-2-ylpyrrolidine-1-carbonyl)pyridin-2-yl]-3-piperidyl]acetic acid | 1H NMR (400.13 MHz, CDCl3) 0.99 (3H, t), 1.27 (1H, m), 1.50-1.62 (1H, m), 1.63-1.78 (3H, m), 1.85-1.99 (1H, m), 2.00-2.10 (1H, m), 2.20-2.45 (4H, m), 2.68-2.80 (1H, m), 2.90-3.00 (1H, m), 3.01-3.09 (2H, m), 3.57-3.94 (5H, m), 4.10-4.30 (2H, m), 6.29-6.33 (1H, m), 7.19-7.35 (3H, m), 7.60-7.70 (1H, m), 8.58 (1H, d) | 469 |
| | 115 | 2-[(3S)-1-[5-(piperidine-1-carbonyl)-6-propylsulfanyl-pyridin-2-yl]-3-piperidyl]acetic acid | 1H NMR (400.13 MHz, DMSO-d6) 0.94 (3H, t), 1.20-1.30 (1H, m), 1.44-1.49 (6H, m), 1.58-1.70 (5H, m), 1.81-1.89 (2H, m), 2.13-2.26 (2H, m), 2.71-2.76 (2H, m), 2.88-2.95 (1H, m), 2.98-3.09 (2H, m), 4.15 (1H, d), 4.27 (1H, d), 6.40 (1H, d), 7.25 (1H, d), 12.05 (1H, s) | 406 |
| | 116 | 2-[(3S)-1-[6-propylsulfanyl-5-(3-pyrazin-2-ylpyrrolidine-1-carbonyl)pyridin-2-yl]-3-piperidyl]acetic acid | 1H NMR (400.13 MHz, DMSO-d6) 0.94 (3H, s), 1.20-1.30 (1H, m), 1.35-1.50 (1H, m), 1.61-1.65 (3H, m), 1.75-1.90 (2H, m), 2.12-2.34 (4H, m), 2.65-2.75 (1H, m), 2.89-2.95 (1H, m), 2.95-3.01 (2H, m), 3.45-3.65 (5 H, m), 4.10-4.20 (1H, m), 4.23-4.33 (1H, m), 6.50 (1H, s), 7.36 (1H, d), 8.52-8.69 (3H, m), 12.03 (1H, s) | 470 |
| | 117 | 2-[(3S)-1-[5-(4,4-difluoropiperidine-1-carbonyl)-6-propylsulfanyl-pyridin-2-yl]-3-piperidyl]acetic acid | 1H NMR (300.072 MHz, CDCl3) 1.00 (3H, t), 1.31-1.39 (1H, m), 1.53-1.77 (4H, m), 1.92-2.09 (6H, m), 2.32 (2H, d), 2.75-2.82 (1H, m), 2.90-3.05 (1H, m), 3.05-3.15 (2H, m), 3.67 (4H, br s), 4.17-4.30 (2H, m), 6.33 (1H, d), 7.24 (1H, d) | 442 |
| | 118 | 2-[(3S)-1-[6-propylsulfanyl-5-[3-(trifluoromethyl)piperidine-1-carbonyl]pyridin-2-yl]-3-piperidyl]acetic acid | 1H NMR (300.072 MHz, CDCl3) 1.00 (3H, t), 1.23-1.38 (1H, m), 1.50-1.81 (7H, m), 1.93 (1H, d), 2.00-2.15 (4H, m), 2.31 (2H, d), 2.39 (1H, br s), 2.73-3.01 (4H, m), 3.02-3.16 (2H, m), 4.10-4.30 (2H, m), 6.33 (1H, d), 7.22 (1H, d) | 474 |

-continued

| Compound | Ex | Name | ¹H NMR δ | MS m/e MH⁺ |
|---|---|---|---|---|
| | 119 | 2-[(3S)-1-[6-propyl-sulfanyl-5-[4-(trilfuoro-methyl)piperidine-1-carbonyl]pyridin-2-yl]-3-piperidyl]acetic acid | 1H NMR (300.072 MHz, CDCl3) 1.00 (3H, t), 1.28-1.38 (1H, m), 1.50-1.80 (6H, m), 1.83-1.95 (3H, m), 2.00-2.15 (3H, m), 2.22-2.32 (3H, m), 2.70-2.82 (1H, m), 2.83-3.02 (3H, m), 3.04-3.15 (2H, m), 4.22 (2H, m), 6.33 (1H, d), 7.25 (1H, d) | 474 |
| | 120 | 2-[(3S)-1-[5-(4-carbamoyl-piperidine-1-carbonyl)-6-propylsulfanyl-pyridin-2-yl]-3-piperidyl]acetic acid | 1H NMR (400.13 MHz, DMSO-d6) 0.94 (3H, t), 1.18-1.22 (1H, m), 1.40-1.53 (3H, m), 1.63-1.80 (5H, m), 1.81-1.89 (2H, m), 2.14-2.26 (2H, m), 2.30-2.36 (2H, m), 2.67-2.73 (1H, m), 2.88-2.97 (1H, m), 2.99-3.09 (2H, m), 4.16 (1H, d), 4.28 (1H, d), 6.51 (1H, d), 6.81 (1H, s), 7.25 (1H, d), 7.29 (1H, s), 12.17 (1H, s) | 449 |
| | 121 | 2-[(3S)-1-[5-(cyclohexyl-cyclopropyl-carbamoyl)-6-propyl-sulfanyl-pyridin-2-yl]-3-piperidyl]acetic acid | 1H NMR (400.13 MHz, DMSO-d6) 0.43-0.53 (4H, m), 0.94 (3H, t), 1.10-1.20 (1H, m), 1.22-1.31 (3H, m), 1.40-1.50 (1H, m), 1.56-1.70 (5H, m), 1.73-1.91 (7H, m), 2.14-2.26 (2H, m), 2.53-2.62 (1H, m), 2.69-2.74 (1H, m), 2.89-2.96 (1H, m), 2.97-3.10 (2H, m), 3.80-3.90 (1H, m), 4.15 (1H, d), 4.26 (1H, d), 6.47 (1H, d), 7.30 (1H, d), 12.09 (1H, s) | 460 |
| | 122 | 2-[(3S)-1-[5-(cyclohexyl-(cyclopropyl-methyl)carbamoyl)-6-propyl-sulfanyl-pyridin-2-yl]-3-piperidyl]acetic acid | 1H NMR (400.13 MHz, DMSO-d6) 0.20 (2H, s), 0.40 (2H, s), 0.94 (3H, t), 1.08 (3H, s), 1.20-1.35 (2H, m), 1.20-1.59 (13H, m), 1.80-1.93 (2H, m), 2.14-2.25 (2H, m), 2.65-2.75 (1H, m), 2.88-2.98 (1H, m), 3.00-3.20 (3H, m), 4.14 (1H, d), 4.27 (1H, d), 6.50 (1H, d), 7.23 (1H, d), 11.90 (1H, d) | 474 |
| | 123 | 2-[(3S)-1-[5-(cyclohexyl-ethyl-carbamoyl)-6-propylsulfanyl-pyridin-2-yl]-3-piperidyl]acetic acid | 1H NMR (400.13 MHz, DMSO-d6) 0.94 (3H, t), 1.08-1.31 (5H, m), 1.34-1.45 (3H, m), 1.42-1.70 (13H, m), 1.82-1.92 (2H, m), 2.13 2.28 (2H, m), 2.80 (1H, t), 2.95 (1H, t), 3.01-3.10 (2H, m), 4.14 (1H, d), 4.27 (1H, d), 6.50 (1H, d), 7.22 (1H, d), 12.10 (1H, s) | 448 |

| Compound | Ex | Name | ¹H NMR δ | MS m/e MH⁺ |
|---|---|---|---|---|
| | 124 | 2-[(3S)-1-[5-(cyclohexyl-propan-2-yl-carbamoyl)-6-propylsulfanyl-pyridin-2-yl]-3-piperidyl] acetic acid | 1H NMR (400.13 MHz, DMSO-d6) 0.93 (3H, t), 1.10-1.85 (20 H, m), 1.81-1.90 (3H, m), 2.14-2.26 (2H, m), 2.64-2.70 (1H, m), 2.83-2.95 (1H, m), 3.06 (3H, s), 3.58 (1H, s), 4.13 (1H, d), 4.27 (1H, d), 6.48 (1H, d), 7.16 (1H, d), 12.20 (1H, s) | 462 |
| | 125 | 2-[(3S)-1-[5-[(4-hydroxy-cyclohexyl) carbamoyl]-6-propylsulfanyl-pyridin-2-yl]-3-piperidyl] acetic acid | 1H NMR (300.072 MHz, CDCl3) 1.02 (3H, t), 1.31-1.51 (5H, m), 1.52-1.63 (1H, m), 1.67- 1.79 (3H, m), 1.90-2.17 (7H, m), 2.31 (2H, d), 2.79-2.86 (1H, m), 2.93-3.07 (1H, m), 3.08-3.20 (2H, m), 3.62-3.70 (1H, m), 3.85 4.03 (1H, m), 4.18-4.32 (2H, m), 6.35 (1H, d), 6.53 (1H, d), 7.78 (1H, d) | 436 |
| | 126 | 2-[(3S)-1-[6-propylsulfanyl-5-[3-[2-(trifluoromethyl) phenyl]pyrrolidine-1-carbonyl] pyridin-2-yl]-3-piperidyl] acetic acid | 1H NMR (300.073 MHz, DMSO-d6) 0.96 (3H, t), 1.25 (2H, m), 1.64 (7H, m), 1.83-1.90 (4H, m), 2.18 (2H, m), 2.60-3.07 (4H, m), 3.72 (1H, s), 4.00-4.13 (1H, m), 6.49 (1H, s), 7.43 (3H, s), 7.65-7.88 (3H, m), 12.09 (1H, s) | 536; HPLC tR = 2.86 min. |
| | 126b | 2-[(3S)-1-[5-[((2r,5s)-5-methylsulfonyl-2-adamantyl) carbamoyl]-6-propylsulfanyl-pyridin-2-yl]-3-piperidyl] acetic acid | 1H NMR (700.03 MHz, DMSO-d6) 0.97 (3H, t), 1.20-1.32 (2H, m), 1.35-1.49 (3H, m), 1.58-1.70 (3H, m), 1.79-1.90 (2H, m), 1.90-2.00 (4H, m), 2.00-2.10 (5H, m), 2.10-2.25 (3H, m), 2.75 (1H, t), 2.83 (3H, s), 2.90-3.00 (2H, m), 3.00-3.05 (1H, m), 3.90 (1H, s), 4.20 (1H, d), 4.25 (1H, d), 6.50 (1H, d), 7.60 (1H, d), 7.75 (1H, d) | 550; HPLC tR = 2.34 min. |

Intermediate 23 tert-butyl 2-chloro-6-[(3S)-3-(methoxycarbonylmethyl)-1-piperidyl]pyridine-3-carboxylate

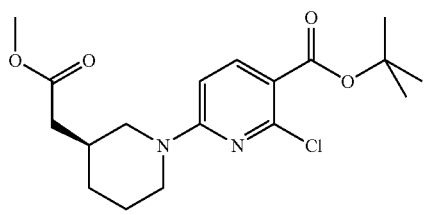 [SMILES: COC(=O)C[C@@H]1CCCN(c2ccc(C(=O)OC(C)(C)C)c(Cl)n2)C1]

Intermediate 23 was prepared from intermediate 19 using an analogous method to that used to prepare intermediate 20

¹H NMR (499.8 MHz, CDCl$_3$) δ1.23-1.31 (1H, m), 1.48-1.60 (10H, m), 1.69-1.74 (1H, m), 1.87-1.90 (1H, m), 2.01-2.05 (1H, m), 2.21-2.33 (2H, m), 2.80-2.85 (1H, m), 3.00-3.05 (1H, m), 3.68 (3H, s), 4.18 (2H, d), 6.45-6.47 (1H, m), 7.90-7.92 (1H, m)

m/z (ESI+) (M+H)+=369; HPLC t$_R$=2.99 min.

119
Intermediate 24 tert-butyl 6-[(3S)-3-(methoxycarbonylmethyl)-1-piperidyl]-2-propylsulfanyl-pyridine-3-carboxylate

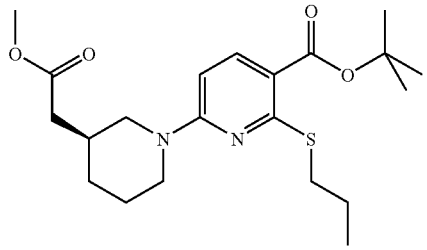 [SMILES: CCCSc1nc(N2CCC[C@@H](CC(=O)OC)C2)ccc1C(=O)OC(C)(C)C]

Intermediate 24 was prepared from intermediate 23 using an analogous method to that used to prepare intermediate 21

$^1$H NMR (400.13 MHz, CDCl$_3$) δ1.04 (3H, t), 1.30-1.37 (1H, m), 1.53-1.63 (10H, m), 1.62-1.79 (3H, m), 1.89-1.93 (1H, m), 2.03-2.10 (1H, m), 2.23-2.34 (2H, m), 2.74-2.87 (1H, m), 2.99-3.10 (3H, m), 3.69 (3H, s), 4.28 (2H, t), 6.28 (1H, d), 7.92 (1H, d)

m/z (ESI+) (M+H)+=409; HPLC t$_R$=3.49 min.

The following Examples were prepared in a similar manner to Example 111, using Intermediate 25 and an appropriate aminoester starting material:

120
Intermediate 25 tert-butyl 2-cyclopentylsulfanyl-6-[(3S)-3-(methoxycarbonylmethyl)-1-piperidyl]pyridine-3-carboxylate

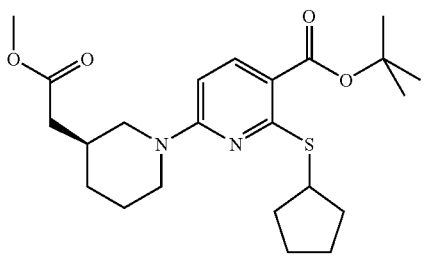 [SMILES: COC(=O)C[C@@H]1CCCN(c2ccc(C(=O)OC(C)(C)C)c(SC3CCCC3)n2)C1]

Intermediate 25 was prepared from intermediate 23 using an analogous method to that used to prepare intermediate 21

The following Examples were prepared in a similar manner to Example 1, using Intermediate 26 and an appropriate aminoester starting material:

| Compound | Ex | Name | $^1$H NMR δ | MS m/e MH+ |
|---|---|---|---|---|
|  | 127 | 2-[(3S)-1-[6-cyclopentyl-sulfanyl-5-(3-pyridin-3-ylpyrrolidine-1-carbonyl)pyridin-2-yl]-3-piperidyl]acetic acid | 1H NMR (400.13 MHz, DMSO-d6) 1.20-1.30 (1H, m), 1.45-1.80 (8H, m), 1.81-1.89 (2H, m), 2.02-2.40 (6H, m), 2.71 (1H, t), 2.92 (1H, t), 3.25-3.65 (4H, m), 3.70 (1H, s), 4.05 (1H, t), 4.14 (1H, d), 4.27 (1H, d), 6.49 (1H, d), 7.30-7.40 (2H, m), 7.73 (1H, s), 8.45 (1H, d), 8.52 (1H, s), 12.05 (1H, s) | 495 |
|  | 128 | 2-[(3S)-1-[6-cyclopentyl-sulfanyl-5-[3-(2-hydroxy-propan-2-yl)piperidine-1-carbonyl]pyridin-2-yl]-3-piperidyl]acetic acid | 1H NMR (400.13 MHz, DMSO-d6) 1.01-1.10 (7H, m), 1.17-1.70 (13H, m), 1.83-1.92 (3H, m), 2.07-2.26 (4H, m), 2.65-2.75 (2H, m), 2.85-2.96 (2H, m), 3.97-4.04 (1H, m), 4.12-4.18 (2H, m), 4.25 (1H, d), 6.49 (1H, d), 7.22 (1H, d), 12.06 (1H, s) | 490 |

| Compound | Ex | Name | ¹H NMR δ | MS m/e MH⁺ |
|---|---|---|---|---|
| 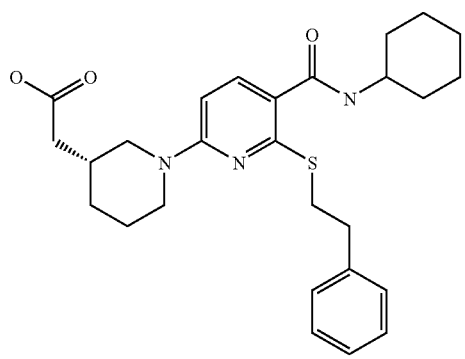 [SMILES: O=C(O)C[C@H]1CCCN(c2ccc(C(=O)NC3CCCCC3)c(SCCc3ccccc3)n2)C1] | 129 | 2-[(3R)-1-[5-(cyclohexyl-carbamoyl)-6-phenethylsulfanyl-pyridin-2-yl]-3-piperidyl] acetic acid | 1H NMR (400.13 MHz, DMSO-d6) 1.10-1.16 (1H, m), 1.20-1.35 (5H, m), 1.38-1.52 (1H, m), 1.57-1.92 (7H, m), 2.09-2.22 (2H, m), 2.72-2.81 (1H, m), 2.91 (2H, t), 2.93-3.05 (1H, m), 3.18-3.35 (3H, m), 3.64-3.67 (1H, m), 4.25 (2H, t), 6.50 (1H, d), 7.18-7.31 (5H, m), 7.64 (1H, d), 7.74 (1H, d), 12.07 (1H, s) | 482 |
| 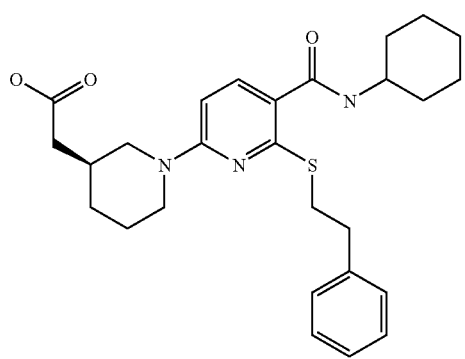 | 130 | 2-[(3S)-1-[5-(cyclohexyl-carbamoyl)-6-phenethylsulfanyl-pyridin-2-yl]-3-piperidyl] acetic acid | 1H NMR (400.13 MHz, CDCl3) 1.18-1.32 (6H, m), 1.35-1.46 (2H, m), 1.53-1.65 (2H, m), 1.65-1.75 (3H, m), 1.91-2.02 (2H, m), 2.24 (2H, d), 2.73-2.80 (1H, m), 2.90-3.10 (3H, m), 3.35-3.49 (2H, m), 3.93-4.02 (1H, m), 4.25-4.33 (2H, m), 6.38 (1H, d), 6.49 (1H, d), 7.19-7.32 (5H, m), 7.81 (1H, d) | 482 |

Intermediate 26

6-chloro-N-cyclohexyl-2-phenethylsulfanyl-pyridine-3-carboxamide

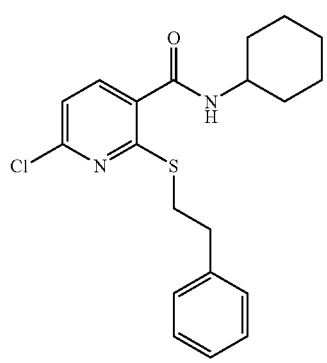 [SMILES: O=C(NC1CCCCC1)c1ccc(Cl)nc1SCCc1ccccc1]

To a solution of 2-phenylethanethiol (295 µl, 2.2 mmol) in DMF (3 ml) was added NaHMDS (2.2 ml, 2.2 mmol). The reaction was stirred at ambient temperature for 2 minutes then added to a solution of 2,6-dichloro-N-cyclohexyl-pyridine-3-carboxamide (Intermediate 1, 600 mg, 2.2 mmol) in DMF (2 ml). The reaction was stirred at ambient temperature for one hour. The solvent was evaporated under reduced pressure and the resulting residue was partitioned between citric acid (20 ml) and EtOAc (40 ml). The layers were separated and the organic layer was washed with sat NaHCO₃ (20 ml), water (20 ml) and brine (10 ml), then dried (MgSO₄), filtered and evaporated to a solid. This solid was triturated with EtOAc/IH (1:9) to yield the product as a white solid (700 mg, 85%).

¹H NMR (400.13 MHz, DMSO-d₆) δ1.11-1.35 (5H, m), 1.57-1.60 (1H, m), 1.70-1.73 (2H, m), 1.78-1.85 (2H, m), 2.85-2.95 (2H, m), 3.25-3.29 (2H, m), 3.65-3.72 (1H, m), 7.20-7.27 (1H, m), 7.28-7.34 (5H, m), 7.79 (1H, d), 8.38 (1H, d)

m/z (ESI+) (M+H)+=375; HPLC $t_R$=3.04 min.

The following Example was prepared in a similar manner to Example 1, using Intermediate 27 and an appropriate aminoester starting material:

| Compound | Ex | Name | ¹H NMR δ | MS m/e MH⁺ |
|---|---|---|---|---|
| | 131 | 2-[(3S)-1-[5-(cyclohexyl-carbamoyl)-6-(2-pyridin-3-ylethylsulfanyl)pyridin-2-yl]-3-piperidyl] acetic acid | 1H NMR (400.13 MHz, DMSO-d6) 1.23 (6H, d), 1.35-1.50 (1H, m), 1.57-1.87 (8H, m), 2.08-2.22 (2H, m), 2.76 (1H, t), 2.90-3.00 (2H, m), 3.20-3.40 (3H, m), 3.63-3.66 (1H, m), 4.26 (2H, t), 6.51 (1H, d), 7.30-7.34 (1H, m), 7.65-7.69 (2H, m), 7.82 (1H, d), 8.41-8.43 (1H, m), 8.45 (1H, d), 12.20 (1H, s) | 483 |

Intermediate 27

6-chloro-N-cyclohexyl-2-(2-pyridin-3-ylethylsulfanyl)pyridine-3-carboxamide

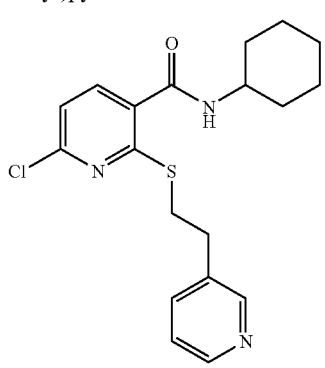

Intermediate 27 was made in an analogous method to intermediate 26

¹H NMR (300.072 MHz, CDCl₃) δ1.16-1.34 (3H, m), 1.35-1.50 (2H, m), 1.61-1.78 (4H, m), 1.95-2.07 (1H, m), 2.97-3.05 (2H, m), 3.38-3.45 (2H, m), 3.92-4.04 (1H, m), 6.16 (1H, d), 7.06 (1H, d), 7.21-7.25 (1H, m), 7.62-7.66 (1H, m), 7.76 (1H, d), 8.45-8.48 (1H, m), 8.55(1H, d)

m/z (ESI+) (M+H)+=376; HPLC t_R=1.49 min.

The following Example was prepared in a similar manner to Example 1, using Intermediate 28 and an appropriate aminoester starting material:

| Compound | Ex | Name | ¹H NMR δ | MS m/e MH⁺ |
|---|---|---|---|---|
| | 132 | 2-[(3S)-1-[5-(cyclohexyl-carbamoyl)-6-(2-pyrazin-2-ylethylsulfanyl)pyridin-2-yl]-3-piperidyl] acetic acid | 1H NMR (400.13 MHz, DMSO-d6) 1.05-1.35 (5H, m), 1.35-1.50 (1H, m), 1.57-1.83 (7H, m), 2.09-2.24 (2H, m), 2.64-2.78 (2H, m), 2.90-3.00 (1H, m), 3.13 (2H, t), 3.30-3.48 (3H, m), 3.62 (1H, s), 4.28 (2H, d), 6.51 (1H, d), 7.67 (1H, d), 7.81 (1H, d), 8.49 (1H, s), 8.56 (2H, s), 12.21 (1H, s) | 484 |

Intermediate 28

6-chloro-N-cyclohexyl-2-(2-pyrazin-2-ylethylsulfanyl)pyridine-3-carboxamide

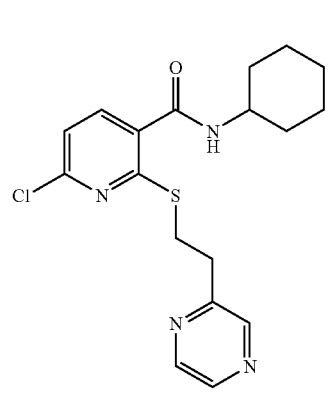 [SMILES: O=C(NC1CCCCC1)c1ccc(Cl)nc1SCCc1cnccn1]

Intermediate 28 was made in an analogous method to intermediate 26

$^1$H NMR (400.13 MHz, DMSO-d$_6$) δ 1.05-1.35 (5H, m), 1.53-1.63 (1H, m), 1.68-1.75 (2H, m), 1.75-1.83 (2H, m), 3.16 (2H, t), 3.46 (2H, t), 3.63-3.68 (1H, m), 7.31 (1H, d), 7.79 (1H, d), 8.37 (1H, d), 8.51 (1H, d), 8.59-8.61 (2H, m) m/z (ESI+) (M+H)+=377; HPLC t$_R$=2.20 min.

The following Example was prepared in a similar manner to Example 1, using Intermediate 29 and an appropriate aminoester starting material:

Intermediate 29

6-chloro-N-cyclohexylnicotinamide

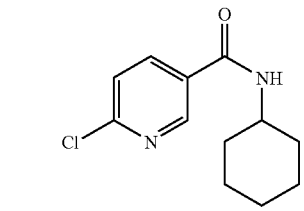 [SMILES: O=C(NC1CCCCC1)c1ccc(Cl)nc1]

To a solution of 6-chloronicotinic acid (778 mg, 5 mmol) and 1-hydroxybenzotriazole (565 mg, 5.43 mmol) stirred in dichloromethane (25 ml) was added triethylamine (1.5 ml, 10.86 mmol), followed by EDAC.HCl (1.04 g, 5.43 mmol). After 5 minutes cyclohexylamine (565 ul, 5 mmol) was added and stirring was continued for a further 16 hours.

The reaction was diluted with dichloromethane (50 ml) and extracted with sat. NaHCO$_3$ solution (50 ml), 1M HCl (50 ml), water (50 ml), brine (50 ml) and then dried over MgSO4, filtered and the solvent removed in vacuo to give 6-chloro-N-cyclohexylnicotinamide (950 mg, 79%) as a cream solid.

$^1$H NMR (400.13 MHz, DMSO-d$_6$) δ 1.12-1.18 (1H, m), 1.24-1.35 (4H, m), 1.61 (1H, d), 1.73-1.75 (2H, m), 1.81-1.82 (1H, m), 1.84 (1H, d), 3.74-3.78 (1H, m), 7.63-7.65 (1H, m), 8.22-8.25 (1H, m), 8.49 (1H, d), 8.81-8.82 (1H, m)

MS m/e (M−H)+ 237

The following Example was prepared in a similar manner to Example 1, using Intermediate 30 and an appropriate aminoester starting material:

| Compound | Ex | Name | $^1$H NMR δ | MS m/e MH$^+$ |
|---|---|---|---|---|
|  | 133 | 3-[(3S)-1-[5-(cyclohexylcarbamoyl)pyridin-2-yl]-3-piperidyl] acetic acid | 1H NMR (400.13 MHz, DMSO-d6) 1.01-1.42 (7H, m), 1.47-2.0 (8H, m), 2.14-2.20 (2H, m), 2.94 (1H, s), 3.12 (1H, s), 3.72- 3.74 (1H, m), 4.24 (2H, d), 7.12 (1H, s), 8.14 (1H, d), 8.22 (1H, S), 8.49 (1H, s) | 346; HPLC tR = 1.31 min |

| Compound | Ex | Name | ¹H NMR δ | MS m/e MH⁺ |
|---|---|---|---|---|
| 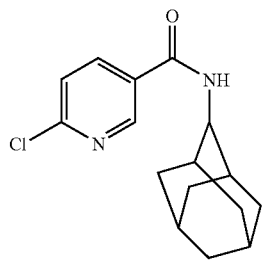 [SMILES: O=C(NC1C2CC3CC(C2)CC1C3)c1ccc(Cl)nc1] | 134 | 2-[(3S)-1-[5-(2-adamantyl-carbamoyl)pyridin-2-yl]-3-piperidyl]acetic acid | 1H NMR (400.13 MHz, DMSO-d6) 1.25-1.44 (2H, m), 1.50 (2H, d), 1.68 (3H, d), 1.82 (8H, d), 1.93 (2H, d), 2.14 (3H, d), 2.23-2.29 (1H, m), 2.85 (2H, d), 4.01 (1H, t), 4.27 (2H, d), 6.82 (1H, d), 7.71 (1H, d), 7.94-7.97 (1H, m), 8.58 (1H, d), 12.18 (1H, s) | 398; HPLC tR = 1.77 min |

Intermediate 30

N-adamantan-2-yl-6-chloronicotinamide

Intermediate 31

6-chloro-N-cyclohexyl-2-[2-(4-fluorophenyl)ethoxy]nicotinamide

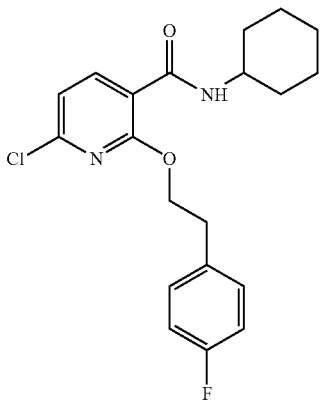 [SMILES: O=C(NC1CCCCC1)c1ccc(Cl)nc1OCCc1ccc(F)cc1]

Intermediate 30 was prepared using an analogous method to that used to prepare intermediate 29

¹H NMR (400.13 MHz, DMSO-d₆) δ1.52 (2H, d), 1.72 (2H, s), 1.78-1.85 (6H, m), 1.98 (2H, s), 2.11 (2H, d), 4.04 (1H, t), 7.61-7.63 (1H, m), 8.21-8.29 (2H, m), 8.79-8.80 (1H, m)

MS m/e (M+H)+ 291

The following Example was prepared in a similar manner to Example 1, using Intermediate 31 and an appropriate aminoester starting material:

2,6-dichloro-N-cyclohexylnicotinamide (Intermediate 1, 273 mg, 1 mmol) was stirred in 1,4-dioxane (4 ml). To this solution was added 4-fluorophenethyl alcohol (154 mg, 1.1 mmol) followed by bis-sodium hexamethyldisilylamide 1.0M in THF (1.1 ml, 1.1 mmol). The tube was sealed and subjected to microwave heating 150° C. (Biotage Initiator 300 W) for 2 hours. The solvent was evaporated and the residue was diluted with water (15 ml) and extracted with dichloromethane (2×20 ml). The combined extract was

| Compound | Ex | Name | ¹H NMR δ | MS m/e MH⁺ |
|---|---|---|---|---|
|  | 135 | 2-[(3S)-1-[5-(cyclohexyl-carbamoyl)-6-[2-(4-fluorophenyl)ethoxy]pyridin-2-yl]-3-piperidyl]acetic acid | 1H NMR (400.13 MHz, DMSO-d6) 0.91-1.04 (3H, m), 1.21-1.28 (4H, m), 1.55-1.64 (7H, m), 1.82 (1H, d), 2.14-2.19 (1H, m), 2.22-2.28 (1H, m), 2.90 (2H, d), 3.10 (2H, t), 3.64 (1H, t), 4.16 (1H, d), 4.25 (1H, d), 4.66-4.70 (2H, m), 6.44 (1H, d), 7.13-7.18 (2H, m), 7.29-7.37 (3H, m), 7.99 (1H, d), 12.19 (1H, s) | 484; HPLC tR = 2.91 min | washed with brine (20 ml) dried over MgSO$_4$, filtered and evaporated. The crude product was purified on SiO$_2$ (40 g) eluting with ethyl acetate/isohexane 0-40% and gave 6-chloro-N-cyclohexyl-2-[2-(4-fluorophenyl)ethoxy]nicotinamide (153 mg, 40%) as a white solid $^1$H NMR (400.13 MHz, DMSO-d$_6$) δ0.99-1.33 (5H, m), 1.54-1.74 (5H, m), 3.10 (2H, t), 3.65-3.72 (1H, m), 4.63 (2H, t), 7.12-7.18 (2H, m), 7.21 (1H, d), 7.35-7.39 (2H, m), 7.70 (1H, d), 8.11 (1H, d)

MS m/e (M+H)$^+$ 377.

The following Example was prepared in a similar manner to Example 1, using Intermediate 32 and an appropriate aminoester starting material:

| Compound | Ex | Name | $^1$H NMR δ | MS m/e MH$^+$ |
|---|---|---|---|---|
| | 136 | 2-[(3S)-1-[5-(cyclohexylcarbamoyl)-6-(3-methylbutoxy)pyridin-2-yl]-3-piperidyl] acetic acid | 1H NMR (400.13 MHz, DMSO-d6) 0.95 (6H, d), 1.17-1.44 (7H, m), 1.55-1.68 (6H, m), 1.74-1.87 (5H, m), 2.12-2.26 (2H, m), 2.77-2.83 (1H, m), 2.96-3.02 (1H, m), 3.77 (1H, t), 4.14 (1H, d), 4.25 (1H, d), 4.39-4.43 (2H, m), 6.43 (1H, d), 7.67 (1H, d), 8.00 (1H, d), 12.19 (1H, bs). | 432; HPLC tR = 3.04 min |

Intermediate 32

6-chloro-N-cyclohexyl-2-isoamylnicotinamide

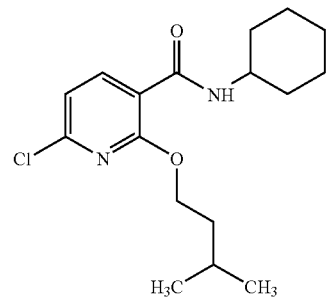 [SMILES: CC(C)CCOc1nc(Cl)ccc1C(=O)NC1CCCCC1]

Intermediate 32 was prepared using an analogous method to that used to prepare intermediate 31

$^1$H NMR (400.13 MHz, DMSO-d$_6$) δ0.94 (6H, d), 1.17-1.24 (1H, m), 1.28 (2H, d), 1.36 (2H, t), 1.55-1.59 (1H, m), 1.63-1.71 (2H, m), 1.66-1.71 (2H, m), 1.75-1.83 (2H, m), 1.85 (1H, s), 3.77 (1H, t), 4.38 (2H, t), 7.20 (1H, d), 7.94 (1H, d), 8.09 (1H, d)

MS m/e (M+H)$^+$325

The following Example was prepared in a similar manner to Example 1, using Intermediate 33 and an appropriate aminoester starting material:

| Compound | Ex | Name | $^1$H NMR δ | MS m/e MH$^+$ |
|---|---|---|---|---|
| | 137 | 2-[(3S)-1-[5-(cyclohexylcarbamoyl)-6-(3-phenylpropoxy)pyridin-2-yl]-3-piperidyl] acetic acid | 1H NMR (400.13 MHz, DMSO-d6) 1.29 (7H, d), 1.54 -1.67 (4H, m), 1.80-1.88 (4H, m), 2.04 2.26 (4H, m), 2.78 (3H, d), 2.96 (1H, d), 3.75-3.82 (1H, m), 4.11 (1H, d), 4.22 (1H, d), 4.34-4.40 (2H, m), 6.43 (1H, d), 7.18-7.24 (3H, m), 7.29-7.32 (2H, m), 7.70 (1H, d), 8.00 (1H, d), 12.17 (1H, s) | 480; HPLC tR = 3.07 min |

Intermediate 33

6-chloro-N-cyclohexyl-2-(3-phenylpropoxy)nicotinamide

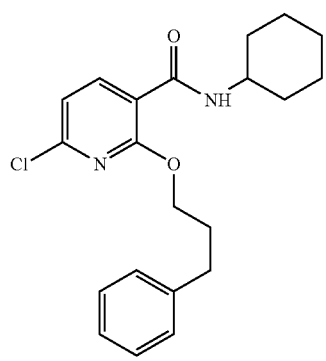 [SMILES: O=C(NC1CCCCC1)c1ccc(Cl)nc1OCCCc1ccccc1]

Intermediate 33 was prepared using an analogous method to that used to prepare intermediate 31

$^1$H NMR (400.13 MHz, DMSO-d$_6$) δ1.23 (5H, d), 1.56 (1H, d), 1.69 (2H, d), 1.86 (2H, d), 2.04-2.11 (2H, m), 2.77 (2H, t), 3.77-3.80 (1H, m), 4.33 (2H, t), 7.18-7.21 (2H, m), 7.22-7.24 (2H, m), 7.28-7.32 (2H, m), 8.02 (1H, d), 8.07 (1H, d)

MS m/e (M+H)$^+$373.

The following Example was prepared in a similar manner to Example 1, using Intermediate 34 and an appropriate aminoester starting material:

Intermediate 34

6-chloro-N-cyclohexyl-2-(2-pyridin-3-ylethoxy) nicotinamide

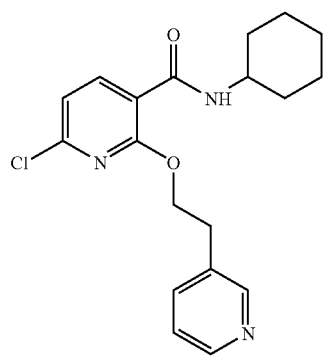 [SMILES: O=C(NC1CCCCC1)c1ccc(Cl)nc1OCCc1cccnc1]

Intermediate 34 was prepared using an analogous method to that used to prepare intermediate 31

$^1$H NMR (400.13 MHz, DMSO-d$_6$) δ1.01-1.05 (1H, m), 1.08 (1H, s), 1.10-1.11 (1H, m), 1.14-1.18 (1H, m), 1.25 (1H, d), 1.53-1.57 (1H, m), 1.62-1.66 (2H, m), 1.69-1.74 (2H, m), 3.13 (2H, t), 3.66-3.70 (1H, m), 4.65 (2H, t), 7.21 (1H, d), 7.33-7.36 (1H, m), 7.73-7.78 (2H, m), 8.08 (1H, d), 8.45-8.46 (1H, m), 8.54 (1H, d)

MS m/e (M+H)$^+$ 360

The following Examples were prepared in a similar manner to Example 1, using Intermediate 35 and an appropriate aminoester starting material:

| Compound | Ex | name | $^1$H NMR δ | MS m/e MH$^+$ |
|---|---|---|---|---|
| | 138 | 2-[(3S)-1-[5-(cyclohexyl-carbamoyl)-6-(2-pyridin-3-ylethoxy)pyridin-2-yl]-3-piperidyl] acetic acid | 1H NMR (400.13 MHz, DMSO-d6) 0.94 (2H, d), 1.05-1.35 (4H, m), 1.39-1.70 (7H, m), 1.84 (2H, d), 2.14-2.20 (1H, m), 2.22- 2.28 (1H, m), 2.83 (1H, d), 3.00 (1H, d), 3.14 (2H, t), 3.64 (1H, t), 4.15 (1H, d), 4.25 (1H, d), 4.69-4.73 (2H, m), 6.44 (1H, d), 7.30 (1H, d), 7.35-7.38 (1H, m), 7.75-7.77 (1H, m), 7.98 (1H, d), 8.45-8.47 (1H, m), 8.54 (1H, d), 12.19 (1H, s) | 467; HPLC tR = 1.67 min |

| Compound | Ex | Name | ¹H NMR δ | MS m/e MH⁺ |
|---|---|---|---|---|
| 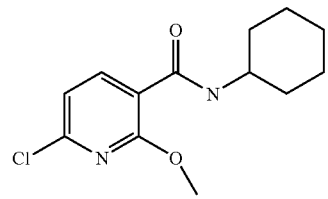 [SMILES: COc1nc(Cl)ccc1C(=O)NC1CCCCC1] | 139 | 2-[(3S)-1-[5-(cyclohexyl-carbamoyl)-6-methoxy-pyridin-2-yl]-3-piperidyl]acetic acid | 1H NMR (400.13 MHz, DMSO-d6) 1.31 (7H, d), 1.62 (4H, d), 1.84 (4H, d), 2.19 (2H, d), 2.79-2.84 (1H, m), 3.01 (1H, d), 3.75-3.78 (1H, m), 3.93 (3H, s), 4.13 (1H, d), 4.30 (1H, d), 6.43 (1H, d), 7.61 (1H, d), 7.99 (1H, d), 12.19 (1H, s) | 376; HPLC tR = 2.45 min |

Intermediate 35

6-chloro-N-cyclohexyl-2-methoxynicotinamide

Intermediate 36

6-chloro-N-cyclohexyl-2-propoxynicotinamide

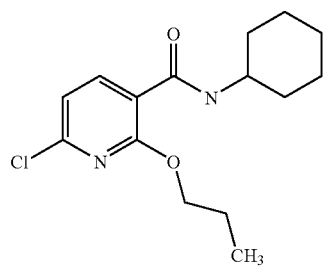 [SMILES: CCCOc1nc(Cl)ccc1C(=O)NC1CCCCC1]

Intermediate 35 was prepared using an analogous method to that used to prepare intermediate 31

¹H NMR (499.8 MHz, DMSO-d₆) δ 1.19 (1H, d), 1.27-1.37 (4H, m), 1.57-1.59 (1H, m), 1.71 (2H, t), 1.83 (2H, d), 3.77 (1H, d), 3.97 (3H, d), 7.19-7.21 (1H, m), 7.97 (1H, d), 8.05-8.07 (1H, m)

MS m/e (M+H)⁺ 269

The following Examples were prepared in a similar manner to Example 1, using Intermediate 36 and an appropriate aminoester starting material:

Intermediate 36 was prepared using an analogous method to that used to prepare intermediate 31

1H NMR (400.13 MHz, DMSO-d6) δ 1.00 (3H, t), 1.17-1.39 (5H, m), 1.54-1.57 (1H, m), 1.67-1.70 (2H, m), 1.75-1.81 (2H, m), 1.84 (2H, s), 3.76-3.79 (1H, m), 4.30 (2H, t), 7.20 (1H, d), 7.97 (1H, d), 8.09 (1H, d)

MS m/e (M+H)⁺ 297

| Compound | Ex | Name | ¹H NMR δ | MS m/e MH⁺ |
|---|---|---|---|---|
| (structure) | 140 | 2-[(3S)-1-[5-(cyclohexylcarbamoyl)-6-propoxy-pyridin-2-yl]-3-piperidyl]acetic acid | 1H NMR (400.13 MHz, DMSO-d6) 1.02 (3H, t), 1.19-1.44 (7H, m), 1.56 (1H, d), 1.66 (3H, d), 1.81 (6H, d), 2.13-2.26 (2H, m), 2.77-2.83 (1H, m), 2.99 (1H, t), 3.77 (1H, t), 4.13 (1H, d), 4.23-4.35 (3H, m), 6.43 (1H, d), 7.70 (1H, d), 8.00 (1H, d), 12.17 (1H, s) | 404; HPLC tR = 2.79 min |

The following Example was prepared in a similar manner to Example 1, using Intermediate 37 and an appropriate aminoester starting material:

| Compound | Ex | Name | ¹H NMR δ | MS m/e MH⁺ |
|---|---|---|---|---|
| | 141 | 2-[(3S)-1-[5-(cyclohexylcarbamoyl)-6-(1-piperidyl)pyridin-2-yl]-3-piperidyl]acetic acid | 1H NMR (400.13 MHz, DMSO-d6) 1.16 (1H, d), 1.21 (1H, s), 1.25 (2H, d), 1.31 (1H, s), 1.34 (1H, s), 1.42 (1H, d), 1.54 (2H, d), 1.63-1.64 (5H, m), 1.71 (2H, d), 1.81 (2H, d), 1.86 (2H, s), 1.90 (1H, s), 2.12-2.17 (1H, m), 2.20-2.26 (1H, m), 2.72-2.97 (2H, m), 3.01-3.03 (4H, m), 3.71 (1H, t), 4.15 (1H, d), 4.22 (1H, d), 6.44 (1H, d), 7.83 (1H, d), 8.69 (1H, d), 12.16 (1H, s) | 429; HPLC tR = 1.82 min |

Intermediate 37

6-chloro-N-cyclohexyl-2-piperidin-1-ylnicotinamide

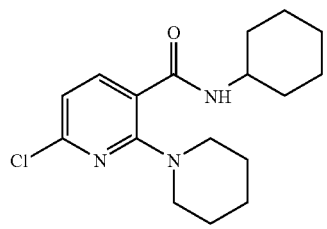 [SMILES: O=C(NC1CCCCC1)c1ccc(Cl)nc1N1CCCCC1]

2,6-dichloro-N-cyclohexylnicotinamide (273 mg, 1 mmol), piperidine (109 ul, 1.1 mmol) and potassium carbonate (345 mg, 2.5 mmol) in butyronitrile (4 ml) were sealed in a microwave tube and heated (Biotage initiator) at 150° C. for 1 hour. The reaction was diluted with water (25 ml) and extracted with dichloromethane (2×25 ml). The combined extracts were dried over MgSO₄, filtered and evaporated. The crude product was purified on SiO₂ (12 g) eluting with ethyl acetate/isohexane 0-30% and gave 6-chloro-2(piperidine)-N-cyclohexylnicotinamide (100 mg, 33%) as a white powder.

¹H NMR (400.13 MHz, DMSO-d₆) δ1.21 (5H, d), 1.56-1.60 (7H, m), 1.69-1.73 (2H, m), 1.83 (2H, d), 3.29-3.30 (4H, m), 3.65-3.68 (1H, m), 6.80 (1H, d), 7.55 (1H, d), 8.31 (1H, d) MS m/e (M+H)⁺ 322

The following Example was prepared in a similar manner to Example 1, using Intermediate 38 and an appropriate aminoester starting material:

| Compound | Ex | Name | ¹H NMR δ | MS m/e MH⁺ |
|---|---|---|---|---|
| | 142 | 2-[(3S)-1-[6-[2-(4-chlorophenyl)ethylamino]-5-(cyclohexylcarbamoyl)pyridin-2-yl]-3-piperidyl]acetic acid | 1H NMR (400.13 MHz, DMSO-d6) 1.12 (1H, d), 1.25 (5H, s), 1.39 (1H, d), 1.45 (1H, d), 1.58 -1.87 (8H, m), 2.12-2.17 (1H, m), 2.20-2.26 (1H, m), 2.74 (1H, d), 2.79-2.86 (2H, m), 2.86 (1H, m), 3.54 (2H, q), 3.64 (1H, s), 4.20 (2H, d), 5.95 (1H, d), 7.25 (2H, d), 7.34 (2H, d), 7.59 (1H, d), 7.76 (1H, t), 12.15 (1H, bs). | 498; HPLC tR = 3.16 min |

Intermediate 38

6-chloro-2-{[2-(4-chlorophenyl)ethyl]amino}-N-cyclohexylnicotinamide

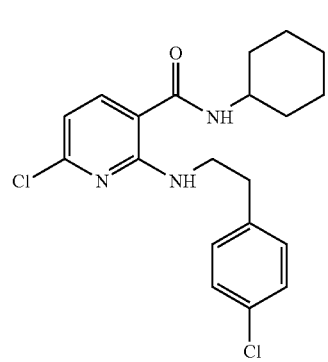 [SMILES: O=C(NC1CCCCC1)c1ccc(Cl)nc1NCCc1ccc(Cl)cc1]

Intermediate 38 was prepared using an analogous method to that used to prepare intermediate 37

$^1$H NMR (400.13 MHz, DMSO-$d_6$) δ1.09-1.29 (5H, m), 1.58-1.78 (5H, m), 2.85 (2H, t), 3.57 (2H, q), 3.68 (1H, d), 6.62 (1H, d), 7.28 (2H, d), 7.35 (2H, d), 7.94 (1H, d), 8.25 (1H, d), 8.62 (1H, t)

MS m/e (M+H)$^+$393.

The following Example was prepared in a similar manner to Example 1, using Intermediate 39 and an appropriate aminoester starting material:

Intermediate 39

6-chloro-N-cyclohexyl-2-[3-(4-fluorophenyl)pyrrolidin-1-yl]nicotinamide

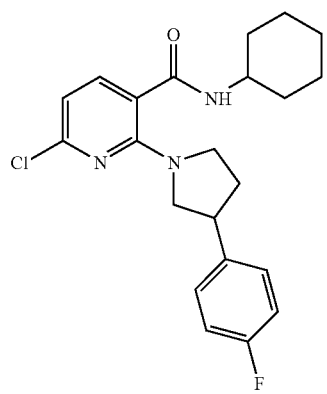 [SMILES: O=C(NC1CCCCC1)c1ccc(Cl)nc1N1CCC(c2ccc(F)cc2)C1]

Intermediate 39 was prepared using an analogous method to that used to prepare intermediate 37

$^1$H NMR (400.13 MHz, DMSO-$d_6$) δ1.19 (5H, d), 1.66 (5H, d), 1.96-2.02 (1H, m), 2.26-2.28 (1H, m), 3.39 (1H, d), 3.44 (1H, d), 3.51-3.55 (2H, m), 3.63-3.66 (1H, m), 3.71-3.75 (1H, m), 6.65 (1H, d), 7.14-7.19 (2H, m), 7.32-7.36 (2H, m), 7.46 (1H, d), 8.31 (1H, d)

MS m/e (M+H)$^+$ 402.

The following Example was prepared in a similar manner to Example 1, using Intermediate 40 and an appropriate aminoester starting material:

| Compound | Ex | Name | $^1$H NMR δ | MS m/e MH$^+$ |
|---|---|---|---|---|
|  | 143 | 2-[(3S)-1-[5-(cyclohexylcarbamoyl)-6-[3-(4-fluorophenyl)pyrrolidin-1-yl]pyridin-2-yl]-3-piperidyl]acetic acid | 1H NMR (400.13 MHz, DMSO-d6) 1.09-1.30 (7H, m), 1.45 (1H, d), 1.38-1.80 (10H, m), 2.11-2.34 (3H, m), 2.64-2.73 (1H, m), 2.89 (1H, d), 3.52 (2H, d), 3.56 (1H, d), 3.61 (1H, d), 3.69 (1H, t), 4.18 (2H, d), 6.05 (1H, d), 7.12-7.17 (2H, m), 7.33 (3H, m), 7.79 (1H, d) | 509; HPLC tR = 2.76 min |

| Compound | Ex | Name | ¹H NMR δ | MS m/e MH⁺ |
|---|---|---|---|---|
| (structure) | 144 | 2-[(3S)-1-[5-(cyclohexylcarbamoyl)-6-(3,4-dihydro-1H-isoquinolin-2-yl)pyridin-2-yl]-3-piperidyl]acetic acid | 1H NMR (400.13 MHz, DMSO-d6) 1.01-1.11 (3H, m), 1.20-1.30 (3H, m), 1.32-1.67 (4H, m), 1.68-1.93 (4H, m), 2.12-2.25 (2H, m), 2.71-2.77 (1H, m), 2.94-3.0 (3H, m), 3.49 (2H, t), 3.68 (1H, t), 4.10 (1H, d), 4.25 (1H, d), 4.30 (2H, s), 6.36 (1H, d), 7.15 (5H, d), 7.71 (1H, d), 8.36 (1H, d), 12.11 (1H, bs) | 477; HPLC tR = 2.85 min |

Intermediate 40

6-chloro-N-cyclohexyl-2-(3,4-dihydroisoquinolin-2 (1H)-yl)nicotinamide

Intermediate 41

6-chloro-N-cyclohexyl-2-(4-phenylpiperazin-1-yl) nicotinamide

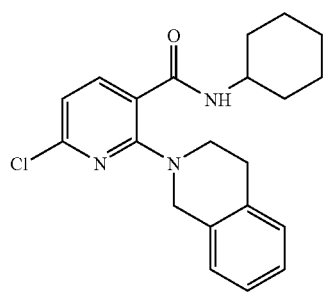 [SMILES: O=C(NC1CCCCC1)c1ccc(Cl)nc1N1CCc2ccccc2C1]

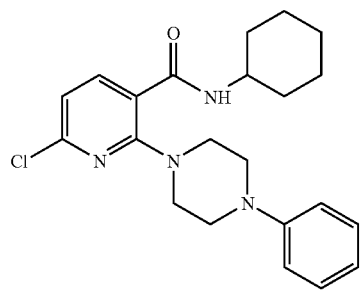 [SMILES: O=C(NC1CCCCC1)c1ccc(Cl)nc1N1CCN(c2ccccc2)CC1]

Intermediate 40 was prepared using an analogous method to that used to prepare intermediate 37

¹H NMR (400.13 MHz, DMSO-d₆) δ1.05-1.40 (5H, m), 1.53-1.61 (1H, m), 1.71 (1H, d), 1.68-1.73 (1H, m), 1.85 (2H, d),2.90 (2H, m) 3.63 (2H, t), 3.68-3.76 (1H, m), 4.47-4.57 (2H, m), 6.82 (1H, t), 7.15-7.19 (4H, m), 7.56 (1H, d), 8.35 (1H, d)

MS m/e (M+H)+ 370

The following Example was prepared in a similar manner to Example 1, using Intermediate 41 and an appropriate aminoester starting material:

Intermediate 41 was prepared using an analogous method to that used to prepare intermediate 37

¹H NMR (400.13 MHz, DMSO-d₆) δ1.15-1.33 (5H, m), 1.51-1.61 (1H, m), 1.68-1.77 (2H, m), 1.80-1.91 (2H, m), 3.22 (1H, s), 3.24 (3H, t), 3.49 (4H, t), 3.71 (1H, t), 6.80 (1H, t), 6.88 (1H, d), 6.96-6.99 (2H, m), 7.22-7.26 (2H, m), 7.61 (1H, d), 8.32 (1H, d)

MS m/e (M+H)⁺ 399.

The following Example was prepared in a similar manner to Example 1, using Intermediate 42 and an appropriate aminoester starting material:

| Compound | Ex | Name | ¹H NMR δ | MS m/e MH⁺ |
|---|---|---|---|---|
| (structure) | 145 | 2-[(3S)-1-[5-(cyclohexylcarbamoyl)-6-(4-phenylpiperazin-1-yl)pyridin-2-yl]-3-piperidyl]acetic acid | 1H NMR (400.13 MHz, DMSO-d6) 1.03-1.28 (7H, m), −1.29-1.51 (2H, m), 1.51-1.68 (3H, m), 1.68-1.84 (4H, m), 2.23-2.37 (3H, m), 2.76 -2.82 (1H, m), 2.94-3.01 (1H, m), 3.24 (1H, s), 3.25 (6H, m), 3.72-3.75 (1H, m), 4.14 (1H, d), 4.23 (1H, d), 6.45 (1H, d), 6.81 (1H, t), 6.99 (2H, d), 7.22-7.26 (2H, m), 7.80 (1H, d), 8.43 (1H, d) | 505; HPLC tR = 3.28 min |

| Compound | Ex | Name | ¹H NMR δ | MS m/e MH⁺ |
|---|---|---|---|---|
| | 146 | 2-[(3S)-1-[5-(cyclohexyl-carbamoyl)-6-[4-(4-fluorobenzoyl)piperazin-1-yl]pyridin-2-yl]-3-piperidyl]acetic acid | 1H NMR (400.13 MHz, DMSO-d6) 1.05-1.43 (8H, m), 1.55-1.90 (8H, m), 2.11-2.25 (2H, m),, 2.45-2.47 (1H, m), 2.71-2.77 (1H, m), 2.94 (1H, d), 3.15 (4H, s), 3.69-3.74 (4H, m), 4.11 (1H, d), 4.24 (1H, d), 6.41 (1H, d), 7.29 (2H, t), 7.51-7.55 (2H, m), 7.72 (1H, d), 8.25 (1H, d) | 552; HPLC tR = 2.53 min |

Intermediate 42

6-chloro-N-cyclohexyl-2-[4-(4-fluorobenzoyl)piperazin-1-yl]nicotinamide

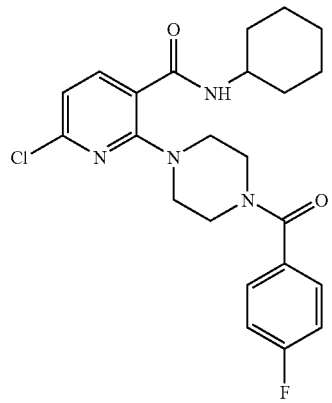 [SMILES: O=C(NC1CCCCC1)c1ccc(Cl)nc1N1CCN(C(=O)c2ccc(F)cc2)CC1]

Intermediate 42 was prepared using an analogous method to that used to prepare intermediate 37

¹H NMR (400.13 MHz, DMSO-d₆) δ1.02-1.35 (6H, m), 1.58 (1H, d), 1.71 (2H, d), 1.83 (2H, d), 3.39 (5H, s), 3.64-3.69 (3H, m), 6.90 (1H, d), 7.27-7.32 (2H, m), 7.51-7.54 (2H, m), 7.61 (1H, d), 8.36 (1H, d)

MS m/e (M+H)⁺ 445.

The following Example was prepared in a similar manner to Example 1, using Intermediate 43 and an appropriate aminoester starting material:

| Compound | Ex | Name | ¹H NMR δ | MS m/e MH⁺ |
|---|---|---|---|---|
| | 147 | 2-[(3S)-1-[6-(4-acetylpiperazin-1-yl)-5-(cyclohexylcarbamoyl)pyridin-2-yl]-3-piperidyl]acetic acid | 1H NMR (400.13 MHz, DMSO-d6) 1.02-1.48 (7H, m), 1.51-1.98 (8H, m), 2.03 (3H, s), 2.18 (2H, d), 2.70-2.76 (1H, m), 2.94 (1H, t), 3.06 (2H, t), 3.12 (2H, t), 3.54 (4H, d), 3.70-3.72 (1H, m), 4.12 (1H, d), 4.25 (1H, d), 6.41 (1H, d), 7.73 (1H, d), 8.29 (1H, d), 11.98 (1H, vbs). | 472; HPLC tR = 1.99 min |

Intermediate 43

2-(4-acetylpiperazin-1-yl)-6-chloro-N-cyclohexylnicotinamide

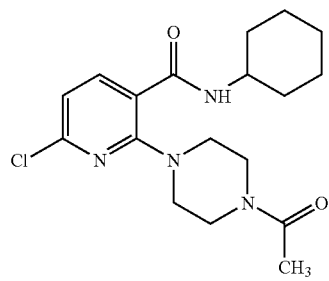 [SMILES: CC(=O)N1CCN(c2nc(Cl)ccc2C(=O)NC2CCCCC2)CC1]

Intermediate 43 was prepared using an analogous method to that used to prepare intermediate 37

$^1$H NMR (400.13 MHz, DMSO-$d_6$) δ1.21 (5H, d), 1.59 (1H, d), 1.72 (2H, d), 1.84 (2H, d), 2.01 (3H, s), 3.36-3.39 (4H, m), 3.52 (4H, q), 3.66-3.70 (1H, m), 6.88 (1H, d), 7.60 (1H, d), 8.36 (1H, d)

MS m/e (M+H)$^+$ 365.

The following Example was prepared in a similar manner to Example 1, using Intermediate 44 and an appropriate aminoester starting material:

| Compound | Ex | Name | $^1$H NMR δ | MS m/e MH$^+$ |
|---|---|---|---|---|
| | 148 | 2-[(3S)-1-[5-(cyclohexylcarbamoyl)-6-(4-ethylsulfonyl-piperazin-1-yl)pyridin-2-yl]-3-piperidyl]acetic acid | 1H NMR (400.13 MHz, DMSO-d6) 1.07-1.50 (11H, m), 1.57-1.86 (8H, m), 2.13-2.25 (2H, m), 2.67-2.74 (1H, m), 2.94 (1H, d), 3.12 (2H, q), 3.28 (4H, d), 3.29 (4H, d), 4.10 (1H, d), 4.29 (1H, d), 6.39 (1H, d), 7.69 (1H, d), 8.14 (1H, d), 12.19 (1H, s) | 522; HPLC tR = 2.34 min |

Intermediate 44

6-chloro-N-cyclohexyl-2-[4-(ethylsulfonyl)piperazin-1-yl]nicotinamide

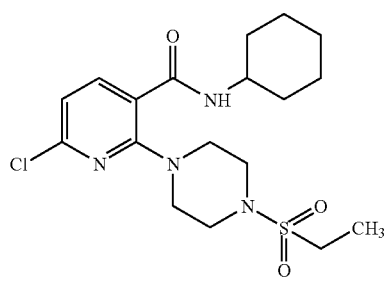 [SMILES: CCS(=O)(=O)N1CCN(c2nc(Cl)ccc2C(=O)NC2CCCCC2)CC1]

Intermediate 44 was prepared using an analogous method to that used to prepare intermediate 37

1H NMR (400.13 MHz, DMSO-$d_6$) δ 1.11-1.35 (8H, m), 1.54-1.62 (1H, m), 1.71 (2H, d), 1.83 (2H, s), 3.11 (2H, q), 3.25 (4H, t), 3.39-3.42 (4H, m), 3.63-3.70 (1H, m), 6.90 (1H, d), 7.60 (1H, d), 8.36 (1H, d)

MS m/e (M+H)$^+$ 415

The following Example was prepared in a similar manner to Example 1, using Intermediate 45 and an appropriate aminoester starting material:

| Compound | Ex | Name | ¹H NMR δ | MS m/e MH⁺ |
|---|---|---|---|---|
| 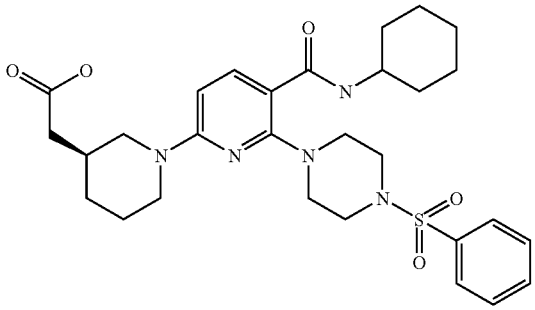 [SMILES: O=C(O)C[C@@H]1CCCN(c2ccc(C(=O)NC3CCCCC3)c(N3CCN(S(=O)(=O)c4ccccc4)CC3)n2)C1] | 149 | 2-[(3S)-1-[6-[4-(benzenesulfonyl)piperazin-1-yl]-5-(cyclohexyl-carbamoyl)pyridin-2-yl]-3-piperidyl]acetic acid | 1H NMR (400.13 MHz, DMSO-d6) 0.74-1.42 (7H, m), 1.5-1.71 (7H, m), 1.79-1.90 (2H, m), 2.13-2.24 (2H, m), 2.68-2.74 (1H, m), 2.99 (4H, s), 3.13 (4H, t), 3.52-3.59 (1H, m), 4.06 (1H, d), 4.28 (1H, d), 6.43 (1H, s), 7.68-7.73 (3H, m), 7.76-7.78 (2H, m), 7.80 (1H, s), 8.16 (1H, d), 12.22 (1H, s) | 570; HPLC tR = 2.66 min |

Intermediate 45

6-chloro-N-cyclohexyl-2-[4-(phenylsulfonyl)piperazin-1-yl]nicotinamide

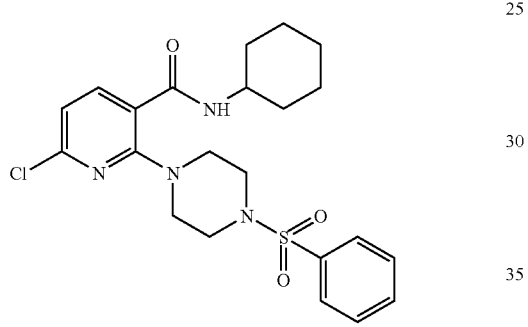

Intermediate 45 was prepared using an analogous method to that used to prepare intermediate 37
MS m/e (M+H)⁺ 464.

The following Example was prepared in a similar manner to Example 1, using Intermediate 46 and an appropriate aminoester starting material:

| Compound | Ex | Name | ¹H NMR δ | MS m/e MH⁺ |
|---|---|---|---|---|
| 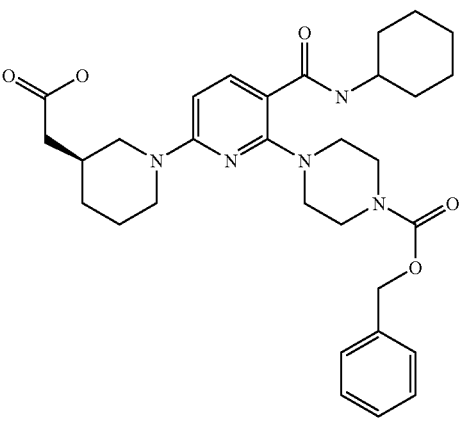 [SMILES: O=C(O)C[C@@H]1CCCN(c2ccc(C(=O)NC3CCCCC3)c(N3CCN(C(=O)OCc4ccccc4)CC3)n2)C1] | 150 | 2-[(3S)-1-[5-(cyclohexylcarbamoyl)-6-(4-phenylmethoxy-carbonylpiperazin-1-yl)pyridin-2-yl]-3-piperidyl]acetic acid | 1H NMR (400.13 MHz, DMSO-d6) 1.08-1.49 (7H, m), 1.53-1.87 (8H, m), 2.16-2.22 (2H, m), 2.72-2.78 (1H, m), 2.90-3.00 (1H, m), 3.11 (4H, t), 3.55 (4H, s), 3.71 (1H, s), 4.08 (1H, d), 4.24 (1H, d), 5.12 (2H, s), 6.41 (1H, d), 7.33-7.39 (5H, m), 7.75 (1H, d), 8.25 (1H, d), 12.12 (1H, bs) | 564; HPLC tR = 2.83 min |

Intermediate 46 benzyl 4-[6-chloro-3-(cyclohexylcarbamoyl)pyridin-2-yl]piperazine-1-carboxylate

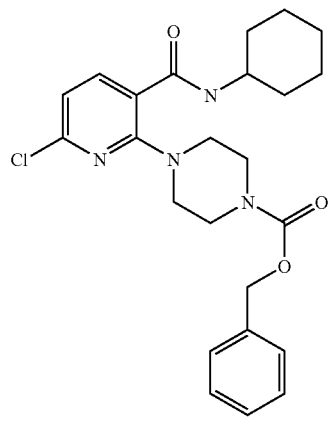 [SMILES: O=C(NC1CCCCC1)c1ccc(Cl)nc1N1CCN(C(=O)OCc2ccccc2)CC1]

Intermediate 46 was prepared using an analogous method to that used to prepare intermediate 37

1H NMR (400.13 MHz, DMSO-$d_6$) δ 1.05-1.35 (5H, m), 1.58 (1H, d), 1.71 (2H, d), 1.83 (2H, d), 3.4-3.48(4H, m), 3.50 (4H, s), 3.69 (1H, d), 5.11 (2H, s), 6.88 (1H, d), 7.32-7.39 (5H, m), 7.60 (1H, d), 8.35 (1H, d)

MS m/e (M+H)$^+$ 457

The following Example was prepared in a similar manner to Example 1, using Intermediate 47 and an appropriate aminoester starting material:

| Compound | Ex | Name | $^1$H NMR δ | MS m/e MH$^+$ |
|---|---|---|---|---|
|  | 151 | 2-[(3S)-1-[5-(cyclohexylcarbamoyl)-6-propylamino-pyridin-2-yl]-3-piperidyl]acetic acid | 1H NMR (400.13 MHz, DMSO-d6) 0.90 (3H, t), 1.27-1.30 (7H, m), 1.61-1.74 (10H, m), 2.10-2.24 (2H, m), 2.90-2.80 (2H, m), 3.27 (2H, t), 3.67 (1H, bs), 4.19-4.24 (2H, m), 5.92 (1H, d), 7.58 (1H, d), 7.75 (1H, d), 8.76 (1H, bs), 12.12 (1H, bs) | 403; HPLC tR = 2.71 min |

Intermediate 47

6-chloro-N-cyclohexyl-2-(propylamino)nicotinamide

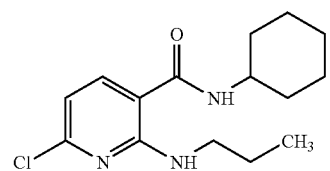 [SMILES: CCCNc1nc(Cl)ccc1C(=O)NC1CCCCC1]

Intermediate 47 was prepared using an analogous method to that used to prepare intermediate 37

$^1$H NMR (400.13 MHz, DMSO-$d_6$) δ0.91 (3H, t), 1.21-35 (5H, m), 1.57 (3H, d), 1.75 (4H, d), 3.27-3.31 (2H, m), 3.70 (1H, m), 6.59 (1H, d), 7.95 (1H, d), 8.26 (1H, d), 8.68 (1H, t)

MS (M+H)=296

The following Example was prepared in a similar manner to Example 1, using Intermediate 48 and an appropriate aminoester starting material:

| Compound | Ex | Name | ¹H NMR δ | MS m/e MH⁺ |
|---|---|---|---|---|
| | 152 | 2-[(3S)-1-[5-(cyclohexylcarbamoyl)-6-(phenethylamino)pyridin-2-yl]-3-piperidyl]acetic acid | 1H NMR (400.13 MHz, DMSO-d6) 1.08-1.48 (7H, m), 1.58-1.88 (8H, m), 2.11-2.17 (1H, m), 2.21-2.26 (1H, m), 2.77 (4H, d), 3.55 (2H, s), 3.65 (1H, s), 4.24 (2H, d), 5.95 (1H, d), 7.17-7.31 (5H, m), 7.59 (1H, s), 7.76 (1H, d), 8.81 (1H, s), 12.16 (1H, s) | 465; HPLC tR = 2.98 min |

Intermediate 48

6-chloro-N-cyclohexyl-2-[(2-phenylethyl)amino]nicotinamide

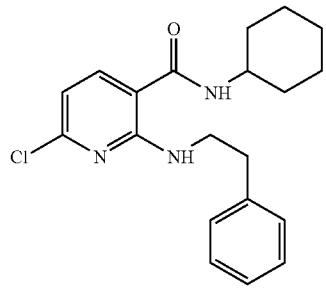 [SMILES: O=C(NC1CCCCC1)c1ccc(Cl)nc1NCCc1ccccc1]

Intermediate 48 was prepared using an analogous method to that used to prepare intermediate 37

¹H NMR (400.13 MHz, DMSO-d₆) δ1.24-1.30 (5H, m), 1.75 (5H, d), 2.85 (2H, t), 3.55-3.60 (2H, m), 3.60-3.71 (1H, m), 6.62 (1H, d), 7.21-7.32 (5H, m), 7.94 (1H, d), 8.25 (1H, d), 8.65 (1H, s)

MS (M+H)=358

The following Example was prepared in a similar manner to Example 1, using Intermediate 49 and an appropriate aminoester starting material:

Intermediate 49

6-chloro-N-cyclohexyl-2-[methyl(2-phenylethyl)amino]nicotinamide

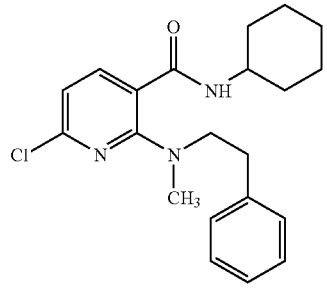 [SMILES: CN(CCc1ccccc1)c1nc(Cl)ccc1C(=O)NC1CCCCC1]

Intermediate 49 was prepared using an analogous method to that used to prepare intermediate 37

¹H NMR (400.13 MHz, DMSO-d₆) δ1.10-1.33 (5H, m), 1.50-1.80 (5H, m), 2.83 (2H, t), 2.94 (3H, s), 3.57 (1H, d), 3.59 (1H, d), 3.64-3.67 (1H, m), 6.69 (1H, d), 7.19-7.22 (1H, m), 7.25-7.32 (4H, m), 7.46 (1H, d), 8.32 (1H, d)

MS (M+H)=372

The following Example was prepared in a similar manner to Example 1, using Intermediate 50 and an appropriate aminoester starting material:

| Compound | Ex | Name | ¹H NMR δ | MS m/e MH⁺ |
|---|---|---|---|---|
| | 153 | 2-[(3S)-1-[5-(cyclohexylcarbamoyl)-6-(methyl-phenethyl-amino)pyridin-2-yl]-3-piperidyl]acetic acid | 1H NMR (400.13 MHz, DMSO-d6) 1.19 (7H, d), 1.61 (8H, d), 1.81-1.89 (2H, m), 2.12-2.26 (1H, m), 2.70-2.75 (1H, m), 2.82 (4H, d), 2.93 (1H, t), 3.47-3.56 (2H, m), 3.62-3.66 (1H, m), 4.20 (2H, d), 6.26 (1H, d), 7.19 (3H, t), 7.27 (2H, d), 7.54 (1H, d), 8.00 (1H, d), 12.15 (1H, bs). | 479; HPLC tR = 2.12 min |

| Compound | Ex | Name | ¹H NMR δ | MS m/e MH⁺ |
|---|---|---|---|---|
|  | 154 | 2-[(3S)-1-[5-(cyclohexylcarbamoyl)-6-(methyl-propyl-amino)pyridin-2-yl]-3-piperidyl]acetic acid | 1H NMR (400.13 MHz, DMSO-d6) 0.82 (3H, t), 1.08-1.71 (13H, m), 1.81 (4H, d), 2.10-2.22 (2H, m), 2.64 -2.71 (1H, m), 2.76 (3H, s), 2.86 (1H, d), 3.14-3.25 (2H, m), 3.63-3.68 (1H, m), 4.11 (1H, d), 4.20 (1H, d), 6.18 (1H, d), 7.49 (1H, d), 8.22 (1H, d), 12.16 (1H, s) | 417; HPLC tR = 1.64 min |

Intermediate 50

6-chloro-N-cyclohexyl-2-[methyl(propyl)amino]nicotinamide

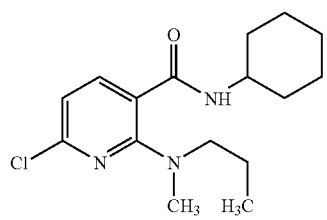 [SMILES: CCCN(C)c1nc(Cl)ccc1C(=O)NC1CCCCC1]

Intermediate 50 was prepared using an analogous method to that used to prepare intermediate 37

¹H NMR (400.13 MHz, DMSO-d₆) δ0.81 (3H, t), 1.10-1.34 (5H, m), 1.48-1.60 (3H, m), 1.69-1.73 (2H, m), 1.81 (2H, d), 2.89 (3H, s), 3.30-3.40 (2H, m), 3.63-3.67 (1H, m), 6.64 (1H, d), 7.42 (1H, d), 8.32 (1H, d)

MS (M+H)=310

The following Example was prepared in a similar manner to Example 1, using Intermediate 51 and an appropriate aminoester starting material:

Intermediate 51

6-chloro-N-cyclohexyl-2-pyrrolidin-1-ylnicotinamide

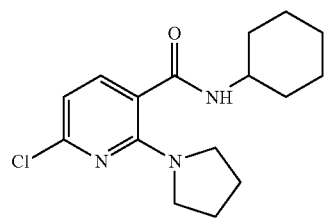 [SMILES: O=C(NC1CCCCC1)c1ccc(Cl)nc1N1CCCC1]

Intermediate 51 was prepared using an analogous method to that used to prepare intermediate 37

¹H NMR (400.13 MHz, DMSO-d₆) δ1.00-1.35 (6H, m) 1.50-1.71 (4H, m), 1.80-1.87 (6H, m), 3.33-3.37 (2H,m), 3.64-3.67 (1H, m), 6.60 (1H, d), 7.41 (1H, d), 8.28 (1H, d)

MS (M+H)=308.

The following Example was prepared in a similar manner to Example 1, using Intermediate 52 and an appropriate aminoester starting material:

| Compound | Ex | Name | ¹H NMR δ | MS m/e MH⁺ |
|---|---|---|---|---|
|  | 155 | 2-[(3S)-1-[5-(cyclohexylcarbamoyl)-6-pyrrolidin-1-yl-pyridin-2-yl]-3-piperidyl]acetic acid | 1H NMR (400.13 MHz, DMSO-d6) 1.47-1.91(19H, m), 2.14-2.21(2H, m), 2.64(1H, d), 2.86(1H, s), 3.48(4H, s), 3.68(1H, m), 4.09(1H, d), 4.19(1H, d), 6.00(1H, d), 7.29(1H, d), 7.81(1H, d), 12.16(1H, bs) | 415; HPLC tR = 1.85 min |

| Compound | Ex | Name | $^1$H NMR δ | MS m/e MH$^+$ |
|---|---|---|---|---|
| 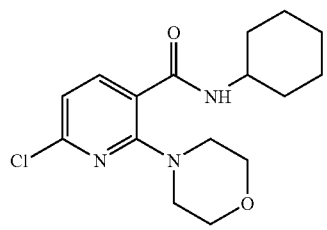 [SMILES: O=C(NC1CCCCC1)c1ccc(Cl)nc1N1CCOCC1] | 156 | 2-[(3S)-1-[5-(cyclohexylcarbamoyl)-6-morpholin-4-yl-pyridin-2-yl]-3-piperidyl]acetic acid | 1H NMR (400.13 MHz, DMSO-d6) 1.10-1.48(7H, m), 1.58-1.73(4H, m), 1.75-1.92(4H, m), 2.12-2.26(2H, m), 2.73-2.79(1H, m), 2.97(1H, d), 3.09 (4H, t), 3.68-3.73(5H, m), 4.12(1H, d), 4.24(1H, d), 6.41(1H, d), 7.75(1H, d), 8.33(1H, d), 12.10(1H, s) | 431; HPLC tR = 2.24 min |

Intermediate 52

6-chloro-N-cyclohexyl-2-morpholin-4-ylnicotinamide

Intermediate 53

6-chloro-N-cyclohexyl-N-methyl-2-(propylamino)nicotinamide

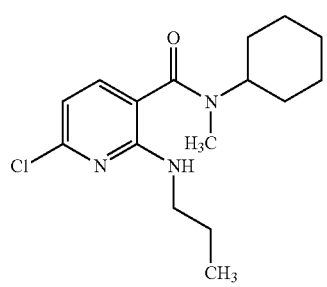 [SMILES: CCCNc1nc(Cl)ccc1C(=O)N(C)C1CCCCC1]

Intermediate 52 was prepared using an analogous method to that used to prepare intermediate 37

$^1$H NMR (400.13 MHz, DMSO-d$_6$) δ1.02-1.33 (5H, m), 1.52-1.65 (1H, d), 1.70-1.80 (2H, m), 1.81-1.90 (2H, m), 3.30-3.40 (4H, m), 3.68-3.72 (5H, m), 6.88 (1H, d), 7.59 (1H, d), 8.30 (1H, d)

MS (M+H)=324.

The following Example was prepared in a similar manner to Example 1, using Intermediate 53 and an appropriate aminoester starting material:

Intermediate 53 was prepared using an analogous method to that used to prepare intermediate 37 m/z (EI+) (M+H)+=310; HPLC t$_R$=2.93 min.

The following Example was prepared in a similar manner to Example 1, using Intermediate 54 and an appropriate aminoester starting material:

| Compound | Ex | Name | $^1$H NMR δ | MS m/e MH$^+$ |
|---|---|---|---|---|
|  | 157 | 2-[(3S)-1-[5-(cyclohexyl-methyl-carbamoyl)-6-propylamino-pyridin-2-yl]-3-piperidyl]acetic acid | 1H NMR (400.13 MHz, DMSO-d6) 0.83-0.93(3H, t), 1.04-1.27(4H, m), 1.35-1.74(9H, m), 1.74-1.91(4H, m), 2.11-2.24(2H, m), 2.62-2.70(1H, m), 2.79(3H, s), 2.88(1H, m), 3.24-3.39 (2H, m), 3.82-3.88(1H, m), 4.14(1H, d), 4.21(1H, d), 5.91(1H, d), 6.51(1H, t), 7.17(1H, d), 12.10(1H, bs). | 417; HPLC tR = 2.66 min |

| Compound | Ex | Name | ¹H NMR δ | MS m/e MH⁺ |
|---|---|---|---|---|
| (structure) | 158 | 2-[(3S)-1-[5-(cyclohexyl-methyl-carbamoyl)-6-(methyl-propyl-amino)pyridin-2-yl]-3-piperidyl]acetic acid | 1H NMR (500.13 MHz, DMSO-d6) 0.86(3H, t), 1.11-1.33(4H, m), 1.47-1.71(10H, m), 1.78(2H, d), 1.84-1.88 (1H, m), 1.92-1.97(1H, m), 2.14-2.24 (2H, m), 2.75(2H, d), 2.77(3H, s), 2.87 (3H, s), 2.95(2H, m), 4.02(1H, d), 4.11-4.15(1H, m), 6.04(1H, d), 7.09(1H, d), 11.85(1H, vbs). | 431; HPLC tR = 2.47 min |

Intermediate 54

6-chloro-N-cyclohexyl-N-methyl-2-[methyl(propyl)amino]nicotinamide

Intermediate 55

6-chloro-N-cyclohexyl-2-methylnicotinamide

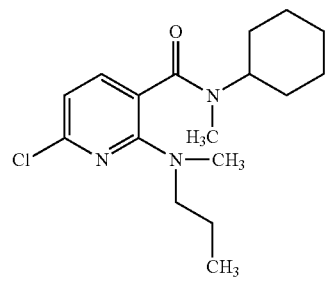 [SMILES: CCCN(C)c1nc(Cl)ccc1C(=O)N(C)C1CCCCC1]

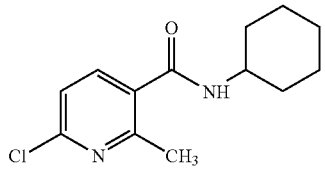 [SMILES: Cc1nc(Cl)ccc1C(=O)NC1CCCCC1]

A solution of 2-methyl-6-chloronicotinic acid (300 mg, 1.75 mmol) and 1-hydroxybenzotriazole (260 mg, 1.92 mmol) was stirred in dichloromethane (25 ml) then triethylamine (561 ul, 4.02 mmol) and EDAC (401 mg, 2.1 mmol) were added and stirred for 5 minutes then cyclohexylamine (201 ul, 1.75 mmol) was added and the reaction was stirred for a further 16 hours at room temperature. The reaction was diluted with dichloromethane (25 ml), washed with sat. NaHCO3, 1M HCl, water, brine and dried over MgSO₄, filtered and the solvent evaporated to give 6-chloro-2-methyl-N-cyclohexylnicotinamide (340 mg, 77%) as a fawn coloured powder ¹H NMR (400.13 MHz, DMSO-d₆) δ1.23 (5H, d), 1.58 (1H, s), 1.70-1.74 (2H, m), 1.82-1.85 (2H, m), 2.47 (3H, s), 3.72 (1H, t), 7.39 (1H, d), 7.73 (1H, d), 8.37 (1H, d)

MS m/e (M+H)+253

Intermediate 54 was prepared using an analogous method to that used to prepare intermediate 37 m/z (EI+) (M+H)+=324; HPLC t$_R$=2.90 min.

The following Example was prepared in a similar manner to Example 1, using Intermediate 55 and an appropriate aminoester starting material:

| Compound | Ex | Name | ¹H NMR δ | MS m/e MH⁺ |
|---|---|---|---|---|
| (structure) | 159 | 2-[(3S)-1-[5-(cyclohexylcarba-moyl)-6-methyl-pyridin-2-yl]-3-piperidyl]acetic acid | 1H NMR (400.13 MHz, DMSO-d6) 1.20(7H, d), 1.71(8H, d), 2.10-2.16 (1H, m), 2.22-2.27(1H, m), 2.39(3H, s), 2.65-2.71(1H, m), 2.87(1H, d), 3.66-3.69(1H, m), 4.18-4.23(2H, m), 6.59(1H, d), 7.47(1H, d), 7.87(1H, s), 12.16(1H, s) | 360; HPLC tR = 1.18 min |

The following Example was prepared in a similar manner to Example 1, using Intermediate 56 and an appropriate aminoester starting material:

| Compound | Ex | Name | ¹H NMR δ | MS m/e MH⁺ |
|---|---|---|---|---|
|  | 160 | 2-[(3S)-1-[5-(1-adamantylcarbamoyl)-6-methyl-pyridin-2-yl]-3-piperidyl]acetic acid | 1H NMR (400.13 MHz, DMSO-d6) 1.18-1.28(1H, m), 1.35-1.45(1H, m), 1.64(7H, s), 1.80-1.86(2H, m), 2.02 (9H, s), 2.10-2.16(1H, m), 2.21-2.27 (1H, m), 2.37(3H, s), 2.64-2.69(1H, m), 2.83-2.89(1H, m), 4.16-4.22(2H, m), 6.57(1H, d), 7.41(1H, d), 7.45(1H, s), 12.16(1H, s) | 412; HPLC tR = 1.50 min |

Intermediate 56

N-adamantan-1-yl-6-chloro-2-methylnicotinamide

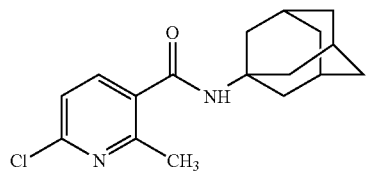 [SMILES: Cc1nc(Cl)ccc1C(=O)NC12CC3CC(CC(C3)C1)C2]

Intermediate 56 was prepared using an analogous method to that used to prepare intermediate 55

¹H NMR (400.13 MHz, DMSO-d₆) δ1.65 (6H, s), 2.04 (9H, s), 2.47 (3H, d), 7.36 (1H, d), 7.37-7.40 (1H, m), 7.68 (1H, d), 7.96 (1H, s)

MS m/e (M+H)+ 305

The following Example was prepared in a similar manner to Example 1, using Intermediate 57 and an appropriate aminoester starting material:

Intermediate 57

N-adamantan-2-yl-6-chloro-2-methylnicotinamide

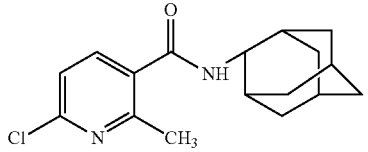 [SMILES: Cc1nc(Cl)ccc1C(=O)NC1C2CC3CC(C2)CC1C3]

Intermediate 57 was prepared using an analogous method to that used to prepare intermediate 55

¹H NMR (400.13 MHz, DMSO-d₆) δ1.52 (2H, d), 1.71 (2H, s), 1.78-1.82 (5H, m), 1.85 (1H, s), 1.94 (2H, s), 2.03 (2H, d), 2.47 (3H, s), 4.04 (1H, d), 7.38-7.40 (1H, m), 7.73 (1H, d), 8.39 (1H, d)

MS m/e (M+H)+ 305

The following Examples were prepared in a similar manner to Example 1, using Intermediate 63 and an appropriate aminoester starting material:

| Compound | Ex | Name | ¹H NMR δ | MS m/e MH⁺ |
|---|---|---|---|---|
|  | 161 | 2-[(3S)-1-[5-(2-adamantylcarbamoyl)-6-methyl-pyridin-2-yl]-3-piperidyl]acetic acid | 1H NMR (400.13 MHz, DMSO-d6) 1.23(1H, t), 1.40(1H, t), 1.50(2H, d), 1.63-1.67(1H, m), 1.70(2H, s), 1.82 (8H, d), 1.92(2H, s), 2.06(2H, d), 2.11-2.28(2H, m), 2.40(3H, s), 2.66-2.71 (1H, m), 2.88(1H, d), 3.98(1H, t), 4.21 (2H, d), 6.60(1H, d), 7.48(1H, d), 7.88 (1H, d), 12.18(1H, bs) | 412; HPLC tR = 1.52 min |

| Compound | Ex | Name | ¹H NMR δ | MS m/e MH⁺ |
|---|---|---|---|---|
| 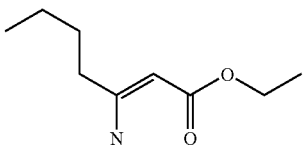 | 162 | 2-[(3S)-1-[5-(2-adamantylcarba-moyl)-6-butyl-pyridin-2-yl]-3-piperidyl]acetic acid | 1H NMR (400.13 MHz, DMSO-d6) 0.87(3H, t), 1.24-1.33(3H, m), 1.37-1.52(3H, m), 1.57-1.66(3H, m), 1.71 (2H, s), 1.79(6H, d), 1.85(2H, s), 1.93 (2H, s), 2.05-2.27(4H, m), 2.68-2.76 (3H, m), 2.90(1H, d), 3.99(1H, d), 4.21 (2H, d), 6.58(1H, d), 7.44(1H, d), 7.86 (1H, d), 12.09(1H, bs) | 454; HPLC tR = 2.08 min |
| 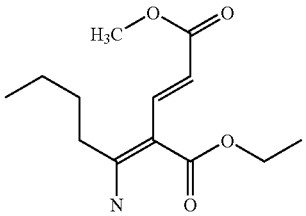 [SMILES: CCCC/C(N)=C(\C=C\C(=O)OC)C(=O)OCC] | 163 | 3-[5-(2-adamantylcarba-moyl)-6-butyl-pyridin-2-yl]-3-azabicyclo[3.1.0]hexane-6-carboxylic acid | 1H NMR (500.13 MHz, DMSO-d6) 0.90(3H, t), 1.35(2H, q), 1.40(1H, t), 1.56(2H, d), 1.64-1.70(2H, m), 1.76 (2H, s), 1.81-1.88(6H, m), 1.98(2H, s), 2.06(2H, d), 2.19(2H, s), 2.81(2H, t), 3.50(2H, d), 3.82(2H, d), 4.03(1H, s), 6.30(1H, d), 7.37(1H, d), 7.49(1H, d) | 438; HPLC tR = 1.84 min |

Intermediate 58

Ethyl)-3-aminohept-2-enoate

Ethyl 3-oxoheptanoate (8.28 g, 48.13 mmol) and ammonium acetate (18.55 g, 240 mmol) were stirred in ethanol (80 ml) at room temperature for 96 hours. The solvent was evaporated and the residue stirred in dichloromethane (100 ml) for 30 minutes. The solid formed was filtered and the filtrate was washed with water (50 ml), saturated brine (50 ml) and dried over MgSO₄ filtered and evaporated to give ethyl 3-aminohept-2-enoate (7.8 g, 94%) as a pale yellow oil.

1H NMR (300.072 MHz, CDCl₃) δ 0.90 (3H, t), 1.19-1.29 (3H, m), 1.31-1.38 (2H, m), 1.47-1.57 (2H, m), 2.06-2.13 (2H, m), 4.09 (2H, q), 4.52 (1H, s)
MS m/e (M+H)+172.

Intermediate 59

5-ethyl 1-methyl-4-(1-aminopentylidene)pent-2-enedioate

Ethyl-3-aminohept-2-enoate (7.8 g, 45.16 mmol) was stirred in toluene (80 ml), methyl propiolate (4.865 ml, 54.73 mmol) was added and the reaction was stirred under N₂ at 100° C. for 96 hours. The solvent was evaporated to give a orange oil. Chromatography (SiO₂) eluting with ethyl acetate/isohexane 20-40% gave 5-ethyl 1-methyl-4-(1-aminopentylidene) pent-2-enedioate (9.5 g, 81%) as a yellow oil.

1H NMR (300.072 MHz, CDCl₃) δ 0.96 (3H, q), 1.35-1.50 (5H, m), 1.60-1.68 (2H, m), 2.05 (1H, s), 2.54 (2H, t), 3.74 (3H, s), 4.13 (1H, q), 4.26 (2H, q), 6.21 (1H, d), 7.64-7.70 (1H, m)
MS m/e (M+H)+ 256.

Intermediate 60 ethyl 2-butyl-6-oxo-1,6-dihydropyridine-3-carboxylate

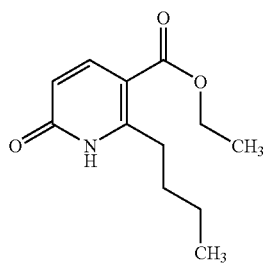 [SMILES: CCCCc1[nH]c(=O)ccc1C(=O)OCC]

5-ethyl 1-methyl-4-(1-aminopentylidene) pent-2-enedioate (2 g, 7.8 mmol) and sodium tertButoxide (100 mg, 1 mmol) were stirred in NMP (20 ml). The solution was heated at 180° C. for 4 hours giving a very dark solution. On cooling the reaction was diluted with ice/water (50 ml) and the resulting precipitate was filtered and washed with water (10 ml) and dried to give ethyl 2-butyl-6-oxo-1,6-dihydropyridine-3-carboxylate (1.35 g, 78%) as a grey powder.

¹H NMR (400.13 MHz, DMSO-d₆) δ0.90 (3H, t), 1.28 (3H, t), 1.31-1.38 (2H, m), 1.50-1.58 (2H, m), 2.90 (2H, m), 4.22 (2H, q), 6.21 (1H, d), 7.82 (1H, d), 11.97 (1H, s)

MS m/e (M+H)+224.

Intermediate 61 ethyl 2-butyl-6-chloronicotinate

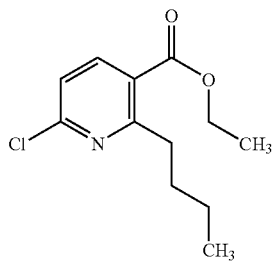 [SMILES: CCCCc1nc(Cl)ccc1C(=O)OCC]

Ethyl 2-butyl-6-oxo-1,6-dihydropyridine-3-carboxylate (450 mg, 2.02 mmol) was stirred in phosphorous oxychloride (10 ml, 30.5 mmol) and heated to 120° C. for 2 hours giving a clear brown solution. The reaction was evaporated and the residue was taken up in EtOAc (25 ml), washed with water (25 ml), saturated brine (25 ml) then dried over MgSO₄ filtered and evaporated. Chromatography of the residue (SiO₂) eluting with ethyl acetate/isohexane 10-30% gave ethyl 2-butyl-6-chloronicotinate (395 mg, 81%) as a clear oil.

¹H NMR (400.13 MHz, DMSO-d₆) δ0.91 (3H, t), 1.30-1.39 (5H, m), 1.58-1.65 (2H, m), 3.02 (2H, t), 4.34 (2H, q), 7.48 (1H, d), 8.16-8.19 (1H, m)

MS m/e (M+H)+ 242

Intermediate 62

2-butyl-6-chloronicotinic acid

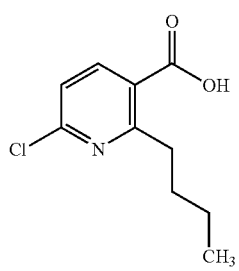

Ethyl 2-butyl-6-chloronicotinate (395 mg, 1.63 mmol) was stirred in methanol (10 ml) and 2M sodium hydroxide (2 ml, 4 mmol) was added. The solution was stirred at room temperature for 16 hours. The solvent was evaporated and the residue taken up in ice/water (10 ml) and acidified with 2M HCl. The milky solution was extracted with dichloromethane (2×15 ml) and the combined extracts were dried over MgSO₄, filtered and evaporated, trituration with isohexane gave 2-butyl-6-chloronicotinic acid (300 mg, 86%) as a white solid.

¹H NMR (400.13 MHz, DMSO-d₆) δ0.90 (3H, t), 1.29-1.38 (2H, m), 1.58-1.66 (2H, m), 3.06 (2H, t), 7.45 (1H, d), 8.17 (1H, d), 13.41 (1H, s)

MS m/e (M+H)+ 214.

Intermediate 63

N-adamantan-2-yl-2-butyl-6-chloronicotinamide

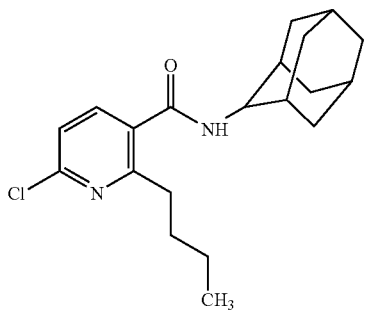 [SMILES: CCCCc1nc(Cl)ccc1C(=O)NC1C2CC3CC(C2)CC1C3]

A solution of oxalyl chloride (0.105 mL, 1.20 mmol) in dichloromethane (2 mL) was added dropwise to a stirred suspension of 2-butyl-6-chloronicotinic acid (214 mg, 1.00 mmol), in dichloromethane (25 mL) over a period of 2 minutes under nitrogen. The resulting solution was stirred at room temperature for 4 hours. The reaction mixture was evaporated to dryness and dissolved in DCM (5 mL). This solution was added dropwise to a stirred solution of 2-adamantanamine hydrochloride (188 mg, 1.00 mmol) and N-ethyldiisopropylamine (0.693 mL, 4.01 mmol) in dichloromethane (20 mL) over a period of 2 minutes under nitrogen. The resulting solution was stirred at room temperature for 16 hours. The reaction mixture was diluted with DCM (20 mL), and washed sequentially with 0.1M HCl (20 mL), saturated NaHCO3 (20 mL), and saturated brine (20 mL). The organic layer was dried over MgSO4, filtered and evaporated to afford N-adamantan-2-yl-2-butyl-6-chloronicotinamide (290 mg, 83%)

1H NMR (400.13 MHz, DMSO-d₆) δ 0.87 (3H, t), 1.24-1.34 (2H, m), 1.50 (2H, d), 1.57-1.64 (2H, m), 1.71 (2H, s), 1.82 (6H, d), 1.92 (2H, s), 2.03 (2H, d), 2.77 (2H, t), 4.05 (1H, t), 7.38 (1H, d), 7.70 (1H, d), 8.43 (1H, d)

MS m/e (M+H)+=347

The following Example was prepared in a similar manner to Example 1, using Intermediate 64 and an appropriate aminoester starting material:

| Compound | Ex | Name | ¹H NMR δ | MS m/e MH⁺ |
|---|---|---|---|---|
| (structure) | 164 | 2-[(3S)-1-[6-butyl-5-(cyclohexylcarbamoyl)pyridin-2-yl]-3-piperidyl]acetic acid | 1H NMR (400.13 MHz, DMSO-d6) 0.87(3H, t), 1.02-1.48(10H, m), 1.55-1.88(9H, m), 2.11-2.27(2H, m),, 2.75 (3H, t), 2.88(1H, d), 3.67(1H, s), 4.20 (2H, t), 6.57(1H, d), 7.42(1H, d), 7.84 (1H, d), 12.07(1H, s) | 402; HPLC tR = 1.65 min |

Intermediate 64

2-butyl-6-chloro-N-cyclohexylnicotinamide

Intermediate 65

6-chloro-N-cyclohexylnicotinamide

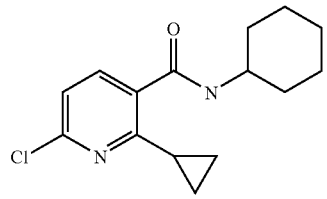

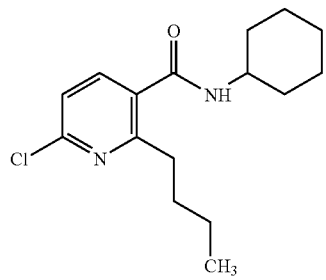 [SMILES: CCCCc1nc(Cl)ccc1C(=O)NC1CCCCC1]

A solution of 6-chloro-2-cyclopropylnicotinoyl chloride (PATENT WO2005/080342) (0.216 g, 1 mmol) in DCM (2.5 mL) was added drop wise to a stirred solution of cyclohexylamine (0.171 mL, 1.50 mmol) and N-ethyldiisopropylamine (0.606 mL, 3.50 mmol) in THF (5 mL) at 20° C., over a period of 2 minutes under nitrogen. The resulting solution was stirred at room temperature for 2 hours. The reaction mixture was diluted with DCM (10 mL) and washed sequentially with 2M HCl (10 mL), saturated NaHCO3 (10 mL), and saturated brine (10 mL). The organic layer was collected from a phase separation cartridge (15 ml) and evaporated to afford crude product. This was triturated with Et2O to give a solid that was collected by filtration and dried under vacuum to give 6-chloro-N-cyclohexyl-2-cyclopropylnicotinamide (79%) as a white solid.

m/z (EI+) (M+H)+=279; HPLC t$_R$=2.43 min.

Intermediate 64 was prepared using an analogous method to that used to prepare intermediate 63

1H NMR (400.13 MHz, DMSO-d₆) δ 0.87 (3H, t), 1.09-1.36 (7H, m), 1.56-1.63 (3H, m), 1.70-1.74 (2H, m), 1.83 (2H, s), 2.78 (2H, t), 3.69-3.76 (1H, m), 7.38 (1H, d), 7.70 (1H, d), 8.39 (1H, d)

MS m/e (M+H)⁺ 295

The following Example was prepared in a similar manner to Example 1, using Intermediate 65 and an appropriate aminoester starting material:

The following Example was prepared in a similar manner to Example 1, using Intermediate 66 and an appropriate aminoester starting material:

| Compound | Ex | Name | ¹H NMR δ | MS m/e MH⁺ |
|---|---|---|---|---|
| (structure) | 165 | 2-[(3S)-1-[5-(cyclohexylcarbamoyl)-6-cyclopropylpyridin-2-yl]-3-piperidyl]acetic acid | 1H NMR (400 .13 MHz, DMSO-d6) 0.78-0.97(6H, m), 1.07-1.45(7H, d), 1.55-1.90(7H, d), 2.10-2.23(2H, m), 2.65-2.70(1H, m), 2.84-2.91(1H, m), 3.68-3.71(1H, m), 4.09(1H, d), 4.17 (1H, d), 6.50(1H, d), 7.41(1H, d), 7.88 (1H, d), 12.09(1H, s) | 386 HPLC tR = 2.2 min |

| Compound | Ex | Name | ¹H NMR δ | MS m/e MH⁺ |
|---|---|---|---|---|
| 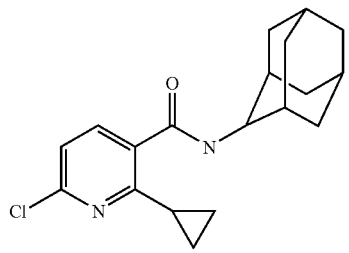 [SMILES: O=C(NC1C2CC3CC(C2)CC1C3)c1ccc(Cl)nc1C1CC1] | 166 | 2-[(3S)-1-[5-(2-adamantylcarba-moyl)-6-cyclopropyl-pyridin-2-yl]-3-piperidyl]acetic acid | 1H NMR (400.13 MHz, DMSO-d6) 0.78-0.81(2H, m), 0.84-1.00(2H, m), 1.20-1.44(2H, m), 1.51(2H, d), 1.61-1.64(1H, m), 1.71(2H, s), 1.83(8H, d), 1.94(2H, s), 2.05-2.22(4H, m), 2.42-2.46(1H, m), 2.65-2.71(1H, m), 2.88(1H, t), 4.01(1H, t), 4.10(1H, d), 4.18(1H, d), 6.52(1H, d), 7.43(1H, d), 7.86(1H, d), 12.01(1H, vbs). | 438 HPLC tR = 2.74 min |

Intermediate 66

N-adamantan-2-yl-6-chloro-2-cyclopropylnicotinamide

Intermediate 66 was prepared using an analogous method to that used to prepare intermediate 65 m/z (EI+) (M+H)+=331; HPLC t_R=2.92 min.

The following Example was prepared in a similar manner to Example 1, using Intermediate 67 and an appropriate aminoester starting material:

Intermediate 67

Trans-4-chloro-2-cyclopropyl-N-((2r,5s)-5-hydroxy-adamantan-2-yl)nicotinamide

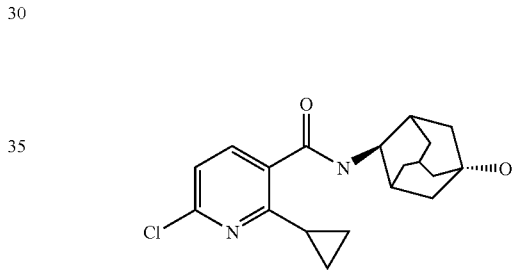

Intermediate 67 was prepared using an analogous method to that used to prepare intermediate 65 m/z (EI+) (M+H)+=347; HPLC t_R=1.86 min.

| Compound | Ex | Name | ¹H NMR δ | MS m/e MH⁺ |
|---|---|---|---|---|
| | 167 | 2-[(3S)-1-[6-cyclopropyl-5-[[(2r,5s)-5-hydroxy-2-adamantyl]carba-moyl]pyridin-2-yl]-3-piperidyl]acetic acid | 1H NMR (400.13 MHz, DMSO-d6) 0.78-0.81(2H, m), 0.91(1H, q), 0.97 (1H, t), 1.25(2H, s), 1.33(2H, d), 1.41 (1H, s), 1.63(4H, d), 1.73(2H, d), 1.79 (2H, d), 1.94(1H, s), 1.98(2H, d), 2.06 (2H, s), 2.10-2.15(1H, m), 2.17-2.22 (1H, m), 2.41-2.46(1H, m), 2.68(1H, d), 2.88(1H, d), 3.92(1H, t), 4.09(1H, d), 4.18(1H, d), 4.37(1H, s), 6.51(1H, d), 7.42(1H, d), 7.83(1H, d), 11.99 (1H, bs) | 454 HPLC tR = 1.75 min |

Example 168

2-[(3R)-1-[5-(Cyclohexyl-methyl-carbamoyl)-6-propylsulfanyl-pyridin-2-yl]-3-piperidyl]acetic acid

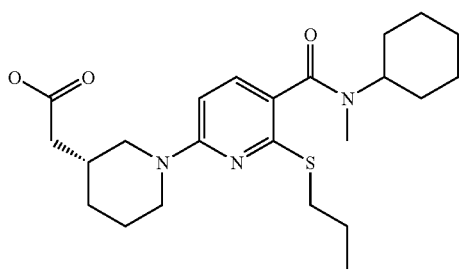 [SMILES: CCCSc1nc(N2CCC[C@H](CC(=O)O)C2)ccc1C(=O)N(C)C1CCCCC1]

6-Chloro-N-cyclohexyl-2-propylsulfanyl-pyridine-3-carboxamide (Intermediate 2, 1.46 g, 4.66 mmol), methyl-(R)-3-piperidine acetate hydrochloride (0.90 g, 4.66 mmol), K$_2$CO$_3$ (1.93 g, 13.98 mmol) and butyronitrile were mixed in a microwave tube and stirred at 170° C. for 2 hours. The mixture changed from a poorly soluble white mixture to an orange solution. Most of the butyronitrile was evaporated under reduced pressure. Water (20 mL) was added and the product was extracted in EtOAc (2×40 mL), washed with brine (10 mL), dried over MgSO$_4$, filtered and evaporated under reduced pressure to give an orange oil. It was preloaded on Celite and purified by flash column chromatography (SiO$_2$, eluent gradient: 0% to 50%, hexane:EtOAc) to afford methyl 2-[(3R)-1-[5-(cyclohexylcarbamoyl)-6-propylsulfanyl-pyridin-2-yl]-3-piperidyl]acetate as a slightly yellow oil which crystallised to give a white solid (1.15 g, 57%).

The crude mixture was then dissolved in THF (25 mL), under N2, in dry glassware and a 1N solution of LiHMDS (2.92 mL, 2.92 mmol) was added at room temperature. After stirring for 2 hours at room temperature MeI (199 μl, 3.12 mmol) was added and the resulting clear yellow solution was stirred at room temperature overnight. The reaction was stopped and partitioned between EtOAc (50 mL) and saturated NH4Cl aq. (20 mL). The aqueous layer was extracted with EtOAc (2×20 mL) and the combined organics were dried over Na2SO4, filtered and evaporated to give a clear yellow gum. Purification by flash column chromatography (SiO$_2$, eluent gradient: hexane:EtOAc, 30% to 80% EtOAc) afforded methyl 2-[(3R)-1-[5-(cyclohexyl-methyl-carbamoyl)-6-propylsulfanyl-pyridin-2-yl]-3-piperidyl]acetate as a colourless gum (400 mg, 34%).

The gum was dissolved in methanol and a 2N aqueous solution of NaOH (2.6 mL, 5.22 mmol) was added. The reaction was stirred at room temperature for 4 hours. TLC showed no more starting material. The MeOH was evaporated under reduced pressure and the remaining solution was acidified to pH 4.6. The product was extracted in DCM (2×25 mL), washed with brine (10 mL), dried over MgSO4 and the solvent evaporated under reduced pressure to give 2-[(3R)-1-[5-(cyclohexyl-methyl-carbamoyl)-6-propylsulfanyl-pyridin-2-yl]-3-piperidyl]acetic acid as a colourless gum. It was triturated in ether and to give a white solid (352 mg, 93%).

$^1$H NMR (400.13 MHz, DMSO-d$_6$) δ 0.94 (3H, t), 1.00-1.09 (2H, m), 1.25-1.40 (2H, m), 1.47-1.55 (4H, m), 1.56-1.81 (8H, m), 1.84-1.91 (2H, m), 2.20-2.26 (2H, m), 2.70-2.90 (4H, m), 2.95 (1H, m), 2.97-3.11 (2H, m), 4.15 (1H, d), 4.27 (1H, d), 6.50 (1H, d), 7.23 (1H, d), 12.22 (1H, br s)

MS m/e MH$^+$ 434

The following Example was prepared in a similar manner to Example 168, using Intermediate 2 and an appropriate aminoester starting material:

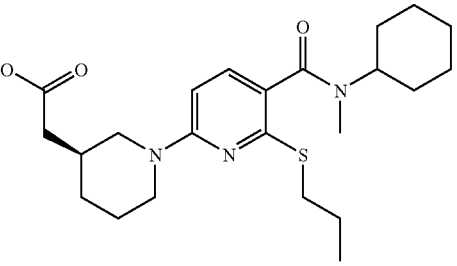 [SMILES: CCCSc1nc(N2CCC[C@@H](CC(=O)O)C2)ccc1C(=O)N(C)C1CCCCC1]

| Compound | Ex | Name | $^1$NMR δ | MS m/e MH$^+$ |
|---|---|---|---|---|
| | 169 | 2-[(3S)-1-[5-(cyclohexyl-methyl-carbamoyl)-6-propylsulfanyl-pyridin-2-yl]-3-piperidyl]acetic acid | 1H NMR (400.13 MHz, DMSO-d6) 0.94(3H, t), 1.05-1.11(2H, m), 1.20-1.30(2H, m), 1.41-1.51(4H, m), 1.56-1.69(8H, m), 1.80-1.90(2H, m), 2.14-2.26(2H, m), 2.65-2.85(4H, m), 2.85-2.95(1H, m), 2.99-3.09(2H, m), 4.15 (1H, d), 4.28(1H, d), 6.50(1H, d), 7.23 (1H, d), 12.15(1H, br s) | 434 |

Example 170

[(3S)-1-[5-[((2r,5s)-5-Methoxyadamantan-2-yl)(methyl)carbamoyl]-6-(propylthio)pyridin-2-yl]piperidin-3-yl]acetic acid

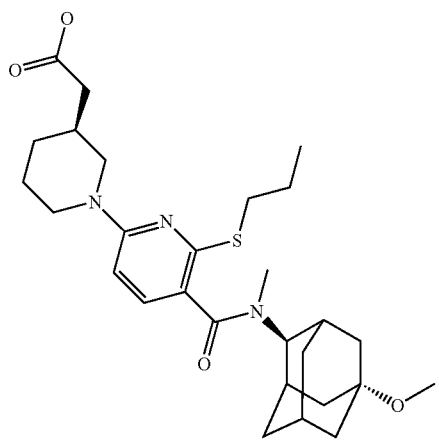 [SMILES: CCCSc1nc(N2CCC[C@@H](CC(=O)O)C2)ccc1C(=O)N(C)[C@H]1C2CC3CC1C[C@](OC)(C3)C2]

A solution of sodium hydroxide (0.036 g, 0.9 mmol) in water (0.45 mL) was added dropwise to a stirred solution of methyl [(3S)-1-{5-[((2r,5s)-5-methoxyadamantan-2-yl)(methyl)carbamoyl]-6-(propylthio)pyridin-2-yl}piperidin-3-yl] acetate (Intermediate 69, 96 mg, 0.18 mmol) in MeOH (5 mL) at 18° C., over a period of 1 minute. The resulting solution was stirred at 18° C. for 45 hours. The reaction mixture was adjusted to pH 4.5 with 2M HCl and the reaction mixture was diluted with EtOAc (50 mL), and washed sequentially with water (20 mL) and saturated brine (20 mL). The organic layer was dried over MgSO4, filtered and evaporated to afford crude product. The crude product was purified by preparative HPLC (Phenomenex Gemini C18 110A (axia) column, 5μ silica, 21 mm diameter, 100 mm length), using decreasingly polar mixtures of water (containing 0.5% NH3) and MeCN as eluents. Fractions containing the desired compound were concentrated under reduced pressure to remove the bulk of the CH3CN. The colourless solution was adjusted to pH 4.5 with 2M HCl and the white solid filtered off and washed with water (2×5 ml), dried under vacuum to afford [(3S)-1-{5-[((2r,5s)-5-methoxyadamantan-2-yl)(methyl)carbamoyl]-6-(propylthio)pyridin-2-yl}piperidin-3-yl]acetic acid (54 mg, 58%) as a white solid.

1H NMR (400.13 MHz, DMSO-d$_6$) δ 0.95 (3H, t), 1.21-1.33 (1H, m), 1.40-1.53 (3H, m), 1.58-1.77 (9H, m), 1.80-2.00 (4H, m), 2.14-2.26 (3H, m), 2.39-2.45 (2H, m), 2.70-2.75 (1H, m), 2.91-3.13 (9H, m), 4.01-4.04 (1H, m), 4.11-4.19 (1H, m), 4.25-4.28 (1H, m), 6.51 (1H, d), 7.27 (1H, d), 12.09 (1H, s)

m/z (ESI+) (M+H)+=516; HPLC $t_R$=2.67 min

Intermediate 68

6-chloro-N-((2r,5s)-5-methoxyadamantan-2-yl)-N-methyl-2-(propylthio)nicotinamide and 6-chloro-N-((2r,5s)-5-hydroxyadamantan-2-yl)-N-methyl-2-(propylthio)nicotinamide

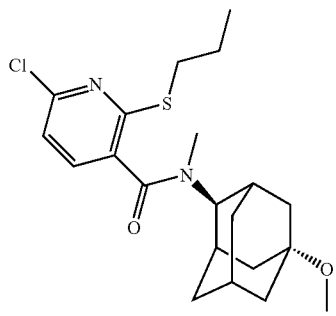 [SMILES: CCCSc1nc(Cl)ccc1C(=O)N(C)[C@H]1C2CC3CC1C[C@](OC)(C3)C2]

6-chloro-N-((2r,5s)-5-hydroxyadamantan-2-yl)-2-(propylthio)nicotinamide (Intermediate 12, 0.38 g, 1 mmol) was added portionwise to sodium hydride (60% dispersion in oil) (0.043 g, 1.07 mmol) in DMF (5 mL) cooled to 0° C. over a period of 2 minutes under nitrogen. The resulting suspension was warmed and stirred at 20° C. for 1 hour. The temperature was decreased to 0° C. and methyl iodide (0.069 ml, 1.1 mmol) was added in one portion and the suspension was warmed and stirred at 20° C. for a further 18 hours. The reaction mixture was quenched with saturated aqueous ammonium chloride (5 mL) then diluted with EtOAc (50 mL), and washed sequentially with water (10 mL) and saturated brine (10 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford 6-chloro-N-((2r,5s)-5-methoxyadamantan-2-yl)-N-methyl-2-(propylthio)nicotinamide (0.077 g, 19%) as a clear glass and 6-chloro-N-((2r,5s)-5-hydroxyadamantan-2-yl)-N-methyl-2-(propylthio) nicotinamide (0.303 g, 77%) as a white solid.

6-chloro-N-((2r,5 s)-5-methoxyadamantan-2-yl)-N-methyl-2-(propylthio)nicotinamide 1H NMR (400.13 MHz, DMSO-d$_6$) δ 0.97 (1H, t), 1.49-1.55 (2H, m), 1.61-1.77 (8H, m), 1.92-1.99 (2H, m), 2.15-2.20 (1H, m), 2.39-2.46 (2H, m), 2.99 (3H, s), 3.11-3.16 (5H, m), 3.95-4.15 (1H, m), 7.29 (1H, d), 7.64 (1H, d)

m/z (ESI+) (M+H)+=409; HPLC $t_R$=2.88 min 6-chloro-N-((2r,5s)-5-hydroxyadamantan-2-yl)-N-methyl-2-(propylthio)nicotinamide 1H NMR (400.13 MHz, DMSO-d$_6$) δ 0.97 (1H, t), 1.46-1.52 (2H, m), 1.59-1.77 (8H, m), 1.90-1.98 (2H, m), 2.10-2.14 (1H, m), 2.29-2.37 (2H, m), 3.00 (3H, s), 3.14 (2H, t), 3.95-4.12 (1H, m), 4.41 (1H, s), 7.29 (1H, d), 7.64 (1H, d)

m/z (ESI+) (M+H)+=395; HPLC $t_R$=2.42 min

Intermediate 69

Methyl [(3S)-1-{5-[((2r,5s)-5-methoxyadamantan-2-yl)(methyl)carbamoyl]-6-(propylthio)pyridin-2-yl}piperidin-3-yl]acetate

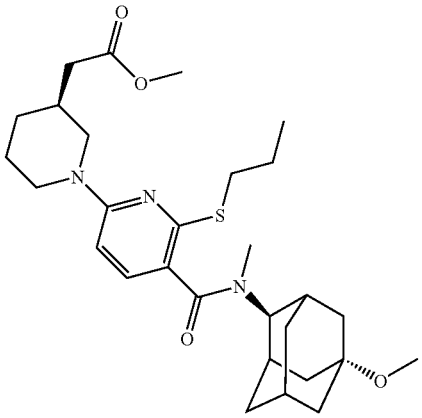 [SMILES: CCCSc1nc(N2CCC[C@@H](CC(=O)OC)C2)ccc1C(=O)N(C)[C@H]1C2CC3CC1C[C@](OC)(C3)C2]

6-chloro-N-((2r,5s)-5-methoxyadamantan-2-yl)-N-methyl-2-(propylthio)nicotinamide (0.074 g, 0.18 mmol) was added to (S)-methyl 2-(piperidin-3-yl)acetate. HCl (0.053 g, 0.27 mmol) and Potassium carbonate (0.088 g, 0.63 mmol) in Butyronitrile (3 mL) warmed to 130° C. over a period of 1 hour under nitrogen. The resulting suspension was stirred at 130° C. for 168 hours. The reaction mixture was diluted with EtOAc (50 mL), and washed sequentially with water (20 mL) and brine (20 mL). The organic layer was dried over MgSO4, filtered and evaporated to afford crude product, methyl [(3S)-1-{5-[((2r,5s)-5-methoxyadamantan-2-yl)(methyl)carbamoyl]-6-(propylthio)pyridin-2-yl}piperidin-3-yl]acetate (97 mg, 100%) as a yellow gum.

m/z (ESI+) (M+H)+=530; HPLC $t_R$=3.13 min

Example 171

[(3S)-1-{5-[((2r,5s)-5-Hydroxyadamantan-2-yl)(methyl)carbamoyl]-6-(propylthio)pyridin-2-yl}piperidin-3-yl]acetic acid

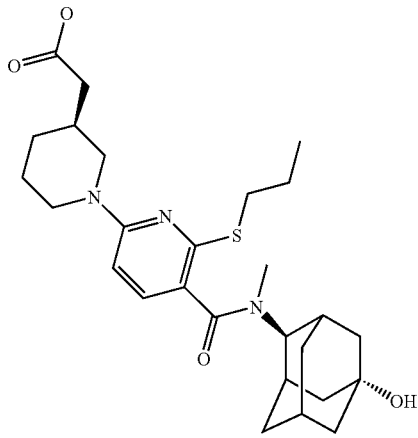 [SMILES: CCCSc1nc(N2CCC[C@@H](CC(=O)O)C2)ccc1C(=O)N(C)[C@H]1C2CC3CC1C[C@](O)(C3)C2]

A solution of sodium hydroxide (0.066 g, 1.65 mmol) in water (0.83 mL) was added dropwise to a stirred solution of methyl [(3S)-1-{5-[(5-hydroxyadamantan-2-yl)(methyl)carbamoyl]-6-(propylthio)pyridin-2-yl}piperidin-3-yl]acetate (171 mg, 0.33 mmol) in MeOH (5 mL) at 18° C., over a period of 1 minute. The resulting solution was stirred at 18° C. for 20 hours. The reaction mixture was adjusted to pH 4.5 with 2M HCl and the reaction mixture was diluted with EtOAc (50 mL), and washed sequentially with water (20 mL) and saturated brine (20 mL). The organic layer was dried over MgSO4, filtered and evaporated to afford crude product. The residue was dissolved in DCM (10 ml) and the slight suspension filtered through a nylon millipore filter to remove the solid. Evaporation gave the product, [(3S)-1-{5-[((2r,5s)-5-hydroxyadamantan-2-yl)(methyl)carbamoyl]-6-(propylthio)pyridin-2-yl]piperidin-3-yl]acetic acid (162 mg, 98%), as a white solid 1H NMR (400.13 MHz, DMSO-$d_6$) δ 0.95 (3H, t), 1.24-1.29 (2H, m), 1.41-1.52 (3H, m), 1.57-1.72 (8H, m), 1.82-2.00 (4H, m), 2.10-2.26 (3H, m), 2.30-2.35 (2H, m), 2.69-2.75 (1H, m), 2.90-3.11 (6H, m), 3.99-4.03 (1H, m), 4.11-4.88 (1H, m), 4.24-4.30 (1H, m), 4.38 (1H, s), 6.51 (1H, d), 7.26 (1H, d), 12.09 (1H, s)

m/z (ESI+) (M+H)+=502; HPLC $t_R$=2.29 min

Intermediate 70

Methyl [(3S)-1-{5-[((2r,5s)-5-hydroxyadamantan-2-yl)(methyl)carbamoyl]-6-(propylthio)pyridin-2-yl}piperidin-3-yl]acetate

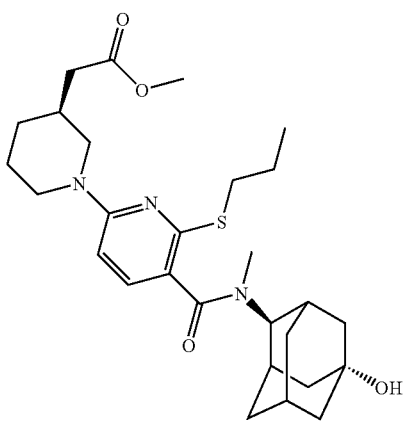 [SMILES: CCCSc1nc(N2CCC[C@@H](CC(=O)OC)C2)ccc1C(=O)N(C)[C@H]1C2CC3CC1C[C@](O)(C3)C2]

6-chloro-N-((2r,5s)-5-hydroxyadamantan-2-yl)-N-methyl-2-(propylthio)nicotinamide (0.289 g, 0.73 mmol) was added to (S)-methyl 2-(piperidin-3-yl)acetate.HCl (0.213 g, 1.1 mmol) and potassium carbonate (0.354 g, 2.56 mmol) in butyronitrile (5 mL) warmed to 130° C. over a period of 1 hour under nitrogen. The resulting suspension was stirred at 130° C. for 168 hours. The reaction mixture was diluted with EtOAc (50 mL), and washed sequentially with water (20 mL) and brine (20 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford methyl [(3S)-1-{5-[((2r,5s)-5-hydroxyadamantan-2-yl)(methyl)carbamoyl]-6-(propylthio)pyridin-2-yl}piperidin-3-yl]acetate (0.282 g, 75%) as a white solid.

1H NMR (400.13 MHz, DMSO-$d_6$) δ 0.95 (3H, t), 1.27-1.32 (1H, m), 1.41-1.52 (3H, m), 1.58-1.70 (9H, m), 1.79-2.00 (4H, m), 2.11 (1H, s), 2.25-2.36 (4H, m), 2.71-2.77 (1H, m), 2.90-3.10 (6H, m), 3.62 (3H, s), 3.99-4.03 (1H, m), 4.11-4.17 (1H, m), 4.22-4.28 (1H, m), 4.38 (1H, s), 6.52 (1H, d), 7.27 (1H, d)

m/z (ESI+) (M+H)+=516; HPLC $t_R$=2.68 min

Example 172

{(3S)-1-[5-(Adamantan-1-ylcarbamoyl)-6-(Propylthio)pyridin-2-yl]piperidin-3-yl}acetic acid

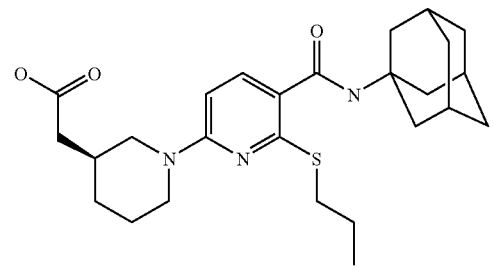 [SMILES: CCCSc1nc(N2CCC[C@@H](CC(=O)O)C2)ccc1C(=O)NC12CC3CC(CC(C3)C1)C2]

A solution of lithium hydroxide (0.053 g, 1.26 mmol) in water (1 mL) was added dropwise to a stirred solution of methyl {(3S)-1-[5-(adamantan-1-ylcarbamoyl)-6-(propylthio)pyridin-2-yl]piperidin-3-yl}acetate (Intermediate 73, 204 mg, 0.42 mmol) in MeOH (3 mL) and THF (2 mL) at 18° C., over a period of 1 minute. The resulting solution was stirred at 18° C. for 20 hours. The reaction mixture was adjusted to pH 4.5 with 2M HCl and the reaction mixture was diluted with EtOAc (50 mL), and washed sequentially with water (20 mL) and saturated brine (20 mL). The organic layer was dried over MgSO4, filtered and evaporated to afford {(3S)-1-[5-(adamantan-1-ylcarbamoyl)-6-(propylthio)pyridin-2-yl]piperidin-3-yl}acetic acid (180 mg, 91%), as a white solid.

$^1$H NMR (400.13 MHz, DMSO-$d_6$) δ0.95 (3H, t), 1.21-1.49 (2H, m), 1.55-1.70 (9H, m), 1.78-1.89 (2H, m), 1.99-2.06 (9H, m), 2.11-2.25 (2H, m), 2.70-2.76 (1H, m), 2.87-3.03 (3H, m), 4.19 (1H, d), 4.27 (1H, d), 6.45 (1H, d), 7.31 (1H, s), 7.53 (1H, d)

m/z (ESI+) (M+H)+=472; HPLC $t_R$=3.12 min

Intermediate 71

N-adamantan-1-yl-2,6-dichloronicotinamide

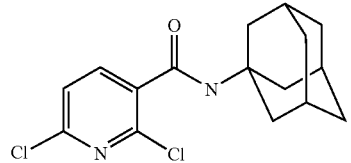 [SMILES: O=C(NC12CC3CC(CC(C3)C1)C2)c1ccc(Cl)nc1Cl]

A solution of 2,6-dichloronicotinoyl chloride (4.21 g, 20 mmol) in DCM (20 mL) was added dropwise to a stirred suspension of 1-aminoadamantane (3.03 g, 20 mmol) and N-ethyldiisopropylamine (4.19 mL, 24 mmol) in DCM (20 mL) at 0° C., over a period of 30 minutes under nitrogen. The resulting suspension was stirred at room temperature for 18 hours. The reaction mixture was diluted with EtOAc (500 mL), and washed sequentially with water (100 mL) and saturated brine (50 mL). The organic layer was dried over MgSO4, filtered and evaporated to afford crude product. The crude product was purified by flash silica chromatography, elution gradient 0 to 5% Et2O in DCM. Pure fractions were evaporated to dryness to afford N-adamantan-1-yl-2,6-dichloronicotinamide (5.57 g, 76%) as a white solid.

$^1$H NMR (400.13 MHz, DMSO-$d_6$) δ1.63-1.67 (6H, m), 2.01-2.08 (9H, m), 7.61 (1H, d), 7.90 (1H, d), 8.12 (1H, s)

m/z (ESI+) (M+H)+=366; HPLC $t_R$=2.66 min

Intermediate 72

N-adamantan-1-yl-6-chloro-2-(propylthio)nicotinamide

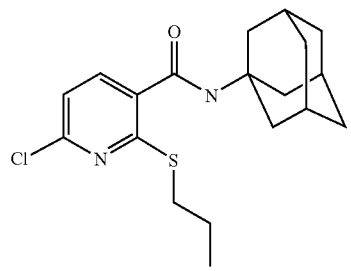 [SMILES: CCCSc1nc(Cl)ccc1C(=O)NC12CC3CC(CC(C3)C1)C2]

1-Propanethiol (0.499 mL, 5.50 mmol) was added dropwise to N-adamantan-1-yl-2,6-dichloronicotinamide (1.63 g, 5 mmol) and potassium carbonate (2.07 g, 15.00 mmol) in butyronitrile (15 mL) at 20° C. over a period of 2 minutes under nitrogen. The resulting suspension was heated at 150° C. for 2 hours. The reaction mixture was diluted with EtOAc (60 mL), and washed sequentially with water (20 mL) and saturated brine (20 mL). The organic layer was dried over MgSO4, filtered and evaporated to afford N-adamantan-1-yl-6-chloro-2-(propylthio)nicotinamide (2.21 g, 100%) as a white solid.

$^1$H NMR (400.13 MHz, DMSO-$d_6$) δ0.97 (3H, t), 1.61-1.66 (8H, m), 2.01-2.07 (9H, m), 3.04 (2H, t), 7.24 (1H, d), 7.67 (1H, d), 7.94 (1H, s)

m/z (ESI+) (M+H)+=365; HPLC $t_R$=3.30 min

Intermediate 73

Methyl {(3S)-1-[5-(adamantan-1-ylcarbamoyl)-6-(propylthio)pyridin-2-yl]piperidin-3-yl}acetate

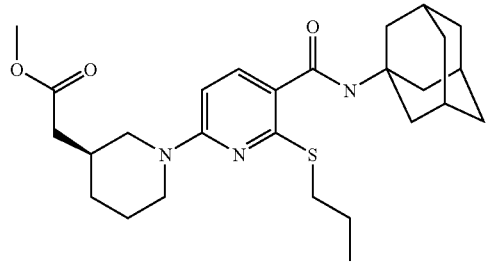 [SMILES: CCCSc1nc(N2CCC[C@@H](CC(=O)OC)C2)ccc1C(=O)NC12CC3CC(CC(C3)C1)C2]

N-adamantan-1-yl-6-chloro-2-(propylthio)nicotinamide (0.365 g, 1 mmol) was added to (S)-methyl 2-(piperidin-3-yl)acetate.HCl (0.194 g, 1 mmol) and potassium carbonate (0.415 g, 3 mmol) in butyronitrile (4 mL) was heated at 150° C. for 2 hours. The reaction mixture was diluted with EtOAc (50 mL), and washed sequentially with water (20 mL) and brine (20 mL). The organic layer was dried over MgSO4, filtered and evaporated to afford crude product. The crude product was purified by flash silica chromatography, elution gradient 0 to 50% EtOAc in hexane. Pure fractions were evaporated to dryness to afford methyl {(3S)-1-[5-(adamantan-1-ylcarbamoyl)-6-(propylthio)pyridin-2-yl]piperidin-3-yl}acetate (0.215 g, 44%) as a white solid.

$^1$H NMR (400.13 MHz, DMSO-$d_6$) δ0.96 (3H, t), 1.22-1.33 (1H, m), 1.37-1.48 (1H, m), 1.55-1.69 (9H, m), 1.76-1.91 (2H, m), 1.99-2.06 (9H, m), 2.23-2.35 (2H, m), 2.72-2.78 (1H, m), 2.87-3.02 (3H, m), 3.61 (3H, s), 4.18 (1H, d), 4.26 (1H, d), 6.46 (1H, d), 7.31 (1H, s), 7.54 (1H, d)

m/z (ESI+) (M+H)+=486; HPLC $t_R$=3.54 min

Example 173

3S)-1-[6-(Propylthio)-5-(tetrahydro-2H-pyran-4-ylcarbamoyl)pyridin-2-yl]piperidin-3-yl]acetic acid

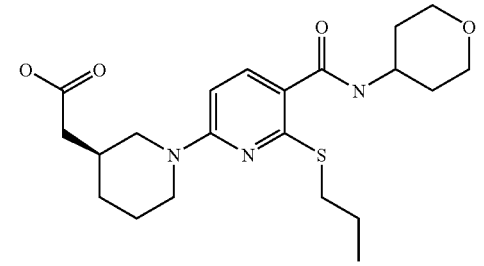 [SMILES: CCCSc1nc(N2CCC[C@@H](CC(=O)O)C2)ccc1C(=O)NC1CCOCC1]

A solution of lithium hydroxide (0.055 g, 1.29 mmol) in water (1 mL) was added dropwise to a stirred solution of methyl {(3S)-1-[6-(propylthio)-5-(tetrahydro-2H-pyran-4-ylcarbamoyl)pyridin-2-yl]piperidin-3-yl}acetate (188 mg, 0.43 mmol) in MeOH (3 mL) and THF (2 mL) at 18° C., over a period of 1 minute. The resulting solution was stirred at 18° C. for 20 hours. The reaction mixture was adjusted to pH 4.5 with 2M HCl and the reaction mixture was diluted with EtOAc (50 mL), and washed sequentially with water (20 mL) and saturated brine (20 mL). The organic layer was dried over MgSO4, filtered and evaporated to afford {(3S)-1-[6-(propylthio)-5-(tetrahydro-2H-pyran-4-ylcarbamoyl)pyridin-2-yl]piperidin-3-yl}acetic acid (191 mg, 100%), as a white solid.

$^1$H NMR (400.13 MHz, DMSO-$d_6$) δ0.95 (3H, t), 1.25-1.88 (11H, m), 2.13-2.25 (2H, m), 2.72-2.77 (1H, m), 2.85-3.02 (3H, m), 3.33-3.40 (2H, m), 3.84-3.90 (3H, m), 4.21 (1H, d), 4.30 (1H, d), 6.49 (1H, d), 7.64 (1H, d), 7.91 (1H, d), 12.18 (1H, s)

m/z (ESI+) (M+H)+=422; HPLC $t_R$=2.05 min

Intermediate 74

2,6-dichloro-N-(tetrahydro-2H-pyran-4-yl)nicotinamide

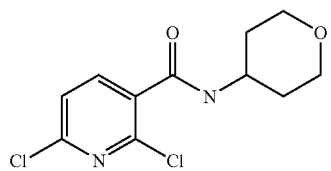 [SMILES: O=C(NC1CCOCC1)c1ccc(Cl)nc1Cl]

A solution of 2,6-dichloronicotinoyl chloride (4.21 g, 20 mmol) in DCM (20 mL) was added dropwise to a stirred suspension of 4-aminotetrahydropyran (2.03 g, 20 mmol) and N-ethyldiisopropylamine (4.19 mL, 24 mmol) in DCM (20 mL) at 0° C., over a period of 30 minutes under nitrogen. The resulting suspension was stirred at room temperature for 18 hours. The reaction mixture was diluted with DCM (200 mL), and washed sequentially with water (50 mL) and saturated brine (50 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford 2,6-dichloro-N-(tetrahydro-2H-pyran-4-yl)nicotinamide (5.03 g, 92%) as a white solid.

$^1$H NMR (400.13 MHz, DMSO-$d_6$) δ1.43-1.53 (2H, m), 1.78-1.83 (2H, m), 3.37-3.43 (2H, m), 3.83-3.88 (2H, m), 3.91-4.00 (1H, m), 7.66 (1H, d), 7.98 (1H, d), 8.65 (1H, d)

m/z (ESI+) (M+H)+=273; HPLC $t_R$=1.28 min

Intermediate 75

6-chloro-2-(propylthio)-N-(tetrahydro-2H-pyran-4-yl)nicotinamide

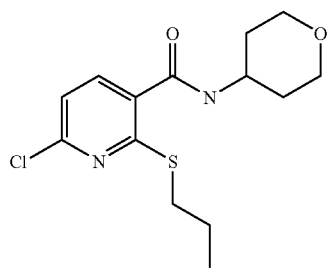

Sodium hexamethyldisilazide (1M in THF) (9 mL, 9 mmol) was added to a solution of 1-propanethiol (0.684 g, 9 mmol) in DMF (14 mL) under N2. This solution was added to a solution of 2,6-dichloro-N-(tetrahydro-2H-pyran-4-yl)nicotinamide (2.93 g, 9 mmol) in DMF (14 mL) under N2 and stirred for 18 hours. The reaction mixture was diluted with EtOAc (200 mL), and washed sequentially with water (50 mL) and saturated brine (50 mL). The organic layer was dried over MgSO4, filtered and evaporated to afford crude product. The crude product was purified by flash silica chromatography, elution gradient 0 to 50% EtOAc in DCM. Pure fractions were evaporated to dryness to afford 2,6-dichloro-N-(tetrahydro-2H-pyran-4-yl)nicotinamide (2.60 g, 92%) as a white solid.

$^1$H NMR (400.13 MHz, DMSO-$d_6$) δ0.97 (3H, t), 1.45-1.55 (2H, m), 1.59-1.68 (2H, m), 1.75-1.79 (2H, m), 3.04 (2H, t), 3.34-3.43 (2H, m), 3.84-3.96 (3H, m), 7.29 (1H, d), 7.78 (1H, d), 8.49 (1H, d)

m/z (ESI+) (M+H)+=315; HPLC $t_R$=2.17 min

Intermediate 76

Methyl {(3S)-1-[6-(propylthio)-5-(tetrahydro-2H-pyran-4-ylcarbamoyl)pyridin-2-yl]piperidin-3-yl}acetate

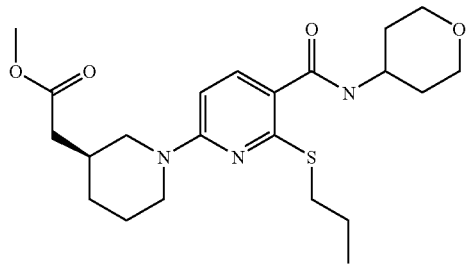 [SMILES: CCCSc1nc(N2CCC[C@@H](CC(=O)OC)C2)ccc1C(=O)NC1CCOCC1]

6-chloro-2-(propylthio)-N-(tetrahydro-2H-pyran-4-yl)nicotinamide (0.205 g, 0.65 mmol) was added to (S)-methyl 2-(piperidin-3-yl)acetate. HCl (0.189 g, 0.98 mmol) and potassium carbonate (0.607 g, 2.93 mmol) in butyronitrile (3 mL) was heated at 150° C. for 4 hours. The reaction mixture was diluted with DCM (50 mL), and washed sequentially with water (20 mL) and brine (20 mL). The organic layer was dried over MgSO4, filtered and evaporated to afford crude product. The crude product was purified by flash silica chromatography, elution gradient 0 to 100% EtOAc:MeOH (19:1) in hexane. Pure fractions were evaporated to dryness to afford Methyl {(3S)-1-[6-(propylthio)-5-(tetrahydro-2H-pyran-4-ylcarbamoyl)pyridin-2-yl]piperidin-3-yl}acetate (0.214 g, 76%) as a white solid.

$^1$H NMR (400.13 MHz, DMSO-$d_6$) δ0.95 (3H, t), 1.23-1.34 (1H, m), 1.37-1.93 (10H, m), 2.24-2.35 (2H, m), 2.73-2.79 (1H, m), 2.86-3.00 (3H, m), 3.33-3.41 (2H, m), 3.61 (3H, s), 3.83-3.93 (3H, m), 4.19 (1H, d), 4.29 (1H, d), 6.50 (1H, d), 7.64 (1H, m), 7.92 (1H, m)

m/z (ESI+) (M+H)+=436; HPLC $t_R$=2.46 min

Example 174

[(3S)-1-{5-[Methyl(tetrahydro-2H-pyran-4-yl)carbamoyl]-6-(propylthio)pyridin-2-yl}piperidin-3-yl] acetic acid

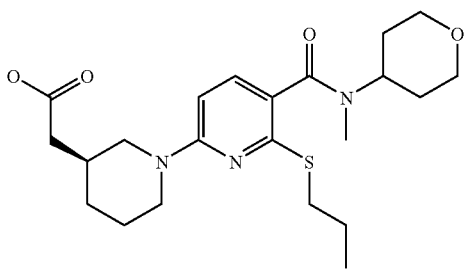 [SMILES: CCCSc1nc(N2CCC[C@@H](CC(=O)O)C2)ccc1C(=O)N(C)C1CCOCC1]

A solution of sodium hydroxide (0.130 g, 3.25 mmol) in water (1.63 mL) was added dropwise to a stirred solution of methyl [(3S)-1-{5-[methyl(tetrahydro-2H-pyran-4-yl)carbamoyl]-6-(propylthio)pyridin-2-yl}piperidin-3-yl]acetate (293 mg, 0.65 mmol) in MeOH (5 mL) at 18° C., over a period of 1 minute. The resulting solution was stirred at 18° C. for 20 hours. The reaction mixture was adjusted to pH 4.5 with 2M HCl and the reaction mixture was diluted with EtOAc (50 mL), and washed sequentially with water (20 mL) and saturated brine (20 mL). The organic layer was dried over MgSO4, filtered and evaporated to afford crude product. The residue was dissolved in DCM (10 ml) and the slight suspension filtered through a nylon millipore filter to remove the solid. Evaporation gave the product, [(3S)-1-{5-[methyl(tetrahydro-2H-pyran-4-yl)carbamoyl]-6-(propylthio)pyridin-2-yl}piperidin-3-yl]acetic acid (281 mg, 100%), as a white solid $^1$H NMR (400.13 MHz, DMSO-$d_6$) δ0.93 (3H, t), 1.23-1.29 (1H, m), 1.40-1.92 (10H, m), 2.14-2.26 (2H, m), 2.67-3.55 (9H, m), 3.89 (2H, d), 4.15 (1H, d), 4.28 (1H, d), 4.36-4.66 (1H, m), 6.51 (1H, d), 7.26 (1H, d), 12.16 (1H, s)

m/z (ESI+) (M+H)+=434; HPLC $t_R$=2.13 min

Intermediate 77

6-chloro-N-methyl-2-(propylthio)-N-(tetrahydro-2H-pyran-4-yl)nicotinamide

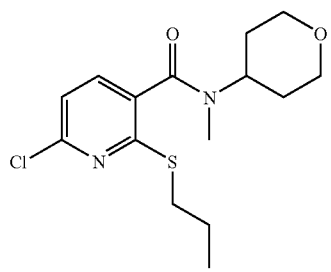 [SMILES: CCCSc1nc(Cl)ccc1C(=O)N(C)C1CCOCC1]

6-chloro-2-(propylthio)-N-(tetrahydro-2H-pyran-4-yl) nicotinamide (0.410 g, 1.3 mmol) in DMF (4 mL) was added portionwise to sodium hydride (60% dispersion in oil) (0.063 g, 1.56 mmol) in DMF (2 mL) cooled to 0° C. over a period of 2 minutes under nitrogen and stirred for 25 minutes. Methyl iodide (0.069 ml, 1.1 mmol) was added in one portion and the suspension was warmed and stirred at 20° C. for 72 hours. The reaction mixture was quenched with saturated aqueous ammonium chloride (5 mL) then diluted with EtOAc (50 mL), and washed sequentially with water (10 mL) and saturated brine (10 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford 6-chloro-N-methyl-2-(propylthio)-N-(tetrahydro-2H-pyran-4-yl)nicotinamide (0.422 g, 99%) as a colourless clear gum.

$^1$H NMR (400.13 MHz, DMSO-$d_6$) (Rotamers) δ0.95 (3H+3H, q), 1.18 (1H, t), 1.50-1.68 (4H+4H, m), 1.75-1.85 (2H+2H, m), 2.67 (3H, s), 2.89 (3H, s), 3.07-3.18 (3H+3H, m), 3.27-3.37 (1H, m), 3.42 (1H+1H, d), 3.81 (1H+1H, d), 3.93-3.97 (1H+1H, m), 4.53-4.63 (1H, m), 7.28-7.31 (1H+1H, m), 7.64-7.68 (1H+1H, m)

m/z (ESI+) (M+H)+=329; HPLC $t_R$=2.28 min

Intermediate 78

Methyl [(3S)-1-{5-[methyl(tetrahydro-2H-pyran-4-yl)carbamoyl]-6-(propylthio)pyridin-2-yl}piperidin-3-yl]acetate

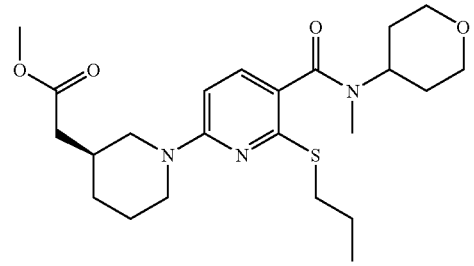 [SMILES: CCCSc1nc(N2CCC[C@@H](CC(=O)OC)C2)ccc1C(=O)N(C)C1CCOCC1]

6-chloro-N-methyl-2-(propylthio)-N-(tetrahydro-2H-pyran-4-yl)nicotinamide (0.398 g, 1.21 mmol) was added to (S)-methyl 2-(piperidin-3-yl)acetate.HCl (0.353 g, 1.82 mmol) and potassium carbonate (0.753 g, 5.45 mmol) in butyronitrile (3 mL) was heated at 150° C. for 4 hours. The reaction mixture was diluted with DCM (60 mL), and washed sequentially with water (20 mL) and brine (20 mL). The organic layer was dried over MgSO4, filtered and evaporated to afford crude product. The crude product was purified by flash silica chromatography, elution gradient 0 to 100% EtOAc in DCM. Pure fractions were evaporated to dryness to afford methyl [(3S)-1-{5-[methyl(tetrahydro-2H-pyran-4-yl) carbamoyl]-6-(propylthio)pyridin-2-yl}piperidin-3-yl]acetate (0.310 g, 57%) as a white solid.

$^1$H NMR (400.13 MHz, DMSO-$d_6$) δ0.94 (2H, t), 1.25-1.31 (1H, m), 1.44-1.93 (10H, m), 2.25-2.36 (2H, m), 2.68-2.84 (4H, m), 2.88-3.11 (3H, m), 3.13-3.49 (2H, m), 3.83-3.94 (2H, M), 4.14 (1H, d), 4.24-4.27 (1H, m), 6.52 (1H, d), 7.26 (1H, d)

m/z (ESI+) (M+H)+=450; HPLC $t_R$=2.52 min

Example 175

2-[(3S)-1-[6-Cyclohexylsulfanyl-5-[[(2r,5s)-5-(difluoromethoxy)-2-adamantyl]carbamoyl]pyridin-2-yl]pyrrolidin-3-yl]acetic acid

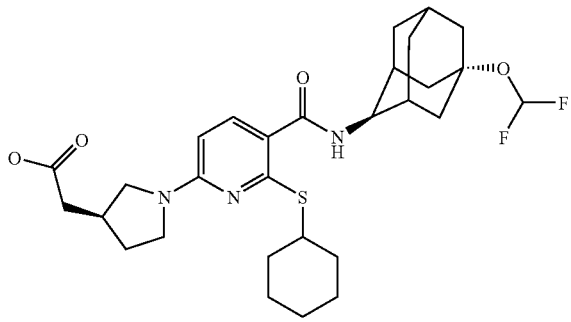 [SMILES: O=C(O)C[C@@H]1CCN(c2ccc(C(=O)N[C@H]3C4CC5CC3C[C@](OC(F)F)(C5)C4)c(SC3CCCCC3)n2)C1]

To a solution of methyl 2-[(3S)-1-[6-cyclohexylsulfanyl-5-[[(2r,5s)-5-(difluoromethoxy)-2-adamantyl]carbamoyl]pyridin-2-yl]pyrrolidin-3-yl]acetate (600 mg, 1.04 mmol) in methanol (30 mL) was added 2M sodium hydroxide (5.19 mL, 10.39 mmol) and the mixture was stirred at ambient temperature for 20 hours.

The reaction was acidified with 1M citric acid (30 mL), evaporated to approximately half volume then ethyl acetate (50 mL) was added and the mixture was washed sequentially with water (2×25 mL) and saturated brine (25 mL). The organic layer was dried over MgSO4, filtered and evaporated to afford the desired product (430 mg, 73%) as a white powder.

1H NMR (400.13 MHz, DMSO-$d_6$) δ 1.22-1.47 (7H, m), 1.55-1.64 (1H, m), 1.66-1.79 (3H, m), 1.81-2.25 (14H, m), 2.36-2.46 (2H, m), 2.55-2.64 (1H, m), 3.08 (1H, dd), 3.36-3.40 (1H, m), 3.5-3.6 (1H, m), 3.7-3.85 (2H, m), 3.9-3.96 (1H, m), 6.12 (1H, d), 6.86 (1H, t), 7.6 (1H, d), 7.62 (1H, d), 12.15 (1H, s)

m/z (ESI+) (M+H)+=564; HPLC $t_R$=3.12 min.

Intermediate 79

6-chloro-2-cyclohexylsulfanyl-N-((2r,5s)-5-hydroxy-2-adamantyl)pyridine-3-carboxamide

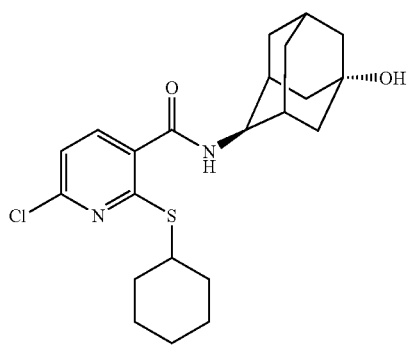 [SMILES: O=C(N[C@H]1C2CC3CC1C[C@](O)(C3)C2)c1ccc(Cl)nc1SC1CCCCC1]

Anhydrous sodium carbonate (1.104 mL, 26.37 mmol) was added in one portion to 2,6-dichloro-N-((2r,5s)-5-hydroxy-2-adamantyl)pyridine-3-carboxamide (3 g, 8.79 mmol) and cyclohexyl mercaptan (1.022 g, 8.79 mmol) in DMF (50 mL) under nitrogen. The resulting suspension was stirred at 60° C. for 6 hours.

The reaction mixture was concentrated and diluted with DCM (150 mL), and washed sequentially with water (2×75 mL) and saturated brine (75 mL). The organic layer was dried over MgSO4, filtered and evaporated to afford crude product that was triturated with 4:1 isohexane:EtOAc to give the desired product (3.5 g, 95%) as a white powder.

1H NMR (400.13 MHz, DMSO-$d_6$) δ 1.32-1.5 (7H, m), 1.59-1.8 (10H, m), 1.94-2.05 (5H, m), 2.06-2.15 (2H, m), 3.7-3.85 (1H, m), 3.91-3.97 (1H, m), 4.39 (1H, s), 7.25 (1H, d), 7.69 (1H, d), 8.23 (1H, d)

m/z (ESI+) (M+H)+=421; HPLC $t_R$=2.7 min.

Intermediate 80 methyl 2-[(3S)-1-[6-cyclohexylsulfanyl-5-[((2r,5s)-5-hydroxy-2-adamantyl)carbamoyl]pyridin-2-yl]pyrrolidin-3-yl]acetate

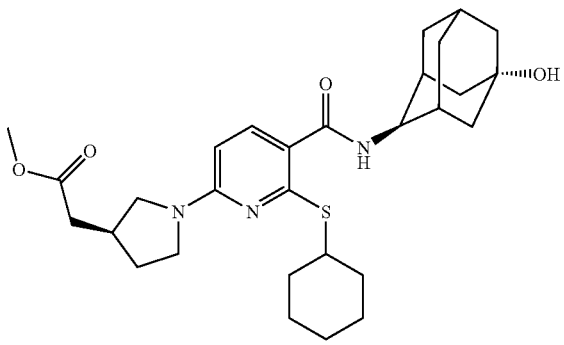 [SMILES: COC(=O)C[C@@H]1CCN(c2ccc(C(=O)N[C@H]3C4CC5CC3C[C@](O)(C5)C4)c(SC3CCCCC3)n2)C1]

Anhydrous potassium carbonate (0.985 g, 7.13 mmol) was added in one portion to (S)-methyl 2-(pyrrolidin-3-yl)acetate hydrochloride (0.427 g, 2.38 mmol) and 6-chloro-2-cyclohexylsulfanyl-N-((2r,5s)-5-hydroxy-2-adamantyl)pyridine-3-carboxamide (1.0 g, 2.38 mmol) in butyronitrile (15 mL). The resulting suspension was stirred at 115° C. for 3 days.

The reaction mixture was cooled, diluted with EtOAc (50 mL), washed with water (2×30 mL) and brine (30 mL), the organic phase dried (MgSO$_4$), filtered and evaporated to an orange oil.

The crude product was purified by flash silica chromatography with EtOAc. Pure fractions were evaporated to dryness to afford methyl 2-[(3S)-1-[6-cyclohexylsulfanyl-5-[((2r,5s)-5-hydroxy-2-adamantyl)carbamoyl]pyridin-2-yl]pyrrolidin-3-yl]acetate (740 mg, 59%) as a pale yellow foam.

1H NMR (400.13 MHz, DMSO-$d_6$) δ 1.22-1.45 (7H, m), 1.57-1.8 (10H, m), 1.92-2.09 (7H, m), 2.14-2.23 (1H, m), 2.53-2.65 (1H, m), 3.1 (1H, dd), 3.36-3.44 (1H, m), 3.5-3.6 (1H, m), 3.63 (3H, s), 3.66-3.84 (2H, m), 3.84-3.9 (1H, m), 4.37 (1H, s), 6.12 (1H, d), 7.54 (1H, d), 7.63 (1H, d)

m/z (ESI+) (M+H)+=528; HPLC $t_R$=2.84 min.

181

Intermediate 81 methyl 2-[(3S)-1-[6-cyclohexylsulfanyl-5-[[(2r,5s)-5-(difluoromethoxy)-2-adamantyl]carbamoyl]pyridin-2-yl]pyrrolidin-3-yl]acetate

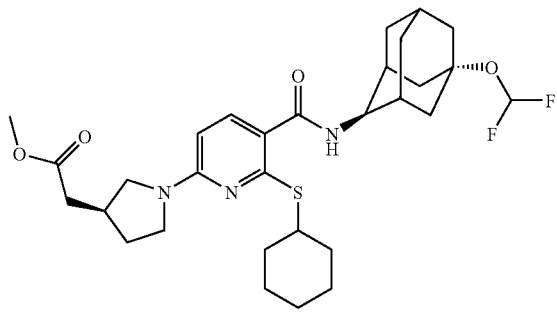 [SMILES: COC(=O)C[C@@H]1CCN(c2ccc(C(=O)N[C@H]3C4CC5CC3C[C@](OC(F)F)(C5)C4)c(SC3CCCCC3)n2)C1]

A solution of 2-(fluorosulphonyl)difluoroacetic acid (0.286 mL, 2.77 mmol) in anhydrous acetonitrile (3 mL) was added dropwise to a solution of methyl 2-[(3S)-1-[6-cyclohexylsulfanyl-5-[((2r,5s)-5-hydroxy-2-adamantyl)carbamoyl]pyridin-2-yl]pyrrolidin-3-yl]acetate (730 mg, 1.38 mmol) and copper (I) iodide (52.7 mg, 0.28 mmol) in anhydrous acetonitrile (27 mL) and warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over MgSO4, filtered and evaporated to afford crude product as an orange oil. The crude product was purified by flash silica chromatography, elution gradient 20 to 50% EtOAc in isohexane. Pure fractions were evaporated to dryness to afford the desired product (640 mg, 80%) as a pale yellow foam.

1H NMR (400.13 MHz, DMSO-$d_6$) δ 1.1-1.34 (8H, m), 1.43-1.52 (1H, m), 1.53-1.67 (3H, m), 1.72-1.83 (4H, m), 1.84-2.1 (11H, m), 2.4-2.58 (1H, m), 2.99 (1H, dd), 3.23-3.33 (1H, m), 3.39-3.47 (1H, m), 3.5 (3H, s), 3.54-3.7 (2H, m), 3.79-3.85 (1H, m), 6.12 (1H, d), 6.75 (1H, t), 7.48 (1H, d), 7.51 (1H, d).

m/z (ESI+) (M+H)+=578; HPLC $t_R$=3.6 min.

Example 176

2-[(3S)-1-[6-Cyclohexylsulfanyl-5-[[(2r,5s)-5-(difluoromethoxy)-2-adamantyl]carbamoyl]pyridin-2-yl]-3-piperidyl]acetic acid

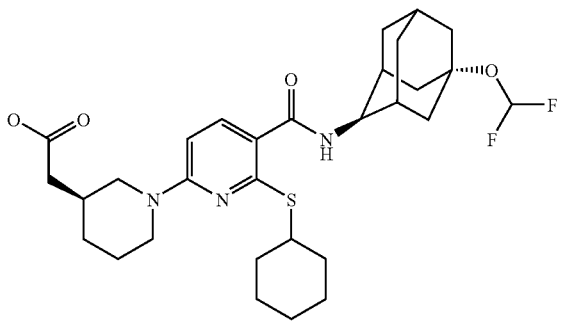 [SMILES: O=C(O)C[C@@H]1CCCN(c2ccc(C(=O)N[C@H]3C4CC5CC3C[C@](OC(F)F)(C5)C4)c(SC3CCCCC3)n2)C1]

To a solution of methyl 2-[(3S)-1-[6-cyclohexylsulfanyl-5-[[(2r,5s)-5-(difluoromethoxy)-2-adamantyl]carbamoyl]pyridin-2-yl]-3-piperidyl]acetate (600 mg, 1.01 mmol) in methanol (30 mL) was added 2M sodium hydroxide (5.07 mL, 10.14 mmol) and the mixture was stirred at ambient temperature for 20 hours.

The mixture was acidified with 1M citric acid (30 mL), evaporated to approximately half volume then ethyl acetate (50 mL) added, and the mixture was washed sequentially with water (2×25 mL) and saturated brine (25 mL). The organic layer was dried over MgSO4, filtered and evaporated to afford desired product (500 mg, 85%) as a white foam.

1H NMR (400.13 MHz, DMSO-$d_6$) δ 1.26-1.5 (10H, m), 1.55-1.78 (4H, m), 1.8-2.08 (12H, m), 2.10-2.3 (4H, m), 2.75 (1H, dd), 2.97 (1H, dd), 3.68-3.78 (1H, m), 3.92-3.97 (1H, m), 4.18-4.3 (2H, m), 6.49 (1H, d), 6.87 (1H, t), 7.60 (1H, d), 7.68 (1H, d), 12.07 (1H, s)

m/z (ESI+) (M+H)+=578; HPLC $t_R$=3.28 min.

Intermediate 82 methyl 2-[(3S)-1-[6-cyclohexylsulfanyl-5-[((2r,5s)-5-hydroxy-2-adamantyl)carbamoyl]pyridin-2-yl]-3-piperidyl]acetate

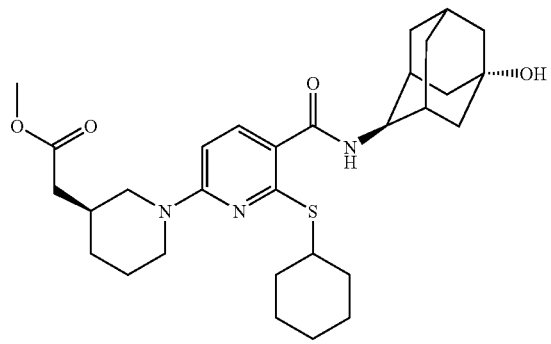 [SMILES: COC(=O)C[C@@H]1CCCN(c2ccc(C(=O)N[C@H]3C4CC5CC3C[C@](O)(C5)C4)c(SC3CCCCC3)n2)C1]

Anhydrous potassium carbonate (0.985 g, 7.13 mmol) was added in one portion to (S)-methyl 2-(piperidin-3-yl)acetate hydrochloride (0.460 g, 2.38 mmol) and 6-chloro-2-cyclohexylsulfanyl-N-((2r,5s)-5-hydroxy-2-adamantyl)pyridine-3-carboxamide (1 g, 2.38 mmol) in butyronitrile (15 mL). The resulting suspension was stirred at 115° C. for 3 days.

The reaction mixture was cooled, diluted with EtOAc (50 mL), washed with water (2×30 mL) and brine (30 mL) and the organic phase was dried (MgSO4), filtered and evaporated to an orange oil.

The crude product was purified by flash silica chromatography with ethyl acetate. Pure fractions were evaporated to dryness to afford methyl 2-[(3S)-1-[6-cyclohexylsulfanyl-5-[((2r,5s)-5-hydroxy-2-adamantyl)carbamoyl]pyridin-2-yl]-3-piperidyl]acetate (960 mg, 74%) as a pale yellow foam.

1H NMR (400.13 MHz, DMSO-$d_6$) δ 1.15-1.43 (9H, m), 1.48-1.69 (10H, m), 1.70-2.0 (9H, m), 2.14-2.31 (2H, m), 2.71 (1H, dd), 2.85-2.95 (1H, m), 3.54 (3H, s), 3.6-3.7 (1H, m), 3.77-3.83 (1H, m), 4.07-4.21 (2H, m), 4.3 (1H, s), 6.43 (1H, d), 7.53 (2H, d), 7.55 (1H, d)

m/z (ESI+) (M+H)+=542; HPLC $t_R$=3.00 min.

Intermediate 83 methyl 2-[(3S)-1-[6-cyclohexylsulfanyl-5-[[(2r,5s)-5-(difluoromethoxy)-2-adamantyl]carbamoyl]pyridin-2-yl]-3-piperidyl]acetate

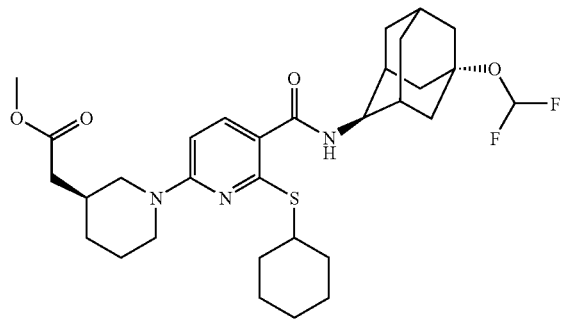

A solution of 2-(fluorosulphonyl)difluoroacetic acid (0.362 mL, 3.51 mmol) in anhydrous acetonitrile (3 mL) was added dropwise to a solution of methyl 2-[(3S)-1-[6-cyclohexylsulfanyl-5-[((2r,5s)-5-hydroxy-2-adamantyl)carbamoyl]pyridin-2-yl]-3-piperidyl]acetate (950 mg, 1.75 mmol) and copper (I) iodide (66.8 mg, 0.35 mmol) in anhydrous acetonitrile (27 mL) warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over MgSO4, filtered and evaporated to afford crude product as an orange oil.

The crude product was purified by flash silica chromatography, elution gradient 20 to 50% EtOAc in isohexane. Pure fractions were evaporated to dryness to afford the desired product (650 mg, 62%) as a pale yellow foam.

1H NMR (400.13 MHz, DMSO-$d_6$) δ 1.26-1.52 (10H, m), 1.58-2.08 (15H, m), 2.09-2.12 (3H, m), 2.24-2.39 (2H, m), 2.78 (1H, dd), 2.94-3.01 (1H, m), 3.62 (3H, s), 3.68-3.77 (1H, m), 3.92-3.97 (1H, m), 4.15-4.3 (2H, m), 6.49 (1H, d), 6.87 (1H, t), 7.61 (1H, d), 7.69 (1H, d)

m/z (ESI+) (M+H)+=592; HPLC $t_R$=3.72 min.

Example 177

2-[(3S)-1-[6-Cyclopentylsulfanyl-5-[[(2r,5s)-5-(difluoromethoxy)-2-adamantyl]carbamoyl]pyridin-2-yl]pyrrolidin-3-yl]acetic acid

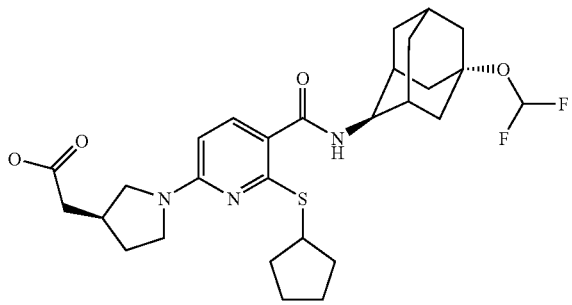 [SMILES: O=C(O)C[C@@H]1CCN(c2ccc(C(=O)N[C@H]3C4CC5CC3C[C@](OC(F)F)(C5)C4)c(SC3CCCC3)n2)C1]

To a solution of methyl 2-[(3S)-1-[6-cyclopentylsulfanyl-5-[[(2r,5s)-5-(difluoromethoxy)-2-adamantyl]carbamoyl]pyridin-2-yl]pyrrolidin-3-yl]acetate (700 mg, 1.24 mmol) in methanol (30 mL) was added 2M sodium hydroxide (6.21 mL, 12.42 mmol) and the mixture was stirred at ambient temperature for 20 hours.

The mixture was acidified with 1M citric acid (30 mL), evaporated to approximately half volume then ethyl acetate (50 mL) was added and the mixture was washed sequentially with water (2×25 mL) and saturated brine (25 mL). The organic layer was dried over MgSO4, filtered and evaporated to afford desired product (560 mg, 82%) as a white powder.

1H NMR (400.13 MHz, DMSO-$d_6$) δ 1.42 (2H, d), 1.49-1.75 (7H, m), 1.84-2.25 (14H, m), 2.42 (2H, d), 2.55-2.62 (1H, m), 3.08 (1H, dd), 3.37-3.41 (1H, m), 3.5-3.6 (1H, m), 3.69-3.74 (1H, m), 3.92-4.05 (2H, m), 6.12 (1H, d), 6.86 (1H, t), 7.58 (1H, d), 7.64 (1H, d), 12.15 (1H, s)

m/z (ESI+) (M+H)+=550; HPLC $t_R$=3.01 min.

Intermediate 84

6-chloro-2-cyclopentylsulfanyl-N-((2r,5s)-5-hydroxy-2-adamantyl)pyridine-3-carboxamide

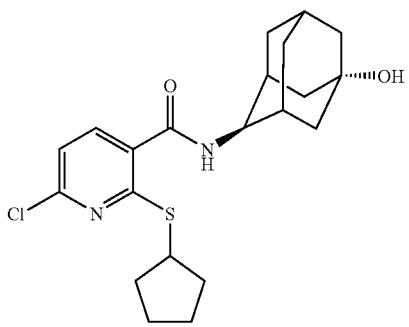 [SMILES: O=C(N[C@H]1C2CC3CC1C[C@](O)(C3)C2)c1ccc(Cl)nc1SC1CCCC1]

Anhydrous sodium carbonate (1.104 mL, 26.37 mmol) was added in one portion to 2,6-dichloro-N-((2r,5s)-5-hydroxy-2-adamantyl)pyridine-3-carboxamide (3 g, 8.79 mmol) and cyclopentyl mercaptan (0.946 mL, 8.79 mmol) in DMF (50 mL) under nitrogen. The resulting suspension was stirred at 60° C. for 6 hours.

The reaction mixture was concentrated and diluted with DCM (150 mL), and washed sequentially with water (2×75 mL) and saturated brine (75 mL). The organic layer was dried over MgSO4, filtered and evaporated to afford crude product that was triturated with 4:1 isohexane:EtOAc to give the desired product (3.2 g, 89%) as a white powder.

1H NMR (400.13 MHz, DMSO-$d_6$) δ 1.38 (2H, d), 1.47-1.6 (2H, m), 1.64-1.85 (10H, m), 1.94-2.08 (3H, m), 2.1-2.15 (2H, m), 2.16-2.28 (2H, m), 3.90-3.97 (2H, m), 4.45 (1H, s), 7.3 (1H, d), 7.70-7.75 (1H, m), 8.28 (1H, d)

m/z (ESI+) (M+H)+=407; HPLC $t_R$=2.55 min.

Intermediate 85 methyl 2-[(3S)-1-[6-cyclopentylsulfanyl-5-[((2r,5s)-5-hydroxy-2-adamantyl)carbamoyl]pyridin-2-yl]pyrrolidin-3-yl]acetate

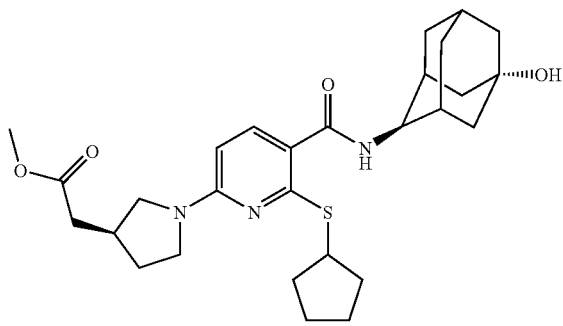 [SMILES: COC(=O)C[C@@H]1CCN(c2ccc(C(=O)N[C@H]3C4CC5CC3C[C@](O)(C5)C4)c(SC3CCCC3)n2)C1]

Anhydrous potassium carbonate (1.019 g, 7.37 mmol) was added in one portion to (S)-methyl 2-(pyrrolidin-3-yl)acetate hydrochloride (0.441 g, 2.46 mmol) and 6-chloro-2-cyclopentylsulfanyl-N-((2r,5s)-5-hydroxy-2-adamantyl)pyridine-3-carboxamide (1.0 g, 2.46 mmol) in butyronitrile (15 mL). The resulting suspension was stirred at 115° C. for 3 days.

The reaction mixture was cooled, diluted with EtOAc (50 mL), washed with water (2×30 mL) and brine (30 mL) and the organic phase dried (MgSO₄), filtered and evaporated to an orange oil.

The crude product was purified by flash silica chromatography with EtOAc. Pure fractions were evaporated to dryness to afford methyl 2-[(3S)-1-[6-cyclopentylsulfanyl-5-[((2r,5s)-5-hydroxy-2-adamantyl)carbamoyl]pyridin-2-yl]pyrrolidin-3-yl]acetate (1.0 g, 79%) as a pale yellow foam.

1H NMR (400.13 MHz, DMSO-d₆) δ 1.3-1.4 (2H, m), 1.48-1.78 (13H, m), 1.9-2.22 (8H, m), 2.55-2.7 (1H, m), 3.1 (1H, dd), 3.35-3.45 (1H, m), 3.52-3.6 (1H, m), 3.63 (3H, s), 3.68-3.73 (1H, m), 3.85-3.92 (1H, m), 3.98-4.05 (1H, m), 4.37 (1H, s), 6.12 (1H, d), 7.52 (1H, d), 7.64 (1H, d)

m/z (ESI+) (M+H)+=514; HPLC $t_R$=2.68 min.

Intermediate 86 methyl 2-[(3S)-1-[6-cyclopentylsulfanyl-5-[[(2r,5s)-5-(difluoromethoxy)-2-adamantyl]carbamoyl]pyridin-2-yl]pyrrolidin-3-yl]acetate

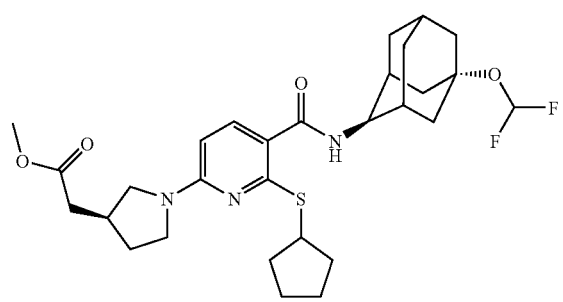 [SMILES: COC(=O)C[C@@H]1CCN(c2ccc(C(=O)N[C@H]3C4CC5CC3C[C@](OC(F)F)(C5)C4)c(SC3CCCC3)n2)C1]

A solution of 2-(fluorosulphonyl)difluoroacetic acid (0.382 mL, 3.70 mmol) in anhydrous acetonitrile (3 mL) was added dropwise to a solution of methyl 2-[(3S)-1-[6-cyclopentylsulfanyl-5-[((2r,5s)-5-hydroxy-2-adamantyl)carbamoyl]pyridin-2-yl]pyrrolidin-3-yl]acetate (950 mg, 1.85 mmol) and copper (I) iodide (70.4 mg, 0.37 mmol) in anhydrous acetonitrile (27 mL) warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over MgSO4, filtered and evaporated to afford crude product as an orange oil. The crude product was purified by flash silica chromatography, elution gradient 20 to 50% EtOAc in isohexane. Pure fractions were evaporated to dryness to afford the desired product (740 mg, 71%) as a pale yellow foam.

1H NMR (400.13 MHz, DMSO-d₆) δ 1.27-1.36 (2H, m), 1.37-1.65 (7H, m), 1.73-1.82 (5H, m), 1.83-1.92 (5H, m), 1.96-2.1 (6H, m), 2.4-2.57 (1H, m), 3.0 (1H, dd), 3.25-3.35 (1H, m), 3.4-3.5 (1H, m), 3.51 (3H, s), 3.55-3.65 (1H, m), 3.8-3.93 (2H, m), 6.12 (1H, d), 6.57 (1H, t), 7.49 (1H, d), 7.54 (1H, d)

m/z (ESI+) (M+H)+=564; HPLC $t_R$=3.46 min.

Example 178

2-[(3S)-1-[6-Cyclopentylsulfanyl-5-[[(2r,5s)-5-(difluoromethoxy)-2-adamantyl]carbamoyl]pyridin-2-yl]-3-piperidyl]acetic acid

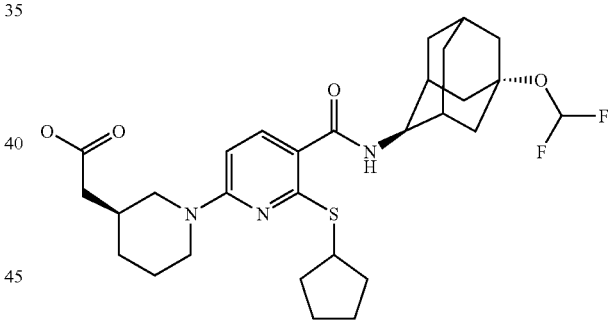

To a solution of methyl 2-[(3S)-1-[6-cyclopentylsulfanyl-5-[[(2r,5s)-5-(difluoromethoxy)-2-adamantyl]carbamoyl]pyridin-2-yl]-3-piperidyl]acetate (700 mg, 1.21 mmol) in methanol (30 mL) was added 2M sodium hydroxide (6.06 mL, 12.12 mmol) and the mixture was stirred at ambient temperature for 20 hours.

The mixture was acidified with 1M citric acid (30 mL), evaporated to approximately half volume then ethyl acetate (50 mL) was added and the mixture was washed sequentially with water (2×25 mL) and saturated brine (25 mL). The organic layer was dried over MgSO4, filtered and evaporated to afford desired product (620 mg, 91%) as a white foam.

1H NMR (400.13 MHz, DMSO-d₆) δ 1.23-1.35 (1H, m), 1.38-1.75 (10H, m), 1.8-1.93 (6H, m), 1.95-2.06 (4H, m), 2.08-2.27 (7H, m), 2.75 (1H, dd), 2.98 (1H, dd), 3.9-4.03 (2H, m), 4.15-4.23 (1H, m), 4.25-4.34 (1H, m), 6.49 (1H, d), 6.87 (1H, t), 7.61 (1H, d), 7.68 (1H, d), 12.1 (1H, s).

m/z (ESI+) (M+H)+=564; HPLC $t_R$=3.13 min.

Intermediate 87 methyl 2-[(3S)-1-[6-cyclopentylsulfanyl-5-[((2r,5s)-5-hydroxy-2-adamantyl)carbamoyl]pyridin-2-yl]-3-piperidyl]acetate

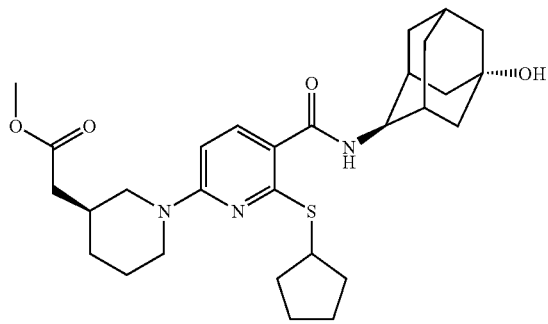 [SMILES: COC(=O)C[C@@H]1CCCN(c2ccc(C(=O)N[C@H]3C4CC5CC3C[C@](O)(C5)C4)c(SC3CCCC3)n2)C1]

Anhydrous potassium carbonate (1.019 g, 7.37 mmol) was added in one portion to (S)-methyl 2-(piperidin-3-yl)acetate hydrochloride (0.476 g, 2.46 mmol) and 6-chloro-2-cyclopentylsulfanyl-N-((2r,5s)-5-hydroxy-2-adamantyl)pyridine-3-carboxamide (1.0 g, 2.46 mmol) in butyronitrile (15 mL). The resulting suspension was stirred at 115° C. for 3 days.

The reaction mixture was cooled, diluted with EtOAc (50 mL), washed with water (2×30 mL) and brine (30 mL) and the organic phase was dried (MgSO$_4$), filtered and evaporated to an orange oil.

The crude product was purified by flash silica chromatography with EtOAc. Pure fractions were evaporated to dryness to afford methyl 2-[(3S)-1-[6-cyclopentylsulfanyl-5-[(2r,5s)-(5-hydroxy-2-adamantyl)carbamoyl]pyridin-2-yl]-3-piperidyl]acetate (1.15 g, 89%) as a white foam.

1H NMR (400.13 MHz, DMSO-d$_6$) δ 1.28-1.75 (17H, m), 1.79-2.2 (9H, m), 2.25-2.35 (2H, m), 2.77 (1H, dd), 2.92-3.02 (1H, m), 3.61 (3H, s), 3.84-3.87 (1H, m), 3.92-4.0 (1H, m), 4.12-4.18 (1H, m), 4.24-4.30 (1H, m), 4.37 (1H, s), 6.49 (1H, d), 7.59 (1H, d), 7.61 (1H, d)

m/z (ESI+) (M+H)+=528; HPLC t$_R$=2.86 min.

Intermediate 88 methyl 2-[(3S)-1-[6-cyclopentylsulfanyl-5-[[(2r,5s)-5-(difluoromethoxy)-2-adamantyl]carbamoyl]pyridin-2-yl]-3-piperidyl]acetate

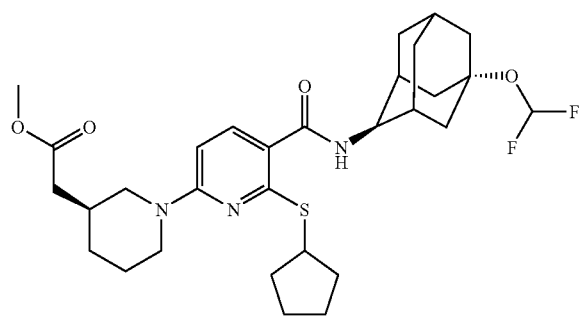 [SMILES: COC(=O)C[C@@H]1CCCN(c2ccc(C(=O)N[C@H]3C4CC5CC3C[C@](OC(F)F)(C5)C4)c(SC3CCCC3)n2)C1]

A solution of 2-(fluorosulphonyl)difluoroacetic acid (0.431 mL, 4.17 mmol) in anhydrous acetonitrile (3 mL) was added dropwise to a solution of methyl 2-[(3S)-1-[6-cyclopentylsulfanyl-5-[((2r,5s)-5-hydroxy-2-adamantyl)carbamoyl]pyridin-2-yl]-3-piperidyl]acetate (1.1 g, 2.08 mmol) and copper (I) iodide (0.079 g, 0.42 mmol) in anhydrous acetonitrile (27 mL) warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over MgSO4, filtered and evaporated to afford crude product as an orange oil.

The crude product was purified by flash silica chromatography, elution gradient 20 to 50% EtOAc in isohexane. Pure fractions were evaporated to dryness to afford the desired product (750 mg, 62%) as a pale yellow foam.

1H NMR (400.13 MHz, DMSO-d$_6$) δ 1.24-1.34 (1H, m), 1.40-1.74 (10H, m), 1.81-1.94 (6H, m), 1.95-2.21 (9H, m), 2.23-2.37 (2H, m), 2.78 (1H, dd), 2.94-3.01 (1H, m), 3.62 (3H, s), 3.90-4.00 (2H, m), 4.16-4.19 (1H, m), 4.27-4.32 (1H, m), 6.49 (1H, d), 6.89 (1H, t), 7.61-7.63 (1H, d), 7.67 (1H, d)

m/z (ESI+) (M+H)+=578; HPLC t$_R$=3.55 min.

Example 179

2-[(3S)-1-[5-[[(2r,5s)-5-(Difluoromethoxy)-2-adamantyl]carbamoyl]-6-propylsulfanyl-pyridin-2-yl]-3-piperidyl]acetic acid

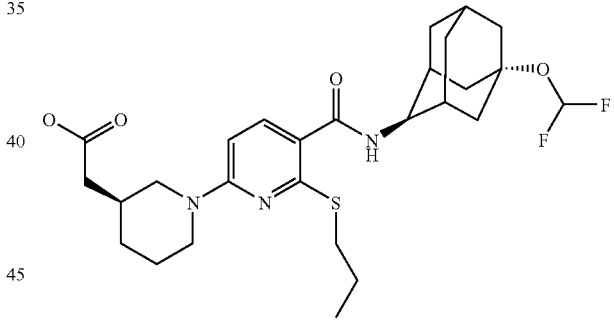

To a solution of methyl 2-[(3S)-1-[5-[[(2r,5s)-5-(difluoromethoxy)-2-adamantyl]carbamoyl]-6-propylsulfanyl-pyridin-2-yl]-3-piperidyl]acetate (850 mg, 1.54 mmol) in methanol (30 mL) was added 2M sodium hydroxide (7.70 mL, 15.41 mmol) and the mixture was stirred at ambient temperature for 20 hours.

The mixture was acidified with 1M citric acid (30 mL), evaporated to approximately half volume then ethyl acetate (50 mL) was added and the mixture washed sequentially with water (2×25 mL) and saturated brine (25 mL). The organic layer was dried over MgSO4, filtered and evaporated to afford desired product (750 mg, 91%) as a white foam.

1H NMR (400.13 MHz, DMSO-d$_6$) δ 0.96 (3H, t), 1.22-1.33 (1H, m), 1.40-1.52 (3H, m), 1.58-1.7 (3H, m), 1.8-1.94 (6H, m), 1.95-2.07 (4H, m), 2.11-2.3 (5H, m), 2.80 (1H, dd), 2.9-3.1 (3H, m), 3.9-3.98 (1H, m), 4.17-4.25 (1H, m), 4.27-4.32 (1H, m), 6.49 (1H, d), 6.87 (1H, t), 7.61 (1H, d), 7.68 (1H, d), 12.09 (1H, s)

m/z (ESI+) (M+H)+=538; HPLC t$_R$=2.96 min.

Intermediate 89 methyl 2-[(3S)-1-[5-[((2r,5s)-5-hydroxy-2-adamantyl)carbamoyl]-6-propylsulfanyl-pyridin-2-yl]-3-piperidyl]acetate

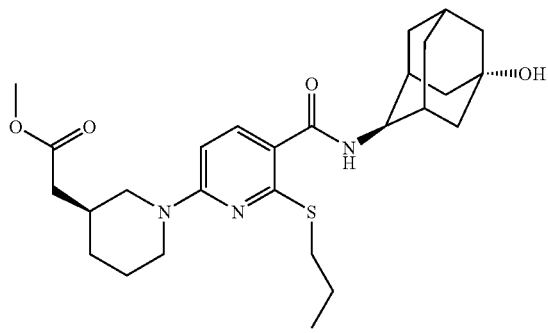 [SMILES: CCCSc1nc(N2CCC[C@@H](CC(=O)OC)C2)ccc1C(=O)N[C@H]1C2CC3CC1C[C@](O)(C3)C2]

Anhydrous potassium carbonate (1.088 g, 7.88 mmol) was added in one portion to (S)-methyl 2-(piperidin-3-yl)acetate hydrochloride (0.508 g, 2.63 mmol) and 6-chloro-N-(5-hydroxy-2-adamantyl)-2-propylsulfanyl-pyridine-3-carboxamide (1 g, 2.63 mmol) in butyronitrile (15 mL). The resulting suspension was stirred at 115° C. for 3 days.

The reaction mixture was cooled, diluted with EtOAc (50 mL), washed with water (2×30 mL) and brine (30 mL), the organic phase dried (MgSO$_4$), filtered and evaporated to an orange oil.

The crude product was purified by flash silica chromatography with EtOAc. Pure fractions were evaporated to dryness to afford methyl 2-[(3S)-1-[5-[((2r,5s)-5-hydroxy-2-adamantyl)carbamoyl]-6-propylsulfanyl-pyridin-2-yl]-3-piperidyl]acetate (1.11 g, 84%) as a pale yellow foam.

1H NMR (400.13 MHz, DMSO-d$_6$) δ 0.96 (3H, t), 1.25-1.36 (3H, m), 1.40-1.46 (1H, m), 1.57-1.77 (9H, m), 1.79-2.1 (7H, m), 2.24-2.38 (2H, m), 2.7 (1H, dd), 2.93-3.06 (3H, m), 3.62 (3H, s), 3.82-3.9 (1H, m), 4.13-4.21 (1H, m), 4.24-4.3 (1H, m), 4.37 (1H, s), 6.50 (1H, d), 7.60 (1H, d), 7.62 (1H, d)

m/z (ESI+) (M+H)+=502; HPLC t$_R$=2.64 min.

Intermediate 90 methyl 2-[(3S)-1-[5-[[(2r,5s)-5-(difluoromethoxy)-2-adamantyl]carbamoyl]-6-propylsulfanyl-pyridin-2-yl]-3-piperidyl]acetate

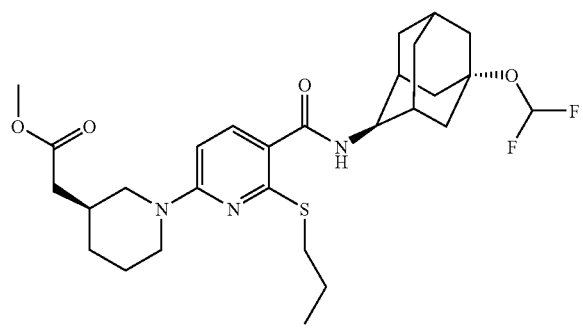 [SMILES: CCCSc1nc(N2CCC[C@@H](CC(=O)OC)C2)ccc1C(=O)N[C@H]1C2CC3CC1C[C@](OC(F)F)(C3)C2]

A solution of 2-(fluorosulphonyl)difluoroacetic acid (0.453 mL, 4.39 mmol) in anhydrous acetonitrile (3 mL) was added dropwise to a solution of methyl 2-[(3S)-1-[5-[((2r,5s)-5-hydroxy-2-adamantyl)carbamoyl]-6-propylsulfanyl-pyridin-2-yl]-3-piperidyl]acetate (1.1 g, 2.19 mmol) and copper (I) iodide (0.084 g, 0.44 mmol) in anhydrous acetonitrile (27 mL) warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over MgSO4, filtered and evaporated to afford crude product as an orange oil.

The crude product was purified by flash silica chromatography, elution gradient 20 to 50% EtOAc in isohexane. Pure fractions were evaporated to dryness to afford the desired product (875 mg, 72%) as a pale yellow foam.

1H NMR (400.13 MHz, DMSO-d$_6$) δ 0.96 (3H, t), 1.24-1.34 (1H, m), 1.38-1.5 (3H, m), 1.58-1.71 (3H, m), 1.76-2.08 (10H, m), 2.09-2.2 (3H, m), 2.24-2.35 (2H, m), 2.81 (1H, dd), 2.91-3.08 (3H, m), 3.62 (3H, s), 3.92-3.98 (1H, m), 4.15-4.22 (1H, m), 4.24-4.32 (1H, m), 6.50 (1H, d), 6.87 (1H, t), 7.61 (1H, d), 7.69 (1H, d)

m/z (ESI+) (M+H)+=552; HPLC t$_R$=3.39 min.

Example 180

2-[(3S)-1-[5-[[(2r,5s)-5-(Difluoromethoxy)-2-adamantyl]carbamoyl]-6-propylsulfanyl-pyridin-2-yl]pyrrolidin-3-yl]acetic acid

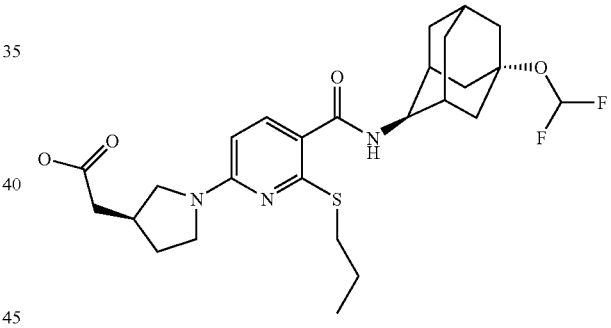

To a solution of methyl 2-[(3S)-1-[5-[[(2r,5s)-5-(difluoromethoxy)-2-adamantyl]carbamoyl]-6-propylsulfanyl-pyridin-2-yl]pyrrolidin-3-yl]acetate (760 mg, 1.41 mmol) in methanol (30 mL) was added 2M sodium hydroxide (7.07 mL, 14.14 mmol) and the mixture was stirred at ambient temperature for 20 hours.

The mixture was acidified with 1M citric acid (30 mL), evaporated to approximately half volume then ethyl acetate (50 mL) was added and the mixture was washed sequentially with water (2×25 mL) and saturated brine (25 mL). The organic layer was dried over MgSO4, filtered and evaporated to afford desired product (670 mg, 91%) as a pale yellow powder.

1H NMR (400.13 MHz, DMSO-d$_6$) δ 0.96 (3H, t), 1.40-1.47 (2H, m), 1.59-1.75 (3H, m), 1.85-2.24 (12H, s), 2.41-2.47 (2H, m), 2.55-2.65 (1H, m), 3.03 (2H, t), 3.1 (1H, dd), 3.37-3.41 (1H, m), 3.52-3.6 (1H, m), 3.7-3.78 (1H, m), 3.92-3.98 (1H, m), 6.13 (1H, d), 6.87 (1H, t), 7.60 (1H, d), 7.64 (1H, d), 12.15 (1H, s)

m/z (ESI+) (M+H)+=524; HPLC t$_R$=2.86 min.

Intermediate 91 methyl 2-[(3S)-1-[5-[((2r,5s)-5-hydroxy-2-adamantyl)carbamoyl]-6-propylsulfanyl-pyridin-2-yl]pyrrolidin-3-yl]acetate

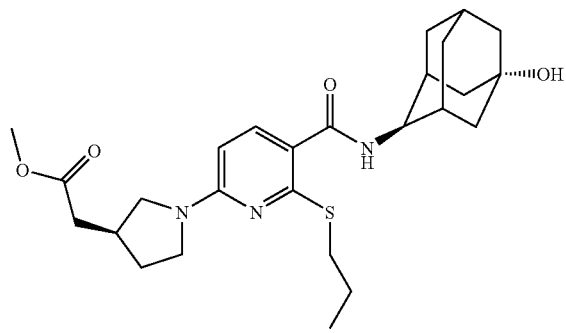 [SMILES: CCCSc1nc(N2CC[C@@H](CC(=O)OC)C2)ccc1C(=O)N[C@H]1C2CC3CC1C[C@](O)(C3)C2]

Anhydrous potassium carbonate (1.088 g, 7.88 mmol) was added in one portion to (S)-methyl 2-(pyrrolidin-3-yl)acetate hydrochloride (0.472 g, 2.63 mmol) and 6-chloro-N-((2r,5s)-5-hydroxy-2-adamantyl)-2-propylsulfanyl-pyridine-3-carboxamide (1.0 g, 2.63 mmol) in butyronitrile (15 mL). The resulting suspension was stirred at 115° C. for 3 days.

The reaction mixture was cooled, diluted with EtOAc (50 mL), washed with water (2×30 mL) and brine (30 mL), the organic phase dried ($MgSO_4$), filtered and evaporated to an orange oil.

The crude product was purified by flash silica chromatography with EtOAc. Pure fractions were evaporated to dryness to afford methyl 2-[(3S)-1-[5-[((2r,5s)-5-hydroxy-2-adamantyl)carbamoyl]-6-propylsulfanyl-pyridin-2-yl]pyrrolidin-3-yl]acetate (980 mg, 77%) as a pale yellow solid.

1H NMR (400.13 MHz, DMSO-$d_6$) δ 0.96 (3H, t), 1.33-1.36 (2H, m), 1.59-1.75 (9H, m), 1.92-2.08 (5H, m), 2.11-2.23 (1H, m), 2.53-2.7 (1H, m), 3.03 (2H, t), 3.08-3.13 (1H, m), 3.39-3.41 (1H, m), 3.52-3.61 (1H, m), 3.63 (3H, s), 3.69-3.74 (1H, m), 3.85-3.92 (1H, m), 4.37 (1H, s), 6.13 (1H, d), 7.53 (1H, d), 7.64 (1H, d)

m/z (ESI+) (M+H)+=488; HPLC $t_R$=2.52 min.

Intermediate 92 methyl 2-[(3S)-1-[5-[[(2r,5s)-5-(difluoromethoxy)-2-adamantyl]carbamoyl]-6-propylsulfanyl-pyridin-2-yl]pyrrolidin-3-yl]acetate

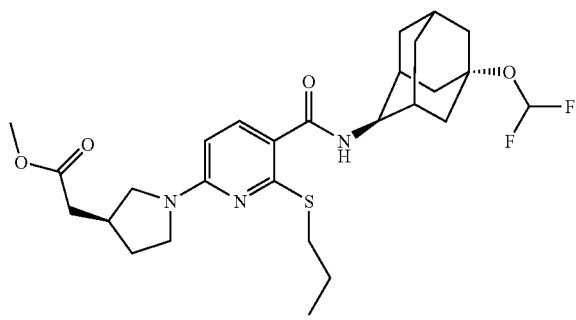 [SMILES: CCCSc1nc(N2CC[C@@H](CC(=O)OC)C2)ccc1C(=O)N[C@H]1C2CC3CC1C[C@](OC(F)F)(C3)C2]

A solution of 2-(fluorosulphonyl)difluoroacetic acid (0.411 mL, 3.98 mmol) in anhydrous acetonitrile (3 mL) was added dropwise to a solution of methyl 2-[(3S)-1-[5-[((2r,5s)-5-hydroxy-2-adamantyl)carbamoyl]-6-propylsulfanyl-pyridin-2-yl]pyrrolidin-3-yl]acetate (970 mg, 1.99 mmol) and copper (I) iodide (76 mg, 0.40 mmol) in anhydrous acetonitrile (27 mL) warmed to 45° C., over a period of 1 hour under nitrogen. The resulting solution was stirred at 45° C. for 30 minutes.

The reaction mixture was concentrated and diluted with EtOAc (50 mL), and washed sequentially with water (2×25 mL) and saturated brine (25 mL). The organic layer was dried over $MgSO4$, filtered and evaporated to afford crude product as an orange oil. The crude product was purified by flash silica chromatography, elution gradient 20 to 50% EtOAc in isohexane. Pure fractions were evaporated to dryness to afford the desired product (790 mg, 74%) as a pale yellow foam.

1H NMR (400.13 MHz, DMSO-$d_6$) δ 0.96 (3H, t), 1.39-1.48 (2H, m), 1.59-1.78 (3H, m), 1.84-1.95 (4H, m), 1.96-2.06 (5H, s), 2.07-2.22 (5H, t), 2.53-2.7 (1H, m), 3.03 (2H, t), 3.1 (1H, dd), 3.33-3.46 (1H, m), 3.52-3.6 (1H, m), 3.63 (3H, s), 3.70-3.77 (1H, m), 3.91-3.97 (1H, m), 6.13 (1H, d), 6.88 (1H, t), 7.60 (1H, d), 7.64 (1H, d)

m/z (ESI+) (M+H)+=538; HPLC $t_R$=3.29 min.

Example 181

2-[(3S)-1-[5-[[(2r,5s)-5-(Difluoromethoxy)-2-adamantyl]carbamoyl]-6-propoxy-pyridin-2-yl]-3-piperidyl]acetic acid

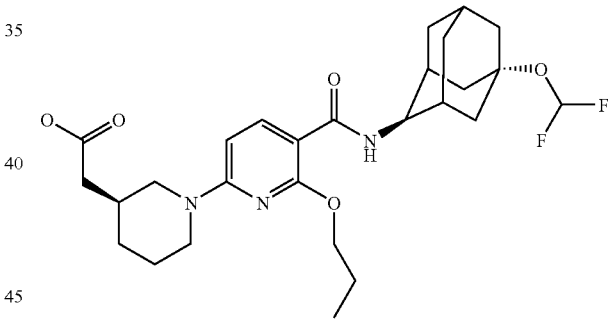

To a solution of methyl 2-[(3S)-1-[5-[[(2r,5s)-5-(difluoromethoxy)-2-adamantyl]carbamoyl]-6-propoxy-pyridin-2-yl]-3-piperidyl]acetate (120 mg, 0.22 mmol) in MeOH (5 mL) was added 2M sodium hydroxide (1 mL, 2.00 mmol). The resulting solution was stirred at ambient temperature for 24 hours.

The mixture was evaporated to approximately quarter volume, water (5 mL) was added and the mixture acidified with 1M citric acid (2 mL) causing formation of a white precipitate. The mixture was stirred for 30 mins, filtered, washed with water and dried in vacuo at 50° C. to afford 2-[(3S)-1-[5-[[5-(difluoromethoxy)-2-adamantyl]carbamoyl]-6-propoxy-pyridin-2-yl]-3-piperidyl]acetic acid (110 mg, 94%)

1H NMR (400.13 MHz, DMSO-$d_6$) δ 1.00 (3H, t), 1.2-1.35 (1H, m), 1.37-1.49 (1H, m), 1.5-1.6 (2H, m), 1.61-1.96 (11H, m), 1.97-2.08 (2H, m), 2.1-2.3 (5H, m), 2.82 (1H, dd), 2.95-3.06 (1H, m), 4.03-4.09 (1H, m), 4.1-4.2 (1H, m), 4.25-4.28 (1H, m), 4.31-4.41 (2H, m), 6.45 (1H, d), 6.9 (1H, t), 7.97 (1H, d), 8.02 (1H, d), 12.2 (1H, s).

m/z (ESI+) (M+H)+=522; HPLC $t_R$=2.97 min.

193
Intermediate 93 methyl 2-[(3S)-1-[5-[((2r,5s)-5-hydroxy-2-adamantyl)carbamoyl]-6-propoxy-pyridin-2-yl]-3-piperidyl]acetate

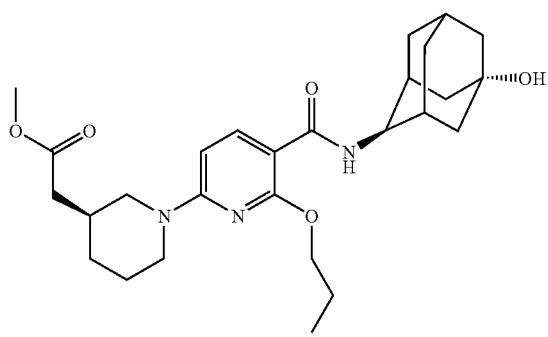

A solution of trimethylsilyldiazomethane (2M solution in ether) (0.329 mL, 0.66 mmol) was added dropwise to a stirred solution of 2-[(3S)-1-[5-[((2r,5s)-5-hydroxy-2-adamantyl)carbamoyl]-6-propoxy-pyridin-2-yl]-3-piperidyl]acetic acid (207 mg, 0.44 mmol) in 3:2 toluene:methanol (5 mL) at 22° C., over a period of 1 minute. The resulting solution was stirred at ambient temperature for 1 hour.

A further 200 μL of 2M TMS diazomethane was added dropwise and the mixture was stirred at ambient temperature for 1 hour.

The mixture was evaporated and the crude product was purified by flash silica chromatography with EtOAc. Pure fractions were evaporated to dryness to afford methyl 2-[(3S)-1-[5-[((2r,5s)-5-hydroxy-2-adamantyl)carbamoyl]-6-propoxy-pyridin-2-yl]-3-piperidyl]acetate (210 mg, 99%) as a colourless oil that crystallised on standing to a white solid.

1H NMR (400.13 MHz, DMSO-$d_6$) δ 1.00 (3H, t), 1.18-1.45 (4H, m), 57-1.9 (13H, m), 1.93-2.05 (3H, m), 2.2-2.32 (2H, m), 2.79 (1H, dd), 2.9-3.0 (1H, m), 3.6 (3H, s), 3.92-3.98 (1H, m), 4.04-4.1 (1H, m), 4.17-4.23 (1H, m), 4.26-4.35 (1H, m), 4.4 (1H, s), 6.4 (1H, d), 7.92 (1H, d), 8.0 (1H, d)

m/z (ESI+) (M+H)+=486; HPLC $t_R$=2.63 min.

194
Intermediate 94 methyl 2-[(3S)-1-[5-[[(2r,5 s)-5-(difluoromethoxy)-2-adamantyl]carbamoyl]-6-propoxy-pyridin-2-yl]-3-piperidyl]acetate

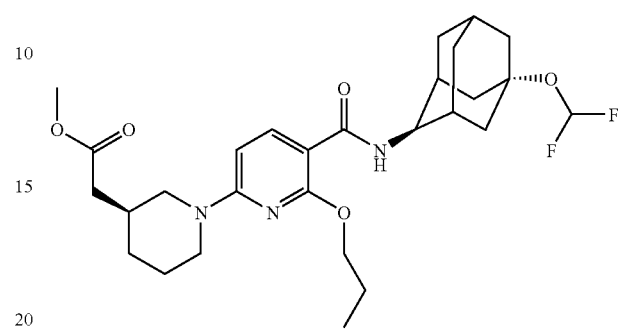

A solution of 2-(fluorosulphonyl)difluoroacetic acid (0.128 mL, 1.24 mmol) in anhydrous acetonitrile (1 mL) was added dropwise to a solution of methyl 2-[(3S)-1-[5-[((2r,5s)-5-hydroxy-2-adamantyl)carbamoyl]-6-propoxy-pyridin-2-yl]-3-piperidyl]acetate (200 mg, 0.41 mmol) and copper (I) iodide (15.69 mg, 0.08 mmol) in anhydrous acetonitrile (5 mL) warmed to 45° C., over a period of 1 hour under nitrogen. The resulting solution was stirred at 45° C. for 30 minutes.

The reaction mixture was concentrated and diluted with EtOAc (25 mL), and washed sequentially with water (2×10 mL) and saturated brine (10 mL). The organic layer was dried over MgSO4, filtered and evaporated to afford crude product as an orange oil.

The crude product was purified by flash silica chromatography, elution gradient 20 to 50% EtOAc in isohexane. Pure fractions were evaporated to dryness to afford the desired product (120 mg, 54%) as a pale yellow foam.

1H NMR (400.13 MHz, CDCl$_3$) δ 1.06 (3H, t), 1.24-1.38 (1H, m), 1.5-1.64 (4H, m), 1.7-1.8 (1H, m), 1.82-2.18 (11H, m), 2.2-2.32 (5H, m), 2.81 (1H, dd), 3.00-3.07 (1H, m), 3.69 (3H, s), 4.10-4.15 (1H, m), 4.2-4.3 (2H, m), 4.36-4.42 (2H, m), 6.28 (1H, d), 6.37 (1H, t), 8.10 (1H, d), 8.26 (1H, d)

m/z (ESI+) (M+H)+=536; HPLC $t_R$=3.46 min.

The following Examples were prepared in a similar manner to Example 175 from the corresponding acid compounds.

| Compound | Ex | Name | $^1$H NMR δ | MS m/e MH+ |
|---|---|---|---|---|
| ![structure] | 182 | (3R)-1-[6-cyclopentylsulfanyl-5-[[(2r,5s)-5-(difluoromethoxy)-2-adamantyl]carbamoyl]pyridin-2-yl]pyrrolidine-3-carboxylic acid | 1H NMR (400.13 MHz, DMSO-d6) 1.36-1.44(2H, m), 1.45-1.73(6H, m), 1.88-1.91(4H, m), 1.92-2.06(4H, m), 2.07-2.3(7H, m), 3.13-3.27(1H, m), 3.43-3.58(2H, m), 3.60-3.72(2H, m), 3.89-3.95(1H, m), 3.96-4.04(1H, m), 6.17(1H, d), 6.9(1H, t), 7.64(1H, d), 7.69(1H, d), 12.5(1H, s). | 536; HPLC tR = 2.92 min. |

| Compound | Ex | Name | ¹H NMR δ | MS m/e MH⁺ |
|---|---|---|---|---|
| | 183 | (1R,5S)-3-[6-cyclopentylsulfanyl-5-[[(2r,5s)-5-(difluoromethoxy)-2-adamantyl]carbamoyl]pyridin-2-yl]-3-azabicyclo[3.1.0]hexane-6-carboxylic acid | 1H NMR (400.13 MHz, DMSO-d6) 1.32-1.44(2H, m), 1.45-1.74(7H, m), 1.83-1.90(4H, m), 1.92-2.01(4H, m), 2.05-2.21(7H, m), 3.45-3.55(2H, m), 3.72-3.85(2H, m), 3.88-4.02(2H, m), 6.14(1H, d), 6.89(1H, t), 7.60(1H, d), 7.69(1H, d), 12.3(1H, s). | 548; HPLC tR = 2.92 min. |
| | 184 | 2-[(3R)-1-[5-[[(2r,5s)-5-(difluoromethoxy)-2-adamantyl]carbamoyl]-6-propylsulfanylpyridin-2-yl]pyrrolidin-3-yl]acetic acid | 1H NMR (400.13 MHz, DMSO-d6) 0.96(3H, t), 1.37-1.45(2H, m), 1.57-1.77(3H, m), 1.83-1.90(4H, m), 1.93-2.04(4H, m), 2.08-2.22(4H, m), 2.39-2.49(2H, m), 2.53-2.62(1H, m), 3.01 (2H, t), 3.05-3.14(1H, m), 3.3-3.43(1H, m), 3.5-3.62(1H, m), 3.65-3.78(1H, m), 3.9-3.98(1H, m), 6.13(1H, d), 6.9(1H, t), 7.65(1H, d), 7.67(1H, d), 12.20(1H, s). | 524; HPLC tR = 2.84 min. |
| | 185 | 1-[5-[[(2r,5S)-5-(difluoromethoxy)-2-adamantyl]carbamoyl]-6-propylsulfanylpyridin-2-yl]pyrrolidine-3-carboxylic acid | 1H NMR (400.13 MHz, DMSO-d6) 0.9 (3H, t), 1.3-1.4(2H, m), 1.4-1.62(2H, m), 1.77-1.89(4H, m), 1.9-2.0(4H, m), 2.03-2.24(5H, m), 2.96(2H, t), 3.1-3.22 (1H, m), 3.37-3.48(2H, m), 3.52-3.65 (2H, m), 3.83-3.9(1H, m), 6.13(1H, d), 6.84(1H, t), 7.6(1H, d), 7.64(1H, d), 12.5(1H, s). | 5.10; HPLC tR = 2.77 min. |

Example 186

(S)-2-(1-(5-(Cyclohexylcarbamoyl)-3-fluoro-6-(propylthio)pyridin-2-yl)piperidin-3-yl)acetic acid

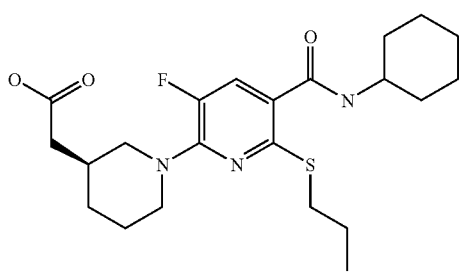 [SMILES: CCCSc1nc(N2CCC[C@@H](CC(=O)O)C2)c(F)cc1C(=O)NC1CCCCC1]

A solution of aqueous 2N sodium hydroxide (1.6 mL, 3.19 mmol) was added to a stirred solution of (S)-methyl 2-(1-(5-(cyclohexylcarbamoyl)-3-fluoro-6-(propylthio)pyridin-2-yl)piperidin-3-yl)acetate (240 mg, 0.53 mmol) in methanol (10 mL) at room temperature. The resulting solution was stirred at 20° C. for 18 hours.

The reaction mixture was evaporated to dryness and dissolved in EtOAc (25 mL), and washed sequentially with 2M HCl (2 mL), and saturated brine (10 mL). The organic layer was dried over MgSO₄, filtered and evaporated to afford (S)-2-(1-(5-(cyclohexylcarbamoyl)-3-fluoro-6-(propylthio)pyridin-2-yl)piperidin-3-yl)acetic acid (225 mg, 97%) as a white solid.

1H NMR (400.13 MHz, DMSO-d₆) δ 0.95 (3H, t), 1.13-1.18 (1H, m), 1.22-1.30 (6H, m), 1.55-1.65 (4H, m), 1.70-1.84 (5H, m), 1.93-2.00 (1H, m), 2.13-2.24 (2H, m), 2.80 (1H, t), 2.93-3.02 (3H, m), 3.62-3.68 (1H, m), 4.03 (1H, d), 4.11 (1H, d), 7.63 (1H, d), 7.95 (1H, d), 12.17 (1H, s)

m/z (ESI+) (M+H)+=438; HPLC t$_R$=2.83 min.

Intermediate 95

2,6-dichloro-N-cyclohexyl-5-fluoronicotinamide

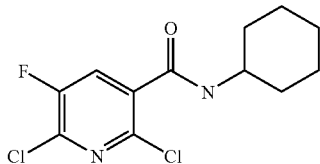 [SMILES: O=C(NC1CCCCC1)c1cc(F)c(Cl)nc1Cl]

Oxalyl chloride (3.74 mL, 42.86 mmol) was added portionwise to 2,6-dichloro-5-fluoronicotinic acid (3.00 g, 14.29 mmol) in dichloromethane (40 mL) at 20° C. The resulting suspension was stirred at 20° C. for 1 hour.

The reaction mixture was evaporated to dryness and dissolved in DCM (10 mL).

This solution was added portionwise to a stirred solution of cyclohexylamine (2.45 mL, 21.4 mmol) in dichloromethane (40 mL) at 20° C. The resulting solution was stirred at 20° C. for 5 hours.

The reaction mixture was diluted with DCM (50 mL), and washed sequentially with 1N HCl (10 mL), water (10 mL), saturated $NaHCO_3$ (10 mL) and saturated brine (10 mL). The organic layer was dried over $MgSO_4$, filtered and evaporated to afford crude product.

1H NMR (400.13 MHz, DMSO-$d_6$) δ 1.28 (5H, t), 1.57 (1H, m), 1.70 (2H, m), 1.84 (2H, m), 3.72 (1H, m), 8.21-8.23 (1H, d), 8.54-8.58 (1H, d)

m/z (ESI+) M+Acetonitrile=332; HPLC $t_R$=2.33 min.

Intermediate 96

6-chloro-N-cyclohexyl-5-fluoro-2-(propylthio)nicotinamide

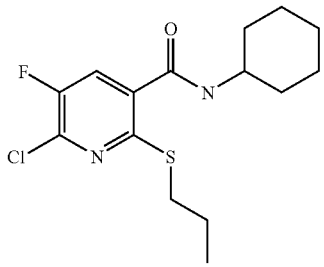 [SMILES: CCCSc1nc(Cl)c(F)cc1C(=O)NC1CCCCC1]

A solution of sodium bis(trimethylsilyl)amide (8.24 mL, 8.24 mmol) in THF (1M) was added to a stirred solution of 1-propanethiol (0.622 mL, 6.87 mmol) in DMF (30 mL) at 5° C., over a period of 3 minutes under air. The resulting suspension was stirred at 20° C. for 15 minutes. 2,6-dichloro-N-cyclohexyl-5-fluoronicotinamide (2.0 g, 6.87 mmol) in DMF (10 mL) was added at room temperature.

The reaction mixture was evaporated to dryness and dissolved in EtOAc (75 mL) and washed sequentially with water (20 mL) and saturated brine (15 mL). The organic layer was dried over $MgSO_4$, filtered and evaporated to afford crude product.

The crude product was purified by flash silica chromatography, elution gradient 0 to 30% EtOAc in isohexane. Pure fractions were evaporated to dryness to afford 6-chloro-N-cyclohexyl-5-fluoro-2-(propylthio)nicotinamide (0.900 g, 40%) as a white solid.

m/z (ESI+) (M+H)+=331; HPLC $t_R$=2.98 min.

Intermediate 97

(S)-methyl 2-(1-(5-(cyclohexylcarbamoyl)-3-fluoro-6-(propylthio)pyridin-2-yl)piperidin-3-yl)acetate

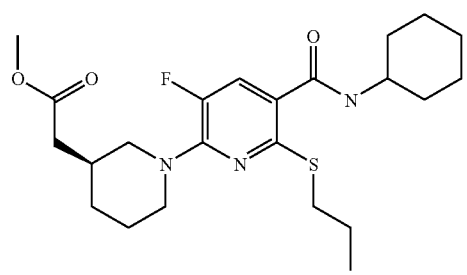 [SMILES: CCCSc1nc(N2CCC[C@@H](CC(=O)OC)C2)c(F)cc1C(=O)NC1CCCCC1]

(S)-methyl 2-(piperidin-3-yl)acetate hydrochloride (263 mg, 1.36 mmol) was added to 6-chloro-N-cyclohexyl-5-fluoro-2-(propylthio)nicotinamide (500 mg, 1.51 mmol) and potassium carbonate (418 μl, 3.02 mmol) in butyronitrile (20 ml) at room temperature and under air. The resulting suspension was stirred at 120° C. for 80 hours.

The reaction mixture was evaporated to dryness and dissolved in EtOAc (50 mL), and washed sequentially with water (20 mL) and saturated brine (10 mL). The organic layer was dried over $MgSO_4$, filtered and evaporated to afford crude product.

The crude product was purified by flash silica chromatography, elution gradient 0 to 50% EtOAc in isohexane. Pure fractions were evaporated to dryness to afford (S)-methyl 2-(1-(5-(cyclohexylcarbamoyl)-3-fluoro-6-(propylthio)pyridin-2-yl)piperidin-3-yl)acetate (240 mg, 35%) as a white solid.

1H NMR (500.13 MHz, DMSO-$d_6$) δ 0.96 (3H, t), 1.10-1.17 (1H, m), 1.24-1.32 (5H, m), 1.54-1.64 (4H, m), 1.70-1.73 (3H, m), 1.80-1.84 (3H, m), 1.97-2.02 (1H, m), 2.26-2.31 (2H, m), 2.82 (1H, t), 2.96 (2H, t), 3.02 (1H, t), 3.61 (3H, s), 3.60-3.66 (1H, m), 4.02 (1H, d), 4.08 (1H, d), 7.63 (1H, d), 7.91 (1H, d)

m/z (ESI+) (M+H)+=452; HPLC $t_R$=3.29 min.

Example 187

(R)-2-(1-(5-(Cyclohexylcarbamoyl)-3-fluoro-6-(propylthio)pyridin-2-yl)piperidin-3-yl)acetic acid

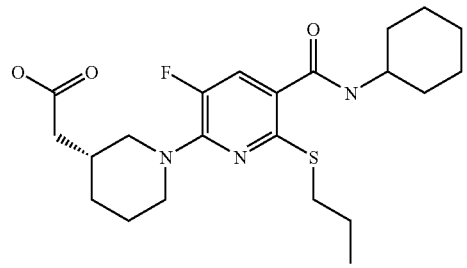 [SMILES: CCCSc1nc(N2CCC[C@H](CC(=O)O)C2)c(F)cc1C(=O)NC1CCCCC1]

Prepared in a similar manner to that described above from 6-chloro-N-cyclohexyl-5-fluoro-2-(propylthio)nicotinamide using (S)-methyl 2-(piperidin-3-yl)acetate hydrochloride followed by an ester hydrolysis as described above to give the desired compound (190 mg) as a white solid.

1H NMR (400.13 MHz, DMSO-$d_6$) δ 0.95 (3H, t), 1.08-1.22 (2H, m), 1.26-1.30 (5H, m), 1.55-1.65 (4H, m), 1.70-1.84 (5H, m), 1.93-1.98 (1H, m), 2.16-2.21 (2H, m), 2.80 (1H, t), 2.93-3.00 (3H, m), 3.60-3.70 (1H, m), 4.02 (1H, d), 4.11 (1H, d), 7.63 (1H, d), 7.95 (1H, d), 12.17 (1H, s)

m/z (ESI+) (M+H)+=438; HPLC $t_R$=2.81 min.

As part of the above program of work, a number of aminoester starting materials were prepared and used according to the following procedures (R)-ethyl 2-(pyrrolidin-3-yloxy)acetate hydrochloride

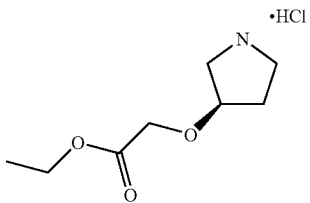

tert-Butyl (3R)-3-(ethoxycarbonylmethoxy)pyrrolidine-1-carboxylate (4.0 g, 15.42 mmol) was dissolved in 4N HCl in 1,4-dioxane (50 mL), stirred at ambient temperature for 3 hrs, evaporated, co-evaporated with 1,4-dioxane (3×50 mL) and dried under high vacuum to give (R)-ethyl 2-(pyrrolidin-3-yloxy)acetate hydrochloride as an orange oil that solidified on standing.

(3.2 g, 100%).

1H NMR (400.13 MHz, DMSO-$d_6$) δ 1.21 (3H, t), 1.89-1.98 (1H, m), 2.05-2.10 (1H, m), 3.14-3.4 (4H, m), 4.14 (2H, q), 4.18 (2H, s), 4.29-4.33 (1H, m), 9.29 (1H, broad s), 9.65 (1H, broad s).

the tert-butyl (3R)-3-(ethoxycarbonylmethoxy)pyrrolidine-1-carboxylate used as starting material was prepared as described below A solution of sodium bis(trimethylsilyl)amide in THF (58.7 mL, 58.75 mmol) was added dropwise to a stirred solution of (R)-tert-butyl 3-hydroxypyrrolidine-1-carboxylate (10 g, 53.41 mmol) in DMF (100 mL) over a period of 10 minutes under nitrogen. The resulting solution was stirred at ambient temperature for 10 minutes. Ethyl bromoacetate (8.92 g, 53.41 mmol) was added dropwise over 10 minutes (exotherm. Temperature kept below 30° C. using a cold water bath) and the reaction was stirred at ambient temperature for 20 hours.

The reaction mixture was evaporated, EtOAc (200 mL) added and washed sequentially with water (4×50 mL), and saturated brine (50 mL). The organic layer was dried over MgSO4, filtered and evaporated to afford crude product (14 g) as an orange oil.

The crude product was purified by flash silica chromatography, elution gradient 20 to 50% EtOAc in isohexane. Pure fractions were evaporated to dryness to afford the product (4.0 g, 28%) as a pale yellow oil.

1H NMR (400.13 MHz, DMSO-$d_6$) δ 1.21 (3H, t), 1.41 (9H, s), 1.83-2.01 (2H, m), 3.2-3.32 (4H, m), 4.12 (2H, s), 4.1-4.2 (5H, m)

(S)-ethyl 2-(pyrrolidin-3-yloxy)acetate hydrochloride

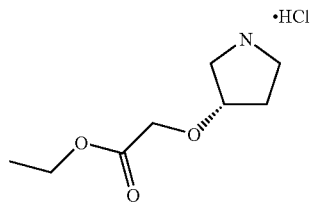

Prepared in a similar manner to that described above from (S)-tert-butyl 3-(2-ethoxy-2-oxoethoxy)pyrrolidine-1-carboxylate (4.7 g, 17.2 mmol) to give the desired product (3.6 g, 100%) as an oil that solidified on standing.

1H NMR (400.13 MHz, DMSO-$d_6$) δ 1.21 (3H, t), 1.86-1.97 (1H, m), 2.04-2.12 (1H, m), 3.1-3.3 (4H, m), 4.12 (2H, q), 4.17 (2H, s), 4.27-4.33 (1H, m), 9.3 (1H, broad s), 9.55 (1H, broad s) the (S)-tert-butyl 3-(2-ethoxy-2-oxoethoxy)pyrrolidine-1-carboxylate used as starting material was prepared as described below Prepared in a similar manner to that above from (S)-tert-butyl 3-hydroxypyrrolidine-1-carboxylate (10 g, 53.41 mmol) to give the desired product (4.7 g, 32%) as a pale yellow oil.

1H NMR (400.13 MHz, DMSO-$d_6$) δ 1.21 (3H, t), 1.41 (9H, s), 1.83-2.01 (2H, m), 3.2-3.32 (4H, m), 4.12 (2H, s), 4.1-4.2 (5H, m)

(R)-methyl 2-(pyrrolidin-3-yl)acetate hydrochloride

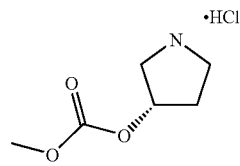

(R)-2-(1-(tert-butoxycarbonyl)pyrrolidin-3-yl)acetic acid (5.0 g, 21.81 mmol) in 4N HCl in dioxane (50 mL) was stirred at ambient temperature for 20 hours. The mixture was evaporated, coevaporated with dioxane (3×30 mL) and dried under high vacuum to give a yellow oil.

This was dissolved in methanol (50 mL) at 10° C. and the solution saturated with HCl gas. The reaction mixture was then allowed to warm to ambient temperature and evaporated. The residue was co-evaporated with methanol (2×30 mL) and toluene (3×30 mL) and dried under high vacuum to give a yellow oil (4.0 g).

1H NMR (400.13 MHz, DMSO-d$_6$) δ 1.52-1.57 (1H, m), 2.063-2.13 (1H, m), 2.47-2.59 (3H, m), 2.7-2.8 (1H, m), 3.03-3.12 (1H, m), 3.14-3.25 (1H, m), 3.27-3.48 (3H, m), 3.61 (3H, s), 9.42 (2H, s)

(S)-methyl 2-(pyrrolidin-3-yl)acetate hydrochloride

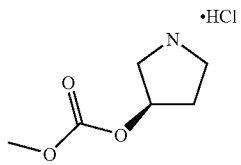

Prepared in a similar manner to that described above from (S)-2-(1-(tert-butoxycarbonyl)pyrrolidin-3-yl)acetic acid (5.0 g, 21.81 mmol) to give the desired compound (4.0 g, 100%) as a yellow oil.

1H NMR (400.13 MHz, DMSO-d$_6$) δ 1.52-1.57 (1H, m), 2.063-2.13 (1H, m), 2.47-2.59 (3H, m), 2.7-2.8 (1H, m), 3.03-3.12 (1H, m), 3.14-3.25 (1H, m), 3.27-3.48 (3H, m), 3.61 (3H, s), 9.42 (2H, s).

Ethyl 2-methyl-2-(3-piperidyl)propanoate hydrochloride

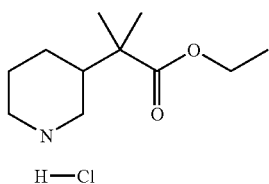

Ethyl 2-methyl-2-pyridin-3-yl-propanoate (1.80 g, 9.3 mmol) in ethanol (100 ml) and 5% rhodium on alumina (180 mg, 0.09 mmol) were stirred under an atmosphere of hydrogen at a pressure of 4 bar and a temperature of 25° C. for 12 hours.

The reaction mixture was filtered through Celite to remove the catalyst. 10 mL of 4N HCl in dioxane was added to form the hydrochloride salt and the solvent was evaporated under reduced pressure to give ethyl 2-methyl-2-(3-piperidyl)propanoate hydrochloride as a brown oil (2.19 g, 100%).

1H NMR (300.073 MHz, DMSO-d$_6$) δ1.07-1.08 (6H, m), 1.20 (3H, t), 1.52-1.70 (2H, m), 1.80 (1H, m), 1.96-2.04 (1H, m), 2.60-2.80 (2H, m), 3.05-3.19 (2H, m), 4.08 (2H, q), 8.75-9.35 (2H, m)

The ethyl 2-methyl-2-pyridin-3-yl-propanoate used as starting material was prepared as described below To a solution of ethyl 3-pyridyl acetate (3.30 g, 20.0 mmol) in DMF (30.0 mL) was added a 0.5M solution of potassium bis(trimethylsilyl)amide in toluene (80.0 mL, 40 mmol). The reaction mixture was stirred at room temperature for 30 minutes before adding MeI (3.99 mL, 64.0 mmol) in one portion. The reaction mixture was then stirred at room temperature for 18 hours.

The reaction mixture was evaporated to dryness and dissolved in DCM (150 mL), and washed sequentially with saturated NH$_4$Cl (25 mL), water (50 mL), and saturated brine (25 mL). The organic layer was dried over MgSO$_4$, filtered and evaporated to afford crude product. The crude product was purified by flash silica chromatography, elution gradient 0 to 50% EtOAc in isohexane. Pure fractions were evaporated to dryness to afford ethyl 2-methyl-2-pyridin-3-yl-propanoate (1.80 g, 9.3 mmol, 47%) as an orange oil.

1H NMR (400.13 MHz, DMSO-d$_6$) δ1.14 (3H, t), 1.55 (6H, s), 4.08 (2H, q), 7.35-7.39 (1H, m), 7.70-7.75 (1H, m), 8.46-8.48 (1H, m), 8.56 (1H, d)

m/z (ESI+) (M+H)+=194; HPLC t$_R$=0.71 min.

Ethyl 1-(3-piperidyl)cyclopropane-1-carboxylate hydrochloride

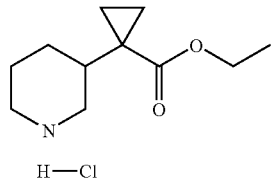

Prepared in a similar manner to that described above by reacting ethyl 2-pyridin-3-ylacetate with 1,2-dibromoethane to give ethyl 1-pyridin-3-ylcyclopropane-1-carboxylate which was then hydrogenated to give the desired compound as a brown oil (quantitative reaction).

$^1$H NMR (400.13 MHz, DMSO-d$_6$) δ1.03-1.22 (5H, m), 1.23-1.28 (2H, m), 1.45-1.83 (5H, m), 2.67-2.93 (2H, m), 3.02-3.36 (2H, m), 4.01-4.08 (2H, m), 8.75-9.35 (2H, m)

Ethyl 1-(3-piperidyl)cyclobutane-1-carboxylate hydrochloride

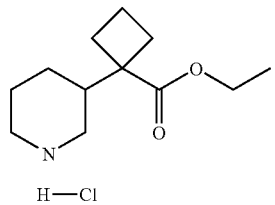

Prepared in a similar manner to that described above by reacting ethyl 2-pyridin-3-ylacetate with 1,3-dibromopropane to give ethyl 1-pyridin-3-ylcyclobutane-1-carboxylate which was then hydrogenated to give the desired compound as a brown oil (quantitative reaction).

$^1$H NMR (400.13 MHz, DMSO-d$_6$) δ1.11-1.18 (1H, m), 1.20-1.26 (3H, t), 1.62-1.79 (5H, m), 2.03-2.31 (5H, m), 2.58-2.78 (2H, m), 3.19 (2H, d), 4.13 (2H, q), 8.90-9.42 (2H, d)

Ethyl 2-methyl-2-(4-piperidyl)propanoate

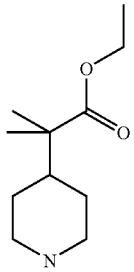

Ethyl 2-methyl-2-pyridin-4-yl-propanoate (1.50 g, 7.77 mmol) in ethanol (100 ml) and 5% rhodium on alumina (150 mg, 0.075 mmol) were stirred under an atmosphere of hydrogen at a pressure of 4 bars and a temperature of 25° C. for 12 hours.

The reaction mixture was filtered through Celite to remove the catalyst. The solvent was evaporated under reduced pressure to give ethyl 2-methyl-2-(4-piperidyl)propanoate as a black oil (quantitative reaction).

1H NMR (300.073 MHz, DMSO-d$_6$) δ 1.04 (6H, s), 1.17 (3H, t), 1.25-1.33 (2H, m), 1.48 (1H, d), 1.52-1.64 (2H, m), 1.80 (1H, s), 2.55-2.61 (2H, m), 3.09 (2H, d), 4.05 (2H, q)

The ethyl 2-methyl-2-pyridin-4-yl-propanoate used as starting material was prepared as described below To a solution of ethyl 4-pyridyl acetate (1.855 mL, 12.12 mmol) in DMF (30.0 mL) was added LiHMDS (15.15 mL, 15.15 mmol). The reaction was stirred at room temperature for 30 minutes before adding methyl iodide (1.21 mL, 19.4 mmol). The reaction mixture was stirred at room temperature for one hour before adding more LiHMDS (15.15 mL, 15.15 mmol). The reaction was stirred for another hour at room temperature before adding more methyl iodide (1.21 mL, 19.4 mmol). The reaction was then stirred at room temperature for two hours.

The reaction mixture was evaporated to dryness and dissolved in DCM (150 mL), and washed sequentially with saturated NH$_4$Cl (25 mL), water (50 mL), and saturated brine (25 mL). The organic layer was dried over MgSO$_4$, filtered and evaporated to afford crude product. The crude product was loaded on Celite and purified by flash silica chromatography, elution gradient 0 to 50% EtOAc in isohexane. Pure fractions were evaporated to dryness to afford ethyl 2-methyl-2-pyridin-4-yl-propanoate (1.061 g, 5.50 mmol, 45%) as a yellow oil.

m/z (ESI+) (M+H)+=194; HPLC t$_R$=2.44 min.

Ethyl 1-(4-piperidyl)cyclobutane-1-carboxylate

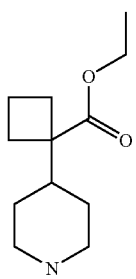

Prepared in a similar manner to that described above by reacting ethyl 4-pyridil acetate with 1,3-dibromopropane to give ethyl 1-pyridin-4-ylcyclobutane-1-carboxylate which was then hydrogenated to give the desired compound as a black oil (quantitative reaction).

1H NMR (300.073 MHz, DMSO-d$_6$) δ 1.06 (2H, t), 1.10-1.23 (5H, m), 1.50-1.54 (2H, m), 1.63-1.75 (3H, m), 1.83 (1H, s), 1.95-2.01 (2H, m), 2.22-2.28 (2H, m), 2.42 (1H, d), 2.99 (1H, d), 4.07 (2H, q)

Ethyl 1-(4-piperidyl)cyclopropane-1-carboxylate

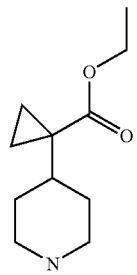

Prepared in a similar manner to that described above by reacting ethyl 4-pyridil acetate with 1,2 dibromoethane to give ethyl 1-pyridin-4-ylcyclopropane-1-carboxylate which was then hydrogenated to give the desired compound as a black oil (quantitative reaction).

1H NMR (300.073 MHz, DMSO-d$_6$) δ 0.73-0.78 (2H, m), 0.92-0.98 (2H, m), 1.14 (3H, t), 1.23-1.32 (2H, m), 1.42-1.50 (2H, m), 2.38 (2H, t), 2.89-2.93 (4H, m), 4.01 (2H, q)

Ethyl 2-(3-piperidyloxy)propanoate

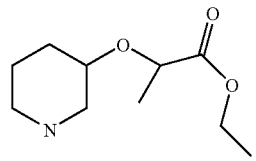

Prepared in a similar manner to that described above from ethyl 2-pyridin-3-yloxypropanoate to give the desired compound as a black gum (quantitative reaction).

1H NMR (300.073 MHz, DMSO-d$_6$) δ 1.17-1.22 (5H, m), 1.25-1.27 (2H, m), 1.38 (2H, d), 1.64-1.68 (2H, m), 1.76-1.86 (2H, m), 2.76-3.05 (2H, m), 3.36-3.42 (1H, m), 4.03-4.18 (3H, m)

Ethyl 2-methyl-2-(3-piperidyloxy)propanoate

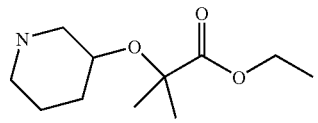

Prepared in a similar manner to that described above from ethyl 2-methyl-2-pyridin-3-yloxy-propanoate to give the desired compound as a black gum (quantitative reaction).

1H NMR (300.073 MHz, DMSO-d$_6$) δ 1.20 (3H, t), 1.23-1.28 (2H, m), 1.30 (6H, s), 1.54-1.59 (1H, m), 1.82-1.91 (1H, m), 2.20-2.29 (2H, m), 2.69 (1H, d), 2.95-2.97 (2H, m), 3.17-3.28 (1H, m), 4.10 (2H, q)

Ethyl 2-(3-piperidyloxy)acetate

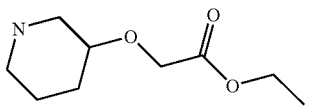

Prepared in a similar manner to that described above from ethyl 2-(2-chloropyridin-3-yl)oxyacetate to give the desired compound as a brown gum (quantitative reaction).

1H NMR (300.073 MHz, DMSO-$d_6$) δ 1.20 (3H, t), 1.54-1.65 (2H, m), 1.76-1.84 (2H, m), 2.89-2.95 (4H, m), 3.13-3.19 (1H, m), 3.68-3.76 (1H, m), 4.12 (2H, q), 4.20 (2H, s)

As part of the above programme of work, a number of ester intermediates of final products were characterised. Representative examples are given below

| Ester | Name | ¹H NMR δ | MS m/e MH⁺ |
|---|---|---|---|
|  | methyl 2-[(3S)-1-[5-[((2r,5s)-5-methylsulfonyl-2-adamantyl)carbamoyl]-6-propylsulfanyl-pyridin-2-yl]-3-piperidyl]acetate | 1H NMR (300.13 MHz, CDCl3) 0.97 (3H, t), 1.15-1.35( 2H, m), 1.55-1.75 (5H, m), 1.82-1.87(1H, m), 1.94-2.26 (14H, m), 2.70-2.80(4H, m), 2.92-3.01(1H, m), 3.07-3.18(2H, m), 3.63 (3H, s), 4.11-4.25(3H, m), 6.32(1H, d), 7.05(1H, d), 7.84(1H, d) | 564; HPLC tR = 2.72 min. |
|  | methyl (1R,5S)-3-[5-(2-adamantylcarbamoyl)-6-methylsulfanyl-pyridin-2-yl]-3-azabicyclo[3.1.0]hex-ane-6-carboylate | 1H NMR (300.072 MHz, CDCl3) 1.59 (t, 1H), 1.64-1.81(m, 4H), 1.82-2.07 (m, 10H), 2.24-2.29(m, 2H), 2.56(s, 3H), 3.58(d, 2H), 3.70(s, 3H), 3.87(d, 2H), 4.20-4.30(m, 1H), 6.05(d, 1H), 6.82-6.93(m, 1H), 7.84(d, 1H) | 442; HPLC $t_R$ = 3.09 min |
|  | methyl (3R)-1-[6-cyclohexylsulfanyl-5-[((2r,5s)-5-hydroxy-2-adamantyl)carbamoyl]pyridin-2-yl]pyrrolidine-3-carboxylate | 1H NMR (300.072 MHz, CDCl3) 1.29-2.38(m, 26H), 3.23(quintet, 1H), 3.47-3.58(m, 1H), 3.59-3.70(m, 1H), 3.72-3.81(m, 5H), 3.94-4.05(m, 1H), 4.19-4.27(m, 1H), 6.11(d, 1H), 7.14-7.20(m, 1H), 7.92(d, 1H) | 514; HPLC $t_R$ = 2.65 min. |

-continued

| Ester | Name | ¹H NMR δ | MS m/e MH⁺ |
|---|---|---|---|
| | methyl (3S)-1-[(2r,5s)-5-(2-adamantylcarbamoyl)-6-propylsulfanyl-pyridin-2-yl]pyrrolidine-3-carboxylate | 1H NMR (300.072 MHz, CDCl3) 1.03 (t, 3H), 1.61-2.09(m, 16H), 2.31(q, 2H), 3.15-3.28(m, 3H), 3.45-3.87(m, 7H), 4.22-4.32(m, 1H), 6.10(d, 1H), 7.04-7.13(m, 1H), 7.90(d, 1H) | 458; HPLC tR = 3.33 min. |
| | methyl 3-[5-(cyclohexylcarbamoyl)-6-propylsulfanyl-pyridin-2-yl]oxybenzoate | 1H NMR (300.072 MHz, CDCl3) 0.70 (t, 3H), 1.20-1.52(m, 7H), 1.58-1.69 (m, 1H), 1.70-1.82(m, 2H), 1.95-2.09 (m, 2H), 2.71(t, 2H), 3.93(s, 3H), 3.96-4.08(m, 1H), 6.31(d, 1H), 6.68(d, 1H), 7.33(d, 1H), 7.48(t, 1H), 7.81(s, 1H), 7.91(d, 1H), 7.95(d, 1H) | 429; HPLC t_R = 3.06 min |
| | methyl 2-[(3R)-1-[5-(2-adamantylcarbamoyl)-6-ethylsulfanyl-pyridin-2-yl]pyrrolidin-3-yl]acetate | 1H NMR (300.072 MHz, CDCl3) 1.38 (t, 3H), 1.61-1.81(m, 5H), 1.81-2.08 (m, 10H), 2.24(q, 1H), 2.49(d, 2H), 2.65-2.79(m, 1H), 3.10-3.21(m, 1H), 3.23(q, 2H), 3.48(q, 1H), 3.59-3.69(m, 1H), 3.71(s, 3H), 3.79(t, 1H), 4.21-4.31(m, 1H), 6.08(d, 1H), 6.99-7.05(m, 1H), 7.88(d, 1H) | 458; HPLC t_R = 3.28 min. |
| | methyl (1R,5S)-3-[6-cyclopentyl sulfanyl-5-(3-pyridin-3-yl pyrrolidine-1-carbonyl)pyridin-2-yl]-3-azabicyclo [3.1.0]hexane-6-carboxylate | 1H NMR (400.13 MHz, CDCl3) 1.63 (4H, m), 1.69-1.80(3H, m), 2.11-2.20 (3H, m), 2.25(2H, s), 2.36(1H, s), 3.52-3.60(4H, m), 3.69(4H, s), 3.74-3.87 (4H, m), 4.05-4.12(2H, m), 5.99(1H, d), 7.21-7.29(2H, m), 7.57(1H, s), 8.41-8.47(1H, m) | 493 |
| | methyl 2-[(3S)-1-[6-cyclopentylsulfanyl-5-[3-(2-hydroxypropan-2-yl)piperidine-1-carbonyl]pyridin-2-yl]-3-piperidyl]acetate | 1H NMR (300.072 MHz, CDCl3) 1.10-1.40(10H, m), 1.52-1.80(12H, m), 1.86-1.95(2H, m), 2.08-2.16(3H, m), 22.6-2.29(2H, m), 2.60(1H, s), 2.72-2.79(2H, m), 2.92-3.01(1H, m), 3.69 (3H, s), 4.03-4.16(2H, m), 4.24(1H, d), 6.31(1H, d), 7.19(1H, d) | 504 |

-continued

| Ester | Name | ¹H NMR δ | MS m/e MH⁺ |
|---|---|---|---|
| 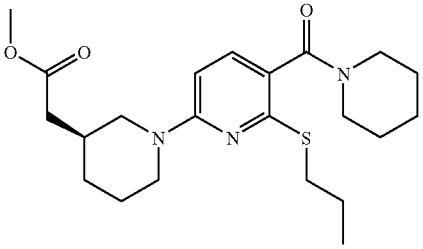 [SMILES: CCCSc1nc(N2CCC[C@@H](CC(=O)OC)C2)ccc1C(=O)N1CCCCC1] | methyl 2-[(3S)-1-[5-(piperidine-1-carbonyl)-6-propylsulfanyl-pyridin-2-yl]-3-piperidyl]acetate | 1H NMR (300.072 MHz, CDCl3) 1.01 (3H, t), 1.22-1.35(1H, m), 1.62-1.78 (11H, m), 1.87-1.93(1H, m), 2.03-2.13(1H, m), 2.22-2.35(2H, m), 2.71-2.80(1H, m), 2.92-3.02(1H, m), 3.05-3.17(2H, m), 3.43-3.65(3H, m), 3.69 (3H, s), 4.13-4.25(2H, m), 6.32(1H, d), 7.21(1H, d) | 420 |
| 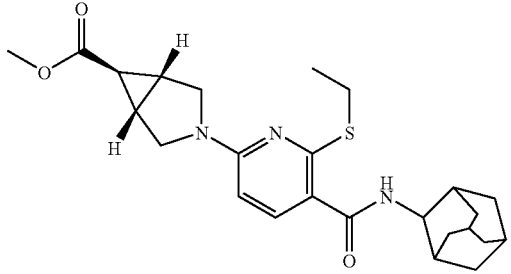 [SMILES: CCSc1nc(N2C[C@@H]3[C@H](C2)[C@H]3C(=O)OC)ccc1C(=O)NC1C2CC3CC(C2)CC1C3] | methyl(1S,5R)-3-[5-(2-adamantylcarbamoyl)-6-ethylsulfanyl-pyridin-2-yl]-3-azabicyclo[3.1.0]hexane-6-carboxylate | 1H NMR (400.13 MHz, DMSO-d6) 1.26(3H, t), 1.49-1.54(3H, m), 1.71 (2H, s), 1.77-1.81(5H, m), 1.84(1H, s), 1.91(2H, s), 2.05-2.08(2H, m), 2.23-2.24(2H, m), 3.03(2H, q), 3.51(2H, d), 3.62(2H, s), 3.81(2H, d), 3.92-3.97 (1H, m), 4.01-4.09(1H, m), 6.15(1H, d), 7.62-7.67(2H, m) | 456; HPLC tR = 3.31 min. |
| 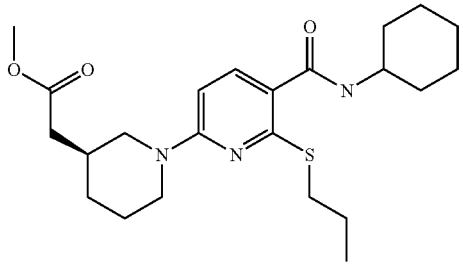 [SMILES: CCCSc1nc(N2CCC[C@@H](CC(=O)OC)C2)ccc1C(=O)NC1CCCCC1] | methyl 2-[(3S)-1-[5-(cyclohexylcarbamoyl)-6-propylsulfanyl-pyridin-2-yl]-3-piperidyl]acetate | 1H NMR (400.13 MHz, DMSO-d6) 0.95 (3H, t), 1.10-1.18( 1H, m), 1.20-1.30 (5H, m), 1.42(1H, d), 1.60(3H, m), 1.64-1.69(2H, m), 1.73(1H, m), 1.79(3H, t), 1.85-1.90(1H, m), 2.29(2H, m), 2.73-2.79(1H, m), 2.86-3.00(3H, m), 3.63(4H, d), 4.18(1H, d), 4.27(1H, d), 6.48(1H, d), 7.62(1H, d), 7.79(1H, d) | 434; HPLC t_R = 3.14 min. |
| 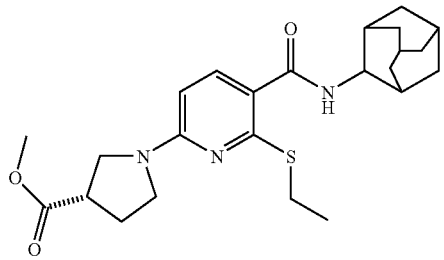 [SMILES: CCSc1nc(N2CC[C@H](C(=O)OC)C2)ccc1C(=O)NC1C2CC3CC(C2)CC1C3] | methyl (3S)-1-[5-(2-adamantylcarbamoyl)-6-ethylsulfanyl-pyridin-2-yl]pyrrolidine-3-carboxylate | 1H NMR (400.13 MHz, DMSO-d6) 1.27(3H, t), 1.52(2H, d), 1.72(2H, s), 1.78-1.86(6H, m), 1.92(2H, s), 2.08 (2H, d), 2.15-2.21(1H, m), 2.24-2.30 (1H, m), 3.06(2H, q), 3.27-3.36(2H, m), 3.48-3.58(2H, m), 3.67(3H, s), 3.70-3.75(1H, m), 3.95-3.99(1H, m), 6.19(1H, d), 7.58(1H, d), 7.67(1H, d) | 444; HPLC t_R = 3.25 min. |
| 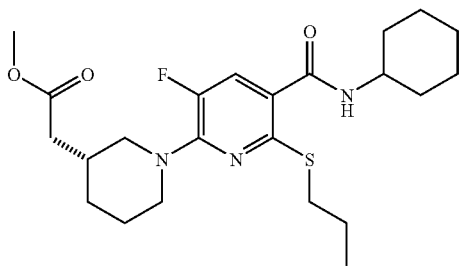 | methyl 2-[(3R)-1-[5-(cyclohexylcarbamoyl)-3-fluoro-6-propylsulfanyl-pyridin-2-yl]-3-piperidyl]acetate | 1H NMR (500.13 MHz, DMSO-d6) 0.96(3H, t), 1.06-1.11(1H, m), 1.24-1.32(5H, m), 1.54-1.64(4H, m), 1.70-1.73(3H, m), 1.80-1.84(3H, m), 1.97-2.02(1H, m), 2.26-2.31(2H, m), 2.82 (1H, t), 2.96(2H, t), 3.02(1H, t), 3.61 (3H, s), 3.60-3.66(1H, m), 4.02(1H, d), 4.08(1H, d), 7.63(1H, d), 7.91(1H, d) | 452; HPLC t_R = 3.29 min. |

-continued

| Ester | Name | ¹H NMR δ | MS m/e MH⁺ |
|---|---|---|---|
| | ethyl 1-[1-[5-(cyclohexylcarbamoyl)-6-cyclopentylsulfanyl-pyridin-2-yl]-3-piperidyl]cyclopropane-1-carboxylate | 1H NMR (300.073 MHz, DMSO-d6) 0.81-0.88(2H, m), 1.00-1.08(2H, m), 1.15(3H, t), 1.25(3H, m), 1.35-1.41 (1H, m), 1.44-1.50(5H, m), 1.48-1.74 (10H, m), 1.75-1.82(2H, m), 2.03-2.11(2H, m), 2.71-2.89(2H, m), 3.60-3.65(1H, m), 3.87-3.93(1H, m), 3.98-4.07(2H, q), 4.32-4.45(2H, m), 6.47 (1H, d), 7.57-7.60(1H, d), 7.72(1H, d) | 500; HPLC tR = 3.71 min. |
| | methyl 4-[[[5-(cyclohexylcarbamoyl)-6-propylsulfanyl-pyridin-2-yl]amino]methyl]cyclohexane-1-carboxylate | 1H NMR (400.13 MHz, CDCl3) 0.87-0.98(5H, m), 1.12-1.25(3H, m), 1.29-1.41(4H, m), 1.49-1.55(2H, m), 1.61-1.70(4H, m), 1.83(2H, d), 1.92-1.97 (4H, m), 2.14-2.22(1H, m), 3.06(2H, t), 3.15(2H, t), 3.59(3H, s), 3.82-3.83 (1H, m), 4.90(1H, s), 6.01(1H, d), 6.43 (1H, d), 7.62(1H, d) | 448; HPLC tR = 3.09 min. |
| | ethyl 2-[1-[5-(cyclohexylcarbamoyl)-6-propylsulfanyl-pyridin-2-yl]-3-piperidyl]-2-methyl-propanoate | 1H NMR (400.13 MHz, CDCl3) 0.96 (3H, t), 1.12(3H, s), 1.15(3H, s), 1.17-1.22(4H, m), 1.23(1H, d), 1.30-1.38 (2H, m), 1.45-1.55(2H, m), 1.58-1.75 (9H, m), 1.92-1.96(2H, m), 2.59-2.65 (1H, m), 2.70-2.74(1H, m), 2.96-3.03 (1H, m), 3.12-3.19(1H, m), 3.88-3.95 (1H, m), 4.09(2H, q), 4.33(2H, d), 6.25 (1H, d), 6.38(1H, d), 7.70(1H, d) | 476; HPLC tR = 3.48 min. |
| | methyl 2-[(3S)-1-[5-(cyclohexylcarbamoyl)-6-(2-pyrazin-2-ylethylsulfanyl)pyridin-2-yl]-3-piperidyl]acetate | ¹H NMR (400.13 MHz, DMSO-d₆) 1.09-1.15(1H, m), 1.21-1.31(5H, m), 1.40-1.48(1H, m), 1.57-1.65(2H, m), 1.69-1.75(4H, m), 1.81-1.91(1H, m), 2.19-2.32(2H, m), 2.73-2.79(1H, m), 2.90-3.00(1H, m), 3.12(2H, t), 3.35(2H, t), 3.39-3.46(1H, m), 3.56(3H, s), 3.58-3.63(1H, m), 4.22(1H, d), 4.32(1H, d), 6.52(1H, d), 7.67(1H, d), 7.82(1H, d), 8.49(1H, d), 8.52-8.55(2H, m) | 498 |

| Ester | Name | $^1$H NMR δ | MS m/e MH$^+$ |
|---|---|---|---|
| 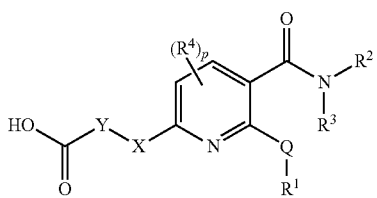 | methyl 2-[(3S)-1-[5-(cyclohexylcarbamoyl)-6-phenethylsulfanyl-pyridin-2-yl]-3-piperidyl]acetate | $^1$H NMR (400.13 MHz, CDCl$_3$) 1.21-1.33(3H, m), 1.41-1.50(3H, m), 1.53-1.63(2H, m), 1.68-1.73(3H, m), 1.88-1.92(1H, m), 1.96-2.00(2H, m), 2.03-2.09(1H, m), 2.22(2H, d), 2.75-2.81 (1H, m), 2.98-3.04(3H, m), 3.36-3.47 (2H, m), 3.65(3H, s), 3.90-4.03(1H, m), 4.23-4.30(2H, m), 6.33-6.43(2H, m), 7.19-7.32(5H, m), 7.78(1H, d) | 496 |

The invention claimed is:

1. A compound of formula (1):

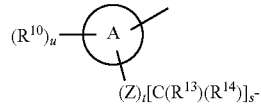

(1)

wherein:

Q is —S—;

$R^1$ is $C_{1-6}$alkyl, $C_{3-7}$cycloalkyl or $C_{3-7}$cycloalkyl$C_{1-3}$alkyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5$CON(R^{5'})$—, $(R^{5'})(R^{5''})$NC(O)—, $R^{5'}$OC(O)— and $(R^{5'})(R^{5''})$NSO$_2$— (wherein $R^5$ is $C_{1-3}$alkyl optionally substituted by 1, 2 or 3 substituents independently selected from hydroxyl, halo and cyano; and $R^{5'}$ and $R^{5''}$ are independently selected from the group consisting of hydrogen and $C_{1-3}$alkyl optionally substituted by 1, 2 or 3 substituents independently selected from the group consisting of hydroxyl, halo, $C_{1-3}$alkoxy, carboxy and cyano;

$R^2$ is $C_{3-7}$cycloalkyl(CH$_2$)$_m$— or $C_{6-12}$polycycloalkyl (CH$_2$)$_m$—; m is 0, 1, or 2 and the rings are optionally substituted by 1, or 2 substituents independently selected from $R^6$ where $R^6$ is independently selected from the group consisting of hydroxyl, halo, and triflouromethyl);

$R^3$ is hydrogen;

p is 0;

—X—Y— together represents a group of the formula:

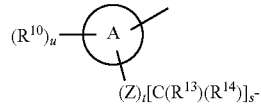

wherein:

ring A is linked to the pyridine group and —(Z)$_t$[C(R$^{13}$)(R$^{14}$)]$_s$— is linked to the carboxy group; and A is a piperidine ring containing a ring nitrogen atom by which it is attached to the pyridine ring;

Z is —O—, —S— or —N(R$^{16}$)— wherein R$^{16}$ is hydrogen, $C_{1-3}$alkyl or $C_{1-3}$alkanoyl;

t is 0 or 1 provided that when s is 0 then t is 0;

$R^{10}$ is independently selected from $C_{1-3}$alkyl and $C_{1-3}$alkoxy; and u is 0 or 1;

$R^{13}$ and $R^{14}$ are independently selected from hydrogen and from $C_{1-3}$alkyl or $R^{13}$ and $R^{14}$ may together with the carbon atom to which they are attached form a $C_{3-7}$cycloalkyl ring; and s is 0, 1 or 2;

or a pharmaceutically-acceptable salt thereof.

2. A compound according to claim 1, which is:

1-[5(cyclohexylcarbamoyl)-6-propylsulfanyl-pyridin-2-yl]piperidine-3-carboxylic acid;

1-[5(cyclohexylcarbamoyl)-6-propylsulfanyl-pyridin-2-yl]piperidine-4-carboxylic acid;

2-[1[5-(cyclohexylcarbamoyl)-6-propylsulfanyl-pyridin-2-yl]-4-piperidyl]-acetic acid;

2-[1[5-(cyclohexylcarbamoyl)-6-propylsulfanyl-pyridin-2-yl]-3-piperidyl]-acetic acid;

1-[5-(cyclohexylcarbamoyl)-6-propylsulfanyl-pyridin-2-yl]piperidine-2-carboxylic acid;

2-[1[5-(cyclohexylcarbamoyl)-6-propylsulfanyl-pyridin-2-yl]-4-piperidyl]propanoic acid;

2-[[1[5-(cyclohexylcarbamoyl)-6-propylsulfanyl-pyridin-2-yl]-3-piperidyl]oxy]propanoic acid;

2-[[1[5-(cyclohexylcarbamoyl)-6-propylsulfanyl-pyridin-2-yl]-3-piperidyl]oxy]acetic acid;

2-[(3R)-1-[5-(cyclohexylcarbamoyl)-6-cyclohexylsulfanyl-pyridin-2-yl]-3-piperidyl]acetic acid;

2-[(3S)-1-[5-(cyclohexylcarbamoyl)-6-cyclopentylsulfanyl-pyridin-2-yl]-3-piperidyl]acetic acid;

2-[(3R)-1-[5-(cyclohexylcarbamoyl)-6-cyclopentylsulfanyl-pyridin-2-yl]-3-piperidyl]acetic acid;

2-[(3S)-1-[5-(2-adamantylcarbamoyl)-6-propylsulfanyl-pyridin-2-yl]-3-piperidyl]acetic acid;

2-[(3S)-1-[5-[(2r,5s)-5-hydroxy-2-adamantyl]carbamoyl]-6-propylsulfanyl-pyridin-2-yl]-3-piperidyl]acetic acid;

1-[5-[[(2r,5s)-5-hydroxy-2-adamantyl]carbamoyl]-6-propylsulfanyl-pyridin-2-yl]-piperidine-4-carboxylic acid;
2-[(3R)-1-[5-[[(2r,5s)-5-hydroxy-2-adamantyl]carbamoyl]-6-propylsulfanyl-pyridin-2-yl]-3-piperidyl]acetic acid;
2-[1-[5-[[(2r,5s)-5-hydroxy-2-adamantyl]carbamoyl]-6-propylsulfanyl-pyridin-2-yl]-4-piperidyl]acetic acid;
3-[1-[5-[[(2r,5s)-5-hydroxy-2-adamantyl]carbamoyl]-6-propylsulfanyl-pyridin-2-yl]-3-piperidyl]propanoic acid;
1-[6-cyclopentylsulfanyl-5-[((2r,5s)-5-hydroxy-2-adamantyl]carbamoyl]-pyridin-2-yl]-piperidine-4-carboxylic acid;
2-[(3S)-1-[6-cyclohexylsulfanyl 5-[[(2r,5s)-5-hydroxy-2-adamantyl]carbamoyl]pyridin-2-yl]-3-piperidyl]acetic acid;
2-[(3S)-1-[5-[[(2r,5s)-5-hydroxy-2-adamantyl]carbamoyl]-6-(3-methylbutylsulfanyl)pyridin-2-yl]-3-piperidyl]acetic acid;
2-[(3S)-1-[5-(cyclohexyl-ethyl-carbamoyl-6-propylsulfanyl-pyridin-2-yl]-3-piperidyl]acetic acid;
2-[(3S)-1-[5-[(4-hydroxycyclohexyl)carbamoyl]-6-propylsulfanyl-pyridin-2-yl]-3-piperidyl]acetic acid;
{(3S)-1-[5-(adamantan-1-ylcarbamoyl-6-(propylthio)pyridin-2-yl]piperidin-3-yl}acetic acid;
or a pharmaceutically-acceptable salt thereof.

3. A pharmaceutical composition, which comprises a compound according to claim 1 in association with a pharmaceutical-acceptable diluent or carrier.

\* \* \* \* \*